(12) United States Patent
Schein et al.

(10) Patent No.: US 11,566,032 B2
(45) Date of Patent: Jan. 31, 2023

(54) RADIO-PROTECTIVE AND CHEMO-PROTECTIVE SUBSTITUTED THIOLS

(71) Applicants: TONIX PHARMACEUTICALS, INC., Chatham, NJ (US); TONIX PHARMACEUTICALS HOLDING CORP., Chatham, NJ (US)

(72) Inventors: Philip S. Schein, Stuart, FL (US); Darryl C. Rideout, Milford, PA (US)

(73) Assignees: TONIX PHARMACEUTICALS, INC., Chatham, NJ (US); TONIX PHARMACEUTICALS HOLDING CORP., Chatham, NJ (US)

( * ) Notice: Subject to any disclaimer, the term of this patent is extended or adjusted under 35 U.S.C. 154(b) by 0 days.

(21) Appl. No.: 17/315,258

(22) Filed: May 7, 2021

(65) Prior Publication Data
US 2021/0388011 A1    Dec. 16, 2021

Related U.S. Application Data

(60) Provisional application No. 63/021,937, filed on May 8, 2020.

(51) Int. Cl.
| | |
|---|---|
| *A61K 31/095* | (2006.01) |
| *C07C 321/06* | (2006.01) |
| *C07F 9/24* | (2006.01) |
| *A61P 39/00* | (2006.01) |
| *A61K 45/06* | (2006.01) |
| *C07D 241/04* | (2006.01) |
| *C07D 243/08* | (2006.01) |
| *C07D 243/10* | (2006.01) |
| *C07D 401/04* | (2006.01) |
| *C07D 487/04* | (2006.01) |
| *C07F 9/6574* | (2006.01) |

(52) U.S. Cl.
CPC ............ *C07F 9/24* (2013.01); *A61K 45/06* (2013.01); *A61P 39/00* (2018.01); *C07D 241/04* (2013.01); *C07D 243/08* (2013.01); *C07D 243/10* (2013.01); *C07D 401/04* (2013.01); *C07D 487/04* (2013.01); *C07F 9/65742* (2013.01); *C07B 2200/13* (2013.01)

(58) Field of Classification Search
CPC ............................ A61K 31/095; C07C 321/06
USPC ............................................... 514/706; 568/18
See application file for complete search history.

(56) References Cited

U.S. PATENT DOCUMENTS

| | | |
|---|---|---|
| 3,681,352 A | 8/1972 | Rosenfeld |
| 6,949,528 B1 | 9/2005 | Goddard |

| | | |
|---|---|---|
| 2008/0125483 A1 | 5/2008 | Hwang |
| 2014/0107216 A1 | 4/2014 | Fahl |
| 2014/0248242 A1 | 9/2014 | Dousson |

FOREIGN PATENT DOCUMENTS

| | | | |
|---|---|---|---|
| CN | 108948084 | | 12/2018 |
| WO | WO 2000/044731 | * | 8/2000 |
| WO | WO2009069100 | | 6/2009 |
| WO | WO2016041877 | | 3/2016 |
| WO | WO2019034866 | | 2/2019 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Guelman et al., "Ionizing radiation-induced damage on developing cerebellar granule cells cultures can be prevented by an early amifostine post-treatment," International Journal of Developmental Neuroscience, 23(1):1-7 (2005).
Warner et al., "Reaction of a poly dentate cysteine-based ligand and its nickel(II) complex with electrophilic and nucleophilic methyl-transfer reagents—from S-methylation to acetyl coenzyme A synthase reactivity," Dalton Transactions, 44(42):18378-18385 (2015).
Akbulut et al., "Cytoprotective effects of amifostine, ascorbic acid and N-acetylcysteine against methotrexate-induced hepatotoxicity in rats," World Journal of Gastroenterology, 20(9):10158-10165 (2014).
Bazin et al., "Phospholipidation of TLR7/8-active imidazoquinolines using a tandem phosphoramidite method," Tetrahedron Letters, 57(19):2063-2066 (2016).
Birkus et al., "Intracellular Activation of Tenofovir Alafenamide and the Effect of Viral and Host Protease Inhibitors," Antimicrobial Agents and Chemotherapy, 60(1):316-322 (2015).
Brand et al., "Reduction of X-ray-induced DNA damage in normal human cells treated with the PrC-210 radioprotector," Biology Open, bio035113. doi:10.1242/bio.035113 (2018) (6 pages).
Bushberg, "Radiation Exposure and Contamination," Merck Manual (2020) (18 pages).
Carroll et al., "S-[2-[(2'-carbamoylethyl)amino]ethyl] phosphorothio-ate and related compounds as potential antiradiation agents," Journal of Medicinal Chemistiy, 33(9):2501-2508 (1990).

(Continued)

*Primary Examiner* — Douglas M Willis
(74) *Attorney, Agent, or Firm* — Haley Guiliano LLP; James F. Haley, Jr.; Stacey W. Chung

(57) ABSTRACT

The present disclosure relates to prodrugs, double prodrugs, derivatives and analogues of 3-(methylamino)-2-((methylamino)methyl)propane-1-thiol. The compounds of this disclosure also relate to

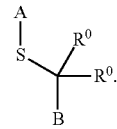

formula I The use of these compounds as radio— and chemo—protectors is also described.

25 Claims, 1 Drawing Sheet

(56) References Cited

OTHER PUBLICATIONS

Chevolot et al., "DNA-Based Carbohydrate Biochips: A Platform for Surface Glyco-Engineering," Communications, Angewandte Chemie International Edition, 46:2390-2402 (2007).
Chok et al., "Renoprotective potency of amifostine in rat renal ischaemia-reperfusion," Nephrology Dialysis Transplantation, 25:3845-3851 (2010).
Chronidou et al., "Beneficial effect of the oxygen free radical scavenger amifostine (WR-2721) on spinal cord ischemia/reperfusion injury in rabbits," Journal of Thoracic and Cardiovascular Surgery, 4(50):doi: 10.1186/1749-8090-4-50 (2009).
Copp et al., "Synthesis and growth regulatory activity of a prototype member of a new family of aminothiol radioprotectors," Bioorganic & Medicinal Chemistry Letters, 21(24):7426-7430 (2011).
Cucinotta et al., "Space radiation risks to the central nervous system," Life Sciences in Space Research, 2:54-69 (2014).
Cullen et al., "A Nuclear Magnetic Resonance Study of the Conformation of Six-membered Chelate Rings in Four-coordinate Complexes," Canadian Journal of Chemistry, 53(3):366-372 (1975).
Dorfmueller et al., "Substrate and product analogues as human O-GlcNAc transferase inhibitors," Amino Acids, 40(3):781-792 (2011).
Dugave et al., "Synthesis of Activated Disulfide Adducts Containing a 4-Diazocyclohexa-2,5-dienone Precursor for Photoaffinity Labelling," Tetrahedron Letters, 35(51):9557-9560 (1994).
Egron et al., "Effect of the Thioalkyl Chain Variation the Efficiency of Sate Pronucleotides," Nucleosides and Nucleotides, 17(9-11):1725-1729 (1998).
Eliel et al., "O NMR Spectra of Cycli Phophites, Phospates, and Thioposphates," Journal of the American Chemical Society, 108:6651-6661 (1986).
Erion et al., "Design, synthesis, and characterization of a series of cytochrome P(450) 3A-activated prodrugs (HepDirect prodrugs) useful for targeting phosph(on)ate-based drugs to the liver," Journal of the American Chemical Society, 126(16):5154-5163 (2004).
Foldi et al., "Addition of thiol compounds to the double bond. Part I. Preparation of tertiary mercapto-acids," Journal of Chemical Sciences (Bangalore), pp. 1683-1685 (1948).
Fu et al., "Amifostine reduces lung vascular permeability via suppression of inflammatory signalling," European Respiratory Journal, 33(3):612-624 (2009).
Greene-Schloesser et al., "Radiation-induced cognitive impairment—from bench to bedside," Neuro-Oncology, 14(4):iv37-iv44 (2012).
Hayashi et al., "Oxidative stress in inherited mitochondrial diseases," Free Radical Biology and Medicine, 88(pt A):10-17 (2015).
Hu et al., "A Convenient Trimethylsilylthioxy-Dehalogenation Reaction for the Preparation of Functionalized Thiols," Journal of Organic Chemistry, 64(13):4959-4961 (1999).
Kiuru et al., "2,2-Disubstituted 4-Acylthio-3-oxobutyl Groups as Esterase- and Thermolabile Protecting Groups of Phosphodiesters," Journal of Organic Chemistiy, 78(3):950-959 (2012).
Kiuru et al., "2-[(Acetyloxy)methyl]-4-(acetylsulfanyl)-2-(ethoxycarbonyl)-3-oxobutyl Group: A Thermolabile Protecting Group for Phosphodiesters," Helvetica Chimica Acta, 96(11):1997-2008 (2013).
Knapp et al., "Synthesis of alpha-GalNAc thioconjugates from an alpha-GalNAc mercaptan," Journal of Organic Chemistry, 67(9):2995-2999 (2002).
Kregel et al., "An integrated view of oxidative stress in aging: basic mechanisms, functional effects, and pathological considerations," American Journal of Physiology—Regulatory, Integrative and Comparative Physiology, 292(1):R18-R36 (2007).
Kulesza et al., "Synthesis of Stable Dolichylphosphomannose Analogues," Helvetica Chimica Acta, 87(12):3106-3118 (2004).

Laval et al., "Radioprotective effect of low doses of 2-(1-naphthylmethyl)-2-imidazoline alone or associated with phosphorothioates," European Journal of Medicinal Chemistry, 28(9):709-714 (1993).
Majer et al., "Discovery of Orally Available Prodrugs of the Glutamate Carboxypeptidase II (GCPII) Inhibitor 2-Phosphonomethylpentanedioic Acid (2-PMPA)," Journal of Medicinal Chemistiy, 59:2810-2819 (2016).
Matsumoto et al, "An approach to a chiral cycloalkanone-mediated asymmetric epoxidation of stilbene with oxone," Chemical and Pharmaceutical Bulletin, 49(12):1653-1657 (2001).
Mittal et al., "Reactive Oxygen Species in Inflammation and Tissue Injury," Antioxidants & Redox Signaling, 20(7):1126-1167 (2014).
Moene et al., "Reactivity of ether- and amine-complexed dimers and tetramers of alkyllithiums towards triphenylmethane," Chemistry—A European Journal, 6(2):225-236 (2000).
NIH, "Radiation Therapy for Cancer," National Cancer Institute (2019) (4 pages).
Nudelman et al., "Prodrugs of butyric acid. Novel derivatives possessing increased aqueous solubility and potential for treating cancer and blood diseases," European Journal of Medicinal Chemistry, 36(1):63-74 (2001).
Parihar et al., "What happens to your brain on the way to Mars," Science Advances, 1(4):e1400256, DOI: 10.1126/sciadv.1400256 (2015).
Peebles et al., "ROS-scavenger and radioprotective efficacy of the new PrC-210 aminothiol," Radiation Research, 178(1):57-68. doi:10.1667/rr2806.1 (2012).
Piper et al., "Heteroalicyclic Analogs of 2 and 3 Aminoalkanethiols," Journal of Organic Chemistry, 28(4):981-985 (1963).
Ponaire et al., "Growth inhibition of *Mycobacterium smegmatis* by prodrugs of deoxyxylulose phosphate reducto-isomerase inhibitors, promising anti-mycobacterial agents," European Journal of Medicinal Chemistry, 51:277-285 (2012).
Redd, "Radiation Remains a Problem for Any Mission to Mars," May 17, 2016, Smithsonian (4 pages).
Richter et al., "Penicillamine: An Extractable Chiral Auxiliary Providing Excellent Stereocontrol," Tetrahedron: Asymmetry, 7(2):427-434 (1996).
Romanucci et al., "Synthesis, biophysical characterization and anti-HIV activity of d(TG3 AG) Quadruplexes bearing hydrophobic tails at the 5'-end," Bioorganic & Medicinal Chemistry, 22(3):960-966 (2014).
Singh et al., "The efficacy and safety of amifostine for the acute radiation syndrome," Expert Opinion on Drug Safety, 18(11):1077-1090 (2019).
Tsukada et al., "A prodrag approach towards the development of tricyclic-based FBPase inhibitors," Bioorganic and Medicinal Chemistry Letters, 20:2938-2941 (2010).
Uttara et al., "Oxidative stress and neurodegenerative diseases: a review of upstream and downstream antioxidant therapeutic options," Current Neuropharmacology, 7(1):65-74 (2009).
Walli et al., "Tautomerism in Bis(oxzoline)s," European Journal of Organic Chemistry, 31:7044-7049 (2013).
Washburn et al., "Prediction of the effective radioprotective dose of WR-2721 in humans through an interspecies tissue distribution study," Radiation Research, 66(1):100-105 (1976).
Weitz et al., "Synthesis of a Trisubstituted 1,4-Diazepin-3-one-Based Dipeptidomimetic as a Novel Molecular Scaffold," Journal of Organic Chemistiy, 62:2527-2534 (1997).
Wondrak et al., "Identification of alpha-dicarbonyl scavengers for cellular protection against carbonyl stress," Biochemical Pharmacology, 63(3):361-373 (2002).
Wu et al., "Amifostine Pretreatment Attenuates Myocardial Ischemia/Reperfusion Injury by Inhibiting Apoptosis and Oxidative Stress," Oxidative Medicine and Cellular Longevity, doi: 10.1155/2017/4130824 (2017).

* cited by examiner

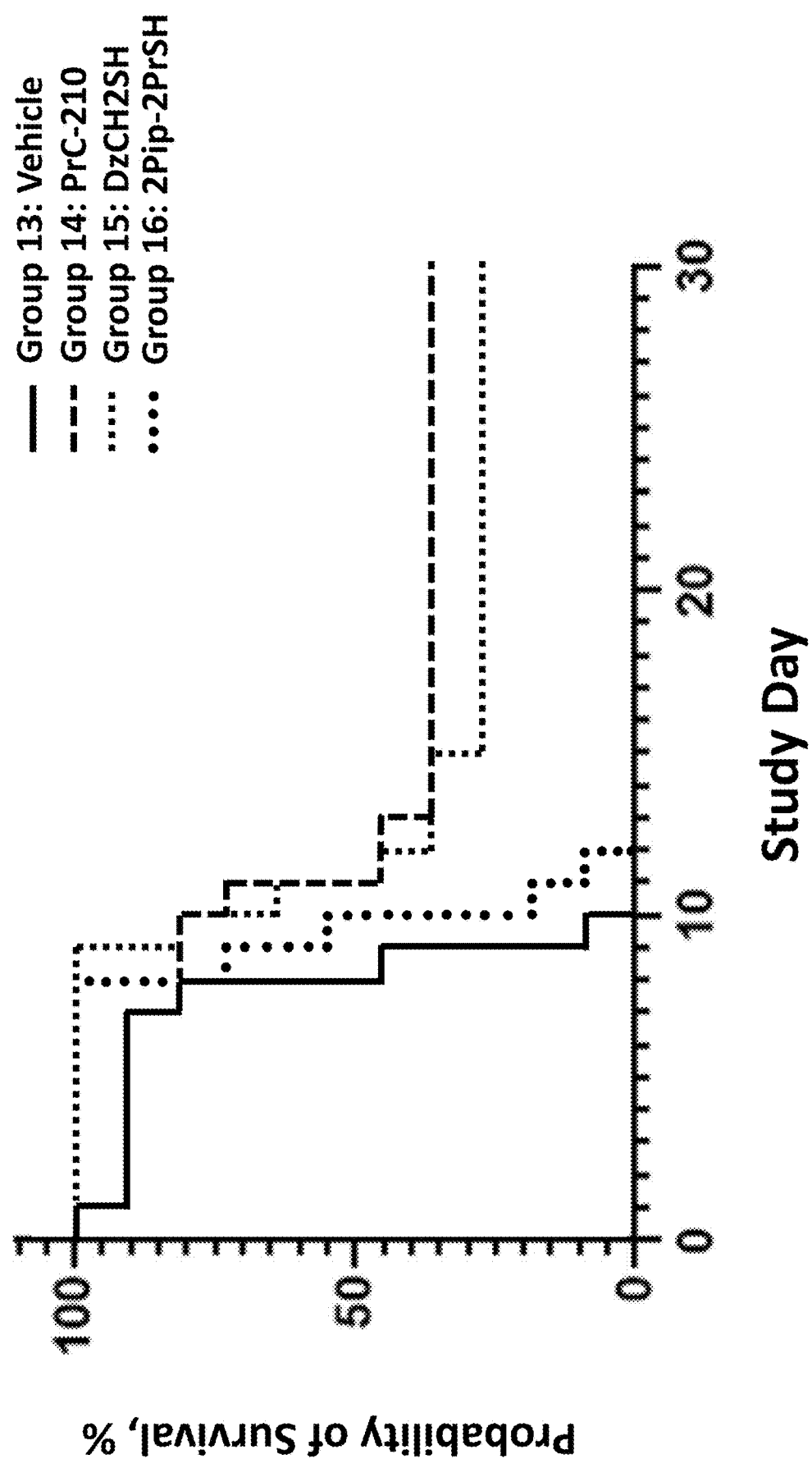

RADIO-PROTECTIVE AND CHEMO-PROTECTIVE SUBSTITUTED THIOLS

CROSS-REFERENCE TO RELATED APPLICATIONS

This application claims priority and benefit from U.S. Provisional Application No. 63/021,937, filed May 8, 2020, the contents of which are hereby incorporated by reference in its entirety.

FIELD OF THE DISCLOSURE

The present disclosure relates to compounds that are radio— and chemo-protective agents, pharmaceutical compositions comprising those compounds, and methods of preventing or reducing a syndrome, toxicity, disease or condition associated with exposure to ionizing radiation or chemotherapy.

BACKGROUND OF THE DISCLOSURE

In humans, exposure to high doses of radiation can lead to the development of Acute Radiation Syndrome (ARS) often referred to as radiation sickness. Irradiation of the body has cytotoxic effects on cells and tissues as it damages essential molecular structures within the cells such as DNA, RNA, proteins, etc. Hematopoietic, gastrointestinal, and neurovascular cells are most vulnerable to the adverse effects of ionizing radiation. Depletion of these cells is responsible for many of the observed symptoms of ARS.

Depending on the radiation dose and extent of exposure, ARS can manifest as bone marrow syndrome, gastrointestinal syndrome, and/or cutaneous and cardiovascular (CV)/central nervous system (CNS) syndrome. The syndrome has three distinct stages—the prodromal phase, the latent asymptomatic phase, and the overt systemic illness phase—each of which is characterized by the different symptoms of ARS that develop over time (Bushberg, Jerrold T. "Radiation Exposure and Contamination" Merck Manual (2020)). In many cases, ARS is fatal due to irreparable damage to the body's organs and tissues. In cases where the individual survives, however, recovery from ARS can take up to two years (Acute Radiation Syndrome: A Fact Sheet for Physicians. CDC (2005)).

Individuals, such as first-responders, nuclear power plant workers, pilots, flight attendants and astronauts can be exposed to high doses of radiation in the occupation setting. Emergency personnel, such as policemen, firefighters, and military members, can likewise be exposed to radiation while responding to an attack or accident involving radioactive material or during the decommissioning reactors. Individuals whose professions require space travel are also more likely to be exposed to harmful amounts of space radiation. In particular, space radiation exhibits increased ionization and is composed of many different types of radiation, including that from solar flares, coronal mass ejections, galactic cosmic rays, and radioactive particles within the Earth's magnetic field. NASA estimates that crews on the International Space Station are subjected to radiation doses ranging from 80 mSv-160 mSv during a six-month mission (NASA Facts: Understanding Space Radiation. National Aeronautics and Space Administration (2004)). Furthermore, the average radiation exposure experienced by astronauts is increased during spacewalk excursions outside of the space station or vehicle. Longer, extended deep space flight (such as the 3-year mission to Mars projected to be completed by the 2030s) would expose astronauts to even higher levels of radiation, levels which could effectively put an entire mission at risk (Redd, Nola Taylor "Radiation Remains a Problem for Any Mission to Mars," May 17, 2016, Smithsonian). Engineers have yet to develop effective methods to shield astronauts from increased radiation exposure and radiation scientists emphasize the need for research and development in the coming years as an adjunct to prudent planning for a such a mission to Mars (Redd, Nola Taylor "Radiation Remains a Problem for Any Mission to Mars," May 17, 2016, Smithsonian).

Therapeutic radiation for the treatment of cancer and other conditions is a more common source of radiation exposure among humans. For example, by applying radiation to proliferative cancer cells, this therapy aims to eliminate or to reduce the size of malignant tumors in the body. Despite efforts to target the radiation to isolated areas of abnormal tissue, therapeutic radiation still exposes normal healthy tissue to the cytotoxic effects of ionizing radiation leading to side effects. Currently, amifostine (Ethyol®):

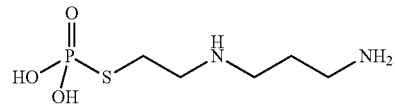 [SMILES: NCCCNCCSP(=O)(O)O]

is the only FDA-approved radioprotector for individuals undergoing therapeutic radiation treatment for cancer (Radiation Therapy for Cancer. National Cancer Institute (2019)). This agent, however, is only approved for protecting salivary glands from the damaging effects of radiation, and must be administered intravenously. In addition, this agent is associated with toxicities that can limit its use, such as transient hypotension and nausea and vomiting. Aside from the use of leucovorin to protect against the toxicity of methotrexate, there is no oral, multi-organ radioprotector available for subjects undergoing chemotherapy and/or therapeutic radiation. There is, therefore, a glaring need for an oral chemo- and radio-protector that has ease of administration, reduced costs and likely reduced adverse reactions, with minimal loss of efficacy for the treated tumor, versus the currently available intravenous therapy.

There is also a need to develop an effective orally bio-available radioprotective compound that is capable of providing systemic protection from the harmful effects of ionizing radiation to the body's healthy tissues. An easily-administered pharmaceutical composition would be the most practical means of protection in both radiological emergencies and exposures and therapeutic radiation treatments.

Exposure to radiation can also lead to oxidative stress, i.e., an imbalance between free radicals and antioxidants in the body. Oxidative stress results in damage to biomolecules such as lipids, proteins and DNA. This damage often leads to the development of chronic diseases such as atherosclerosis, cancer, diabetes, rheumatoid arthritis, post-ischemic perfusion injury, myocardial infarction, cardiovascular diseases, chronic inflammation, stroke, septic shock, aging and other degenerative diseases (Uttara, B., et al., Oxidative Stress and Neurodegenerative Diseases: A Review of Upstream and Downstream Antioxidant Therapeutic Options, *Current Neuropharmacology*, 2009, 7, 65-74). Oxidative stress is also considered a contributing factor in aging (Kregel, K. C., et al, "An integrated view of oxidative stress in aging: basic mechanisms, functional effects, and pathological considerations", *Am. J. Physiol. Regul. Integr. Comp. Physiol,* 2007, 292, R18-R36) and inflammatory disorders (Mittal, M., et al., "Reactive Oxygen Species in Inflammation and Tissue Injury", *Antioxidants & Redox Signaling,* 2014, 20(7), 1126-1167). Additionally, hereditary conditions that are associated with mutations in mitochondrially expressed genes have been linked to oxidative stress, including Friedreich ataxia, Leber's hereditary optic neuropathy (LHON), myoclonus epilepsy, ragged red fiber disease (MERRF), mitochondrial encephalomyapathy, lactic acidosis and stroke-like episodes (MELAS) (Hayashi, G.; Cortopassi, G., "Oxidative stress in inherited mitochondrial diseases", *Free Radical Biology and Medicine,* 2015, 88, 10-17). Thus, there is a need to develop an effective reactive oxygen species (ROS) scavenger that is capable of treating diseases, disorders or conditions associated with oxidative stress.

SUMMARY OF THE DISCLOSURE OF THE APPLICATION

In one aspect, the disclosure is directed to a compound having a structure according to formula I.

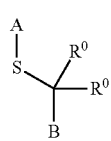

formula I or a pharmaceutically acceptable salt, solvate, hydrate, or polymorph thereof, or a solvate, hydrate, or polymorph of the pharmaceutically acceptable salt, wherein;
each $R^0$ is independently hydrogen, (C1-C3)alkyl, or —SH;
A is selected from hydrogen, Moiety $A^1$, Moiety $A^2$ or Moiety $A^3$:

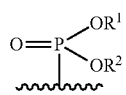

Moiety $A^1$ wherein each of $R^1$ and $R^2$ is independently selected from the group consisting of hydrogen, —(CH($R^6$))—O—C(O)$R^{10}$, —(CH($R^6$))$_m$—S—C(O)$R^{10}$ and —CH$_2$—(C($R^{11}$)$_2$)—C(O)—CH$_2$—S—C(O)$R^{10}$; wherein m is an integer selected from the group consisting of 0, 1, 2, 3, and 4; or $R^1$ and $R^2$, one of which is CH$_2$ or the other is CH$_2$CH$_2$, taken with the —O—P—O— linkage to which they are attached, form a 6-membered heterocycloalkyl ring that is independently substituted with 1-2 Ra and 0-3 $R^b$;
wherein each Ra is independently hydrogen, (C1-C6)alkyl, (C6-C10)aryl- or a 5- to 10-membered heteroaryl-, provided that at least one $R^a$ group is (C6-C10)aryl- or a 5- to 10-membered heteroaryl-, wherein said alkyl, aryl and heteroaryl $R^a$ is substituted with 0-3 $R^c$;
wherein, when present, each $R^b$ is —(C1-C3)alkyl;
wherein each $R^c$ is independently selected from the group consisting of halogen, (C1-C3)alkyl, —CN, —O—(C1-C3)alkyl, —S—(C1-C3)alkyl, —C(O)O—(C1-C3)alkyl, —N(R')$_2$, —CF$_3$ and —OCF$_3$;
wherein each $R^6$ is independently hydrogen or (C1-C3)alkyl;
wherein each $R^{10}$ is selected from the group consisting of —(C1-C6)alkyl, —O—(C1-C6)alkyl, —O—(C6-C10)aryl, —(C6-C10)aryl, (5- to 10-membered)heteroaryl, (4- to 10-membered)heterocycloalkyl, (C3-C10)cycloalkyl, —O—(5- to 10-membered)heteroaryl, —O—(4- to 10-membered)heterocycloalkyl, —O—(C3-C10)cycloalkyl, —O—(4- to 20-membered)heteroalkyl,-(4- to 20-membered)heteroalkyl, —[(CH$_2$)$_y$O]$_z$—R, —CH$_2$—O—[(CH$_2$)$_y$O]$_z$—R and —O—[(CH$_2$)$_y$O]$_z$—R, wherein each of said heteroalkyl, heterocycloalkyl, and heteroaryl independently have 1-6 oxygen atoms, wherein y is an integer between 1 and 4, wherein z is an integer between 1 and 10, wherein R is hydrogen or (C1-C6)alkyl and wherein each $R^{10}$ is independently substituted with 0-3 $R^c$;
wherein each $R^{11}$ is independently selected from the group consisting of hydrogen, —(C1-C6)alkyl, —CH$_2$—O—C(O)R", —C(O)—OR", —(4- to 20-membered)heteroalkyl, —O—(4- to 20-membered)heteroalkyl, —[(CH$_2$)$_y$O]$_z$—R, —CH$_2$—O—[(CH$_2$)$_y$O]$_z$—R and —O—[(CH$_2$)$_y$O]$_z$—R, wherein each of said heteroalkyls independently has 1-6 oxygen atoms, wherein y is an integer between 1 and 4, wherein z is an integer between 1 and 10, and wherein R is hydrogen or (C1-C6)alkyl;

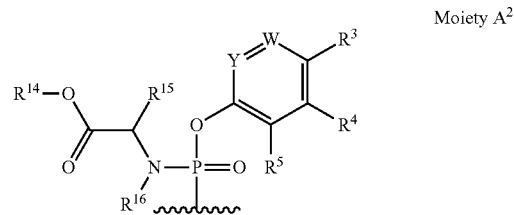

Moiety $A^2$ wherein W and Y are independently selected from N or CH;
wherein $R^3$ is hydrogen, halogen, (C1-C6)alkyl, (C3-C7)cycloalkyl, (5- to 8-membered)heterocycloalkyl, —O—(C1-C6)alkyl, —O—(C3-C7)cycloalkyl, —O—(5- to 8-membered)heterocycloalkyl, (C2-C6)alkenyl, —CH$_2$OH, phenyl, (5- to 6-membered)heteroaryl, or (5- to 6-membered)heterocycloalkyl, wherein $R^3$ is substituted with 0-3 substituents selected from the group consisting of halogen, oxo, —CN, —(C1-C6)alkyl, —O—(C1-C6)alkyl, and —C(O)O(C1-C3)alkyl;
wherein $R^4$ is hydrogen, —CN, (C1-C6)alkyl, —O—(C1-C6)alkyl, (C2-C6)alkenyl or —CH$_2$OH;
or $R^4$ and $R^3$ are taken together with the carbon atoms to which they are attached to form a (C5-C6)cycloalkyl, (C6-C10)aryl, (5- to 10-membered)heterocycloalkyl or (5- to 10-membered)heteroaryl;
wherein $R^5$ is hydrogen, halogen, (C1-C6)alkyl or —O—(C1-C6)alkyl; or
$R^5$ and $R^4$ are taken together with the carbon atoms to which they are attached to form a (C5-C6)cycloalkyl, phenyl, (5- or 6-membered)heterocycloalkyl, or (5- or 6-membered)heteroaryl; wherein $R^{14}$ is —(C1-C6)alkyl;
wherein $R^{15}$ is hydrogen, —(C1-C6)alkyl, —CH$_2$—phenyl, or —CH$_2$-(5—to 10-membered)heteroaryl, wherein the —(C1-C6)alkyl, —CH₂—phenyl, or —CH₂-(5—to 10-membered)heteroaryl are substituted with 0-3 substituents selected from the group consisting of —OH, —SH, —SCH₃, —C(O)NH₂, —C(O)OH, —NH₂ and —NH—C(=NH)NH₂;
wherein R¹⁶ is hydrogen or —(C1-C6)alkyl;

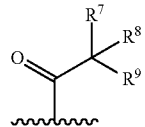

Moiety A³ wherein R⁷ is selected from the group consisting of —(C1-C3)alkyl, —(C3-C6)cycloalkyl, and —(4- to 6-membered)heterocycloalkyl, wherein R⁷ is substituted with 0-3 R";
wherein R⁸ and R⁹ are independently selected from the group consisting of hydrogen, —(C1-C3)alkyl, —(C3-C6)cycloalkyl, and —(4- to 6-membered)heterocycloalkyl, wherein R⁸ and R⁹ are independently substituted with 0-3 R";
wherein R" is hydrogen, halogen, —(C1-C6)alkyl, —O—(C2-C6)alkyl, —(4- to 20-membered)heteroalkyl, or —[(CH₂)ᵧO]_z—R, wherein said heteroalkyl has 1-6 oxygen atoms, wherein y is an integer between 1 and 4, wherein z is an integer between 1 and 10, and wherein R is hydrogen or (C1-C6)alkyl;
wherein B is a (6- to 8-membered)heterocycloalkyl containing two N atoms, wherein B is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4) alkenyl and (C1-C4)alkynyl, wherein the (C1-C4)alkyl, (C1-C4)alkenyl and (C1-C4)alkynyl are optionally substituted with 1-3 halogen or (C1-C4)alkoxy;
or is selected from Moiety B¹ or Moiety B², wherein Moiety B¹ has the structure:

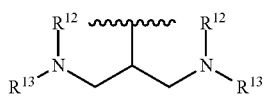

Moiety B¹ wherein each occurrence of R¹² and R¹³ is independently selected from the group consisting of hydrogen, —(C1-C10)alkyl, —(C3-C10)cycloalkyl, —(4- to 10-membered) heteroaryl, and —(4- to 10-membered)heterocycloalkyl, wherein each of R¹² and R¹³ is independently substituted with 0-3 R'; or
wherein two R¹³ groups taken with the nitrogen atoms to which they are attached combine to form a (7- to 8-membered)heterocycloalkyl, wherein the (7- to 8-membered)heterocycloalkyl is substituted with 0-3 (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4) alkenyl and (C1-C4)alkynyl, wherein the (C1-C4)alkyl,
(C1-C4)alkenyl and (C1-C4)alkynyl are optionally substituted with 1-3 halogen or (C1-C4)alkoxy;
wherein R is selected from hydrogen, halogen, (C1-C4) alkyl, or —O—(C1-C4)alkyl; and wherein Moiety B² has the structure:

Moiety B² wherein n is an integer selected from the group consisting of 1, 2, 3, and 4; and provided that the compound is not

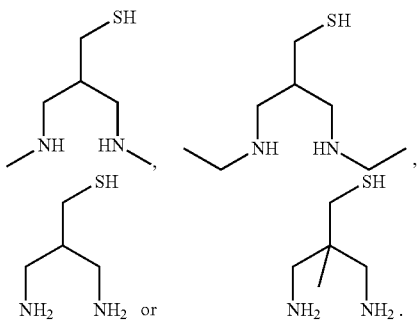

In one embodiment, the disclosure is directed to a compound having a structure according to formula II,

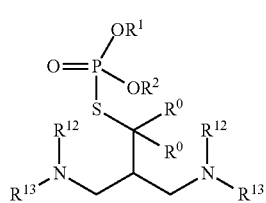

formula II or a pharmaceutically acceptable salt, solvate, hydrate, or polymorph thereof, or a solvate, hydrate, or polymorph of the pharmaceutically acceptable salt, wherein R⁰, R¹, R², R¹², and R¹³ are as defined in formula I.

In another embodiment, the disclosure is directed to a compound having a structure according to formula III,

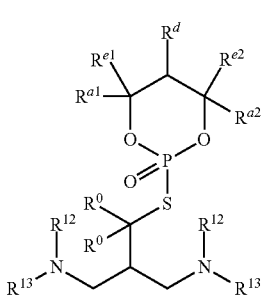

formula III or a pharmaceutically acceptable salt, solvate, hydrate, or polymorph thereof, or a solvate, hydrate, or polymorph of the pharmaceutically acceptable salt, wherein $R^0$, $R^{12}$, and $R^{13}$ are as defined in formula I, and wherein:

$R^{a1}$ and $R^2$ are independently selected from hydrogen, (C1-C6)alkyl, (C6-C10)aryl or a 5- to 10-membered heteroaryl, wherein said alkyl, aryl and heteroaryl are substituted with 0-3 $R^c$, provided that at least one of $R^{a1}$ and $R^{a2}$ is (C6-C10)aryl or a 5- to 10-membered heteroaryl;

$R^d$ is hydrogen or (C1-C3)alkyl; and $R^{e1}$ and $R^{e2}$ are independently hydrogen or (C1-C3)alkyl, provided that when $R^{a1}$ is (C6-C10)aryl or a 5- to 10-membered heteroaryl, $R^{e1}$ is hydrogen, and that when $R^{a2}$ is (C6-C10)aryl or a 5- to 10-membered heteroaryl, $R^{e2}$ is hydrogen.

In another embodiment, the disclosure is directed to a compound having a structure according to formula IV,

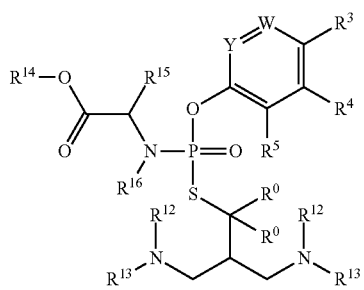

formula IV or a pharmaceutically acceptable salt, solvate, hydrate, or polymorph thereof, or a solvate, hydrate, or polymorph of the pharmaceutically acceptable salt, wherein Y, W, $R^0$, $R^4$, $R^5$, $R^{12}$, $R^{13}$, $R^{14}$, $R^{15}$, and $R^{16}$ are as defined in formula I, and wherein:

$R^3$ is (C1-C6)alkyl, (C3-C7)cycloalkyl, (5- to 8-membered)heterocycloalkyl, —O—(C1-C6)alkyl, —O—(C3-C7)cycloalkyl, —O—(5- to 8-membered)heterocycloalkyl, (C2-C6)alkenyl, —CH$_2$OH, phenyl, (5- or 6-membered)heteroaryl, or (5- or 6-membered)heterocycloalkyl, wherein $R^3$ is substituted with 0-3 substituents selected from the group consisting of halogen, oxo, —(C1-C5)alkyl, —O—(C2-C4)alkyl, and —C(O)O(C1-C3)alkyl.

In one embodiment, the disclosure is directed to a compound having a structure according to formula V,

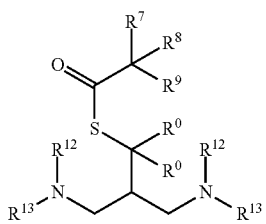

formula V or a pharmaceutically acceptable salt, solvate, hydrate, or polymorph thereof, or a solvate, hydrate, or polymorph of the pharmaceutically acceptable salt, wherein $R^0$, $R^7$, $R^1$, $R^9$, $R^{12}$, and $R^{13}$ are as defined in formula I, and wherein:

R" is halogen, —(C1-C6)alkyl or —O—(C2-C6)alkyl.

In another embodiment, the disclosure is directed to a compound having a structure according to formula VI:

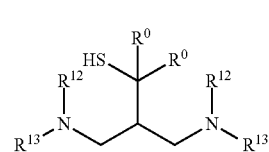

formula VI or a pharmaceutically acceptable salt, solvate, hydrate, polymorph, prodrug or double prodrug thereof, or a solvate, hydrate, or polymorph of the pharmaceutically acceptable salt, wherein $R^0$, $R^{12}$, and $R^{13}$ are as defined in formula I, provided that the compound is not

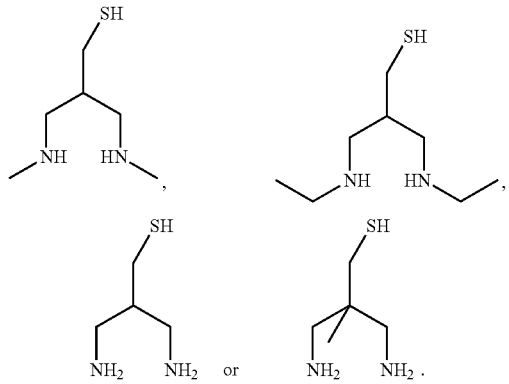

In another embodiment, the disclosure is directed to a compound having a structure according to formula VII:

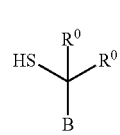

formula VII or a pharmaceutically acceptable salt, solvate, hydrate, polymorph, prodrug or double prodrug thereof, or a solvate, hydrate, or polymorph of the pharmaceutically acceptable salt, wherein $R^0$ and B are as defined in formula I, provided that the compound is not

-continued

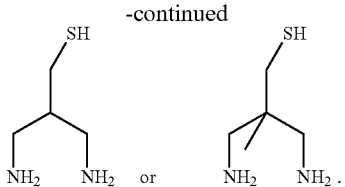

In one aspect, this disclosure is directed to a method of treating or preventing a toxicity or condition associated with ionizing radiation exposure in a subject in need of said radiation, comprising administering to the subject a therapeutically effective or protective amount of a compound of this disclosure, or of a pharmaceutical composition thereof.

In another aspect, this disclosure is directed to a method of protecting normal tissues in a subject against toxicities associated with radiation therapy with minimal adverse effects on the tumor response to those treatments, the method comprising administering to said subject a therapeutically effective amount of a compound or pharmaceutical composition of this disclosure.

In one aspect, this disclosure is directed to a method of protecting normal tissues in a subject against toxicities associated with chemotherapy with minimal adverse effects on the tumor response to those treatments, the method comprising administering to said subject a therapeutically effective amount of a compound or pharmaceutical composition this disclosure.

In another aspect, this disclosure is directed to a method of reducing the risk of secondary tumor induction in a subject being treated with radiation therapy, the method comprising administering to said subject a therapeutically effective amount of a compound or pharmaceutical composition of this disclosure.

In one aspect, this disclosure is directed to a method of reducing the risk of secondary tumor induction in a subject being treated with chemotherapy, the method comprising administering to said subject a therapeutically effective amount of a compound or pharmaceutical composition of this disclosure.

In another aspect, this disclosure is directed to a method of reducing the risk of tumor induction in a subject who has been exposed to, is being exposed to, or will be exposed to ionizing radiation, the method comprising administering to said subject a protective amount of a compound or pharmaceutical composition of this disclosure.

In another aspect, this disclosure is directed to a method of slowing the aging process in a subject, wherein the method comprises administering a compound or pharmaceutical composition of this disclosure.

In another aspect, this disclosure is directed to a method of treating a disease or condition in a subject in need thereof comprising administering a compound or a pharmaceutical composition of this disclosure.

In one aspect, this disclosure is directed to a pharmaceutical composition or a crystalline salt form of one of the aspects of this disclosure and a pharmaceutically acceptable carrier.

In one embodiment, the pharmaceutical composition of this disclosure further comprises an antioxidant.

In one embodiment, a pharmaceutical composition of this disclosure is co-administered (concurrently, separately or sequentially) with an antioxidant as described herein. In another embodiment, the antioxidant is selected from the group consisting of ascorbic acid, ascorbate, vitamin C, N-acetylcysteine, glutathione, lipoic acid, uric acid, alpha-tocopherol, vitamin E, beta-carotene, vitamin A, retinol, and ubiquinol.

BRIEF DESCRIPTION OF THE DRAWINGS

FIG. 1 shows a Kaplan-Meier plot with survival curves of mice treated with vehicle, PrC-210, DzCH2SH or 2Pip-PrSH prior to total body irradiation with 9.9 Gy.

DETAILED DESCRIPTION OF THE DISCLOSURE

Exemplary Embodiments

Exemplary Embodiments of the Disclosure Include

1. A compound having a structure according to formula I:

or a pharmaceutically acceptable salt, solvate, hydrate, or polymorph thereof, or a solvate, hydrate, or polymorph of the pharmaceutically acceptable salt, wherein; each $R^0$ is independently hydrogen, (C1-C3)alkyl, or —SH; A is selected from hydrogen, Moiety $A^1$, Moiety $A^2$ or Moiety $A^3$:

wherein each of $R^1$ and $R^2$ is independently selected from the group consisting of hydrogen, —(CH($R^6$))—O—C(O)$R^{10}$, —(CH($R^6$))$_m$—S—C(O)$R^{10}$ and —CH$_2$—(C($R^{11}$)$_2$)—C(O)—CH$_2$—S—C(O)$R^{10}$; wherein m is an integer selected from the group consisting of 0, 1, 2, 3, and 4;

or $R^1$ and $R^2$, one of which is CH$_2$ or the other of which is CH$_2$CH$_2$, taken with the —O—P—O— linkage to which they are attached form a 6-membered heterocycloalkyl ring that is independently substituted with 1-2 $R^a$ and 0-3 $R^b$;

wherein each $R^a$ is independently hydrogen, (C1-C6)alkyl, (C6-C10)aryl- or a 5- to 10-membered heteroaryl-, wherein said alkyl, aryl and heteroaryl is substituted with 0-3 $R^c$, provided that at least one $R^a$ group is (C6-C10)aryl- or a 5- to 10-membered heteroaryl-;

wherein when present, each $R^b$ is —(C1-C3)alkyl;

wherein when present each $R^c$ is independently selected from the group consisting of halogen, (C1-C3)alkyl, —CN, —O—(C1-C3)alkyl, —S—(C1-C3)alkyl, —C(O)O—(C1-C3)alkyl, —N(R')$_2$, —CF$_3$ and —OCF$_3$;

wherein each $R^6$ is independently hydrogen or (C1-C3)alkyl; wherein each $R^{10}$ is selected from the group consisting of —(C1-C6)alkyl, —O—(C1-C6)alkyl, —O—(C6-C10)aryl, —(C6-C10)aryl, (5- to 10-membered)heteroaryl, (4- to 10-membered)heterocycloalkyl, (C3-C10)cycloalkyl, —O—(5- to 10-membered)heteroaryl, —O—(4- to 10-membered)heterocycloalkyl, —O—(C3-C10)cycloalkyl, —O—(4- to 20-membered)heteroalkyl, —(4- to 20-membered)heteroalkyl, —[(CH$_2$)$_y$O]$_z$—R, —CH$_2$—O—[(CH$_2$)$_y$O]$_z$—R and —O—[(CH$_2$)$_y$O]$_z$—R, wherein each of said heteroalkyl, heterocycloalkyl and heteroaryl independently have 1-6 oxygen atoms, wherein y is an integer between 1 and 4, wherein z is an integer between 1 and 10, wherein R is hydrogen or (C1-C6)alkyl, and wherein each R$^{10}$ is independently substituted with 0-3 R$^c$;

each R$^{11}$ is independently selected from the group consisting of hydrogen, —(C1-C6)alkyl, —CH$_2$—O—C(O)R", —C(O)—OR", —(4- to 20-membered)heteroalkyl, —O—(4- to 20-membered)heteroalkyl, —[(CH$_2$)$_y$O]$_z$—R, —CH$_2$—O—[(CH$_2$)$_y$O]$_z$—R and —O—[(CH$_2$)$_y$O]$_z$—R, wherein each of said heteroalkyl independently has 1-6 oxygen atoms, wherein y is an integer between 1 and 4, wherein z is an integer between 1 and 10, and wherein R is hydrogen or (C1-C6)alkyl;

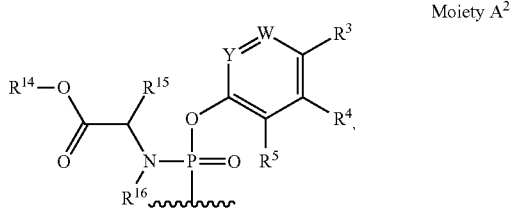

Moiety A$^2$ wherein W and Y are independently selected from N or CH;

wherein R$^3$ is hydrogen, halogen, (C1-C6)alkyl, (C3-C7)cycloalkyl, (5- to 8-membered)heterocycloalkyl, —O—(C1-C6)alkyl, —O—(C3-C7)cycloalkyl, —O—(5- to 8-membered)heterocycloalkyl, (C2-C6)alkenyl, —CH$_2$OH, phenyl, (5- to 6-membered)heteroaryl, or (5- to 6-membered)heterocycloalkyl, wherein R$^3$ is substituted with 0-3 substituents selected from the group consisting of halogen, oxo, cyano, —(C1-C6)alkyl, —O—(C1-C6)alkyl, and —C(O)O(C1-C3)alkyl;

wherein R$^4$ is hydrogen, —CN, (C1-C6)alkyl, —O—(C1-C6)alkyl, —(C2-C6)alkenyl or —CH$_2$OH; or R$^4$ and R$^3$ are taken together with the carbon atoms to which they are attached to form a (C5-C6)cycloalkyl, (C6-C10)aryl, (5- to 10-membered)heterocycloalkyl or (5- to 10-membered)heteroaryl;

wherein R$^5$ is hydrogen, halogen, (C1-C6)alkyl or —O—(C1-C6)alkyl; or R$^5$ and R$^4$ are taken together with the carbon atoms to which they are attached to form a (C5-C6)cycloalkyl, phenyl, (5- or 6-membered)heterocycloalkyl, or (5- or 6-membered)heteroaryl;

wherein R$^{14}$ is —(C1-C6)alkyl;

wherein R$^{15}$ is hydrogen, —(C1-C6)alkyl, —CH$_2$—phenyl, or —CH$_2$-(5—to 10-membered)heteroaryl, wherein the —(C1-C6)alkyl, —CH$_2$—phenyl, or —CH$_2$-(5—to 10-membered)heteroaryl are substituted with 0-3 substituents selected from the group consisting of —OH, —SH, —SCH$_3$, —C(O)NH$_2$, —C(O)OH, —NH$_2$ and —NH—C(=NH)NH$_2$; R$^{16}$ is hydrogen or —(C1-C6)alkyl;

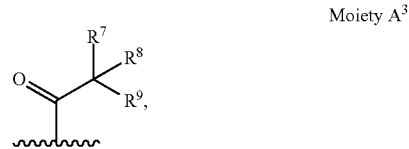

Moiety A$^3$ wherein R$^7$ is selected from the group consisting of —(C1-C3)alkyl, —(C3-C6)cycloalkyl, and —(4- to 6-membered)heterocycloalkyl, wherein R$^7$ is substituted with 0-3 R";

wherein R$^8$ and R$^9$ are independently selected from the group consisting of hydrogen, —(C1-C3)alkyl, —(C3-C6)cycloalkyl, and —(4- to 6-membered)heterocycloalkyl, wherein R$^8$ and R$^9$ are independently substituted with 0-3 R";

wherein R" is hydrogen, halogen, —(C1-C6)alkyl, —O—(C2-C6)alkyl, or —(4- to 20-membered)heteroalkyl, wherein said heteroalkyl has 1-6 oxygen atoms;

wherein B is a (6- to 8-membered)heterocycloalkyl containing two N atoms, Moiety B$^1$, or Moiety B$^2$, wherein B is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4)alkynyl are optionally substituted with 1-3 halogen or (C1-C4) alkoxy;

wherein Moiety B$^1$ has the structure:

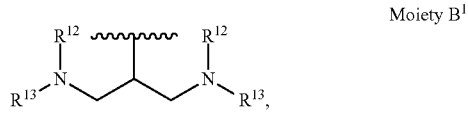

Moiety B$^1$ wherein each occurrence of R$^{12}$ and R$^{13}$ is independently selected from the group consisting of hydrogen, —(C1-C10)alkyl, —(C3-C10)cycloalkyl, —(4- to 10-membered)heteroaryl, and —(4- to 10-membered)heterocycloalkyl, wherein each of R$^{12}$ and R$^{13}$ is independently substituted with 0-3 R'; or wherein two R$^{13}$ groups taken with the nitrogen atoms to which they are attached combine to form a (7- to 8-membered)heterocycloalkyl, wherein the (7- to 8-membered)heterocycloalkyl is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4)alkynyl are optionally substituted with 1-3 halogen or (C1-C4)alkoxy;

wherein R is selected from hydrogen, halogen, (C1-C4)alkyl, or —O—(C1-C4)alkyl; and wherein Moiety B$^2$ has the structure:

Moiety B$^2$ wherein n is an integer selected from the group consisting of 1, 2, 3, and 4; and provided that the compound is not

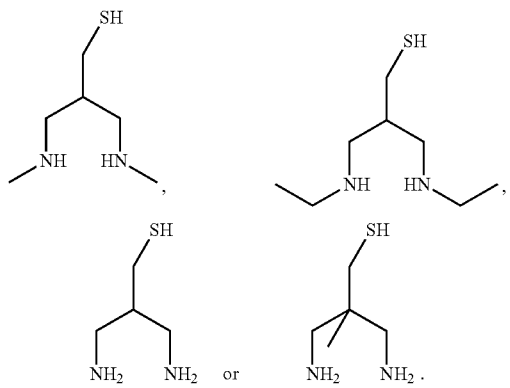

2. The compound according to embodiment 1, or a pharmaceutically acceptable salt, solvate, hydrate, or polymorph thereof, or a solvate, hydrate, or polymorph of the pharmaceutically acceptable salt, wherein B is a heterocycle selected from the group consisting of

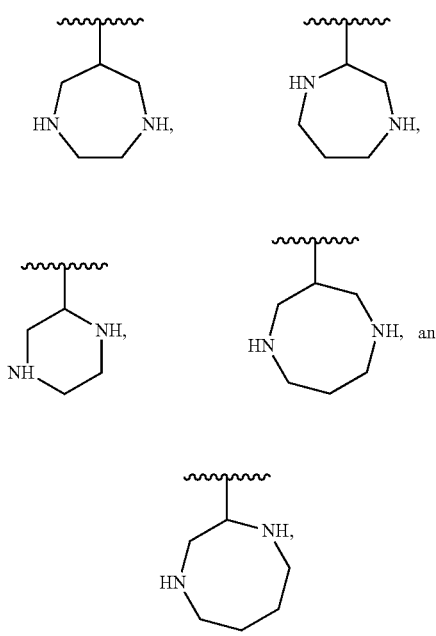

is optionally substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6) aryl, (C5 to C6)heteroaryl, (C1-C4)acyl, (C1-C4)alkenyl and (C1-C4)alkynyl, wherein the (C1-C4)alkyl, (C1-C4) alkenyl and (C1-C4)alkynyl are optionally substituted with 1-3 halogen or (C1-C4)alkoxy.

3. The compound according to embodiment 1, or a pharmaceutically acceptable salt, solvate, hydrate, or polymorph thereof, or a solvate, hydrate, or polymorph of the pharmaceutically acceptable salt, wherein the compound has a structure according to formula II:

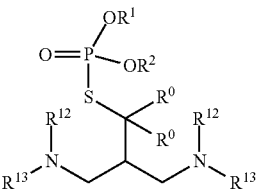

formula II or a pharmaceutically acceptable salt, solvate, hydrate, or polymorph thereof, or a solvate, hydrate, or polymorph of the pharmaceutically acceptable salt.

4. The compound according to embodiment 3, or a pharmaceutically acceptable salt, solvate, hydrate, or polymorph thereof, or a solvate, hydrate, or polymorph of the pharmaceutically acceptable salt, wherein:

each $R^0$ is hydrogen;

wherein each of $R^1$ and $R^2$ is independently hydrogen or —(CH($R^6$))—O—C(O)$R^{10}$;

wherein each $R^6$ is independently hydrogen or (C1-C3) alkyl; and wherein each $R^{10}$ is independently selected from the group consisting of —(C1-C6)alkyl, —O—(C1-C6) alkyl, —(C6-C10)aryl, —(4- to 20-membered)heteroalkyl, —O—(4- to 20-membered)heteroalkyl, —[(CH$_2$)$_y$O]$_z$—R, —CH$_2$—O—[(CH$_2$)$_y$O]$_z$—R and —O—[(CH$_2$)$_y$O]$_z$—R, wherein each of said heteroalkyl independently has 1-6 oxygen atoms, wherein y is an integer between 1 and 4, wherein z is an integer between 1 and 10, wherein R is hydrogen or (C1-C6) alkyl, and wherein each $R^{10}$ is independently substituted with 0-3 $R^c$ groups; wherein $R^0$ is selected from the group consisting of halogen, (C1-C3)alkyl, —CN, —O—(C1-C3)alkyl, —S—(C1-C3)alkyl, and —O—C (0)(C1-C3)alkyl;

wherein each $R^{12}$ is hydrogen; and wherein each $R^{13}$ is (C1-C3)alkyl.

5. The compound according to embodiment 3, or a pharmaceutically acceptable salt, solvate, hydrate, or polymorph thereof, or a solvate, hydrate, or polymorph of the pharmaceutically acceptable salt, wherein:

each $R^0$ is hydrogen;

wherein each of $R^1$ and $R^z$ is independently hydrogen, —(CH($R^6$))$_m$—S—C(O)$R^{10}$ or —CH$_2$—(C($R^{11}$)$_2$)—C (O)—CH$_2$—S—C(O)$R^{10}$;

wherein each $R^{12}$ is hydrogen;

wherein each $R^{13}$ is a (C1-C3)alkyl;

wherein each $R^6$ is hydrogen;

wherein $R^{10}$ is selected from the group consisting of (C1-C6)alkyl, and (C6-C10)aryl, wherein each $R^{10}$ is substituted with 0-3 $R^c$;

each $R^{11}$ is independently selected from the group consisting of hydrogen, —(C1-C6)alkyl, —CH$_2$—O—C (O)R" and —C(O)—OR";

each $R^c$ is (C1-C3)alkyl or —C(O)O—(C1-C3)alkyl;

R" is hydrogen, (C1-C6)alkyl, or —(4- to 20-membered) heteroalkyl, wherein said heteroalkyl has 1-6 oxygen atoms; and m is an integer selected from the group consisting of 0, 1, 2, 3 and 4.

6. The compound according to embodiment 1, wherein the compound has a structure according to formula III:

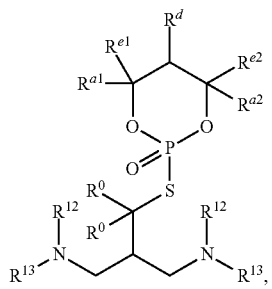

formula III or a pharmaceutically acceptable salt, solvate, hydrate, or polymorph thereof, or a solvate, hydrate, or polymorph of the pharmaceutically acceptable salt, wherein:
$R^{a1}$ and $R^2$ are independently selected from hydrogen, (C1-C6)alkyl, (C6-C10)aryl or a 5- to 10-membered heteroaryl, wherein said alkyl, aryl and heteroaryl are substituted with 0-3 $R^c$, provided that at least one of $R^{a1}$ and $R^{a2}$ is (C6-C10)aryl or a 5- to 10-membered heteroaryl;
wherein each $R^c$ is independently selected from the group consisting of halogen, (C1-C3)alkyl, —CN, —O—(C1-C3)alkyl, —S—(C1-C3)alkyl, —C(O)O—(C1-C3)alkyl, —N(R')$_2$, —CF$_3$ and —OCF$_3$;
wherein $R^d$ is hydrogen or (C1-C3)alkyl; and
wherein $R^{e1}$ and $R^{e2}$ are independently hydrogen or (C1-C3)alkyl, provided that when $R^{a1}$ is (C6-C10)aryl or a 5- to 10-membered heteroaryl, $R^{e1}$ is hydrogen, and that when $R^2$ is (C6-C10)aryl or a 5- to 10-membered heteroaryl, $R^{e2}$ is hydrogen.

7. The compound according to embodiment 6, or a pharmaceutically acceptable salt, solvate, hydrate, or polymorph thereof, or a solvate, hydrate, or polymorph of the pharmaceutically acceptable salt wherein:
each $R^0$ is independently hydrogen;
wherein each $R^{12}$ and $R^{13}$ is independently selected from the group consisting of hydrogen,-(C1-C3)alkyl, —(C3-C10)cycloalkyl, —(4- to 10-membered)heteroaryl, and —(4- to 10-membered)heterocycloalkyl, wherein each of $R^{12}$ and $R^{13}$ is independently substituted with 0-3 R';
wherein $R^{a1}$ and $R^{a2}$ is independently hydrogen, (C1-C6)alkyl, (C6-C10)aryl or a 5- to 10-membered heteroaryl, wherein said alkyl, aryl and heteroaryl are substituted with 0-3 $R^c$, provided that at least one of $R^{a1}$ and $R^{a2}$ is (C6-C10)aryl or a 5- to 10-membered heteroaryl;
wherein $R^c$ is selected from the group consisting of hydrogen, halogen, (C1-C3)alkyl, —CN, —O—(C1-C3)alkyl, —S—(C1-C3)alkyl, —C(O)O—(C1-C3)alkyl, —N(R')$_2$, —CF$_3$ and —OCF$_3$;
wherein $R^d$ is hydrogen or (C1-C3)alkyl;
wherein $R^{e1}$ and $R^{e2}$ are independently hydrogen or (C1-C3)alkyl, provided that when $R^{a1}$ is (C6-C10)aryl or a 5- to 10-membered heteroaryl, $R^{e1}$ is hydrogen, and that when $R^2$ is (C6-C10)aryl or a 5- to 10-membered heteroaryl, $R^{e2}$ is hydrogen; and
wherein R' is hydrogen or —(C1-C4)alkyl.

8. The compound according to embodiment 7, or a pharmaceutically acceptable salt, solvate, hydrate, or polymorph thereof, or a solvate, hydrate, or polymorph of the pharmaceutically acceptable salt, wherein:
each $R^0$ is hydrogen;
wherein each $R^{12}$ is hydrogen;
wherein each $R^{13}$ is (C1-C3)alkyl;
wherein one of $R^{a1}$ and $R^{a2}$ is (C6-C10)aryl or a 5- to 10-membered heteroaryl, and the other is hydrogen, wherein said aryl or heteroaryl is substituted with 1-3 $R^c$;
wherein each $R^c$ is halogen or (C1-C3)alkyl; and
wherein each of $R^d$, $R^{e1}$ and $R^{e2}$ is hydrogen.

9. The compound according to embodiment 1, wherein the compound has a structure according to formula IV:

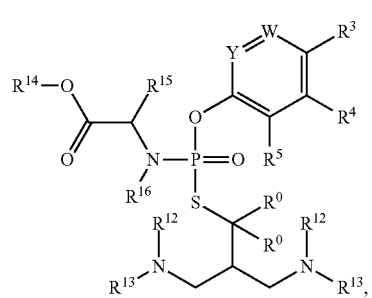

IV or a pharmaceutically acceptable salt, solvate, hydrate, or polymorph thereof, or a solvate, hydrate, or polymorph of the pharmaceutically acceptable salt, wherein:
$R^3$ is substituted with 0-3 substituents selected from the group consisting of halogen, oxo,-(C1-C5)alkyl, —O—(C2-C4)alkyl, and —C(O)O(C1-C3)alkyl;

10. The compound according to embodiment 9, or a pharmaceutically acceptable salt, solvate, hydrate, or polymorph thereof, or a solvate, hydrate, or polymorph of the pharmaceutically acceptable salt, wherein:
each $R^0$ is independently hydrogen or (C1-C3)alkyl;
wherein each $R^{12}$ and $R^{13}$ is independently selected from the group consisting of hydrogen,-(C1-C4)alkyl, —(C3-C10)cycloalkyl, —(4- to 10-membered)heteroaryl, and —(4- to 6-membered)heterocycloalkyl, wherein each $R^{12}$ and $R^{13}$ is independently substituted with 0-3 R';
wherein $R^3$ is hydrogen, halogen, (C1-C6)alkyl, (C3-C7) cycloalkyl, (5- to 8-membered)heterocycloalkyl, —O—(C1-C6)alkyl, —O—(C3-C7)cycloalkyl, —O—(5- to 8-membered)heterocycloalkyl, (C2-C6)alkenyl, —CH$_2$OH, phenyl, (5- or 6-membered)heteroaryl, or (5- or 6-membered)heterocycloalkyl, wherein $R^3$ is substituted with 0-3 substituents selected from the group consisting of halogen, oxo, —(C1-C5)alkyl, —O—(C2-C4)alkyl, and —C(O)O(C1-C3)alkyl;
$R^4$ is hydrogen, —CN, (C1-C6)alkyl, —O—(C1-C6)alkyl, (C2-C6)alkenyl or —CH$_2$OH; or
$R^4$ and $R^3$ are taken together with the carbon atoms to which they are attached to form a (C5-C6)cycloalkyl, (C6-C10)aryl, (5- to 10-membered)heterocycloalkyl or (5- to 10-membered)heteroaryl;
$R^5$ is hydrogen, halogen, (C1-C6)alkyl or —O—(C1-C6) alkyl; or
$R^5$ and $R^4$ are taken together with the carbon atoms to which they are attached to form a (C5-C6)cycloalkyl, phenyl, (5- or 6-membered)heterocycloalkyl, or (5- or 6-membered)heteroaryl;

R¹⁴ is (C1-C6)alkyl;
R¹⁵ is hydrogen, —(C1-C6)alkyl, —CH₂—phenyl, or —CH₂-(5— to 10-membered)heteroaryl, wherein the —(C1-C6)alkyl, —CH₂—phenyl, or —CH₂-(5—to 10-membered)heteroaryl are substituted with 0-3 substituents selected from the group consisting of —OH, —SH, —SCH₃, —C(O)NH₂, —C(O)OH, —NH₂ and —NH—C(=NH)NH₂;
R¹⁶ is hydrogen or —(C1-C6)alkyl; and
R' is selected from hydrogen, halogen, (C1-C4)alkyl, or —O—(C1-C4)alkyl.

11. The compound according to embodiment 10, or a pharmaceutically acceptable salt, solvate, hydrate, or polymorph thereof, or a solvate, hydrate, or polymorph of the pharmaceutically acceptable salt, wherein:
each R⁰ is hydrogen;
each R¹² is H;
each R¹³ is independently hydrogen or —(C1-C10)alkyl;
R³, R⁴ and R⁵ are H;
R¹⁴ is (C1-C3)alkyl;
R¹⁵ is (C1-C3)alkyl; and
R¹⁶ is H.

12. The compound according to embodiment 1, wherein the compound has a structure according to formula V:

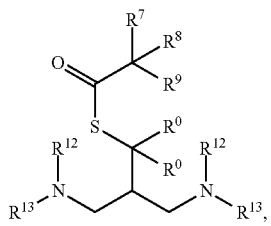

or a pharmaceutically acceptable salt, solvate, hydrate, or polymorph thereof, or a solvate, hydrate, or polymorph of the pharmaceutically acceptable salt, wherein:
R' is halogen, —(C1-C4)alkyl, or —O—(C1-C4)alkyl; and
R" is halogen, —(C1-C6)alkyl or —O—(C2-C6)alkyl.

13. The compound according to embodiment 12, or a pharmaceutically acceptable salt, solvate, hydrate, or polymorph thereof, or a solvate, hydrate, or polymorph of the pharmaceutically acceptable salt, wherein:
each R⁰ is independently hydrogen or (C1-C3)alkyl;
wherein each R¹² and R¹³ is independently selected from the group consisting of hydrogen, —(C1-C3)alkyl, —(C3-C10)cycloalkyl, —(4- to 10-membered)heteroaryl, and —(4- to 10-membered)heterocycloalkyl, wherein each R¹² and R¹³ is independently substituted with 0-3 R';
wherein R⁷ is selected from the group consisting of —(C1-C3)alkyl, —(C3-C6)cycloalkyl, and —(4- to 6-membered)heterocycloalkyl, wherein R⁷ is substituted with 0-3 R";
wherein R⁸ and R⁹ are independently selected from the group consisting of hydrogen, —(C1-C3)alkyl, —(C3-C6)cycloalkyl, and —(4- to 6-membered)heterocycloalkyl, wherein R⁸ and R⁹ are independently substituted with 0-3 R";
wherein R is halogen, (C1-C4)alkyl, or —O—(C1-C4) alkyl; and
wherein R" is halogen, —(C1-C3)alkyl or —O—(C1-C3) alkyl.

14. The compound according to embodiment 13, or a pharmaceutically acceptable salt, solvate, hydrate, or polymorph thereof, or a solvate, hydrate, or polymorph of the pharmaceutically acceptable salt, wherein:
each R⁰ is hydrogen;
each R¹² is H;
each R¹³ is independently —(C1-C3)alkyl; and
R⁷, R⁸ and R⁹ are —(C1-C3)alkyl.

15. The compound according to embodiment 1, wherein the compound has a structure according to formula VI:

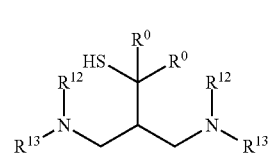

or a pharmaceutically acceptable salt, solvate, hydrate, polymorph, prodrug or double prodrug thereof, or a solvate, hydrate, or polymorph of the pharmaceutically acceptable salt, provided that the compound is not

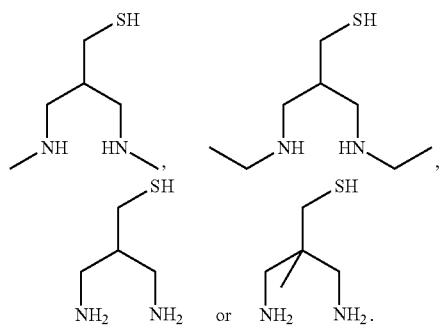

16. The compound according to embodiment 15, or a pharmaceutically acceptable salt, solvate, hydrate, or polymorph thereof, or a solvate, hydrate, or polymorph of the pharmaceutically acceptable salt, wherein:
each R⁰ is independently hydrogen, (C1-C3)alkyl, or —SH;
each R¹² is independently hydrogen, (C1-C3)alkyl or —(4- to 10-membered)heteroaryl;
each R¹³ is taken together with the nitrogen atoms to which they are attached to form a (7- to 8-membered) heterocycloalkyl.

17. The compound according to embodiment 1, wherein the compound has a structure according to formula VII:

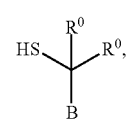

or a pharmaceutically acceptable salt, solvate, hydrate, polymorph, prodrug or double prodrug thereof, or a solvate, hydrate, or polymorph of the pharmaceutically acceptable salt, provided that the compound is not

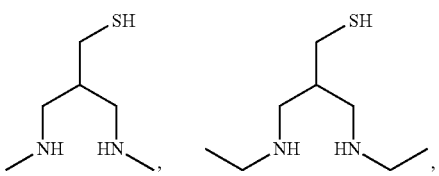

18. The compound according to embodiment 17, or a pharmaceutically acceptable salt, solvate, hydrate, or polymorph thereof, or a solvate, hydrate, or polymorph of the pharmaceutically acceptable salt, wherein:

each $R^0$ is independently hydrogen, (C1-C3)alkyl, or —SH;

wherein B is a (6- to 8-membered)heterocycloalkyl containing two N atoms, wherein B is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4)alkynyl are optionally substituted with 1-3 halogen or (C1-C4)alkoxy or B is Moiety $B^1$;

wherein when present, each occurrence of $R^{12}$ and $R^{13}$ is independently hydrogen, —(C1-C6)alkyl, or —(4- to 10-membered)heteroaryl.

19. The compound according to embodiment 18, or a pharmaceutically acceptable salt, solvate, hydrate, or polymorph thereof, or a solvate, hydrate, or polymorph of the pharmaceutically acceptable salt, wherein B is the heterocycle

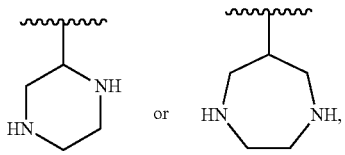 [SMILES: *C1CNCCN1 ; "or" ; *C1CNCCNC1]

wherein the heterocycle is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4)alkynyl are optionally substituted with 1-3 halogen or (C1-C4)alkoxy.

20. The compound according to embodiment 1, wherein the compound is selected from the group consisting of:

| Compound | Structure |
|---|---|
| 1 | 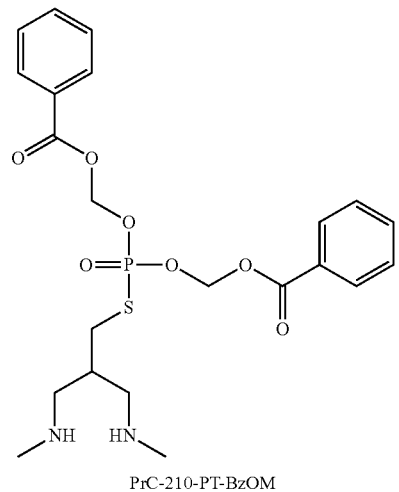 PrC-210-PT |
| 2 | (shown above) PrC-210-PT-BzOM |
| 3 | 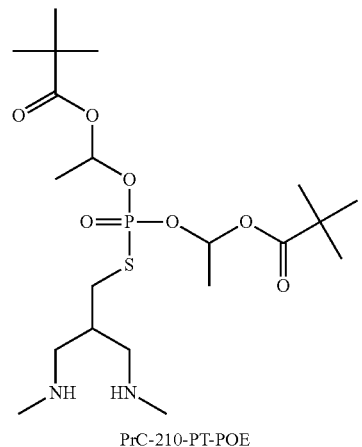 PrC-210-PT-POE |

-continued
| Compound | Structure |
|---|---|
| 4 | 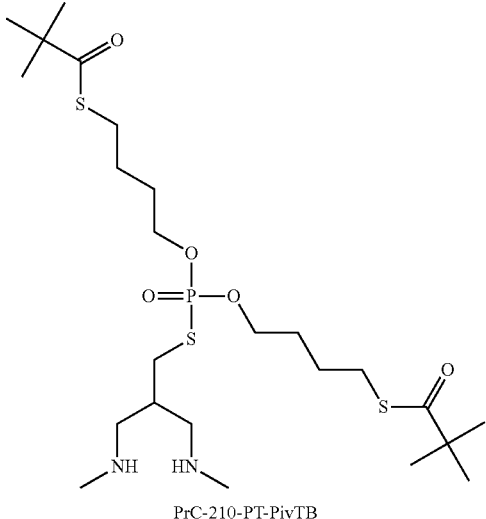<br>PrC-210-PT-PivTB |
| 5 | 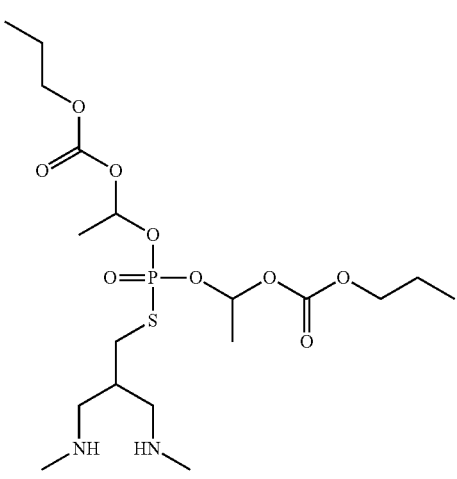 [SMILES: CCCOC(=O)OC(C)OP(=O)(OC(C)OC(=O)OCCC)SCC(CNC)CNC]<br>PrC-210-PT-POCE |
| 6 | 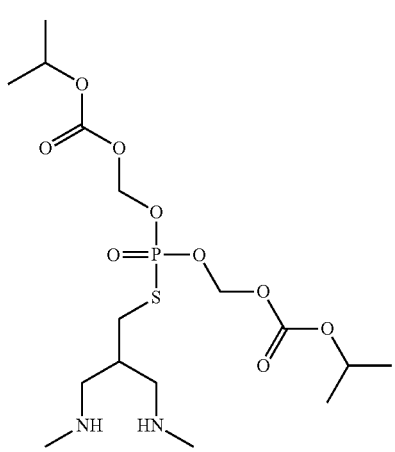 [SMILES: CNCC(CNC)CSP(=O)(OCOC(=O)OC(C)C)OCOC(=O)OC(C)C]<br>PrC-210-PT-POC |
-continued
| Compound | Structure |
|---|---|
| 7 | 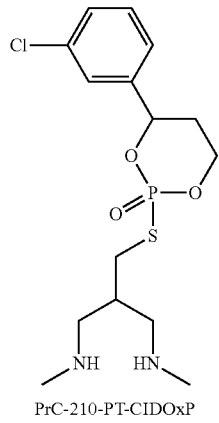<br>PrC-210-PT-ClDOxP |
| 8 | 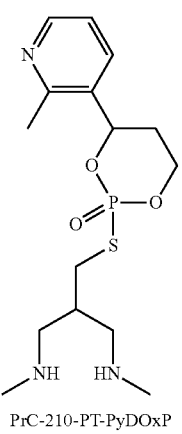<br>PrC-210-PT-PyDOxP |
| 9 | 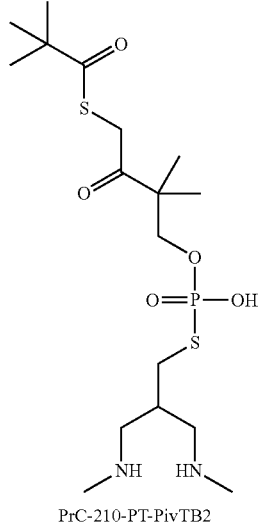<br>PrC-210-PT-PivTB2 |

| Compound | Structure |
|---|---|
| 10 | 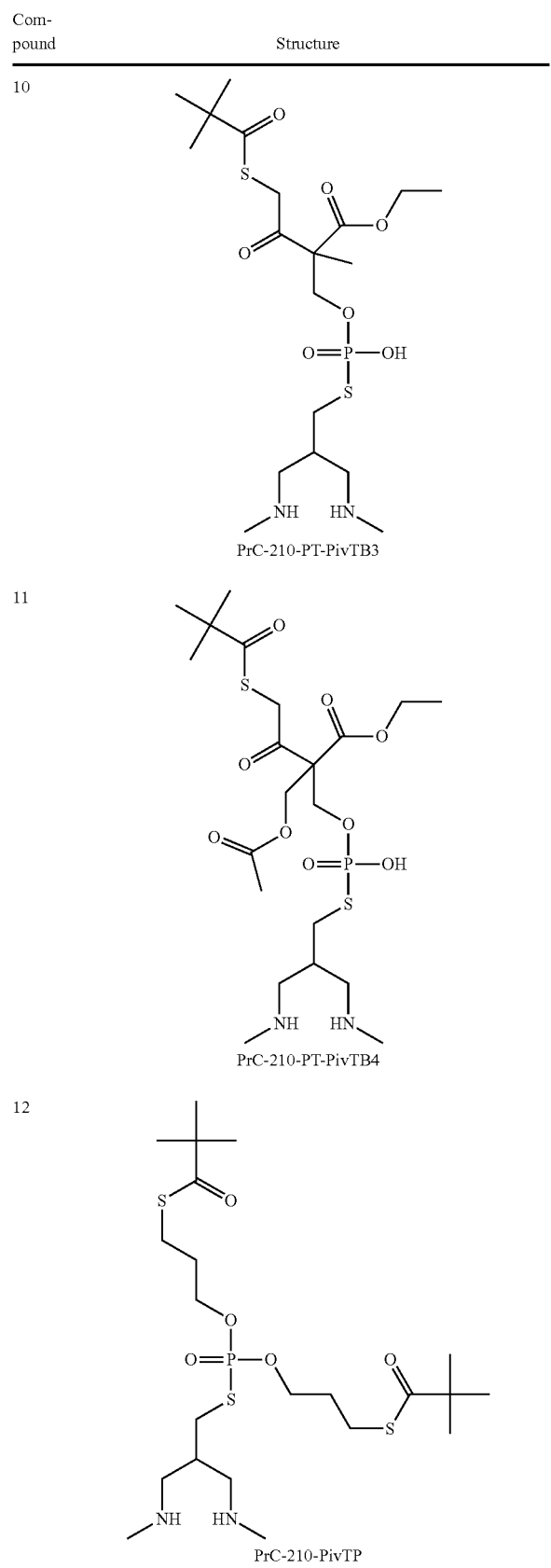
PrC-210-PT-PivTB3 |
| 11 | PrC-210-PT-PivTB4 |
| 12 | PrC-210-PivTP |
| Compound | Structure |
|---|---|
| 13 | 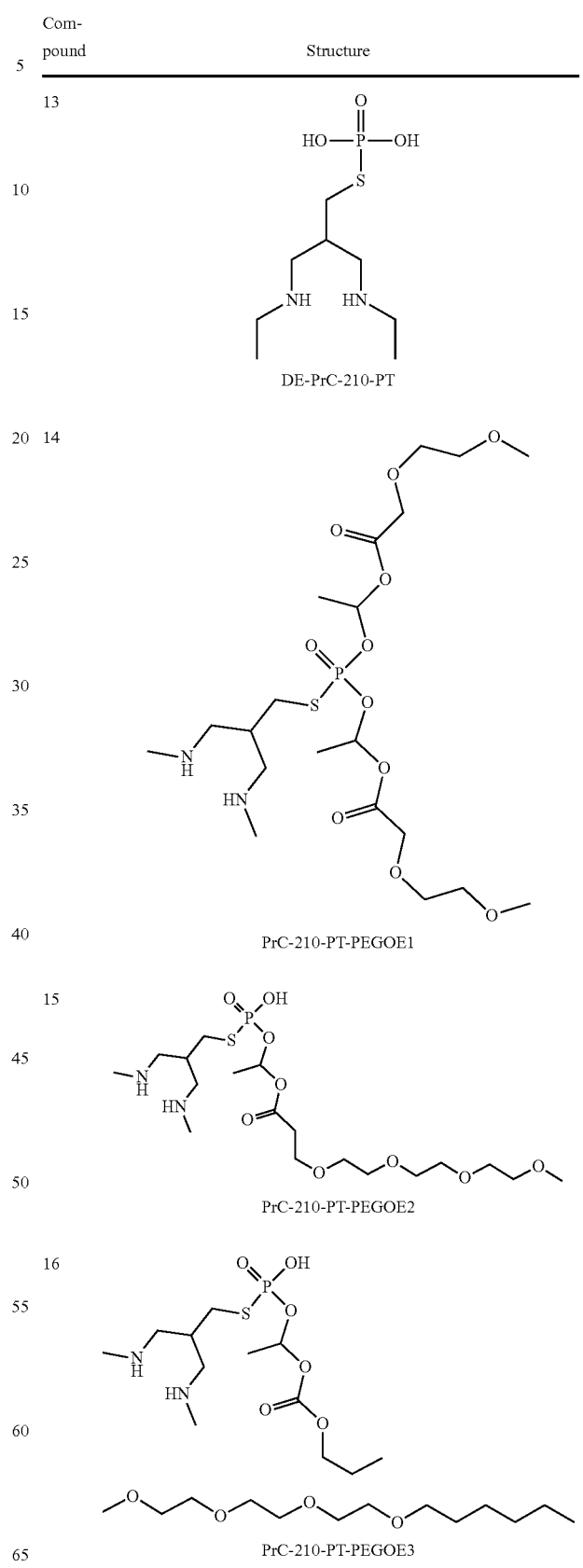
DE-PrC-210-PT |
| 14 | PrC-210-PT-PEGOE1 |
| 15 | PrC-210-PT-PEGOE2 |
| 16 | PrC-210-PT-PEGOE3 |

TABLE 25-continued
| Compound | Structure |
|---|---|
| 17 | 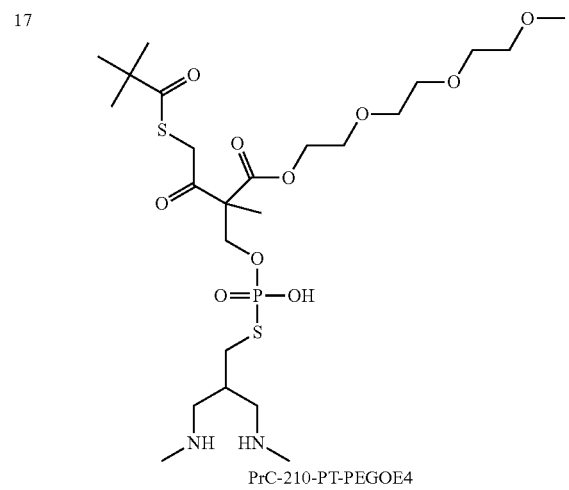
PrC-210-PT-PEGOE4 |
| 18 | 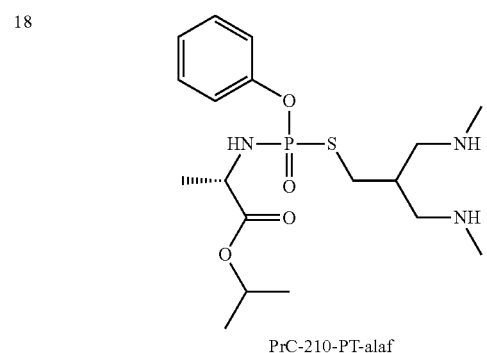
PrC-210-PT-alaf |
| 18-(S,S) | 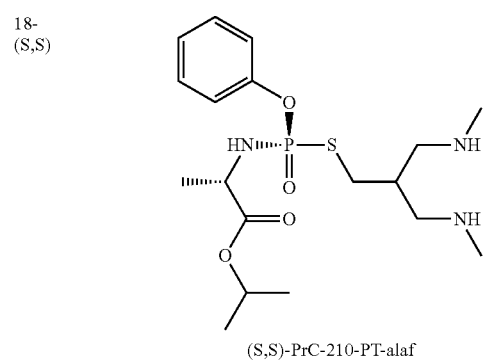
(S,S)-PrC-210-PT-alaf |
| 18-(R,S) | 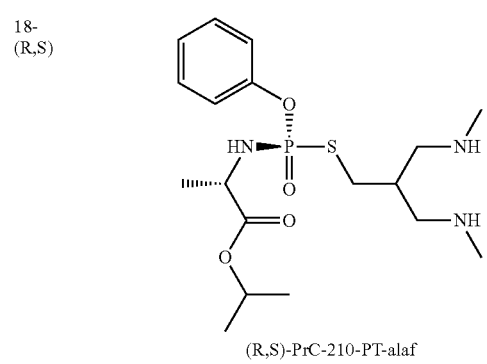
(R,S)-PrC-210-PT-alaf |
TABLE 26-continued
| Compound | Structure |
|---|---|
| 19 | 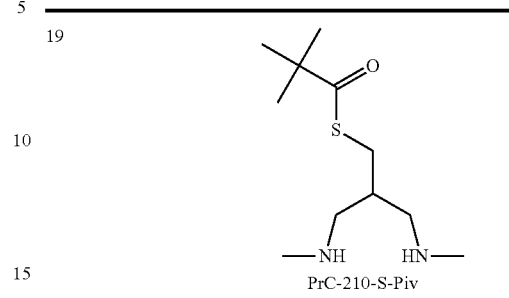
PrC-210-S-Piv |
| 20 | 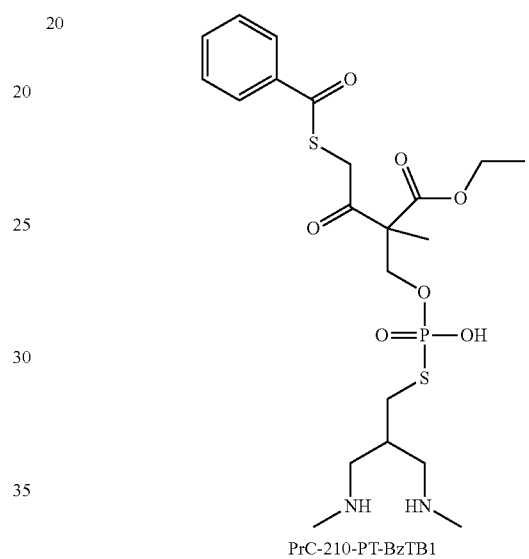
PrC-210-PT-BzTB1 |
| 21 | 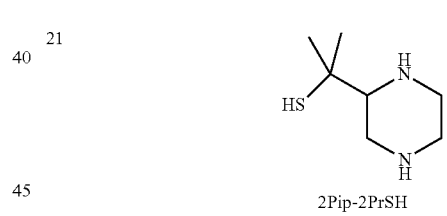
2Pip-2PrSH |
| 22 | 
DzCH2SH |
| 23 | 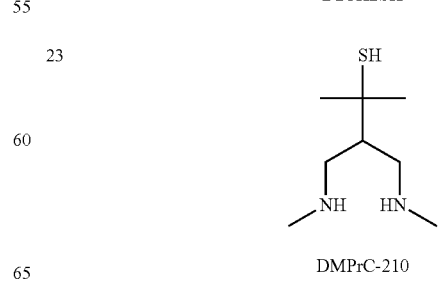
DMPrC-210 |

| Compound | Structure |
|---|---|
| 24 | 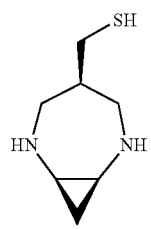<br>[(1R,4s,7S)-2,6-diazabicyclo[5.1.0]octan-4-yl]methanethiol |
| 25 | 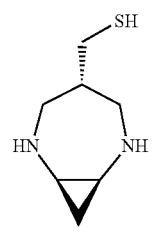<br>[(1R,4r,7S)-2,6-diazabicyclo[5.1.0]octan-4-yl]methanethiol |
| 26 | 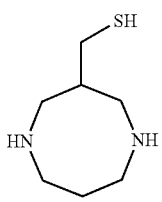<br>(1,5-diazocan-3-yl)methanethiol |
| 27 | 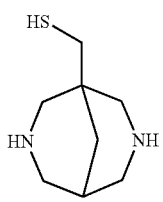<br>{3,7-diazabicyclo[3.3.1]nonan-1-yl}methanethiol |
| 28 | 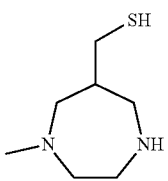<br>(1-methyl-1,4-diazepan-6-yl)methanethiol |
| 29 | 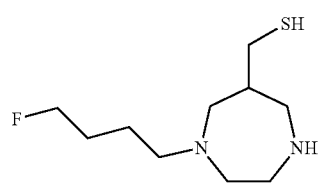<br>[1-(4-fluorobutyl)-1,4-diazepan-6-yl]methanethiol |

| Compound | Structure |
|---|---|
| 30 | 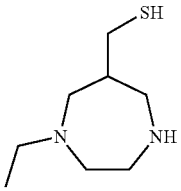<br>(1-ethyl-1,4-diazepan-6-yl)methanethiol |
| 31 | 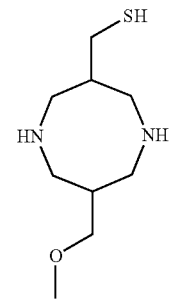<br>[7-(methoxymethyl)-1,5-diazocan-3-yl]methanethiol |
| 32 | 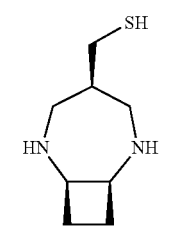<br>[(1R,4S,7S)-2,6-diazabicyclo[5.2.0]nonan-4-yl]methanethiol |
| 33 | 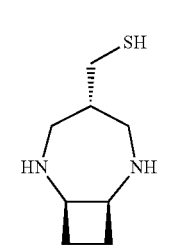<br>[(1R,4R,7S)-2,6-diazabicyclo[5.2.0]nonan-4-yl]methanethiol |
| 34 | 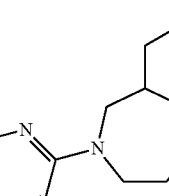<br>[1(pyridin-2-yl)-1,4-diazepan-6-yl]methanethiol |

| Compound | Structure |
|---|---|
| 35 | 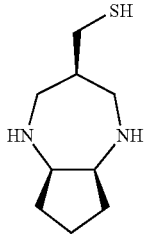<br>[(3S,5aR,8aS)-decahydrocyclopenta[b][1,4]diazepin-3-yl]methanethiol |
| 36 | 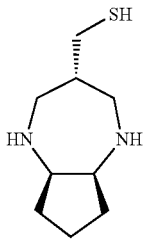<br>[(3R, 5aR, 8aS)-decahydrocyclopenta[b][1,4]diazepin-3-yl]methanethiol |
| 37 | 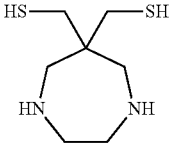<br>[6-(sulfanylmethyl)-1,4-diazepan-6-yl]methanethiol |
| 38 | 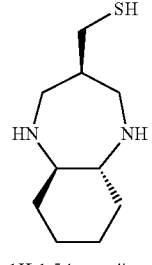<br>[(5aR,9aR)-decahydro-1H-1,5-benzodiazepin-3-yl]methanethiol |
| 39 | 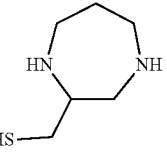<br>(1,4-diazepan-2-yl)methanethiol |
| 40 | 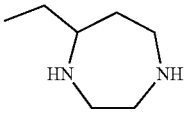<br>(1,4-diazepan-5-yl)methanethiol |
| 41 | 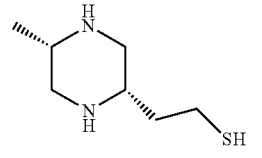<br>2-[(2S,5S)-5-methylpiperazin-2-yl]ethane-1-thiol |
| 42 | 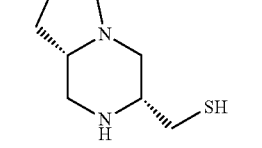<br>[(3R,8aS)-octahydropyrrolo[1,2-a]pyrazin-3-yl]methanethiol |
| 43 | <br>[(2S,5S)-2-methyl-1,4-diazepan-5-yl]methanethiol |
| 44 | 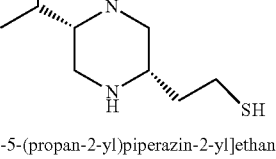<br>2-[(2S,5S)-5-(propan-2-yl)piperazin-2-yl]ethane-1-thiol |
| 45 | 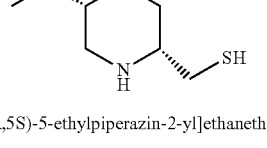<br>[(2R,5S)-5-ethylpiperazin-2-yl]ethanethiol |
| 46 | 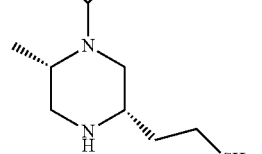<br>2-[(2S,5S)-4-cyclobutyl-5-methylpiperazin-2-yl]ethane-1-thiol |
| 47 | 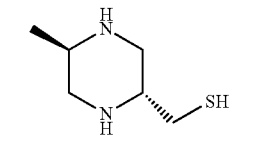<br>[(2R,5R)-5-methylpiperazin-2-yl]ethane-1-thiol |

| Compound | Structure |
|---|---|
| 48 | [(2S,5S)-2-tert-butyl-1,4-diazepan-5-yl]methanethiol |
| 49 | [(2S,5S)-1,2-dimethyl-1,4-diazepan-5-yl]methanethiol |
| 50 | [2-((2R,4aS,8aS)-decahydroquinoxalin-2-yl]ethane-1-thiol | or a pharmaceutically acceptable salt, solvate, hydrate, or polymorph thereof, or a solvate, hydrate, or polymorph of the pharmaceutically acceptable salt.

21. A crystalline salt form of a compound according to any one of embodiments 1-20, or a pharmaceutically acceptable salt, solvate, hydrate, or polymorph thereof or a solvate, hydrate, or polymorph of the pharmaceutically acceptable salt.

22. The crystalline salt form according to embodiment 21, wherein the salt is selected from the group consisting of chloride, benzenesulfonate, 4-toluenesulfonate, cyclohexylsulfamate, fumarate, bromide, maleate, malonate, oxalate, succinate, trifluoroacetate, sulfamate, acetate, ascorbate, mucate, sulfate and 1,5-naphthalenedisulfonate.

23. The crystalline salt form according to any one of embodiments 21-22, wherein the salt form is stable when stored at ambient temperature for at least 1 year.

24. A pharmaceutical composition comprising a compound according to any one of embodiments 1-20, or the crystalline salt form according to any one of embodiments 21-23 and a pharmaceutically acceptable carrier.

25. The pharmaceutical composition according to embodiment 24, wherein the composition further comprises an antioxidant.

26. The pharmaceutical composition according to embodiment 24, wherein the composition is co-administered sequentially, concurrently or separately, with an antioxidant.

27. The pharmaceutical composition according to embodiment 24, wherein the Compound is Compound 42 or Compound 50, and the composition further comprises an antioxidant.

28. The pharmaceutical composition according to any one of embodiments 25-27, wherein the antioxidant is selected from the group consisting of ascorbic acid, ascorbate, vitamin C, N-acetylcysteine, glutathione, lipoic acid, uric acid, α-tocopherol, β-tocopherol, γ-tocopherol, δ-tocopherol, α-tocotrienol, β-tocotrienol, γ-tocotrienol, δ-tocotrienol, vitamin E, carotene, beta-carotene, vitamin A, retinol, selenocysteine, cyanidine-3-glucoside, and ubiquinol.

29. The pharmaceutical composition according to any one of embodiments 25-27, wherein the antioxidant is a non-thiol antioxidant.

30. The pharmaceutical composition according to embodiment 29, wherein the non-thiol antioxidant is selected from the group comprising α-tocopherol, β-tocopherol, γ-tocopherol, δ-tocopherol, α-tocotrienol, β-tocotrienol, γ-tocotrienol, δ-tocotrienol, vitamin E, carotene, beta-carotene, ascorbate, vitamin C, cyanidine-3-glucoside, selenocysteine, or combinations thereof.

31. The pharmaceutical composition according to embodiment 29, wherein the non-thiol antioxidant is selected from the group consisting of α-tocopherol, β-tocopherol, γ-tocopherol, δ-tocopherol, α-tocotrienol, β-tocotrienol, γ-tocotrienol, δ-tocotrienol, vitamin E, carotene, beta-carotene, ascorbate, vitamin C, cyanidine-3-glucoside, selenocysteine, and combinations thereof.

32. The pharmaceutical composition according to embodiment 31, wherein the non-thiol antioxidant is selected from the group consisting of α-tocopherol, γ-tocotrienol, and selenocysteine.

33. The pharmaceutical composition according to any one of embodiments 25-32, wherein the pharmaceutical composition exhibits a synergistic radioprotective effect in mammals, mammalian tissues and/or cultured mammalian cells.

34. The pharmaceutical composition according to any one of embodiments 24-33, wherein the composition is suitable for oral, transmucosal, transdermal, parenteral, topical or cutaneous administration.

35. The pharmaceutical composition according to embodiment 34, wherein the composition is suitable for parenteral administration, and the administration is subcutaneous, intravenous, intramuscular, or intrathecal administration.

36. The pharmaceutical composition according to embodiment 34, wherein the composition is suitable for oral administration.

37. The pharmaceutical composition according to any one of embodiments 24-36, wherein the composition is stable at ambient temperature for at least 1 year.

38. A method of treating or preventing a toxicity or condition associated with ionizing radiation exposure in a subject in need thereof, comprising administering to said subject a therapeutically effective amount of a compound according to any one of embodiments 1-20, or a pharmaceutically acceptable salt, solvate, hydrate, or polymorph thereof or a solvate, hydrate, or polymorph of the pharmaceutically acceptable salt, or of a pharmaceutical composition according to any one of embodiments 24-37.

39. The method according to embodiment 38, wherein the source of the ionizing radiation is nuclear warfare, a nuclear reactor, air travel, or space travel.

40. The method according to embodiment 39, wherein the source of the ionizing radiation is space travel, and the radiation is from one or more of galactic cosmic rays, chronic solar radiation, solar flares or coronal mass ejections.

41. The method according to embodiment 38, wherein the source of ionizing radiation is radiation therapy.
42. The method of any one of embodiments 38-41, wherein the ionizing radiation exposure is acute radiation exposure.
43. The method of any one of embodiments 38-41, wherein the ionizing radiation exposure is chronic radiation exposure.
44. The method according to any one of embodiments 38-43, wherein the subject's risk of developing future carcinogenesis after exposure to ionizing radiation is reduced.
45. The method according to any one of embodiments 38-44, wherein the toxicity is one or more of bone marrow toxicity, central nervous system toxicity, immunological toxicity, gastrointestinal toxicity, neurotoxicity, nephrotoxicity, ototoxicity, cardiotoxicity, hepatotoxicity, cutaneous toxicity, alopecia mucositis, xerostomia, infertility, peripheral neuropathy, pulmonary toxicity or renal toxicity.
46. The method of embodiment 45, wherein the toxicity is a late onset toxicity.
47. The method according to any one of embodiments 38-42, wherein the condition is acute radiation syndrome.
48. The method according to embodiment 47, wherein one or more symptoms of acute radiation syndrome is prevented, eliminated or alleviated.
49. The method according to embodiment 48, wherein the acute radiation syndrome symptom is one or more symptom selected from the group consisting of nausea, vomiting, headache, diarrhea, loss of appetite, fatigue, fever, skin damage and hair loss.
50. The method according to any one of embodiments 38-49, wherein the pharmaceutical composition stimulates bone marrow production.
51. The method according to any one of embodiments 38-43, wherein the condition is a cognitive disorder selected from Alzheimer's disease or dementia.
52. The method according to any one of embodiments 38-43, wherein the condition is premature aging.
53. The method according to any one of embodiments 38-43, wherein the condition is selected from the group consisting of COVID-19-associated cytokine storm, COVID-19-associated multisystem inflammatory syndrome in children (MIS-C), and post-COVID-19 SARS-CoV-2-induced autoimmunity.
54. The method according to any one of embodiments 38-43, wherein the disease or condition is associated with oxidative stress.
55. The method according to embodiment 54, wherein the disease or condition is renal ischemia, myocardial ischemia, spinal cord ischemia and reperfusion injury, Alzheimer's disease, Parkinson's disease, rheumatoid arthritis myocardial infarction, cardiovascular disease, septic shock, chronic inflammation, Friedreich ataxia, Leber's hereditary optic neuropathy, myoclonus epilepsy, ragged red fiber disease, Mitochondrial Encephalopathy, Lactic Acidosis and Stroke (MELAS), radiation-induced cognitive decline, COVID-19-associated cytokine storm, COVID-19-associated multisystem inflammatory syndrome in children (MIS-C), or post-COVID-19 SARS-CoV-2-induced autoimmunity.
56. The method according to any one of embodiments 38-55, wherein the compound or the pharmaceutical composition is administered prior to, during, or after the subject has been or will be exposed to ionizing radiation.
57. A method of protecting normal tissues in a subject against toxicities associated with radiation therapy with minimal effect on the tumor response to those treatments, the method comprising administering to said subject a therapeutically effective amount of a compound according to any one of embodiments 1-20, or a pharmaceutically acceptable salt, solvate, hydrate, or polymorph thereof or a solvate, hydrate, or polymorph of the pharmaceutically acceptable salt, or of a pharmaceutical composition according to any one of embodiments 24-37.
58. The method according to embodiment 57, wherein the radiation therapy is gamma radiation, X-radiation, proton beam radiation, electron beam radiation, gamma radiation from cobalt-60 decay, or in the form of a radiopharmaceutical.
59. The method according to embodiment 57 or 58, wherein the compound or the pharmaceutical composition is administered before, concurrently, separately, sequentially with, or after a radiation therapy.
60. The method according to any one of embodiments 57-59, wherein the radiation therapy is combined with a chemotherapeutic agent or immunotherapy.
61. The method according to embodiment 60, wherein the immunotherapy is selected from the group consisting of immune checkpoint inhibitors, T-cell transfer therapy, monoclonal antibodies, treatment vaccines and immune system modulators.
62. The method according to embodiment or 60, wherein the chemotherapeutic agent is selected from cyclophosphamide, ifosfamide, etoposide, oxaliplatin, cisplatin, carboplatin, mechlorethamine, melphalan, chlorambucil, cyclophosphamide, streptozocin, carmustine, lomustine, bleomycin, busulfan, bendamustine, dacarbazine, doxorubicin, daunoubicin, temozolomide, thiotepa, altretamine, procarbaine, hexamethylmelamine, teniposide or mitoxantrone.
63. A method of protecting normal tissues in a subject against toxicities associated with chemotherapy without adversely affecting the tumor response to those treatments, the method comprising administering to said subject a therapeutically effective amount of a compound according to any one of embodiments 1-20, or a pharmaceutically acceptable salt, solvate, hydrate, or polymorph thereof or a solvate, hydrate, or polymorph of the pharmaceutically acceptable salt, or of a pharmaceutical composition according to any one of embodiments 24-37.
64. The method according to embodiment 63, wherein the chemotherapeutic agent is selected from cyclophosphamide, ifosfamide, etoposide, oxaliplatin, cisplatin, carboplatin, mechlorethamine, melphalan, chlorambucil, cyclophosphamide, streptozocin, carmustine, lomustine, bleomycin, busulfan, bendamustine, dacarbazine, doxorubicin, daunoubicin, temozolomide, thiotepa, altretamine, procarbaine, hexamethylmelamine, teniposide or mitoxantrone.
65. The method according to embodiment 63 or 64, wherein the compound or the pharmaceutical composition is administered before, concurrently, separately, sequentially with, or after a chemotherapeutic agent.
66. The method according to any of embodiments 63-65, wherein the chemotherapy is combined with immunotherapy.

67. The method according to embodiment 66, wherein the immunotherapy is selected from the group consisting of immune checkpoint inhibitors, T-cell transfer therapy, monoclonal antibodies, treatment vaccines and immune system modulators.
68. A method of reducing the risk of secondary tumor induction in a subject being treated with radiation therapy, the method comprising administering to said subject a therapeutically effective amount of a compound according to any one of embodiments 1-20, or a pharmaceutically acceptable salt, solvate, hydrate, or polymorph thereof or a solvate, hydrate, or polymorph of the pharmaceutically acceptable salt, or of a pharmaceutical composition according to any one of embodiments 24-37.
69. The method according to embodiment 68, wherein the radiation therapy is gamma radiation, X-radiation, proton beam radiation or gamma radiation from cobalt-60 decay, or from a radiopharmaceutical.
70. The method according to embodiment 68 or 69, wherein the compound or the pharmaceutical composition is administered before, concurrently, separately, sequentially with, or after a radiation therapy.
71. The method according to any one of embodiments 68-70, wherein the radiation therapy is combined with a chemotherapeutic agent or immunotherapy.
72. The method according to embodiment 71, wherein the immunotherapy is selected from the group consisting of immune checkpoint inhibitors, T-cell transfer therapy, monoclonal antibodies, treatment vaccines and immune system modulators.
73. The method according to embodiment or 71, wherein the chemotherapeutic agent is selected from cyclophosphamide, ifosfamide, etoposide, oxaliplatin, cisplatin, carboplatin, mechlorethamine, melphalan, chlorambucil, cyclophosphamide, streptozocin, carmustine, lomustine, bleomycin, busulfan, bendamustine, dacarbazine, doxorubicin, daunoubicin, temozolomide, thiotepa, altretamine, procarbaine, hexamethylmelamine, teniposide or mitoxantrone.
74. A method of reducing the risk of secondary tumor induction in a subject being treated with chemotherapy, the method comprising administering to said subject a therapeutically effective amount of a compound according to any one of embodiments 1-20, or a pharmaceutically acceptable salt, solvate, hydrate, or polymorph thereof or a solvate, hydrate, or polymorph of the pharmaceutically acceptable salt, or of a pharmaceutical composition according to any one of embodiments 24-37.
75. The method according to embodiment 74, wherein the chemotherapeutic agent is selected from cyclophosphamide, ifosfamide, etoposide, oxaliplatin, cisplatin, carboplatin, mechlorethamine, melphalan, chlorambucil, cyclophosphamide, streptozocin, carmustine, lomustine, bleomycin, busulfan, bendamustine, dacarbazine, doxorubicin, daunoubicin, temozolomide, thiotepa, altretamine, procarbaine, hexamethylmelamine, teniposide or mitoxantrone.
76. The method according to embodiment 74 or 75, wherein the compound or the pharmaceutical composition is administered before, concurrently, separately, sequentially, or after with a chemotherapeutic agent.
77. The method according to any of embodiments 74-76, wherein the chemotherapy is combined with immunotherapy.
78. The method according to embodiment 77, wherein the immunotherapy is selected from the group consisting of immune checkpoint inhibitors, T-cell transfer therapy, monoclonal antibodies, treatment vaccines and immune system modulators.
79. The method of any one of embodiments 38 or 57-78, wherein the subject has cancer and the cancer is hematological cancer, bone cancer, leukemia, lymphoma, myeloma, rectal cancer, colorectal cancer, breast cancer, ovarian cancer, prostate cancer, androgen-dependent prostate cancer, lung cancer, mesothelioma, head and neck cancer, esophageal cancer, gastric cancer, pancreatic cancer, gastrointestinal cancer, renal cell cancer, testicular cancer, germ cell cancer, glioma, cancers of the central nervous system or any other primary or solid tumor.
80. A method of reducing the risk of tumor induction in a subject who has been exposed to, is being exposed to, or will be exposed to ionizing radiation, the method comprising administering to said subject a therapeutically effective amount of a compound according to any one of embodiments 1-20, or a pharmaceutically acceptable salt, solvate, hydrate, polymorph or combination thereof, or of a pharmaceutical composition according to any one of embodiments 24-37.
81. The method according to embodiment 80, wherein the source of the ionizing radiation is nuclear warfare, a nuclear reactor, air travel, or space travel.
82. The method according to embodiment 81, wherein the source of the ionizing radiation is space travel, and the radiation is from one or more of galactic cosmic rays, chronic solar radiation, solar flares or coronal mass ejections.
83. The method according to embodiment 80, wherein the source of ionizing radiation is radiation therapy.
84. The method of any one of embodiments 80-83, wherein the ionizing radiation exposure is acute radiation exposure.
85. The method of any one of embodiment 80-83, wherein the ionizing radiation exposure is chronic radiation exposure.
86. A method of slowing the aging process in a subject, wherein the method comprises administering a compound according to any one of embodiments 1-20, or the pharmaceutical composition according to any one of embodiments 24-37.
87. The method according to embodiment 86, wherein the health span of the subject is increased.
88. A method of treating a disease or condition in a subject in need thereof comprising administering a compound according to any one of embodiments 1-20, or the pharmaceutical composition according to any one of embodiments 24-37.
89. The method according to embodiment 88, wherein the disease or condition is associated with oxidative stress.
90. The method according to embodiment 88 or 89, wherein the disease or condition is renal ischemia, myocardial ischemia, spinal cord ischemia and reperfusion injury, Alzheimer's disease, Parkinson's disease, rheumatoid arthritis myocardial infarction, cardiovascular disease, septic shock, chronic inflammation, Friedreich ataxia, Leber's hereditary optic neuropathy, myoclonus epilepsy, ragged red fiber disease, Mitochondrial Encephalopathy, Lactic Acidosis and Stroke (MELAS), radiation-induced cognitive decline, COVID-19-associated cytokine storm, COVID-19-associated multisystem inflammatory syndrome in children (MIS-C), or post-COVID-19 SARS-CoV-2-induced autoimmunity.

Definitions and General Techniques

Unless otherwise defined herein, scientific and technical terms used in this application shall have the meanings that are commonly understood by those of ordinary skill in the art. In case of conflict, the present specification, including definitions and claims, will control.

Throughout this specification and embodiments, the word "comprise," or variations such as "comprises" or "comprising," will be understood to imply the inclusion of a stated integer or group of integers but not the exclusion of any other integer or group of integers.

The term "including" or "includes" is used to mean "including but not limited to." "Including" and "including but not limited to" are used interchangeably.

Any example(s) following the term "e.g." or "for example" is not meant to be exhaustive or limiting.

Unless otherwise required by context, singular terms shall include pluralities and plural terms shall include the singular.

The articles "a", "an" and "the" are used herein to refer to one or more than one (i.e., to at least one) of the grammatical object of the article.

Notwithstanding that the disclosed numerical ranges and parameters are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g., 1 to 6.1, and ending with a maximum value of 10 or less, e.g., 5.5 to 10.

Where aspects or embodiments are described in terms of a Markush group or other grouping of alternatives, the present application encompasses not only the entire group listed as a whole, but each member of the group individually and all possible subgroups of the main group, and also the main group absent one or more of the group members. The present application also envisages the explicit exclusion of one or more of any of the group members in the disclosure.

Each embodiment of this disclosure may be taken alone or in combination with one or more other embodiments of this disclosure.

Exemplary methods and materials are described herein, although methods and materials similar or equivalent to those described herein can also be used in the practice or testing of the various aspects and embodiments. The materials, methods, and examples are illustrative only and not intended to be limiting.

In order for the disclosure to be more readily understood, certain terms are first defined.

These definitions should be read in light of the remainder of the disclosure as understood by a person of ordinary skill in the art. Unless defined otherwise, all technical and scientific terms used herein have the same meaning as commonly understood by a person of ordinary skill in the art.

Additional definitions are set forth throughout the detailed description.

The term "about", as used herein, refers to a value or parameter that includes (and describes) embodiments that are directed to that value or parameter per se. For example, description referring to "about X" includes description of "X". Numeric ranges are inclusive of the numbers defining the range. Unless specified otherwise, the term "about" when used in the context of a dosage of a compound to be administered to a patient, permits a variation of 10% of a given value or range. For example, about 50 µM would include a range of 45 µM to 55 µM.

The term "derivative" is used herein to refer to the chemical modification of a parent compound. Chemical modifications of a compound can include, for example, replacement of hydrogen by an alkyl or aryl group. Many other modifications are possible.

The term "analogue" is used herein to refer to a compound having a similar structure to that of another compound but differing from it with respect to a certain component. The analogue may differ from the parent compound by virtue of one or more atoms, functional groups or substructures.

The term "substituted", as used herein, means that any hydrogen on the designated atom or moiety or group can be replaced with a selection from the indicated substituent group, provided that the normal valency of the designated atom, moiety or group is not exceeded, and that the substitution results in a stable compound.

The term "alkyl", as used herein, refers to a saturated, branched- or straight-chain alkyl group. Examples of alkyl groups include, but are not limited to, methyl, ethyl, propyl, iso-propyl, tert-butyl, isopentyl, neopentyl and the like. In some embodiments, alkyl as used herein is (C1-C6)alkyl. In some embodiments, alkyl as used herein include an alkyl that is substituted with 0-3 substituents selected from the group consisting of —OH, —SH, —SCH$_3$, —C(O)NH$_2$, —C(O)OH, —NH$_2$ and —NH—C(=NH)NH$_2$. In some embodiments, The term "alkenyl", as used herein, refers to an unsaturated, branched- or straight-chain aliphatic group containing at least one carbon-carbon double bond. Examples of alkenyl groups include, but are not limited to, ethenyl, propenyl, iso-propenyl, butenyl, pentenyl, hexenyl and the like. In some embodiments, alkenyl as used herein includes (C2-C6)alkenyl.

The term "alkynyl", as used herein, refers to an unsaturated, branched- or straight-chain aliphatic group containing at least one carbon-carbon triple bond. Examples of alkynyl groups include, but are not limited to, ethynyl, propynyl, iso-propynyl, butynyl, pentynyl, hexynyl and the like.

The term "aliphatic" as used herein refers to a straight chained or branched alkyl, alkenyl or alkynyl. It is understood that alkenyl or alkynyl embodiments need at least two carbon atoms in the aliphatic chain. Aliphatic groups typically contain from 1 (or two for alkenyl or alkynyl groups) to 12 carbons, such as from 2 to 4 carbons.

As used herein, the carbon atom designations may have the indicated integer and any intervening integer. For example, the number of carbon atoms in a (C1-C3)alkyl group is 1, 2 or 3.

The term "aryl" as used herein refers to a monocyclic or bicyclic carbocyclic aromatic ring system. Aryl as used herein includes a (C6-C12)aryl-. For example, aryl as used herein can be a C6-C10 monocyclic or C8-C12 bicyclic carbocyclic aromatic ring system. In some embodiments, aryl as used herein can be a (C6-C10)aryl. Phenyl (or Ph) is an example of a monocyclic ring system. Bicyclic aromatic ring systems include systems wherein both rings are aromatic, e.g., naphthyl, and systems wherein only one of the two rings is aromatic, e.g., tetralin.

The term "heteroaryl" as used herein refers to a monocyclic or bicyclic aromatic ring system having at least one heteroatom, selected oxygen (O), sulfur (S) or nitrogen (N), in a chemically stable arrangement. Heteroaryl as used herein includes a 5- to 10-membered heteroaryl having 1-4 heteroatoms independently selected from O, N or S. In some embodiments, heteroaryl as used herein can be a 5- to 10-membered heteroaryl having 1-4 heteroatoms independently selected from O, N, or S. For example, heteroaryl as used herein can be a 5- to 10-membered monocyclic or bicyclic aromatic ring system having 1 to 4 heteroatoms selected from O, N, or S in one or both rings in a chemically stable arrangement. As used herein, heteroaryl refers to a monocyclic aromatic ring having 1-4 heteroatoms selected from O, N or S.

As used herein, heteroaryl refers to a bicyclic aromatic ring system wherein one or both rings are aromatic. Examples of monocyclic heteroaryls include, but are not limited to, 6-membered ring substituents such as pyridinyl, pyrazinyl, pyrimidinyl and pyridazinyl; and 5-membered heteroaryls such as triazolyl, imidazolyl, furanyl, isoxazolyl, isothiazolyl, 1,2,3-, 1,2,4, 1,2,5 or 1,3,4-oxadiazolyl, oxazolyl, thiazolyl, isothiazolyl, and pyrazolyl. Examples of bicyclic heteroaryl groups include but are not limited to indolyl, isoindole, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, isobenzothiofuranyl, benzothiofuranyl, quinolinyl, isoquinolinyl, cinnolinyl, quinazolinyl, oxochromanyl, 1,4-benzoxazinyl, 1,2,3,4-tetrahydroquinolinyl, 1,2-dihydroquinolinyl, and indolinyl. In some embodiments, heteroaryl as used herein includes a 5- or 6-membered heteroaryl. In some embodiments, heteroaryl as used herein includes a 5- or 6-membered heteroaryl that is fused to a 6-membered heterocycloalkyl.

As used herein, the term "cycloalkyl" refers to a monocyclic, spirocyclic, fused or bridged bicyclic carbocyclic ring system that is not aromatic. A cycloalkyl may be a monocyclic ring, including but not limited to, cyclopropyl, cyclobutyl, cyclopentyl, cyclohexyl, cycloheptyl and cyclooctyl. A cycloalkyl may be a fused or a bridged bicyclic group. Fused bicyclic groups include, for example, bicyclo[1.1.0]butanyl, bicyclo[2.1.0]pentanyl, bicyclo[2.2.0]hexanyl, bicyclo[3.1.0]hexanyl and the like. Bridged bicyclic groups include, for example, bicyclo[2.2.1]heptanyl and bicyclo[1.1.1]pentanyl. Examples of spirocyclic cycloalkyl groups include, but are not limited to, spiro[5.5]undecanyl, spiropentadienyl, spiro[4.5]decanyl and spiro[3.6]decanyl. Also included in the definition of cycloalkyl are unsaturated non-aromatic cycloalkyls, including, but not limited to, cyclohexenyl, cyclohexadienyl, cyclopentenyl, cycloheptenyl, cyclooctenyl, cyclootadienyl and the like. In some embodiments, cycloalkyl as used herein includes a (C5-C6) cycloalkyl. In some embodiments, cycloalkyl as used herein includes a (C3-C7)cycloalkyl. In some embodiments, cycloalkyl as used herein includes an —O— (C3-C7)cycloalkyl The term "heterocycloalkyl" as used herein refers to a monocyclic, spirocyclic, fused or bridged bicyclic non-aromatic ring system having at least one heteroatom selected from O, N or S (or P in the case of formula I, where $R^1$ and $R^2$, one of which is $CH_2$ or the other is $CH_2CH_2$, are taken together with the —O—P—O linkage to form a 6-membered-heterocycloalkyl ring) in a chemically stable arrangement. For example, heterocycloalkyl as used herein can be a 3- to 10-membered monocyclic or 8-to 12-membered bicyclic non-aromatic ring system having 1 to 4 heteroatom or heteroatom groups in each ring selected from O, N or S in a chemically stable arrangement. In some embodiments, heterocycloalkyl as used herein can be a3-to 10-membered heterocycle-having 1-4 heteroatoms independently selected from O, N, or S. In some embodiments, heterocycloalkyl as used herein includes —O—(C1-C6)alkyl. In some embodiments, heterocycloalkyl as used herein includes —C(O)O(C1-C3)alkyl. In some embodiments, heterocycloalkyl as used herein includes a 5- or 6-membered heterocycloalkyl. In some embodiments, heterocycloalkyl as used herein includes a 5—to 8—membered heterocycloalkyl. In some embodiments, heterocycloalkyl as used herein includes an —O—(5—to 8—membered)heterocycloalkyl. In some embodiments, heterocycloalkyl as used herein includes a 5—to 10—membered heterocycloalkyl. In a bicyclic non-aromatic ring system, one or both rings may contain said heteroatom. A bicyclic heterocycloalkyl can include groups wherein both rings are non-aromatic. A bicyclic heterocycloalkyl can include groups wherein only one of the rings is non-aromatic, and the other is aromatic. Examples of heterocycloalkyl rings include, but are not limited to, 2-tetrahydrofuranyl, 3-tetrahydrouranyl, 2-tetrahydrothiophenyl, 3-tetrahydrothiphenyl, 2-morpholino, 3-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperadinyl, 2-piperidinyl, 3-piperdinyl, 1-pyrazolinyl, 3-pyrazolinyl, 4-pyrazolinyl, 5-pyrazolinyl, 1-piperidinyl, 2-piperidiinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, and benzodithiane. Examples of spirocyclic heterocycloalkyl groups include, but are not limited to 1,4,6-triazaspiro[4.4]nonanyl, 2-oxaspiro[4.4] nonanyl, 3-oxaspiro[5.5]undec-8-enyl, 7-oxaspiro[4.5]decanyl, 7-oxa-1-azaspiro[4.5]decanyl, and 6-oxaspiro[4.5]dec-7-enyl. Also included in the definition of heterocycloalkyl are unsaturated non-aromatic heterocycloalkyl groups. Examples of non-aromatic heterocycloalkyl groups include, but are not limited to, 1,2-dihydroazetyl, 2,5-dihydro-1H-pyrrolyl, 3,6-dihydro-2H-pyranyl, 2,5-dihydrofuranyl, 2,3-dihydrofuranyl, and 4H-pyranyl.

The term "—(4—to 20—membered)heteroalkyl" refers to a saturated straight chain or branched chain alkyl group wherein I to 6 of the atoms are a heteroatom or heteroatom group selected from —O—, —S— and —NH— and the remaining atoms are carbon. In some embodiments, the (4—to 20—membered)heteroalkyl group has 1 to 6 heteroatoms selected from —O— and —S—. In some embodiments, the (4—to 20—membered)heteroalkyl group has 1 to 6—O— atoms. In some embodiments, the (4—to 20—membered)heteroalkyl is a polyethylene glycol (PEG) derivative, having the formula —[($CH_2$)$_2$O]$_x$—R, wherein x is an integer between 1 and 10 and R is hydrogen or a (C1-C6)alkyl group (e.g., methyl, ethyl, propyl and the like). In some embodiments, the (4—to 20—membered)heteroalkyl group is a PEG derivative, having the formula, [($CH_2$)$_y$O]$_z$—R, —$CH_2$—O—[($CH_2$)$_y$O]$_z$—R, or —O—[($CH_2$)$_y$O]$_z$—R, wherein y is an integer between 1 and 4; z is an integer between 1 and 10; and R is hydrogen or a (C1-C6)alkyl group (e.g., methyl, ethyl, propyl, iso-propyl, butyl, tert-butyl, pentyl, neopentyl, hexyl and the like). In some embodiments, the (4—to 20—membered)heteroalkyl includes a —O—(C1-C6)alkyl.

The term "pharmaceutically acceptable salt" refers to salts which retain the biological effectiveness and properties of the compounds of this disclosure and which are not biologically or otherwise undesirable. In some embodiments, the compounds of this disclosure are capable of forming acid and/or base salts by virtue of the presence of amino, thiol, and/or phosphate groups or groups similar thereto. Pharmaceutically acceptable salts can be prepared from inorganic and organic bases or acids.

The term "ionizing radiation" refers to radiation with enough energy to remove electrons from atoms and molecules that it interacts with. Forms of ionizing radiation include alpha, beta and neutron particles, gamma radiation, X-radiation and high energy UV-radiation.

The term "reactive oxygen species" or "ROS" refers to the compounds that are formed when aqueous solutions are exposed to ionizing radiation. Exposure of living tissues to ionizing radiation leads to the formation of ROS which are involved in the initiation and propagation of free radical chain reactions which can be highly damaging to living tissues. Examples of ROS include, but are not limited to superoxide, hydrogen peroxide, hydroxyl, peroxyl, and alkoxyl radicals.

The term "acute onset toxicity" refers to an ionizing toxicity where the symptoms associated with radiation injury present within minutes, hours, days or weeks after exposure to ionizing radiation. In some embodiments, the symptoms associated with acute onset toxicity occur within 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 2 weeks, 3 weeks, 4 weeks, 6 weeks, 8 weeks, 10 weeks or 11 weeks after exposure to ionizing radiation.

The term "late onset toxicity" refers to an ionizing toxicity wherein the symptoms associated with radiation injury do not present until after a latency period. An example of late onset toxicity includes, but is not limited to, the development of cardiotoxicity, in a subject being treated with ionizing radiation for breast cancer, several months or years after completion of the treatment. In some embodiments, the symptoms associated with a late onset toxicity occur after a latency period of several months to years after exposure to ionizing radiation. In some embodiments, the symptoms associated with a late onset toxicity occur 3 months, 4 months, 5 months, 6 months, 7 months, 8 months, 9 months, 10 months, 11 months, 12 months, 1.5 years, 2 years, 2.5 years or 3 years after exposure to ionizing radiation.

The term "chronic radiation exposure" refers to long-term or cumulative exposure to low-levels of ionizing radiation. Examples of chronic radiation exposure include, but are not limited to, exposure to ionizing radiation during air travel (e.g., flight crews and passengers), space travel, radiotherapy, or during the decommissioning and/or installation of nuclear reactors (e.g., naval vessels and nuclear energy plants).

The term "chronic radiation syndrome" refers to a condition that occurs in a subject who has experienced chronic radiation exposure for a period of about 3 years or more.

Symptoms of chronic radiation syndrome include, but are not limited to, sleep and appetite disturbance, generalized weakness and fatigability, altered mood, poor memory, reduced concentration, vertigo, ataxia, parasthesia, headache, syncopal episodes, hot flashes and chills.

The term "acute radiation exposure" refers to short-term exposure to high-levels of ionizing radiation. Examples of acute radiation exposure include, but are not limited to, exposure to ionizing radiation after nuclear reactor accidents, nuclear warfare (e.g., nuclear bomb), nuclear terrorism (e.g., explosive devices that disperse radioactive material (dirty bombs) or space travel.

The term "acute radiation syndrome" or "ARS" refers to a condition that occurs in a subject who has experienced acute radiation exposure. The main manifestations of ARS include bone marrow syndrome, gastrointestinal syndrome and cardiovascular syndrome. There are three recognized phases of ARS including a prodromal phase, latent stage phase, and the overt systemic illness phase. The symptoms associated with the prodromal stage can occur a few hours of radiation exposure, or later. The symptoms include nausea, vomiting, anorexia, and diarrhea, and may last for a few minutes up to several days. In the latent stage of ARS, the subject looks and feels healthy for a period lasting for a few hours up to a few weeks. The overt systemic illness phase is characterized by various symptoms that are based on one or more specific syndromes, i.e., bone marrow syndrome, gastrointestinal syndrome, cutaneous and cardiovascular syndrome.

The term "treating" refers to reversing, alleviating, ameliorating or slowing the progression, of one or more symptoms associated with a condition, toxicity, disease or disorder described herein.

The term "preventing" refers to inhibiting, avoiding, stopping or slowing the development of one or more symptoms associated with a condition, toxicity, disease or disorder described herein.

As used herein, the term "health span" refers to the period of time during which a subject is alive and healthy (e.g., free of serious illness, chronic diseases and/or disabilities of aging).

As used herein, the term "compound" refers to compounds having a structure according to any one of formulae I, II, III, IV, V, VI or VII, and their pharmaceutically acceptable salts, isomers, solvates, hydrates, or polymorphs thereof, or a solvate, hydrate, or polymorph of the pharmaceutically acceptable salt.

As used herein, the term "prodrug" refers to a compound that is administered to a subject in need thereof in its inactive form, that is further metabolized by the body in vivo (e.g., by the action of an enzyme) to produce its active form. In some embodiments, the compounds of the disclosure are double prodrugs, and are metabolized by two different metabolic pathways (e.g., two different enzymatic reactions) to produce the active compound. Without wishing to be bound by theory, the prodrugs of the disclosure are more lipophilic than the parent compounds (i.e., the drug in its active form). The enhanced lipophilicity of the prodrugs and double prodrugs according to the disclosure improves their bioavailability as compared to the parent compound. Additionally, without wishing to be bound by theory, the prodrugs and double prodrugs of this disclosure are more resistant to oxidation as compared to the active form. Therefore, the prodrugs and double prodrugs of this disclosure often have a longer shelf-life. Prodrugs and double prodrugs according to the disclosure have an A group that is characterized by Moiety $A^1$, Moiety $A^2$ or Moiety $A^3$ as described herein.

Compounds of the Disclosure

Ionizing radiation-induced ROS can further combine with lipids to form toxic, reactive alpha-ketoaldehydes (Wondrak, G. T. et al., *Biochem. Pharmacol.* 2002, Vol. 63, pp 361-373). Without wishing to be bound by theory, the compounds according to the disclosure may react with alpha-ketoaldehydes to form less reactive and less toxic adducts. Accordingly, the compounds according to this disclosure may help protect tissues from ionizing radiation (e.g., x rays, gamma rays, or protein beam), radiation inherent in radiotherapy, or ROS in chemotherapy even after the damaging ROS have damaged cellular macromolecules, by inactivating alpha-ketoaldehydes.

Amifostine (3-[3-(methylamino)propylamino]propylsulfanylphosphonic acid) is an FDA approved aminothiophosphonate radioprotector that is administered intravenously (and subcutaneously off label). It is approved for use in reducing renal toxicity associated with repeated exposure to the chemotherapeutic agent, cisplatin, in subjects with ovarian cancer, and to reduce xerostomia in subjects undergoing post-operative radiation treatment for head and neck cancer. It lacks efficacy as a radioprotector when administered orally.

Amifostine is dephosphorylated by alkaline phosphatase in healthy tissues to its active thiol metabolite (2-[(3-aminopropyl)amino]ethane thiol).

A number of adverse side-effects are associated with the administration of Amifostine including hypotension, nausea and vomiting, hypocalcemia, flushing, chills, malaise, pyrexia, rash, dizziness, somnolence, diarrhea, diplopia and blurred vision, and in rare cases, seizures and syncope. Injection site reactions have also been observed.

The aminothiol, 3-(methylamino)-2-((methylamino)methyl)propane-1-thiol (PrC-210):

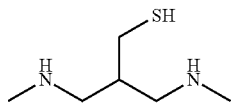

has also been developed as a radioprotector, and has demonstrated radioprotective properties when administered topically and orally in preclinical studies. PrC-210 is reported to be associated with less side effects than Amifostine (see Peebles D D, Soref C M, Copp R R, Thunberg A L, Fahl W E. ROS-scavenger and radioprotective efficacy of the new PrC-210 aminothiol. Radiat Res. 2012; 178(1):57-68. doi: 10.1667/rr2806.1).

The free thiol group of PrC-210, however, may be susceptible to oxidation which can adversely affect its shelf life. Additionally, PrC-210 has not been shown to preferentially protect healthy tissues over tumor tissues. Accordingly, there is a need to develop radioprotective agents that are sufficiently stable, and that protect healthy tissues over tumor tissues for use in conjunction with radiotherapy and/or chemotherapy.

The compounds of this disclosure are novel aminothiols, aminothiophosphonate and aminothioester radioprotectors or prodrugs or double prodrugs of such protectors. They are suitable for oral administration and have fewer side effects when administered to a subject in need thereof to protect normal tissues against ionizing or therapeutic radiation or chemotherapy. The compounds of this disclosure include {[3-(methylamino)-2-[(methylamino)methyl]propyl]sulfanyl} phosphonic acid (PrC-210-PT) and derivatives or analogues thereof as well as prodrugs and double prodrugs thereof. See, e.g., the compounds of formulae I-VII.

In some embodiments, the compounds of the disclosure are characterized by a tertiary alkyl thiol, or are prodrugs thereof (i.e., compounds that are metabolized to tertiary alkyl thiols). Without wishing to be bound by theory, those compounds are less toxic than primary thiols due to the added steric hinderance around the reactive thiol. The steric hinderance prevents the thiol from interacting with macromolecules associated with toxicity, but will still allow detoxification of ROS and ketoaldehydes.

In some embodiments, the compound according to this disclosure has a structure according to formula I.

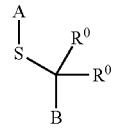

formula I or a pharmaceutically acceptable salt, solvate, hydrate, or polymorph thereof, or a solvate, hydrate, or polymorph of the pharmaceutically acceptable salt, wherein;

each $R^0$ is independently hydrogen, (C1-C3)alkyl, or —SH; A is selected from hydrogen, Moiety $A^1$, Moiety $A^2$ or Moiety $A^3$:

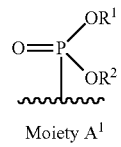

Moiety $A^1$ wherein each of $R^1$ and $R^2$ is independently selected from the group consisting of hydrogen, —(CH($R^6$))—O—C(O)$R^{10}$, —(CH($R^6$))$_m$—S—C(O)$R^{10}$ and —CH$_2$—(C(R")$_2$)—C(O)—CH$_2$—S—C(O)$R^{10}$; m is an integer selected from the group consisting of 0, 1, 2, 3, and 4; or $R^1$ and $R^2$, one of which is CH$_2$ or the other is CH$_2$CH$_2$, taken with the —O—P—O— linkage to which they are attached form a 6—membered heterocycloalkyl ring that is substituted with 1-2 $R^a$ and 0-3 $R^b$;

wherein each $R^a$ is independently hydrogen, (C1-C6) alkyl, (C6-C10)aryl- or a 5—to 10—membered heteroaryl-, wherein said alkyl, aryl and heteroaryl is substituted with 0-3 $R^c$, provided that at least one $R^a$ group is (C6-C10)aryl—or a 5—to 10—membered heteroaryl-;

wherein when present, each $R^b$ is —(C1-C3)alkyl;

wherein each $R^c$ is independently selected from the group consisting of halogen, (C1-C3)alkyl, —CN, —O—(C1-C3)alkyl, —S—(C1-C3)alkyl, —C(O)O—(C1-C3)alkyl, —N(R')$_2$, —CF$_3$ and —OCF$_3$;

wherein each $R^6$ is independently hydrogen or (C1-C3) alkyl;

wherein each $R^0$ is selected from the group consisting of —(C1-C6)alkyl, —O—(C1-C6)alkyl, —O—(C6-C10)aryl, —(C6-C10)aryl, (5—to 10—membered)heteroaryl, (4—to 10—membered)heterocycloalkyl, (C3-C10)cycloalkyl, —O—(5—to 10—membered) heteroaryl, —O— (4—to 10—membered) heterocycloalkyl, —O—(C3-C10)cycloalkyl, —O—(4—to 20—membered)heteroalkyl, —(4—to 20—membered)heteroalkyl, —[(CH$_2$)$_y$O]$_z$—R, —CH$_2$—O—[(CH$_2$)$_y$O]$_z$—R and —O—[(CH$_2$)$_y$O]$_z$—R, wherein each of said heteroalkyl, heterocycloalkyl, and heteroaryl independently have 1-6 oxygen atoms, wherein y is an integer between 1 and 4, wherein z is an integer between 1 and 10, wherein R is hydrogen or (C1-C6)alkyl, and wherein each $R^0$ is independently substituted with 0-3 $R^c$;

wherein each R¹¹ is independently selected from the group consisting of hydrogen, —(C1-C6)alkyl, —CH₂—O—C(O)R", —C(O)—OR", —(4—to 20—membered)heteroalkyl, —O—(4—to 20—membered)heteroalkyl, —[(CH₂)ᵧO]ᵤ—R, —CH₂—O—[(CH₂)ᵧO]ᵤ—R and —O—[(CH₂)ᵧO]ᵤ—R, wherein each of said heteroalkyl independently has 1-6 oxygen atoms, wherein y is an integer between 1 and 4, wherein z is an integer between 1 and 10, and wherein R is hydrogen or (C1-C6)alkyl;

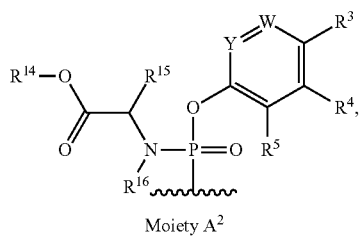

Moiety A² wherein W and Y are independently selected from N or CH;

wherein R³ is hydrogen, halogen, (C1-C6)alkyl, (C3-C7)cycloalkyl, (5—to 8—membered)heterocycloalkyl, —O—(C1-C6)alkyl, —O—(C3-C7)cycloalkyl, —O—(5—to 8—membered)heterocycloalkyl, (C2-C6)alkenyl, —CH₂OH, phenyl, (5—to 6—membered)heteroaryl, or (5—to 6—membered)heterocycloalkyl, wherein R³ is substituted with 0-3 substituents selected from the group consisting of halogen, oxo, —CN, —(C1-C6)alkyl, —O—(C1-C6)alkyl, and —C(O)O(C1-C3)alkyl;

wherein R⁴ is hydrogen, —CN, (C1-C6)alkyl, —O—(C1-C6)alkyl, (C2-C6)alkenyl or —CH₂OH;

or R⁴ and R³ are taken together with the carbon atoms to which they are attached to form a (C5-C6)cycloalkyl, (C6-C10)aryl, (5—to 10—membered)heterocycloalkyl or (5—to 10—membered)heteroaryl;

wherein R⁵ is hydrogen, halogen, (C1-C6)alkyl or —O—(C1-C6)alkyl; or

R⁵ and R⁴ are taken together with the carbon atoms to which they are attached to form a (C5-C6)cycloalkyl, phenyl, (5- or 6—membered)heterocycloalkyl, or (5- or 6—membered)heteroaryl;

wherein each R⁶ is independently hydrogen or (C1-C3)alkyl;

wherein R¹⁴ is —(C1-C6)alkyl;

wherein R¹⁵ is hydrogen, —(C1-C6)alkyl, —CH₂—phenyl, or —CH₂-(5—to 10—membered)heteroaryl, wherein the —(C1-C6)alkyl, —CH₂—phenyl, or —CH₂-(5—to 10—membered)heteroaryl are substituted with 0-3 substituents selected from the group consisting of —OH, —SH, —SCH₃, —C(O)NH₂, —C(O)OH, —NH₂ and —NH—C(=NH)NH₂;

wherein R¹⁶ is hydrogen or —(C1-C6)alkyl;

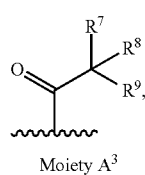

Moiety A³ wherein R⁷ is selected from the group consisting of —(C1-C3)alkyl, —(C3-C6)cycloalkyl, and —(4—to 6—membered)heterocycloalkyl, wherein R⁷ is substituted with 0-3 R";

wherein R⁸ and R⁹ are independently selected from the group consisting of hydrogen, —(C1-C3)alkyl, —(C3-C6)cycloalkyl, and —(4—to 6—membered)heterocycloalkyl, wherein R⁸ and R⁹ are independently substituted with 0-3 R";

wherein R" is hydrogen, halogen, —(C1-C6)alkyl, —O—(C1-C6)alkyl, or —(4—to 20—membered)heteroalkyl, wherein said heteroalkyl has 1-6 oxygen atoms;

wherein B is a (6—to 8—membered)heterocycloalkyl, wherein B is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4)alkynyl are optionally substituted with 1-3 halogen or (C1-C4)alkoxy;

or is selected from Moiety B¹ or Moiety B², wherein Moiety B¹ has the structure:

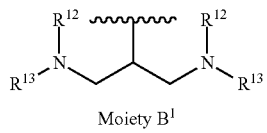

Moiety B¹ wherein each occurrence of R¹² and R¹³ is independently selected from the group consisting of hydrogen, —(C1-C10)alkyl, —(C3-C10)cycloalkyl, —(4—to 10—membered)heteroaryl, and —(4—to 10—membered)heterocycloalkyl, wherein each of R¹² and R¹³ is independently substituted with 0-3 R'; or wherein two R¹³ groups taken with the nitrogen atoms to which they are attached combine to form a (7—to 8—membered)heterocycloalkyl, wherein the (7—to 8—membered)heterocycloalkyl is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4)alkyl, cyclopropyl, cyclobutyl, cyclopentyl and cyclohexyl are optionally substituted with 1-3 halogen or (C1-C4)alkoxy;

wherein R is selected from hydrogen, halogen, (C1-C4)alkyl, or —O—(C1-C4)alkyl; and wherein Moiety B² has the structure:

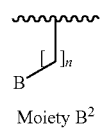

Moiety B² wherein n is an integer selected from the group consisting of 1, 2, 3, and 4; and provided that the compound is not

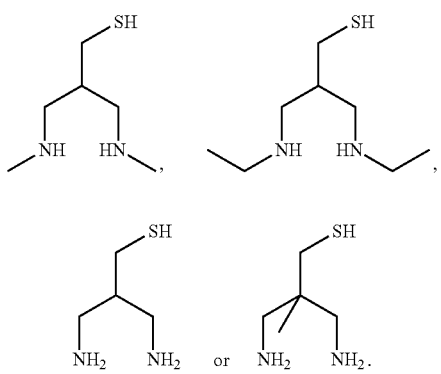

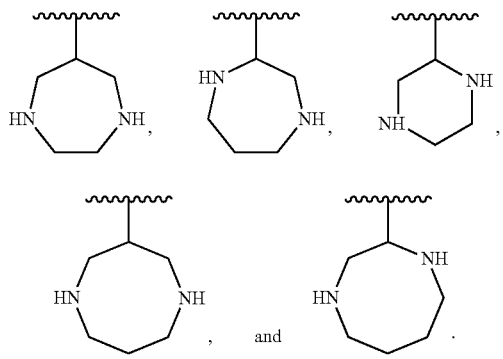

selected from the group consisting of

In one or more embodiments of formula I, B is Moiety $B^1$. In one or more embodiments of formula I, B is Moiety $B^2$. In one or more embodiments of formula I, B is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl. In one or more embodiments of formula I, the (C1-C4)alkyl, (C1-C4)alkenyl and (C1-C4)alkynyl are optionally substituted with 1-3 halogen or (C1-C4)alkoxy. In one or more embodiments of formula I, B is substituted with a (C1-C4) alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4)alkynyl are optionally substituted with 1-3 halogen or (C1-C4)alkoxy.

In some embodiments of the disclosure, the compound according to formula I is a compound having a structure according to formula II:

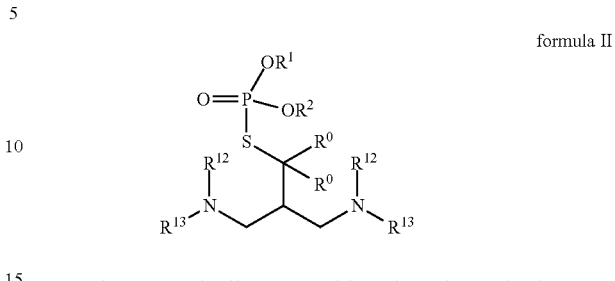

formula II or a pharmaceutically acceptable salt, solvate, hydrate, or polymorph thereof, or a solvate, hydrate, or polymorph of the pharmaceutically acceptable salt, wherein $R^0$, $R^1$, $R^2$, $R^{12}$ and $R^{13}$ are as defined in formula I.

In some embodiments of the compound having a structure according to formula I or II, each of $R^1$ and $R^2$ is independently hydrogen or —(CH($R^6$))—O—C(O)$R^{10}$. In one or more embodiments of formula I or II, one of $R^1$ and $R^2$ is H, and the other is —(CH($R^6$))—O—C(O)$R^{10}$.

In one or more embodiments of formula I or II, both $R^1$ and $R^2$ are —(CH($R^6$))—O—C(O)$R^{10}$. In one or more embodiments of formula I or II, both $R^1$ and $R^2$ are H.

In some embodiments of formula I or II, each of $R^1$ and $R^2$ is independently hydrogen, —(CH($R^6$))$_m$—S—C(O)$R^{10}$ or —CH$_2$—(C($R^{11}$)$_2$)—C(O)—CH$_2$—S—C(O)$R^{10}$, m being selected from the integers of 1, 2, 3 or 4. In one or more embodiments of formula I or II, one of $R^1$ and $R^2$ is H and the other is —CH$_2$—(C($R^1$)$_2$)—C(O)—CH$_2$—S—C(O)$R^{10}$. In one or more embodiments of formula I or II, one of $R^1$ and $R^2$ is H, and the other is —(CH($R^6$))$_m$—S—C(O)$R^{10}$. In one or more embodiments of formula I or II, $R^1$ and $R^2$ are (CH($R^6$))$_m$—S—C(O)$R^{10}$. In one or more embodiments of formula I or II, $R^1$ and $R^2$ are —CH$_2$—(C($R^{11}$)$_2$)—C(O)—CH$_2$—S—C(O)$R^{10}$.

In one or more embodiments of formula I or II, each $R^6$ is independently hydrogen or (C1-C3)alkyl. In one or more embodiments of formula I or II, each $R^6$ is independently hydrogen or (C1-C3)alkyl. In one or more embodiments of formula I or II, each $R^6$ is independently hydrogen, methyl, ethyl, propyl or iso-propyl.

In some embodiments of the compound having a structure according to formula I or II, $R^{10}$ is an optionally substituted —(C1-C6)alkyl, —O—(C1-C6)alkyl, —O—(C6-C10)aryl, —(C6-C10)aryl, (5—to 10—membered)heteroaryl, (4—to 10—membered)heterocycloalkyl, (C3-C10)cycloalkyl, —O—(5—to 10—membered)heteroaryl, —O—(4—to 10—membered)heterocycloalkyl, —O—(C3-C10)cycloalkyl, —O—(4—to 20—membered)heteroalkyl or —(4—to 20—membered)heteroalkyl, wherein each of said heteroalkyl independently has 1-6 oxygen atoms. In one or more embodiments of the compound having a structure according to formula I or II, $R^{10}$ is an optionally substituted —(C1-C6)alkyl, —O—(C1-C6)alkyl, —(C6-C10)aryl, —(4—to 20—membered)heteroalkyl and —O—(4—to 20—membered)heteroalkyl, wherein each of said heteroalkyl independently has 1-6 oxygen atoms. In some embodiments, $R^{10}$ is an optionally substituted —(C1-C6)alkyl, —O—(C1-C6) alkyl, —(C6-C10)aryl, —[(CH$_2$)$_y$O]$_z$—R, —CH$_2$—O—[(CH$_2$)$_y$O]$_z$—R and —O—[(CH$_2$)$_y$O]$_z$—R, wherein y is an integer between 1 and 4; z is an integer between 1 and 10; and R is hydrogen or (C1-C6)alkyl. In some embodiments, $R^{10}$ is an optionally substituted (C1-C6)alkyl, or (C6-C10)

aryl. In some embodiments, $R^{10}$ is methyl, ethyl, propyl, butyl, iso-propyl, tert-butyl or phenyl. In some embodiments, $R^{10}$ is —[(CH$_2$)$_y$O]$_z$—R, —CH$_2$—O—[(CH$_2$)$_y$O]$_z$—R or —O—[(CH$_2$)$_y$O]$_z$—R, wherein y is 2; x is an integer selected from the group consisting of 1, 2, 3 and 4; and R is —(C1-C6)alkyl. In some embodiments $R^{10}$ is —CH$_2$—O—[(CH$_2$)$_{20}$]—(C1-C6)alkyl or —O[(CH$_2$)$_2$O]$_4$-(C1-C6)alkyl.

In some embodiments, $R^{10}$ is unsubstituted. In some embodiments, $R^{10}$ is substituted with 0-3 $R^c$, wherein $R^0$ is selected from the group consisting of halogen (e.g., —F, —Cl, —Br, —I), (C1-C3)alkyl, —CN, —O—(C1-C3)alkyl, —S—(C1-C3)alkyl, and C(O)O—(C1-C3)alkyl. In some embodiments, $R^c$ is (C1-C3)alkyl (e.g., methyl, ethyl, propyl, iso-propyl) or —C(O)O—(C1-C3)alkyl (e.g., —C(O)O-methyl, —C(O)O-ethyl, —C(O)O-propyl, —C(O)O-iso-propyl). In some embodiments, $R^c$ is (C1-C3)alkyl (e.g., methyl, ethyl, propyl, iso-propyl).

In one or more embodiments of formula I or II, each $R^{11}$ is independently selected from the group consisting of hydrogen, —(C1-C6)alkyl, —CH$_2$—O—C(O)R'', —C(O)—OR'', —(4—to 20—membered)heteroalkyl and —O—(4—to 20—membered)heteroalkyl, wherein each of said heteroalkyl independently has 1-6 oxygen atoms. In some embodiments, each $R^{11}$ is independently selected from the group consisting of hydrogen, —(C1-C6)alkyl, —CH$_2$—O—C(O)R'', —C(O)—OR'', —[(CH$_2$)$_y$O]$_z$—R, —CH$_2$—O—[(CH$_2$)$_y$O]$_z$—R and —O—[(CH$_2$)$_y$O]$_z$—R, wherein y is an integer between 1 and 4; z is an integer between 1 and 10; and R is hydrogen or (C1-C6)alkyl (e.g., methyl, ethyl, propyl, iso-propyl, butyl, tert-butyl, pentyl, hexyl). In some embodiments of formula I or II, each $R^{11}$ is independently hydrogen, —(C1-C6)alkyl, —CH$_2$—O—C(O)R'' or —C(O)—OR''.

In some embodiments of formula I or II, each $R^{11}$ is independently hydrogen, —(C1-C3)alkyl, —CH$_2$—O—C(O)R'' and —C(O)—OR'', wherein R'' is hydrogen, (C1-C6)alkyl, or —(4—to 20—membered)heteroalkyl, wherein said heteroalkyl has 1-6 oxygen atoms. In some embodiments of formula I or II, R'' is hydrogen, (C1-C6)alkyl, or —[(CH$_2$)$_y$O]$_z$—R, wherein y is an integer between 1 and 4; z is an integer between 1 and 10; and R is hydrogen or (C1-C6)alkyl (e.g., methyl, ethyl, propyl, iso-propyl, butyl, pentyl or hexyl). In some embodiments of formula I or II, R'' is methyl, ethyl, propyl, iso-propyl, or [(CH$_2$)$_2$O]$_3$—CH$_3$.

In one or more embodiments of formula I or II, each $R^{11}$ of the same $R^1$ or $R^2$ group is a —(C1-C6)alkyl (e.g., methyl, ethyl, propyl, butyl, pentyl, hexyl). In some embodiments, one $R^{11}$ of the same $R^1$ or $R^2$ group is a —(C1-C6)alkyl (e.g., methyl, ethyl, propyl, butyl, pentyl, hexyl), and the other is —CH$_2$—O—C(O)R'' or —C(O)—OR''. In some embodiments, each $R^{11}$ of the same $R^1$ or $R^2$ group is independently —CH$_2$—O—C(O)R'' or —C(O)—OR''.

In one or more embodiments of formula I or II, when $R^{11}$ is —CH$_2$—O—C(O)R'' or —C(O)—OR'', R'' is hydrogen, halogen, —(C1-C6)alkyl, —O—(C2-C6)alkyl, or —(4—to 20—membered)heteroalkyl, wherein said heteroalkyl has 1-6 oxygen atoms. In one or more embodiments of formula I or II, when $R^{11}$ is —CH$_2$—O—C(O)R'' or —C(O)—OR'', R'' is hydrogen, (C1-C6)alkyl, or —(4—to 20—membered) heteroalkyl, wherein said heteroalkyl has 1-6 oxygen atoms. In one or more embodiments of formula I or II, when $R^{11}$ is —CH$_2$—O—C(O)R'' or —C(O)—OR'', R'' is (C1-C6)alkyl, or —(4—to 20—membered)heteroalkyl, wherein said heteroalkyl has 1-6 oxygen atoms. In one or more embodiments of formula I or II, when $R^{11}$ is —CH$_2$—O—C(O)R'' or —C(O)—OR'', R'' is (C1-C6)alkyl or —[(CH$_2$)$_y$O]$_z$—R, wherein y is an integer between 1 and 4; z is an integer between 1 and 10; and R is hydrogen or (C1-C6)alkyl. In one or more embodiments of formula I or II, when $R^{11}$ is —CH$_2$—O—C(O)R'' or —C(O)—OR'', R'' is methyl, ethyl, propyl, iso-propyl, butyl, tert-butyl, pentyl, hexyl or —[(CH$_2$)$_2$O]$_3$—CH$_3$.

In one or more embodiments of formula I or II, $R^1$ and $R^2$, taken with the —O—P—O— linkage to which they are attached form a 6—membered heterocycloalkyl ring that is substituted with 1-2 $R^a$ and 0-3 $R^b$. In one or more embodiments of formula I or II, $R^1$ and $R^2$, one of which is CH$_2$ or the other is CH$_2$CH$_2$, taken with the —O—P—O— linkage to which they are attached form a 6—membered heterocycloalkyl ring that is substituted with 1-2 $R^a$ and 0-3 $R^b$. In some embodiments, when $R^1$ and $R^2$, taken with the —O—P—O— linkage to which they are attached form a 6—membered heterocycloalkyl ring, the heterocycloalkyl ring is 1,3,2-dioxaphosphinane. In some embodiments, when $R^1$ and $R^2$, one of which is CH$_2$ or the other is CH$_2$CH$_2$, taken with the —O—P—O— linkage to which they are attached form a 6—membered heterocycloalkyl ring, the heterocycloalkyl ring is 1,3,2-dioxaphosphinane. In some embodiments, when $R^1$ and $R^2$, taken with the —O—P—O— linkage to which they are attached form a 6—membered heterocycloalkyl ring, the heterocyclalkyl ring is 1,3,2-k-5 dioxaphosphinane. In some embodiments, when $R^1$ and $R^2$, one of which is CH$_2$ or the other is CH$_2$CH$_2$, taken with the —O—P—O— linkage to which they are attached form a 6—membered heterocycloalkyl ring, the heterocyclalkyl ring is 1,3,2-k-5 dioxaphosphinane. In some embodiments, $R^a$ is independently hydrogen, (C1-C6)alkyl, (C6-C10)aryl—or a 5—to 10—membered heteroaryl-, provided that at least one $R^a$ group is (C6-C10)aryl—or a 5—to 10—membered heteroaryl-, wherein said alkyl, aryl and heteroaryl $R^a$ is substituted with 0-3 $R^c$. In some embodiments, $R^a$ is $R^{a1}$ or $R^{a2}$, and $R^{a1}$ and $R^{a2}$ are independently selected from hydrogen, (C1-C6)alkyl, (C6-C10)aryl or a 5—to 10—membered heteroaryl, wherein said alkyl, aryl and heteroaryl are substituted with 0-3 $R^c$, provided that at least one of $R^{a1}$ and $R^{a2}$ is (C6-C10)aryl or a 5—to 10—membered heteroaryl. In some embodiments, $R^b$ is —(C1-C3)alkyl. In some embodiments of formula I or II, $R^b$ is $R^d$, $R^{e1}$ or $R^{e2}$ and $R^d$ is hydrogen or (C1-C3)alkyl; and $R^{e1}$ and $R^{e2}$ are independently hydrogen or (C1-C3)alkyl, provided that when $R^{a1}$ is (C6-C10)aryl or a 5—to 10—membered heteroaryl, R''$^1$ is hydrogen, and that when $R^{a2}$ is (C6-C10)aryl or a 5—to 10—membered heteroaryl, $R^{e2}$ is hydrogen.

In some embodiments of the disclosure, the compound according to formula I or II has a structure according to formula III:

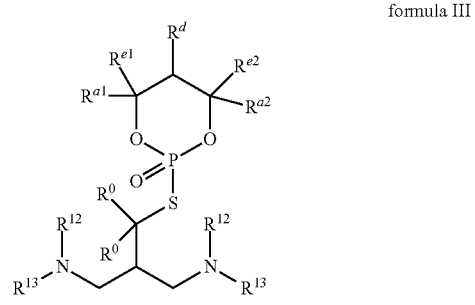

formula III or a pharmaceutically acceptable salt, solvate, hydrate, or polymorph thereof, or a solvate, hydrate, or polymorph of the pharmaceutically acceptable salt, wherein: $R^0$, $R^{12}$ and $R^{13}$ are as defined in formula I;

$R^{a1}$ and $R^2$ are independently selected from hydrogen, (C1-C6)alkyl, (C6-C10)aryl or a 5—to 10—membered heteroaryl, wherein said alkyl, aryl and heteroaryl are substituted with 0-3 $R^c$, provided that at least one of $R^{a1}$ and $R^{a2}$ is (C6-C10)aryl or a 5—to 10—membered heteroaryl;

$R^d$ is hydrogen or (C1-C3)alkyl; and $R^{e1}$ and $R^{e2}$ are independently hydrogen or (C1-C3)alkyl, provided that when $R^{a1}$ is (C6-C10)aryl or a 5—to 10—membered heteroaryl, $R^{e1}$ is hydrogen, and that when $R^{a2}$ is (C6-C10)aryl or a 5—to 10—membered heteroaryl, $R^{e2}$ is hydrogen.

In one or more embodiments of formula I, II or III, $R^{a1}$ is selected from hydrogen, (C1-C6)alkyl, (C6-C10)aryl or 5—to 10—membered heteroaryl, and $R^{a2}$ is selected from hydrogen, (C1-C6)alkyl, (C6-C10)aryl or a 5—to 10—membered heteroaryl, wherein said alkyl, aryl and heteroaryl are substituted with 0-3 $R^e$. In some embodiments, $R^{a1}$ is phenyl or a 5—to 6—membered heteroaryl. In some embodiments, $R^{a2}$ is phenyl or a 5—to 6—membered heteroaryl. In one or more embodiments, one of $R^{a1}$ and $R^{a2}$ is phenyl and the other is hydrogen. In one or more embodiments, one of $R^{a1}$ and $R^{a2}$ is a 5—to 6—membered heteroaryl and the other is hydrogen. In some embodiments, the 5—to 6—membered heteroaryl is a nitrogen containing heteroaryl (e.g., pyridinyl, pyridazinyl, pyrimidinyl, pyrazinyl, pyrrolyl, imidazolyl, pyrazolyl, triazolyl, oxazolyl, or isoxazolyl). In some embodiments, the 5—to 6—membered heteroaryl is pyridinyl.

In one or more embodiments of formula I, II or III, $R^d$ is hydrogen or (C1-C3)alkyl, and $R^{e1}$ and $R^{e2}$ are H. In one or more embodiments of formula I, II or III, Rd, R' and $R^{e2}$ are H.

In one or more embodiments of formula I, II or III, $R^c$ is halogen or (C1-C3)alkyl. In one or more embodiments of formula I, II or III, $R^c$ is chloro, fluoro, bromo, iodo, methyl, ethyl, propyl or iso-propyl. In one or more embodiments of formula I, II or III, $R^c$ is chloro or methyl.

In one or more embodiments of formula I, the compound has a structure according to formula IV:

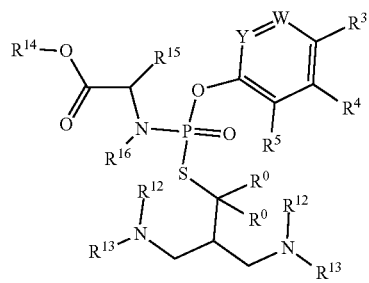

formula IV or a pharmaceutically acceptable salt, solvate, hydrate, or polymorph thereof, or a solvate, hydrate, or polymorph of the pharmaceutically acceptable salt, wherein Y, W, $R^0$, $R^3$, $R^4$, $R^5$, $R^{12}R^{13}$, $R^{14}$, $R^{15}$ and $R^{16}$ are as defined in formula I.

In some embodiments of formula I or IV, Y and W are CH. In some embodiments of formula I or IV, one of Y is CH and the other is N. In some embodiments of formula I or IV, Y and W are N.

In one or more embodiments of formula I or IV, $R^3$ is hydrogen, halogen, (C1-C6)alkyl, (C3-C7)cycloalkyl, (5—to 8—membered)heterocycloalkyl, —O—(C1-C6)alkyl, —O—(C3-C7)cycloalkyl, —O—(5—to 8—membered) heterocycloalkyl, (C2-C6)alkenyl, —CH$_2$OH, phenyl, (5—to 6—membered)heteroaryl, or (5—to 6—membered) heterocycloalkyl, wherein $R^3$ is substituted with 0-3 substituents selected from the group consisting of halogen, oxo, cyano, —(C1-C6)alkyl, —O— (C1-C6)alkyl, and —C(O)O(C1-C3)alkyl. In one or more embodiments of formula I or IV, $R^3$ is hydrogen, halogen, optionally substituted (C1-C6) alkyl, optionally substituted (C2-C6)alkenyl, optionally substituted (C3-C7)cycloalkyl, or —CH$_2$OH. In one or more embodiments of formula I or IV, $R^3$ is hydrogen, halogen, optionally substituted (C1-C6)alkyl or —CH$_2$OH.

In one or more embodiments of formula I or IV, $R^4$ is hydrogen, —CN, (C1-C6)alkyl, —O—(C1-C6)alkyl, —(C2-C6)alkenyl or —CH$_2$OH. In one or more embodiments of formula I or IV, $R^4$ is hydrogen, methyl, ethyl, propyl, iso-propyl, —CN, —CH$_2$OH or methoxy.

In one or more embodiments of formula I or IV, $R^5$ is hydrogen, halogen, (C1-C6)alkyl or —O—(C1-C6)alkyl. In one or more embodiments of formula I or IV, $R^5$ is hydrogen, fluoro, chloro, bromo, methyl, ethyl, propyl, iso-propyl or methoxy.

In one or more embodiments of formula I or IV, $R^3$, $R^4$ and $R^5$ are H.

In one or more embodiments of formula I or IV, $R^{14}$ is —(C1-C6)alkyl. In one or more embodiments of formula I or IV, $R^{14}$ is —(C1-C3)alkyl. In one or more embodiments of formula I or IV, $R^{14}$ is methyl, ethyl, propyl or iso-propyl.

In one or more embodiments of formula I or IV, $R^{15}$ is hydrogen, —(C1-C6)alkyl, —CH$_2$— phenyl, or —CH$_2$-(5—to 10—membered)heteroaryl, wherein the —(C1-C6) alkyl, —CH$_2$—phenyl, or —CH$_2$-(5—to 10—membered) heteroaryl are substituted with 0-3 substituents selected from the group consisting of —OH, —SH, —SCH$_3$, —C(O)NH$_2$, —C(O)OH, —NH$_2$ and —NH—C(=NH)NH$_2$. In one or more embodiments of formula I or IV, $R^{15}$ is hydrogen or —(C1-C6)alkyl, wherein the —(C1-C6)alkyl is substituted with 0-1 substituents selected from the group consisting of —OH, —SH, —SCH$_3$, —C(O)NH$_2$, —C(O)OH, —NH$_2$ and —NH—C(=NH)NH$_2$. In one or more embodiments of formula I or IV, $R^{15}$ is methyl. In one or more embodiments of formula I or IV, $R^{15}$ is —CH$_2$— phenyl substituted with 0-1—OH. In one or more embodiments of formula I or IV, $R^{15}$ is —CH$_2$-(5—to 10—membered)heteroaryl. In one or more embodiments of formula I or IV, $R^{15}$ is —CH$_2$-(5—to 9—membered)heteroaryl wherein the 5—to 9—membered heteroaryl is imidiazolyl or indolyl.

In one or more embodiments of formula I or IV, $R^{16}$ is hydrogen or (C1-C6)alkyl. In one or more embodiments of formula I or IV, $R^{16}$ is hydrogen or (C1-C3)alkyl (e.g., methyl, ethyl, propyl and the like).

In some embodiments of formula I, the compound has a structure according to formula V:

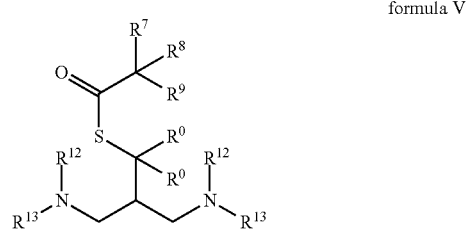

formula V or a pharmaceutically acceptable salt, solvate, hydrate, or polymorph thereof, or a solvate, hydrate, or polymorph of the pharmaceutically acceptable salt, wherein $R^0$, $R^7$, $R^8$, $R^9$, $R^{12}$ and $R^{13}$ are as defined in formula I.

In some embodiments of formula I or V, $R^7$ is —(C1-C3)alkyl, —(C3-C6)cycloalkyl, and —(4—to 6—membered)heterocycloalkyl. In some embodiments of formula I or V, $R^7$ is —(C1-C3)alkyl or —(C3-C6)cycloalkyl. In some embodiments of formula I or V, $R^7$ is (C1-C3)alkyl. In some embodiments of formula I or V, $R^7$ is methyl, ethyl or propyl.

In one or more embodiments of formula I or V, $R^8$ and $R^9$ are independently selected from the group consisting of hydrogen, —(C1-C3)alkyl, —(C3-C6)cycloalkyl, and —(4—to 6—membered)heterocycloalkyl. In one or more embodiments of formula I or V, $R^8$ and $R^9$ are independently selected from the group consisting of hydrogen, —(C1-C3)alkyl or —(C3-C6)cycloalkyl. In one or more embodiments of formula I or V, $R^8$ and $R^9$ are independently selected from the group consisting of hydrogen or —(C1-C3)alkyl. In one or more embodiments of formula I or V, $R^1$ and $R^9$ are independently selected from the group consisting of hydrogen, methyl, ethyl or propyl.

In one or more embodiments of formula I or V, $R^7$, $R^8$ and $R^9$ are substituted with 0-3 R", wherein R" is halogen, —(C1-C6)alkyl or —O—(C1-C6)alkyl. In one or more embodiments of formula I or V, $R^7$, $R^8$ and $R^9$ are unsubstituted.

In some embodiments of formula I, the compound has a structure according to formula VI:

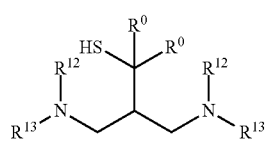

formula VI or a pharmaceutically acceptable salt, solvate, hydrate, polymorph, prodrug or double prodrug thereof, or a solvate, hydrate, or polymorph of the pharmaceutically acceptable salt, wherein $R^0$,

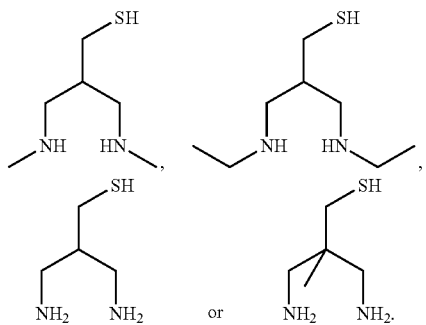

In one or more embodiments of formula I or VI, $R^0$ is independently hydrogen or (C1-C3)alkyl. In one or more embodiments of formula I or VI, one $R^0$ is hydrogen and the other is (C1-C3)alkyl. In one or more embodiments of formula I or VI, $R^0$ is independently hydrogen, (C1-C3)alkyl, or a thiol. In one or more embodiments of formula I or VI, one $R^0$ is hydrogen and the other is a thiol. In one or more embodiments of formula I or VI, each $R^0$ are (C1-C3)alkyl (e.g., methyl, ethyl, propyl, or iso-propyl). In some embodiments, each $R^0$ is methyl.

In some embodiments of formula I or VI, each $R^{12}$ is independently hydrogen or (C1-C3)alkyl. In some embodiments of formula I or VI, each $R^{12}$ is hydrogen.

In some embodiments of formula I or VI, each $R^{13}$ is taken together with the nitrogen atoms to which they are attached to form a (7—to 8—membered)heterocycloalkyl. In some embodiments, each $R^{13}$ is taken together with the nitrogen atoms to which they are attached to form

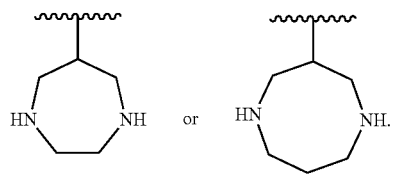 [SMILES: *C1CNCCNC1 ; "or" ; *C1CNCCCNC1]

In some embodiments of formula I, the compound has a structure according to formula VII,

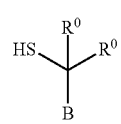

formula VII or a pharmaceutically acceptable salt, solvate, hydrate, polymorph, prodrug or double prodrug thereof, or a solvate, hydrate, or polymorph of the pharmaceutically acceptable salt, wherein $R^0$ and B are as defined in formula I, provided that the compound is not

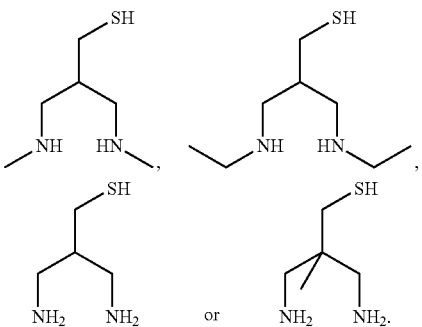

In one or more embodiments of formula I or VII, $R^0$ is independently hydrogen or (C1-C3)alkyl. In one or more embodiments of formula I or VII, one $R^0$ is hydrogen and the other is (C1-C3)alkyl. In one or more embodiments of formula I or VII, $R^0$ is independently hydrogen, (C1-C3)alkyl or a thiol. In one or more embodiments of formula I or VII, one $R^0$ is hydrogen and the other is a thiol. In one or more embodiments of formula I or VII, each $R^0$ are (C1-C3)alkyl (e.g., methyl, ethyl, propyl, iso-propyl). In some embodiments, each $R^0$ is methyl.

In one or more embodiments of formula I or VII, B is a (6—to 8—membered) heterocycloalkyl or Moiety $B^1$, wherein B is substituted with 0-3 (C1-C4)alkyl or cyclopropyl, wherein the (C1-C4)alkyl and cyclopropyl are optionally substituted with 1-3 halogen or (C1-C4)alkoxy. In one or more embodiments of formula I or VII, B is a (6—to 8—membered) heterocycloalkyl or Moiety B¹, wherein B is substituted with a (C1-C4)alkyl, cyclopropyl, cyclobutyl, cyclopentyl or cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6) aryl, (C5 to C6)heteroaryl, (C1-C4)acyl, (C1-C4)alkenyl and (C1-C4)alkynyl, wherein the (C1-C4)alkyl, (C1-C4) alkenyl and (C1-C4)alkynyl are optionally substituted with 1-3 halogen or (C1-C4)alkoxy. In one or more embodiments of formula I or VII, B is a (6—to 8—membered) heterocycloalkyl, Moiety B¹ or Moiety B², wherein B is substituted with a (C1-C4)alkyl, cyclopropyl, cyclobutyl, cyclopentyl cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4) alkynyl are optionally substituted with 1-3 halogen or (C1-C4)alkoxy. In one or more embodiments of formula I or VII, B is Moiety B¹, wherein two R13 groups taken with the nitrogen atoms to which they are attached combine to form a (7—to 8—membered)heterocycloalkyl, wherein the (7—to 8—membered)heterocycloalkyl is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4)alkynyl are optionally substituted with 1-3 halogen or (C1-C4)alkoxy. In some embodiments of formula I or VII, B is a (6—to 8—membered) heterocycloalkyl containing at least two N atoms. In some embodiments, B is selected from the group consisting of

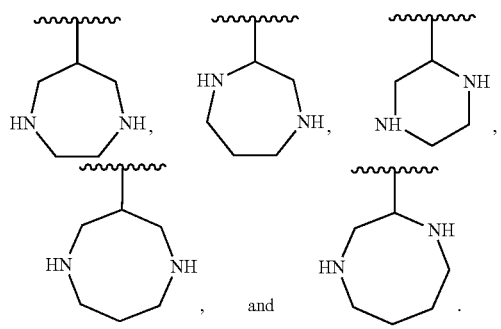

In some embodiments, B is

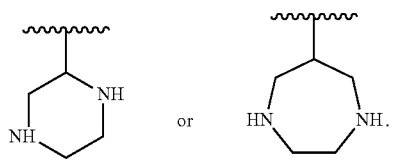 [SMILES: *C1CNCCN1 ; *C1CNCCNC1]

In some embodiments of formula I or VII, B is Moiety B¹, and each $R^{12}$ and $R^{13}$ is C independently hydrogen or —(C1-C6)alkyl. In some embodiments of formula I or VII, B is Moiety B², and each $R^{12}$ and $R^{13}$ is independently hydrogen or —(C1-C6)alkyl. In some embodiments each $R^{12}$ is hydrogen, and each $R^{13}$ is —(C1-C6)alkyl. In some embodiments of formula I or VII, each $R^{12}$ is hydrogen, and each $R^{13}$ is methyl, provided that $R^0$ is not hydrogen. In some embodiments of formula I or VII, $R^{12}$ is independently hydrogen or —(4—to 10—membered)heteroaryl. In some embodiments of formula I or VII, $R^{12}$ is independently hydrogen or pyridine.

In one or more embodiments of formula I, II, III, IV, V, VI or VII, $R^0$ is independently hydrogen or (C1-C3)alkyl. In one or more embodiments of formula I, II, III, IV, V, VI or VII, one $R^0$ is hydrogen and the other is (C1-C3)alkyl. In one or more embodiments of formula I, II, III, IV, V, VI or VII, $R^0$ is independently hydrogen, (C1-C3)alkyl, or a thiol. In one or more embodiments of formula I, II, III, IV, V, VI or VII, one $R^0$ is hydrogen and the other is a thiol. In one or more embodiments of formula I, II, III, IV, V, VI or VII, each $R^0$ are (C1-C3)alkyl (e.g., methyl, ethyl, propyl, or iso-propyl). In some embodiments, each $R^0$ is methyl.

In one or more embodiments of formula I, II, III, IV, V, VI or VII, each $R^{12}$ is independently selected from the group consisting of hydrogen, —(C1-C10)alkyl, —(C3-C10)cycloalkyl, and —(4—to 10—membered)heterocycloalkyl, wherein each $R^{12}$ is independently substituted with 0-3 R'. In one or more embodiments of formula I, II, III, IV, V, VI or VII, each $R^{12}$ is independently selected from the group consisting of hydrogen, —(C1-C10)alkyl, —(C3-C10)cycloalkyl, —(4—to 10—membered)heteroaryl, and —(4—to 10—membered)heterocycloalkyl, wherein each $R^{12}$ is independently substituted with 0-3 R'. In one or more embodiments of formula I, II, III, IV, V, VI or VII, each $R^{12}$ is independently hydrogen or —(C1-C10)alkyl. In one or more embodiments of formula I, II, III, IV, V, VI or VII, each $R^{12}$ is independently hydrogen or —(4—to 10—membered) heteroaryl. In one or more embodiments of formula I, II, III, IV, V, VI or VII, each $R^{12}$ is independently hydrogen or pyridine. In one or more embodiments of formula I, II, III, IV, V, VI or VII, each $R^{12}$ is independently hydrogen, methyl, ethyl, propyl, iso-propyl, butyl, tert-butyl, pentyl, neopentyl, hexyl, heptyl, octyl, nonyl or decyl. In one or more embodiments of formula I, II, III, IV, V, VI or VII, each $R^{12}$ is hydrogen or methyl.

In one or more embodiments of formula I, II, III, IV, V, VI or VII, each $R^{13}$ is independently selected from the group consisting of hydrogen, —(C1-C10)alkyl, —(C3-C10)cycloalkyl, and —(4—to 10—membered)heterocycloalkyl, wherein each $R^{13}$ is independently substituted with 0-3 R'. In one or more embodiments of formula I, II, III, IV, V, VI or VII, each $R^{13}$ is independently hydrogen or —(C1-C10) alkyl. In one or more embodiments of formula I, II, III, IV, V, VI or VII, each $R^{13}$ is independently hydrogen, methyl, ethyl, propyl, iso-propyl, butyl, tert-butyl, pentyl, neopentyl, hexyl, heptyl, octyl, nonyl or decyl. In one or more embodiments of formula I, II, III, IV, V, VI or VII, each $R^{13}$ is hydrogen or methyl.

In some embodiments of formula I, II, III, IV, V, VI or VII, each $R^{13}$ is taken together with the nitrogen atoms to which they are attached to form a (7—to 8—membered) heterocycloalkyl. In some embodiments, each $R^{13}$ is taken together with the nitrogen atoms to which they are attached to form

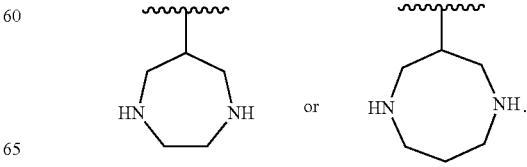

In some embodiments, the disclosure is directed to a compound having a structure according to formula II:

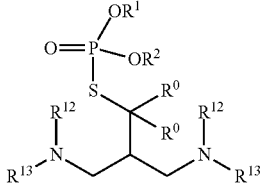

formula II or a pharmaceutically acceptable salt, solvate, hydrate, or polymorph thereof, or a solvate, hydrate, or polymorph of the pharmaceutically acceptable salt, wherein:
each $R^0$ is hydrogen;
each of $R^1$ and $R^2$ is independently hydrogen or —CH($R^6$))-O-C(O)$R^{10}$
each $R^6$ is independently hydrogen or (C1-C3)alkyl;
each $R^{10}$ is independently selected from the group consisting of —(C1-C6)alkyl, —O—(C1-C6)alkyl, —(C6-C10)aryl, —(4—to 20—membered)heteroalkyl, —O—(4—to 20—membered)heteroalkyl, —[(CH$_2$)$_y$O]$_z$—R, —CH$_2$—O—[(CH$_2$)$_y$O]$_z$—R and —O—[(CH$_2$)$_y$O]$_z$—R, wherein each of said heteroalkyl independently has 1-6 oxygen atoms, wherein y is an integer between 1 and 4, wherein z is an integer between 1 and 10, wherein R is hydrogen or (C1-C6) alkyl, and wherein each $R^{10}$ is independently substituted with 0-3 $R^c$ groups;
$R^c$ is selected from the group consisting of halogen, (C1-C3)alkyl, —CN, —O—(C1-C3)alkyl, —S—(C1-C3)alkyl, and —O—C(O)(C1-C3)alkyl;
each $R^{12}$ is hydrogen; and
each $R^{13}$ is (C1-C3)alkyl.

In some embodiments, the disclosure is directed to a compound having a structure according to formula II, or a pharmaceutically acceptable salt, solvate, hydrate, or polymorph thereof, or a solvate, hydrate, or polymorph of the pharmaceutically acceptable salt, wherein:
each $R^0$ is hydrogen;
each of $R^1$ and $R^2$ is independently hydrogen, —(CH($R^6$))$_m$—S—C(O)$R^{10}$ or CH$_2$—S—C(O)$R^{10}$;
each $R^{12}$ is hydrogen;
each $R^{13}$ is a (C1-C3)alkyl;
each $R^6$ is hydrogen;
$R^{10}$ is selected from the group consisting of (C1-C6)alkyl, and (C6-C10)aryl, wherein each $R^{10}$ is substituted with 0-3 $R^c$;
each $R^{11}$ is independently selected from the group consisting of hydrogen, —(C1-C3)alkyl, —CH$_2$—O—C(O)R" and —C(O)—OR";
each $R^c$ is (C1-C3)alkyl or —C(O)O—(C1-C3)alkyl;
R" is hydrogen, (C1-C6)alkyl, or —(4—to 20—membered)heteroalkyl, wherein said heteroalkyl has 1-6 oxygen atoms; and
m is an integer selected from the group consisting of 0, 1, 2, 3 and 4.

In one or more embodiments, the disclosure is directed to a compound having a structure according to formula III,

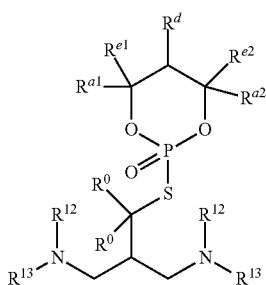

formula III or a pharmaceutically acceptable salt, solvate, hydrate, or polymorph thereof, or a solvate, hydrate, or polymorph of the pharmaceutically acceptable salt, wherein:
each $R^0$ is independently hydrogen;
each $R^{12}$ and $R^{13}$ is independently selected from the group consisting of hydrogen, —(C1-C3)alkyl, —(C3-C6) cycloalkyl, and —(4—to 6—membered)heterocycloalkyl, wherein each of $R^3$ and $R^4$ is independently substituted with 0-3 R';
$R^{a1}$ and $R^{a2}$ is independently hydrogen, (C1-C6)alkyl, (C6-C10)aryl or a 5—to 10—membered heteroaryl, wherein said alkyl, aryl and heteroaryl are substituted with 0-3 $R^c$, provided that at least one of $R^{a1}$ and $R^{a2}$ is (C6-C10)aryl or a 5—to 10—membered heteroaryl;
$R^c$ is selected from the group consisting of hydrogen, halogen, (C1-C3)alkyl, —CN, —O—(C1-C3)alkyl, —S—(C1-C3)alkyl, —C(O)O—(C1-C3)alkyl, —N(R')$_2$, —CF$_3$ and —OCF$_3$;
$R^d$ is hydrogen or (C1-C3)alkyl;
$R^{e1}$ and $R^{e2}$ are independently hydrogen or (C1-C3)alkyl, provided that when $R^{a1}$ is (C6-C10)aryl or a 5—to 10—membered heteroaryl, $R^{e1}$ is hydrogen, and that when $R^{a2}$ is (C6-C10)aryl or a 5—to 10—membered heteroaryl, $R^{e2}$ is hydrogen; and
R' is hydrogen or —(C1-C4)alkyl.

In some embodiments, the disclosure is directed to a compound having a structure according to formula III, or a pharmaceutically acceptable salt, solvate, hydrate, or polymorph thereof, or a solvate, hydrate, or polymorph of the pharmaceutically acceptable salt, wherein:
each $R^0$ is hydrogen;
each $R^{12}$ is hydrogen;
each $R^{13}$ is (C1-C3)alkyl;
one of $R^a$ and $R^{a2}$ is (C6-C10)aryl or a 5—to 10—membered heteroaryl, and the other is hydrogen, wherein said aryl or heteroaryl is substituted with 1-3 $R^c$;
each $R^c$ is halogen or (C1-C3)alkyl; and
each of $R^d$, $R^{e1}$ and $R^{e2}$ is hydrogen.

In some embodiments, the disclosure is directed to a compound having a structure according to formula IV:

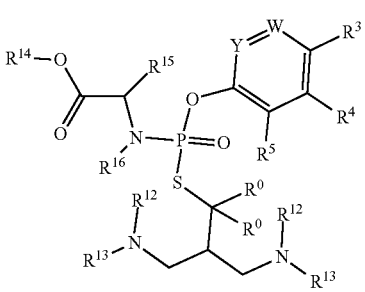

formula IV or a pharmaceutically acceptable salt, solvate, hydrate, or polymorph thereof, or a solvate, hydrate, or polymorph of the pharmaceutically acceptable salt, wherein:

each $R^0$ is independently hydrogen or (C1-C3)alkyl;

each $R^{12}$ and $R^{13}$ is independently selected from the group consisting of hydrogen, —(C1-C4)alkyl, —(C3-C6)cycloalkyl, and —(4—to 6—membered)heterocycloalkyl, wherein each $R^{12}$ and $R^{13}$ is independently substituted with 0-3 $R^1$;

$R^3$ is hydrogen, halogen, (C1-C6)alkyl, (C3-C7)cycloalkyl, (5—to 8—membered)heterocycloalkyl, —O—(C1-C6)alkyl, —O—(C3-C7)cycloalkyl, —O—(5—to 8—membered)heterocycloalkyl, (C2-C6)alkenyl, —CH$_2$OH, phenyl, (5- or 6—membered)heteroaryl, or (5- or 6—membered)heterocycloalkyl, wherein $R^3$ is substituted with 0-3 substituents selected from the group consisting of halogen, oxo, —(C1-C5)alkyl, —O—(C2-C4)alkyl, and —C(O)O(C1-C3)alkyl;

$R^4$ is hydrogen, —CN, (C1-C6)alkyl, —O—(C1-C6)alkyl, (C2-C6)alkenyl or —CH$_2$OH; or $R^4$ and $R^3$ are taken together with the carbon atoms to which they are attached to form a (C5-C6)cycloalkyl, (C6-C10)aryl, (5—to 10—membered)heterocycloalkyl or (5—to 10—membered)heteroaryl;

$R^5$ is hydrogen, halogen, (C1-C6)alkyl or —O—(C1-C6)alkyl; or $R^5$ and $R^4$ are taken together with the carbon atoms to which they are attached to form a (C5-C6)cycloalkyl, phenyl, (5- or 6—membered)heterocycloalkyl, or (5- or 6—membered)heteroaryl;

each $R^6$ is independently selected from hydrogen or (C1-C3)alkyl;

$R^{14}$ is (C1-C6)alkyl;

$R^{15}$ is hydrogen, —(C1-C6)alkyl, —CH$_2$—phenyl, or —CH$_2$-(5—to 10—membered)heteroaryl, wherein the —(C1-C6)alkyl, —CH$_2$—phenyl, or —CH$_2$-(5—to 10—membered)heteroaryl are substituted with 0-3 substituents selected from the group consisting of —OH, —SH, —SCH$_3$, —C(O)NH$_2$, —C(O)OH, —NH$_2$ and —NH—C(=NH)NH$_2$;

$R^{16}$ is hydrogen or —(C1-C6)alkyl; and

R' is selected from halogen, (C1-C4)alkyl, or —O—(C1-C4)alkyl.

In some embodiments, the disclosure is directed to a compound having a structure according to formula IV, or a pharmaceutically acceptable salt, solvate, hydrate, or polymorph thereof, or a solvate, hydrate, or polymorph of the pharmaceutically acceptable salt, wherein:

each $R^0$ is hydrogen;

each $R^{12}$ is H;

each $R^{13}$ is independently hydrogen or —(C1-C6)alkyl;

each $R^6$ is independently selected from hydrogen or (C1-C3)alkyl;

$R^3$, $R^4$ and $R^5$ are H;

$R^{14}$ is (C1-C3)alkyl;

$R^{15}$ is (C1-C3)alkyl; and $R^{16}$ is H.

In another embodiment, the disclosure is directed to a compound having a structure according to formula V:

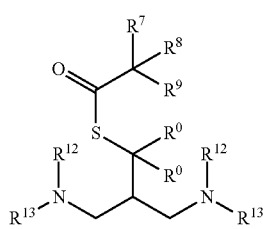

formula V or a pharmaceutically acceptable salt, solvate, hydrate, or polymorph thereof, or a solvate, hydrate, or polymorph of the pharmaceutically acceptable salt, wherein:

each $R^0$ is independently hydrogen or (C1-C3)alkyl each $R^{12}$ and $R^{13}$ is independently selected from the group consisting of hydrogen, —(C1-C3)alkyl, —(C3-C10)cycloalkyl, and —(4—to 10—membered)heterocycloalkyl, wherein each $R^{12}$ and $R^{13}$ is independently substituted with 0-3 $R^1$;

$R^7$ is selected from the group consisting of —(C1-C3)alkyl, —(C3-C6)cycloalkyl, and —(4—to 6—membered)heterocycloalkyl, wherein $R^7$ is substituted with 0-3 R";

$R^8$ and $R^9$ are independently selected from the group consisting of hydrogen, —(C1-C3)alkyl, —(C3-C6)cycloalkyl, and —(4—to 6—membered)heterocycloalkyl, wherein $R^8$ and $R^9$ are independently substituted with 0-3 R";

R' is halogen, (C1-C4)alkyl, or —O—(C1-C4)alkyl; and

R" is halogen, —(C1-C6)alkyl or —O—(C2-C6)alkyl.

In some embodiments, the disclosure is directed to a compound having a structure according to formula VI, or a pharmaceutically acceptable salt, solvate, hydrate, or polymorph thereof, or a solvate, hydrate, or polymorph of the pharmaceutically acceptable salt, wherein:

each $R^0$ is hydrogen;

each $R^{12}$ is H;

each $R^{13}$ is independently —(C1-C3)alkyl; and $R^7$, $R^8$ and $R^9$ are —(C1-C3)alkyl.

In another embodiment, the disclosure is directed to a compound having a structure according to formula VI:

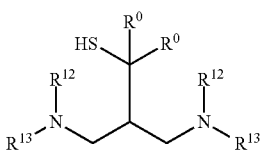

formula VI or a pharmaceutically acceptable salt, solvate, hydrate, polymorph, prodrug or double prodrug thereof, or a solvate, hydrate, or polymorph of the pharmaceutically acceptable salt, wherein:

each $R^0$ is independently hydrogen, (C1-C3)alkyl, or —SH;

each $R^{12}$ is independently hydrogen, (C1-C3)alkyl or —(4—to 10—membered)heteroaryl;

each $R^{13}$ is taken together with the nitrogen atoms to which they are attached to form a (7—to 8—membered)heterocycloalkyl.

In another embodiment, the disclosure is directed to a compound having a structure according to formula VII:

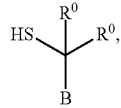
formula VII or a pharmaceutically acceptable salt, solvate, hydrate, polymorph, prodrug or double prodrug thereof, or a solvate, hydrate, or polymorph of the pharmaceutically acceptable salt, wherein:
  each $R^{11}$ is independently hydrogen, (C1-C3)alkyl or —SH;
  B is a (6—to 8—membered)heterocycloalkyl containing two N atoms, Moiety $B^1$, or Moiety $B^2$, wherein B is substituted with a (C1-C4)alkyl, cyclopropyl, cyclobutyl, cyclopentyl, cyclohexyl, so as to form a bicyclic ring, and/or substituted with 0-3 (C1-C4)alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4)alkyl, (C1-C4)alkenyl and (C1-C4)alkynyl are optionally substituted with 1-3 halogen or (C1-C4)alkoxy;
  when present, each occurrence of $R^{12}$ and $R^{13}$ is independently hydrogen, —(C1-C6)alkyl, or —(4-to 10-membered)heteroaryl provided that the compound is not

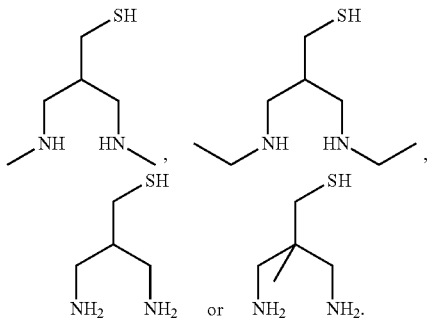

In some embodiments, the disclosure is directed to a compound having a structure according to formula VII, or a pharmaceutically acceptable salt, solvate, hydrate, polymorph, prodrug or double prodrug thereof, or a solvate, hydrate, or polymorph of the pharmaceutically acceptable salt, wherein:
  wherein B is the heterocycle

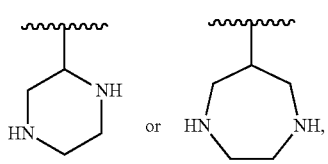 [SMILES: *C1CNCCN1 ; *C1CNCCNC1]

wherein the heterocycle is substituted with a (C1-C4)alkyl, cyclopropyl, cyclobutyl, cyclopentyl, cyclohexyl, so as to form a bicyclic ring, and/or substituted with 0-3 (C1-C4) alkyl, cyclopropyl, cyclobutyl, cyclopentyl, cyclohexyl, heteroaryl, (C1-C6)aryl, (C5 to C6)heteroaryl, (C1-C4)acyl, (C1-C4)alkenyl and (C1-C4)alkynyl, wherein the (C1-C4) alkyl, (C1-C4)alkenyl and (C1-C4)alkynyl are optionally substituted with 1-3 halogen or (C1-C4)alkoxy.

In some embodiments, the compound of this disclosure is selected from the group consisting of:

| Compound | Structure |
|---|---|
| 1 | 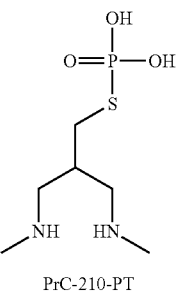<br>PrC-210-PT |
| 2 | 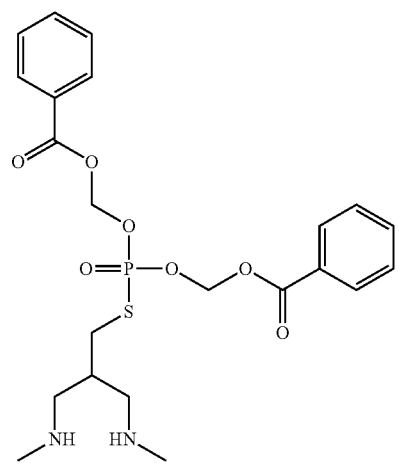<br>PrC-210-PT-BzOM |
| 3 | 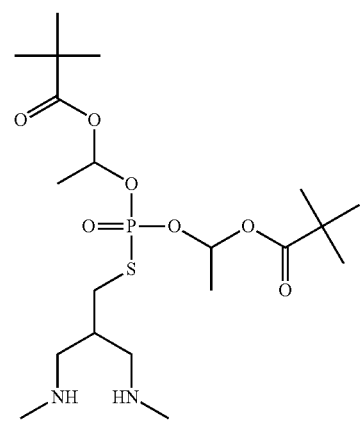<br>PrC-210-PT-POE |

| Compound | Structure |
|---|---|
| 4 | 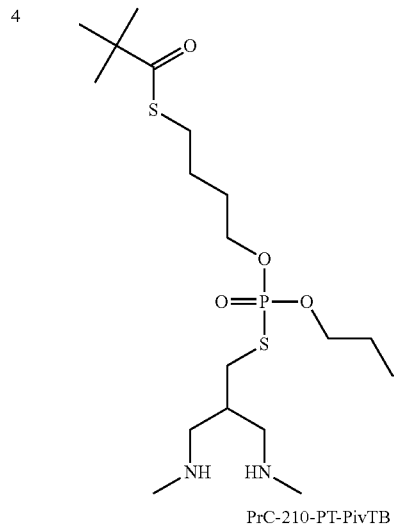<br>PrC-210-PT-PivTB |
| 5 | 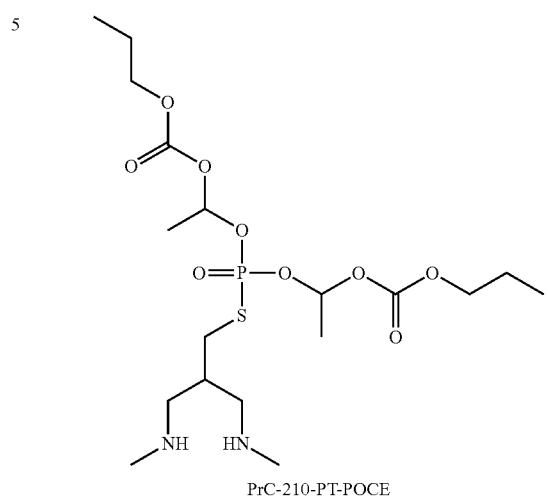<br>PrC-210-PT-POCE |
| 6 | 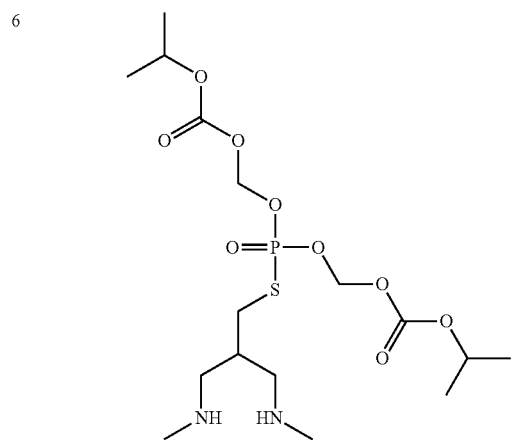<br>PrC-210-PT-POC |
| Compound | Structure |
|---|---|
| 7 | 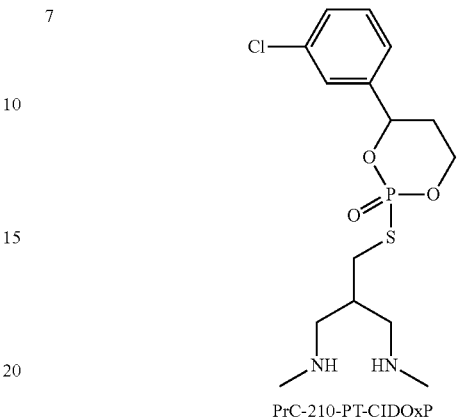<br>PrC-210-PT-ClDOxP |
| 8 | 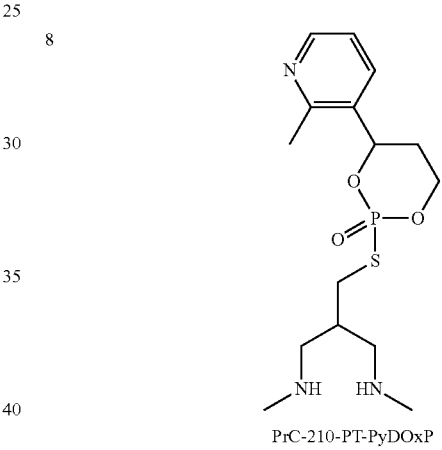<br>PrC-210-PT-PyDOxP |
| 9 | 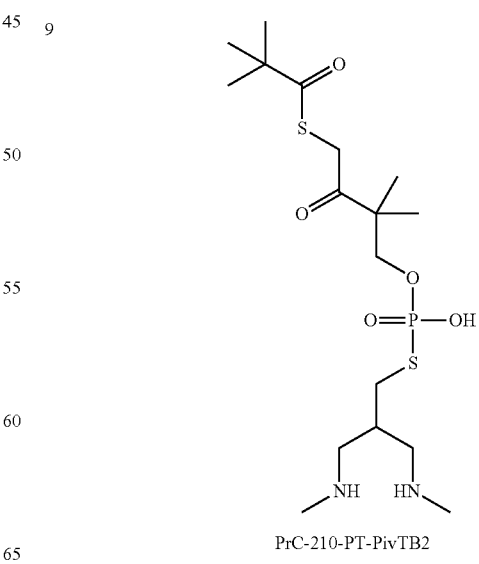<br>PrC-210-PT-PivTB2 |

-continued
| Compound | Structure |
|---|---|
| 10 | 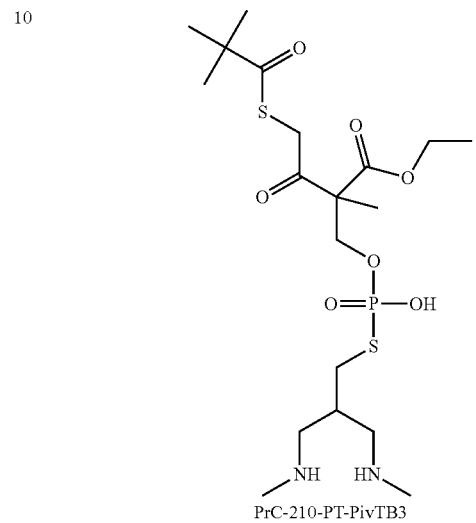
PrC-210-PT-PivTB3 |
| 11 | 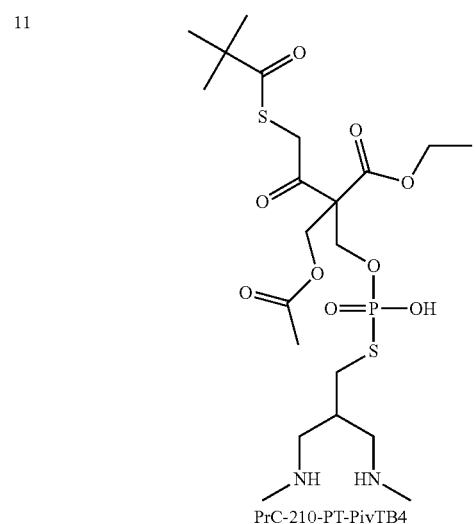
PrC-210-PT-PivTB4 |
| 12 | 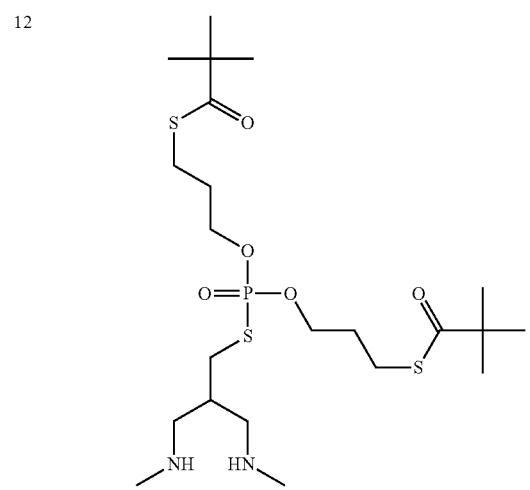
PrC-210-PivTP |
-continued
| Compound | Structure |
|---|---|
| 13 | 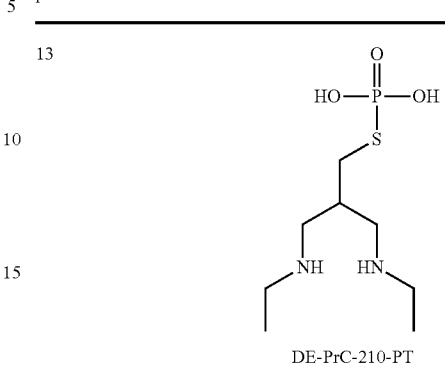
DE-PrC-210-PT |
| 14 | 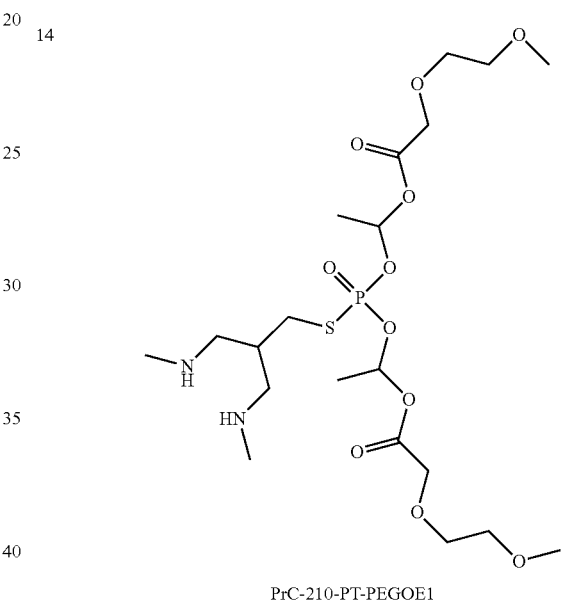
PrC-210-PT-PEGOE1 |
| 15 | 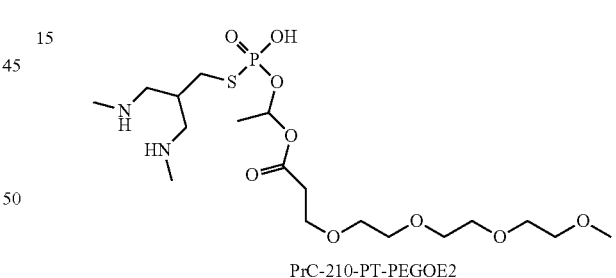
PrC-210-PT-PEGOE2 |
| 16 | 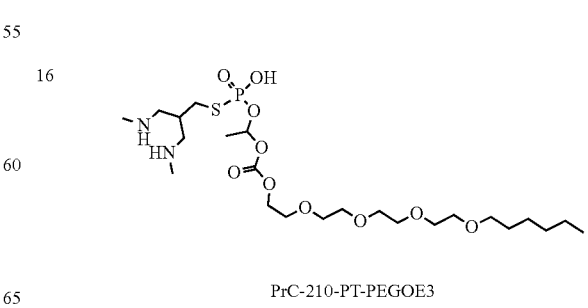
PrC-210-PT-PEGOE3 |

| Compound | Structure |
|---|---|
| 17 | 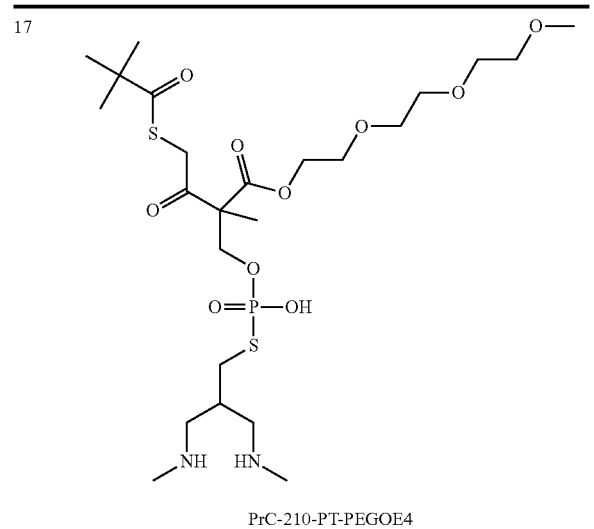<br>PrC-210-PT-PEGOE4 |
| 18 | 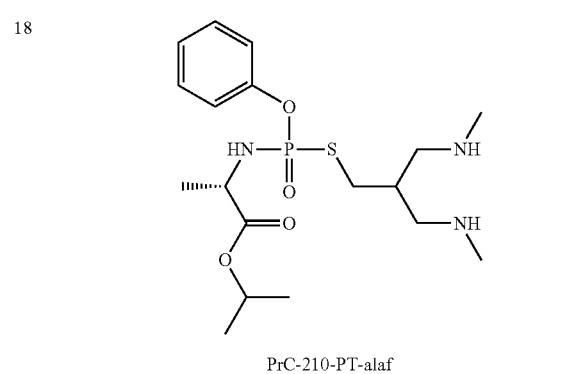<br>PrC-210-PT-alaf |
| 18-(S,S) | 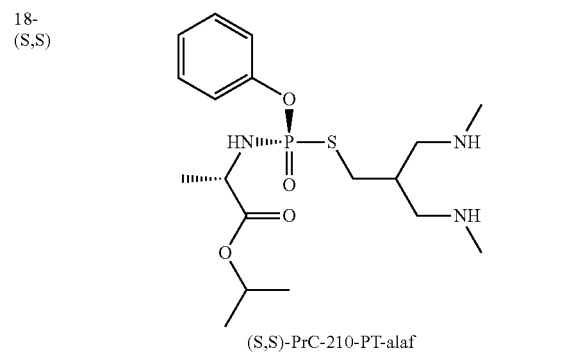<br>(S,S)-PrC-210-PT-alaf |
| 18-(R,S) | 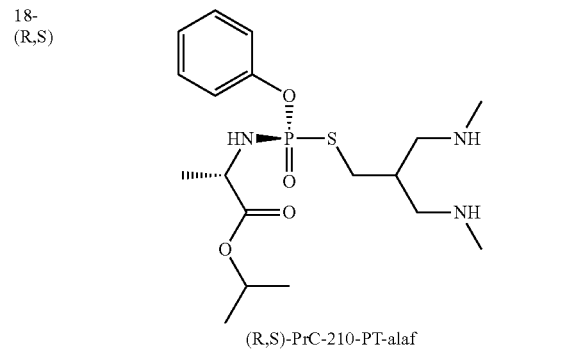<br>(R,S)-PrC-210-PT-alaf |
| Compound | Structure |
|---|---|
| 19 | 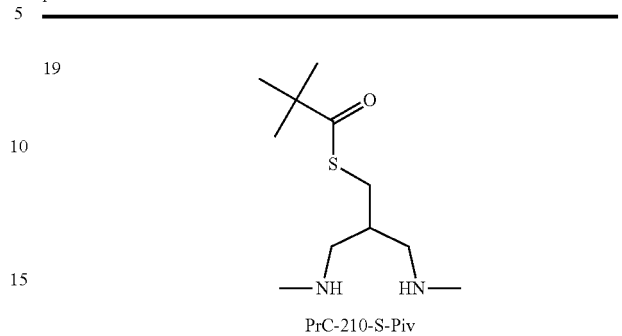<br>PrC-210-S-Piv |
| 20 | 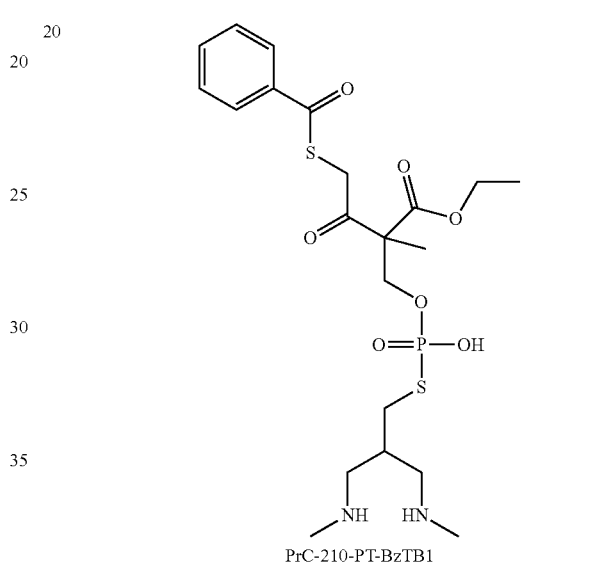<br>PrC-210-PT-BzTB1 |
| 21 | 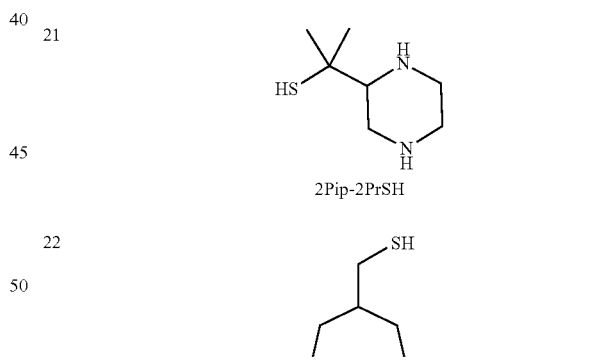<br>2Pip-2PrSH |
| 22 | 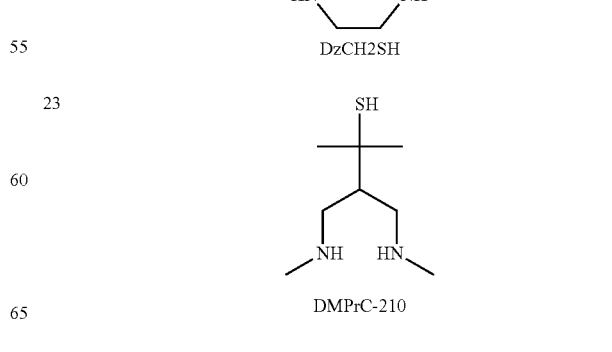<br>DzCH2SH |
| 23 | DMPrC-210 |

| Compound | Structure |
|---|---|
| 24 | [1R,4s,7S)-2,6-diazabicyclo[5.1.0]octan-4-yl]methanethiol |
| 25 | [1R,4s,7S)-2,6-diazabicyclo[5.1.0]octan-4-yl]methanethiol |
| 26 | (1,5-diazocan-3-yl)methanethiol |
| 27 | {3,7-diazabicyclo[3.3.1]nonan-1-yl}methanethiol |
| 28 | (1-methyl-1,4-diazepan-6-yl)methanethiol |
| 29 | [1-(4-flurorobutyl)-1,4-diazepan-6-yl]methanethiol |
| 30 | (1-ethyl-1,4-diazepan-6-yl)methanethiol |
| 31 | [7-(methoxymethyl)-1,5-diazocan-3-yl]methanethiol |
| 32 | [(1R,4S,7S)-2,6-diazabicyclo[5.2.0]nonan-4-yl]methanethiol |
| 33 | [(1R,4S,7S)-2,6-diazabicyclo[5.2.0]nonan-4-yl]methanethiol |
| 34 | [1-(pyridin-2-yl)-1,4-diazepan-6-yl]methanethiol |
| 35 | |

-continued

| Compound | Structure |
|---|---|
| | [(3S,5aR,8aS)-decahydrocyclopenta[b][1,4]diazepin-3-yl]methanethiol |
| 36 | [(3S,5aR,8aS)-decahydrocyclopenta[b][1,4]diazepin-3-yl]methanethiol |
| 37 | [6-(sulfanylmethyl)-1,4-diazepan-6-yl]methanethiol |
| 38 | [(5aR,9aR)-decahydro-1h-1,5-benzodiazepin-3-yl]methanethiol |
| 39 | (1,4-diazepan-2-yl)methanethiol |
| 40 | (1,4-diazepan-2-yl)methanethiol |
| 41 | 2-[(2S,5S)-5-methylpiperazin-2-yl]ethane-1-thiol |
| 42 | [(3R,8aS)-octahydropyrrolo[1,2-a]pyrazin-3-yl]methanethiol |

-continued

| Compound | Structure |
|---|---|
| 43 | 2-[(2S,5S)-2-methyl-1,4-diazepan-5-yl]methanethiol |
| 44 | 2-[(2S,5S)-5-(propan-2-yl)piperazin-2-yl]ethane-1-thiol |
| 45 | [(2R,5S)-5-ethykpiperazin-2-yl]methanethiol |
| 46 | 2-[(2S,5S)-4-cyclobutyl-5-methylpiperazin-2-yl]ethane-1-thiol |
| 47 | [(2R,5R)-5-methylpiperazin-2-yl]methanethiol |
| 48 | [(2S,5S)-2-tert-butyl-1,4-diazepan-5-yl]methanethiol |
| 49 | [(2S,5S)-1,2-dimethyl-1,4-diazepan-5-yl]methanethiol |
| 50 | [2-((2R,4aS,8aS)-decahydroquinoxalin-2yl)ethane-1-thiol] | or a pharmaceutically acceptable salt, solvate, hydrate, polymorph or combination thereof or a solvate, hydrate or polymorph of the salt.

In some embodiments, the compounds of the disclosure are crystalline salts. The salt forms of the compounds of the disclosure will have longer shelf lives compared to the free base form. Without wishing to be bound by theory, the salt forms of the compounds of the disclosure will be more stable to oxidation and other degradation processes, such as rearrangements, that occur after prolonged storage under ambient conditions.

In some embodiments, the compounds of the disclosure are crystalline salts derived from inorganic bases, include by way of example only, sodium, potassium, lithium, ammonium, calcium and magnesium salts.

In some embodiments, the compounds of the disclosure are crystalline salts derived from organic bases including, but not limited to, crystalline salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heterocyclic amines, diheterocyclic amines, triheterocyclic amines, and mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heterocyclic, and the like. In certain such embodiments, also included are amines where the two or three substituents, together with the amino nitrogen, form a heterocyclic group. In certain such embodiments, suitable amines include, by way of example only, isopropylamine, trimethyl amine, diethyl amine, tri(isopropyl) amine, tri(n-propyl) amine, ethanolamine, 2-dimethyl aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

In some embodiments, the compounds of the disclosure are pharmaceutically acceptable crystalline acid addition salts prepared from inorganic and organic acids. In certain such embodiments, inorganic acids that can be used to form acid-addition salt forms include, but are not limited to, hydrochloric acid, hydrobromic acid, sulfuric acid, nitric acid, phosphoric acid, and the like. In some embodiments, crystalline salts derived from organic acids include, but are not limited to, acetic acid, trifluoroacetic acid, sulfamic acid, propionic acid, glycolic acid, pyruvic acid, oxalic acid, malic acid, malonic acid, mucic acid, succinic acid, maleic acid, fumaric acid, tartaric acid, citric acid, benzoic acid, ascorbic acid, cinnamic acid, mandelic acid, methanesulfonic acid, ethanesulfonic acid, p-toluenesulfonic acid, benzenesulfonic acid, cyclohexylsulfamic acid, 1,5-naphthalenedisulfonic acid, salicylic acid, and the like. In some embodiments, the crystalline salt is a hydrochloride salt, benzenesulfonate salt, a 4—toluenesulfonate salt, a cyclohexylsulfamate salt, a fumarate salt, a hydrobromide salt, a maleate salt, a malonate salt, an oxalate salt, a succinate salt, a trifluoroacetate salt, a sulfamate salt, an acetate salt, an ascorbate salt, a mucate salt, a sulfate salt or a 1,5-naphthalenedisulfonate salt. In some embodiments, the crystalline salt is a hydrochloride salt. In some embodiments, the crystalline salt is a benzenesulfonate salt (a besylate salt). In some embodiments, the crystalline salt is a cyclohexylsulfamate salt. In some embodiments, the crystalline salt is a fumarate salt. In some embodiments, the crystalline salt is a hydrobromide salt. In some embodiments, the crystalline salt is a maleate salt. In some embodiments, the crystalline salt is a malonate salt. In some embodiments, the crystalline salt is an oxalate salt. In some embodiments, the crystalline salt is a succinate salt. In some embodiments, the crystalline salt is a trifluoroacetate salt. In some embodiments, the crystalline salt is a sulfamate salt. In some embodiments, the crystalline salt is an acetate salt. In some embodiments, the crystalline salt is an ascorbate salt. In some embodiments, the crystalline salt is a mucate salt. In some embodiments, the crystalline salt is a sulfate salt. In some embodiments, the crystalline salt is a 1,5-naphthalenedisulfonate salt.

In some embodiments, the compounds of this disclosure can exist as various solvates, such as with water (also known as hydrates), methanol, ethanol, dimethylformamide, diethyl ether, acetamide, and the like. Mixtures of such solvates can also be prepared. The source of such solvates can be from the solvent of crystallization, inherent in the solvent of preparation or crystallization, or adventitious to such solvent. Hydrates may be formed, for example, by combining the 3-[3-(methylamino)propylamino]propylsulfanylphosphonic acid and/or 3-[(3-(methylamino) propyl)amino]propane-1-thiol crystalline salts or polymorphs with water. Hydrates may include monohydrates, dehydrates, trihydrates, tetrahydrates, and so on.

In some embodiments, one or more crystalline salt forms of the disclosure are thermally stable at about 4° C. for at least two years. In some embodiments, one or more crystalline salt forms of the disclosure are thermally stable at about ambient temperature for at least two years. In some embodiments, the one or more crystalline salt forms of the disclosure are thermally stable at about 37° C. for at least two years. In some embodiments, the crystalline salt forms of the disclosure are stable at ambient temperature for at least 1 year, 2 years, 3 years, 4 years, 5 years, 6 years, 7 years, 7 years, 8 years, 9 years or 10 years.

In some embodiments, the compounds and salts of this disclosure can exist as various polymorphs, pseudopolymorphs, or in amorphous state. The term "polymorph" refers to different crystalline forms of the same compound and other solid-state molecular forms including pseudo-polymorphs, such as hydrates, solvates, or salts of the same compound. Different crystalline polymorphs have different crystal structures due to a different packing of molecules in the lattice, as a result of changes in temperature, pressure, or variations in the crystallization process. Polymorphs differ from each other in their physical properties, such as X-ray diffraction characteristics, stability, melting points, solubility, or rates of dissolution in certain solvents. Thus, crystalline polymorphic forms are important aspects in the development of suitable dosage forms in pharmaceutical industry.

The disclosure also contemplates all the isomers of the compounds of formulae I, II, III, IV, V, VI and VII. "Isomer" as used herein includes optical isomers (such as stereoisomers, e.g., diastereomers and enantiomers). Many of the compounds useful in the methods and compositions of this disclosure have at least one stereogenic center in their structure. The stereogenic center may be present in an R or S configuration. R and S notation is used in correspondence with the rules described in Pure Appl Chem. (1976), 45, 11-30. The compounds and salts of this disclosure can also be in racemic mixtures.

Any embodiment described herein is also intended to represent unlabeled forms as well as isotopically labeled (or isotope containing) forms of the compound unless otherwise indicated.

Isotopically labeled or containing compounds have structures depicted by the formulas given herein except that one or more atoms are replaced by an atom having a selected atomic mass or mass number. Examples of isotopes that can be incorporated into the compounds of the disclosure include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}F$, $^{31}P$, $^{32}P$, 35S, $^{36}Cl$, 125I respectively. The invention includes various isotopically labeled or containing compounds as defined herein, for example those into which radioactive isotopes, such as $^3H$, $^{13}C$ and $^1C$ are present. Such isotopically labeled compounds are useful in metabolic studies, reaction kinetic studies, detection or imaging techniques. Isotopically labeled or containing compounds with relatively stable isotopes, for example, $^2H$, may also have enhanced stability as compared to their unlabeled counterparts, and therefore, may have longer shelf lives and/or longer half-lives.

Bioconversion of Prodrugs and Double Prodrugs

Some of the compounds and salts of this disclosure are prodrugs and double prodrugs of 3-(methylamino)-2-((methylamino)methyl)propane-1-thiol (PrC-210), or derivatives or analogues thereof. A prodrug is administered to a subject in its inactive form, which is subsequently metabolized in the body into its active form. For example, {[3-(methylamino)-2-[(methylamino)methyl]propyl]sulfanyl}phosphonic acid (PrC-210-PT) is a prodrug of PrC-210.

The PrC-210-PT prodrug is dephosphorylated by alkaline phosphatase into the corresponding thiol (PrC-210), which is the active form of the compound. Due to the polarity of PrC-210-PT, double prodrugs may also be used to enhance the bioavailability of PrC-210 and derivatives or analogues thereof. Accordingly, in some embodiments the double prodrugs of this disclosure are characterized by lipophilic functional groups that aid in enhancing the absorption of the compounds into the bloodstream, thereby enhancing the bioavailability of PrC-210. A double prodrug is administered in its inactive form and is converted to its active form after being metabolized by two separate metabolic pathways. The double prodrugs of this disclosure, for example, PrC-210-PT-BzOM, are metabolized via various enzymes into {[3-(methylamino)-2-[(methylamino)methyl]propyl]sulfanyl}phosphonic acid (PrC-210-PT), or derivatives or analogues thereof. As described above, the PrC-210-PT prodrug is subsequently dephosphorylated by alkaline phosphatase into the corresponding thiol (PrC-210). The double prodrugs of this disclosure are derivatives or analogues of the phosphorothioate compound, PrC-210-PT.

As an example, a bioconversion of the double prodrug compound 2 ({[(benzoyloxy)methoxy]({[3-(methylamino)-2-[(methylamino)methyl]propyl]sulfanyl})phosphoryl}oxy)methyl benzoate (PrC-210-PT-BzOM) is illustrated in Scheme 1. Specifically, serum esterase converts PrC-210-BzOM to the corresponding phosphorothioate compound (PrC-210-PT), which undergoes dephosphorylation in the presence of alkaline phosphatase, resulting in the active thiol, PrC-210. This mechanism of double prodrug activation also applies generically to PrC-210-PT-POE (compound 3), PrC-210-PT-POCE (compound 5), PrC-210-PT-POC (compound 6), PrC-210-PT-PEGOE1 (compound 14), PrC-210-PT-PEGOE2 (compound 15) and PrC-210-PT-PEGOE3 (compound 16).

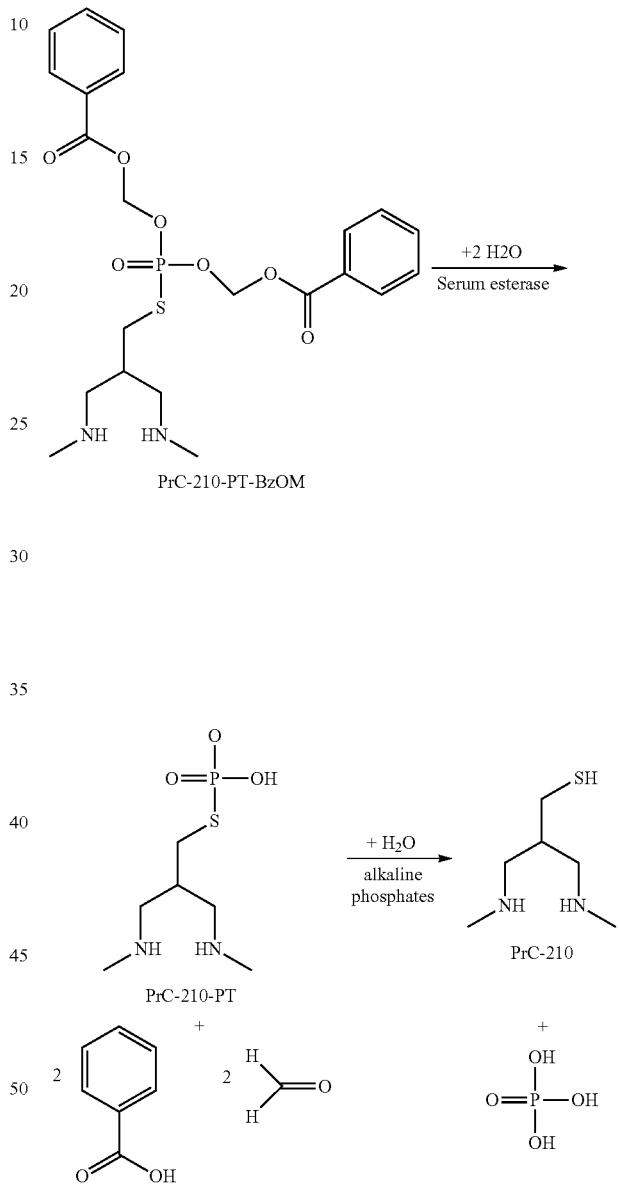

Scheme 1 Bioconversion of double prodrug PrC-210-PT-BzOM (compound 2) to the active thiol (PrC-210).

As another example, a bioconversion of the compound 7 (PrC-210-PT-ClDOxP) is illustrated in Scheme 2. In particular, PrC-210-PT-ClDOxP is converted to the corresponding phosphorothioate derivative in the liver by cytochrome P450 3A4 (CYP3A4). Subsequent dephosphorylation by alkaline phosphatase results in the active compound, PrC-210. This mechanism of double prodrug activation also generically applies to PrC-210-PT-PyDOxP (compound 8).

Scheme 2 Bioconversion of double produg PrC-210-PT-ClDOxP (compound 7) to the active thiol, (PrC-210).

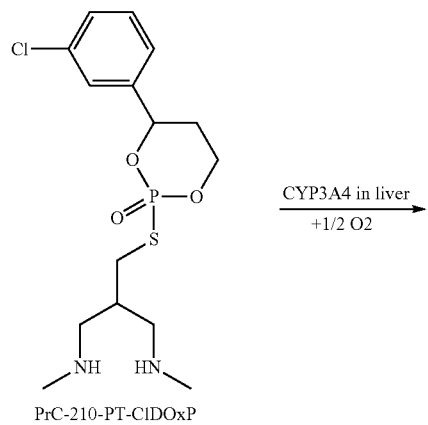

Scheme 3. Bioconversion of double prodrug PrC-210-PT-PivTB (compound 4) to the active thiol, PrC-210.

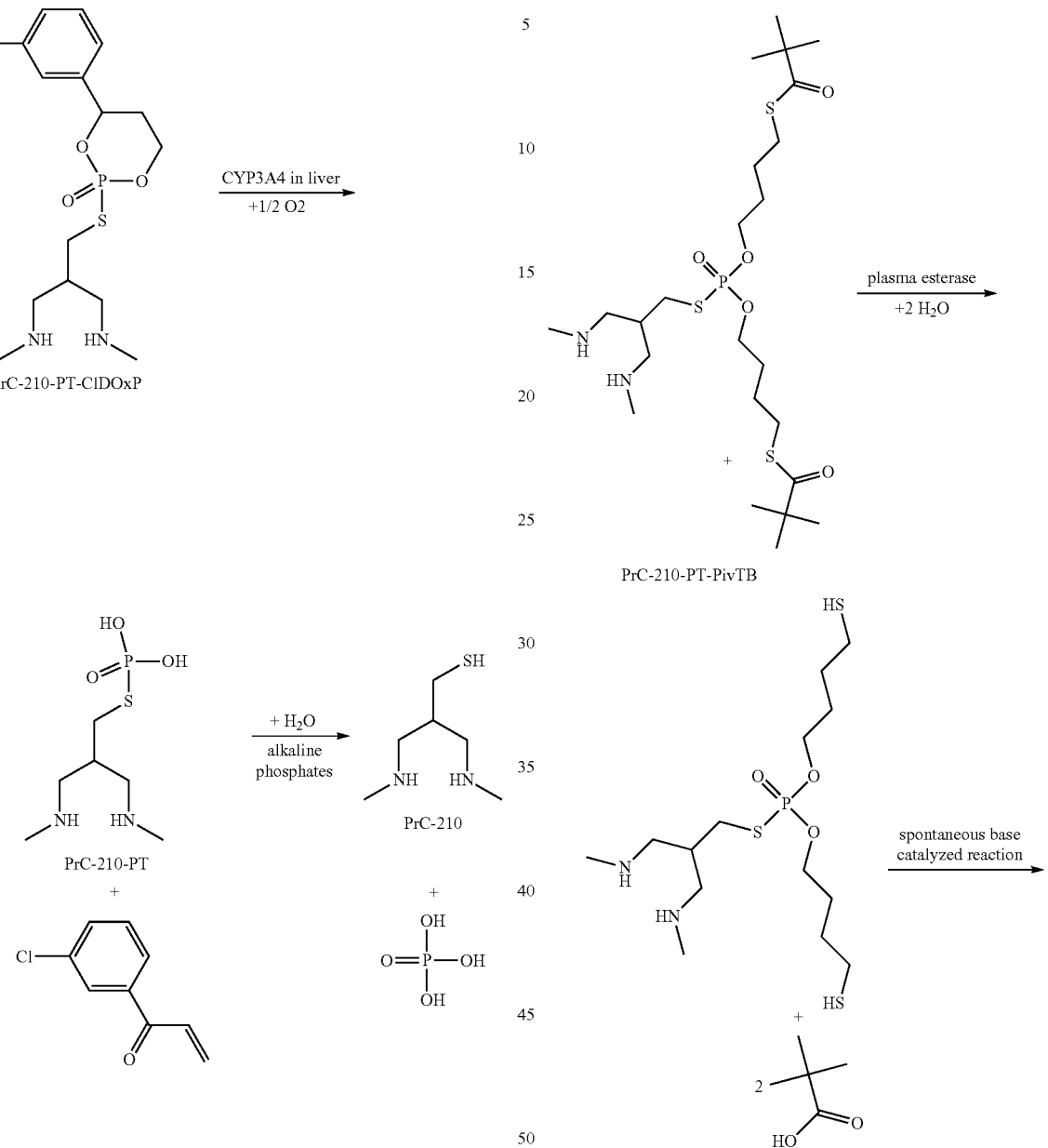

As an additional example, a bioconversion of double prodrug PrC-210-PT-PivTB (compound 4) into PrC-210 is illustrated in Scheme 3. PrC-210-PT-PivTB is hydrolyzed to the corresponding thiol by plasma esterase. A spontaneous base catalyzed reaction subsequently coverts the thiol into the phosphorothioate derivative (PrC-210-PT). Dephosphoylation by alkaline phosphatase furnished the active thiol (PrC-210). This mechanism of double prodrug activation also applies generically to PrC-210-PT-PivTB2 (compound 9), PrC-210-PT-PivTB3 (compound 10), PrC-210-PT-PivTB4 (compound 11), and PrC-210-PT-PivTP (compound 12), PrC-210-PT-PEGOE4 (compound 17) and PrC-210-PT-BzTB1 (compound 20).

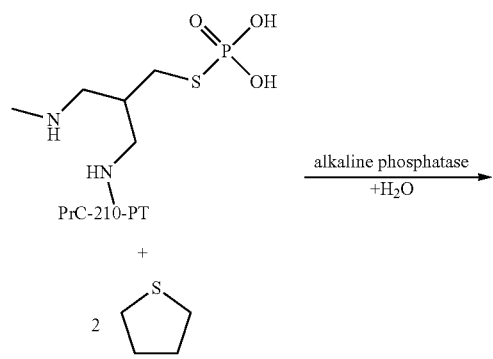

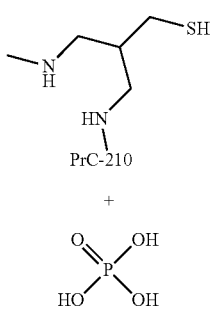

PrC-210

+

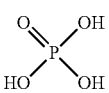

A bioconversion of double prodrug PrC-210-PT-alaf (compound 18) into PrC-210 is illustrated in Scheme 4 (see, for example, Birkus, G. et al., *Antimicrobial Agents and Chemotherapy*, 2016, Vol. 60, pp 316-322). Carboxylesterase 1 (Ces1) cleaves the aryl phosphoester affording the corresponding hydroxide. Subsequently, lysosomes hydrolyze the β-N bond affording PrC-210-PT. Dephosphorylation by alkaline phosphatase furnished the active thiol (PrC-210).

Scheme 4. Bioconversion of double prodrug PrC-210-PT-alaf (compound 18) to the active thiol, PrC-210.

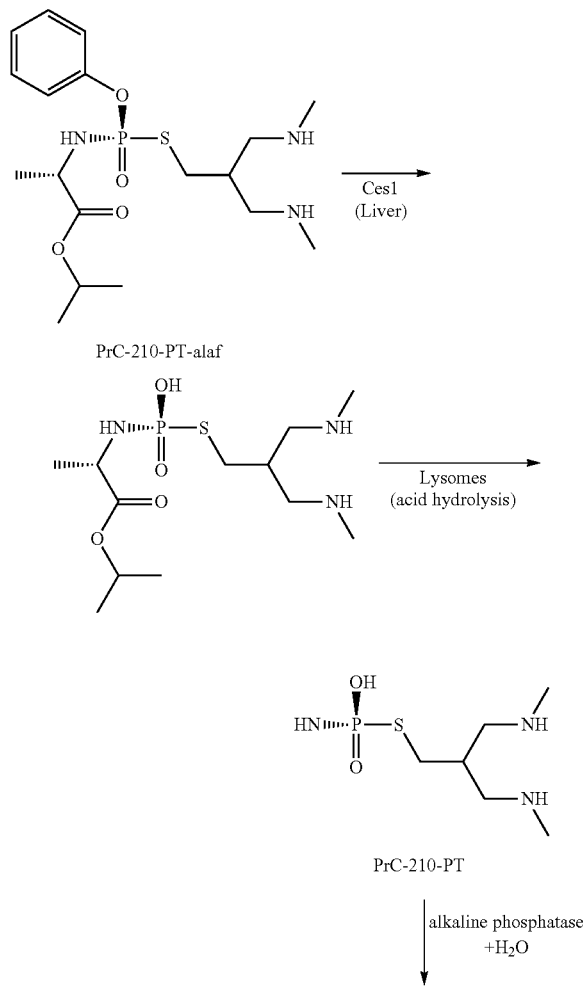

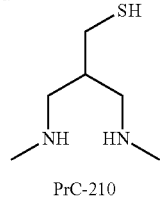

PrC-210

This disclosure also contemplates S-acylated prodrugs of PrC-210 (see, for example, compound 19). S-acylated prodrugs of PrC-210 are more lipophilic than PrC-210, and will exhibit improved bioavailability as compared to PrC-210. Specifically, after oral administration, lipophilic prodrugs of PrC-210 are expected to pass the gut lumen through passive diffusion more readily than the active thiol. These lipophilic prodrugs may also pass the blood brain barrier more readily than PrC-210. The S-acyl prodrugs of this disclosure are believed to be metabolized into the active thiol form, PrC-210, by esterases or lipases in the plasma and cerebrospinal fluid.

Pharmaceutical Compositions

In some embodiments, one or more compounds and salts of the disclosure are useful in the preparation of pharmaceutical compositions. Pharmaceutical compositions in accordance with this disclosure may be formulated in a conventional manner using one or more physiologically acceptable carriers comprising excipients and auxiliaries which facilitate processing of one or more compounds and salts of the disclosure into compositions which can be used pharmaceutically. Formulation is dependent upon the route of administration chosen.

In some embodiments, the pharmaceutical compositions of the disclosure are for oral administration. In certain such embodiments, one or more compounds and salts of the disclosure can be formulated readily by combining the compounds with pharmaceutically acceptable carriers well known in the art. Such carriers enable one or more compounds or salts of the disclosure to be formulated as tablets, pills, dragees, capsules, liquids, gels, syrups, slurries, suspensions and the like, for oral ingestion by a subject to be treated. In some embodiments, pharmaceutical compositions for oral use are obtained using solid excipients, optionally grinding a resulting mixture, and processing the mixture of granules, after adding suitable auxiliaries, if desired, to obtain tablets or dragee cores. Suitable excipients include, but are not limited to, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose; and/or polyvinylpyrrolidone (PVP). If desired, disintegrating agents may be added, such as the cross-linked polyvinyl pyrrolidone, agar, or alginic acid or a salt thereof such as sodium alginate.

In some embodiments, dragee cores are provided with suitable coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize doses of different combinations of one or more compounds of the disclosure.

In some embodiments, pharmaceutical compositions of the disclosure which can be used orally include push-fit capsules made of gelatin, as well as soft, sealed capsules made of gelatin and a plasticizer, such as glycerol or sorbitol. In certain such embodiments, the push-fit capsules can contain the active ingredients in an admixture with fillers such as lactose, binders such as starches, and/or lubricants such as talc or magnesium stearate and, optionally, stabilizers.

In soft capsules, one or more compounds of the disclosure may be dissolved or suspended in suitable liquids, such as fatty oils, liquid paraffin, or liquid polyethylene glycols. In addition, stabilizers may be added.

In some embodiments, the compositions of the disclosure may also optionally contain one or more opacifying agents and may be of a composition such that they release the one or more compounds of the disclosure only, or preferentially, in a certain portion of the gastrointestinal tract, optionally, in a delayed manner. Examples of embedding compositions that can be used include polymeric substances and waxes. The compounds and compositions of this disclosure, or mixtures thereof, can also be in micro-encapsulated form, if appropriate, with one or more of the above-described excipients.

In some embodiments, one or more compounds or salts of the disclosure may be formulated for parenteral administration by injection, e.g., by intramuscular, subcutaneous and intravenous injections, bolus injection or continuous infusion. In some embodiments, compositions for injection can be presented in unit dosage form, e.g., in ampoules or in multi-dose containers, with an added preservative. In some embodiments, one or more compounds or salts of the disclosure can take such forms as suspensions, solutions or emulsions in oily or aqueous vehicles, and can contain formulatory agents such as suspending, stabilizing and/or dispersing agents.

In some embodiments, pharmaceutical compositions for parenteral administration include aqueous solutions of one or more compounds or salts of the disclosure in water-soluble form. In certain such embodiments, suspensions of one or more compounds or salts of the disclosure can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of one or more compounds of the disclosure to allow for the preparation of highly concentrated solutions. For injection, one or more compounds or salts of the disclosure may be formulated in aqueous solutions, for example, physiologically compatible buffers such as Hanks's solution, Ringer's solution, or physiological saline buffer.

In some embodiments, one or more compounds or salts of the disclosure may be in powder form for constitution with a suitable vehicle, e.g., sterile pyrogen-free water, before use.

In some embodiments, one or more compounds or salts of the disclosure are formulated for transmucosal absorption. Transmucosal absorption can occur through any mucosa. Exemplary mucosa include: oral mucosa (e.g., buccal mucosa and sublingual mucosa), nasal mucosa, rectal mucosa, and pulmonary mucosa. For transmucosal administration, penetrants appropriate to the barrier to be permeated are used in the composition. Such penetrants are generally known in the art.

Methods of formulating compounds for transmucosal absorption are well known in the art. For example, a composition may be formulated for buccal absorption using buccal tablets, lozenges, buccal powders, and buccal spray solutions. A composition may be formulated for sublingual absorption using sublingual tablets, sublingual films, liquids, sublingual powders, and sublingual spray solutions.

In some embodiments, the pharmaceutical compositions of the disclosure are for administration by inhalation. In some embodiments, the composition may be formulated for intranasal absorption through nasal sprays. In some embodiments, the composition may be formulated for pulmonary absorption through aerosolized compositions and inhalable dried powders. When formulated for sprays or aerosolized compositions, a composition may be prepared with saline as a solution, employ benzyl alcohol or other suitable preservatives, or include absorption promoters to enhance bioavailability, fluorocarbons, and/or other solubilizing or dispersing agents. In some embodiments, one or more compounds of the disclosure are delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Capsules and cartridges of e.g. gelatin for use in an inhaler or insufflator may be formulated containing a powder mix of the compound and a suitable powder base such as lactose or starch.

In some embodiments, one or more compounds or salts of the disclosure can be formulated in rectal compositions such as suppositories or retention enemas, e.g., containing conventional suppository bases such as cocoa butter or other glycerides.

In some embodiments, one or more compounds or salts of the disclosure can be formulated for transdermal administration. Compositions for transdermal administration include powders, sprays, ointments, pastes, creams, lotions, gels, solutions, patches, and inhalants. One or more compounds of the disclosure may be mixed under sterile conditions with a pharmaceutically acceptable carrier, and with any preservatives, buffers, or propellants that may be required. The ointments, pastes, creams, and gels may contain, in addition to one or more compounds and compositions of this disclosure, excipients, such as animal and vegetable fats, oils, waxes, paraffins, starch, tragacanth, cellulose derivatives, polyethylene glycols, silicones, bentonites, perfuming agents, coloring agents, silicic acid, talc, and zinc oxide, or mixtures thereof.

In some embodiments, one or more compounds or salts of the disclosure can be formulated as a depot composition. Such long acting compositions can be administered by implantation (for example subcutaneously or intramuscularly) or by intramuscular injection.

In some embodiments, one or more compounds or salts of the disclosure can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions of the disclosure can also comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

In some embodiments, one or more pharmaceutical compositions of the disclosure are thermally-stable and sterile and suitable for administration to a subject. In some embodiments, one or more pharmaceutical compositions of the disclosure are thermally stable at about 4° C. for at least two years. In some embodiments, one or more pharmaceutical compositions of the disclosure are thermally stable at about ambient temperature for at least two years. In some embodiments, one or more pharmaceutical compositions of the disclosure are thermally stable at about 37° C. for at least two years. In some embodiments, the pharmaceutical compositions of the disclosure are stable at ambient temperature for at least 1 year, 2 years, 3 years, 4 years, 5 years, 6 years, 7 years, 7 years, 8 years, 9 years or 10 years.

Pharmaceutical compositions of this disclosure include compositions wherein one or more compounds or salts of the disclosure are contained in a therapeutically effective or protective amount, i.e., an amount effective to achieve its intended purpose. Of course, the actual amount of one or more compounds of the disclosure will depend on, among other things, its intended purpose. For example, when administered to cancer subjects as a cytoprotectant in conjunction with radiation or chemotherapy, such compositions will contain an amount of one or more compounds of the disclosure effective to, inter alia, ameliorate the harmful effects of ionizing radiation or chemotherapeutic agents to normal tissues, with minimal effect on the therapeutic purpose of the radiation or chemotherapy on the diseased tissues. When administered to subjects suffering from diseases requiring bone marrow growth, such as myelodysplastic syndromes (MDS), or requiring more rapid recovery of bone marrow function following chemotherapy, compositions of the disclosure will contain an amount of one or more compounds of the disclosure effective to stimulate bone marrow production or function in the subject being treated. Determination of an effective amount is well within the capabilities of those skilled in the art, especially in light of the detailed disclosure herein. In some embodiments, the compositions of the disclosure comprise about 10 mg to about 10,000 mg of one or more compounds or salts of the disclosure.

In some embodiments, the compounds, salts or compositions of the disclosure are useful as cytoprotectants to selectively protect against the toxicities of ionizing radiation or chemotherapeutic agents. In certain such embodiments, a circulating concentration of one or more compounds of the disclosure (and/or and a metabolite thereof) of about 2 µM to about 100 µM is effective as cytoprotectant. In certain such embodiments, the concentration of one or more compounds of the disclosure is about 5 µM to about 50 µM. Alternatively, or in addition to, a tissue concentration of one or more compounds of the disclosure (and/or a metabolite thereof) of about 4 µM to about 700 µM is effective as a cytoprotectant. In certain such embodiments, the effective tissue concentration is about 20 µM to about 350 µM.

In some embodiments, the pharmaceutical compositions of this disclosure further comprise an antioxidant. In some embodiments, the pharmaceutical composition is co-administered (sequentially, concurrently or separately) with an antioxidant. In some embodiments, the antioxidant is a non-thiol antioxidant. In some embodiments, the antioxidant is selected from the group consisting of ascorbic acid, ascorbate, vitamin C, N-acetylcysteine, glutathione, lipoic acid, uric acid, alpha-tocopherol, γ-tocotrienol, vitamin E, beta-carotene, vitamin A, retinol, selenocysteine, cyanidine-3-glucoside, and ubiquinol. In some embodiments, the non-thiol antioxidant comprises α-tocopherol, β-tocopherol, γ-tocopherol, δ-tocopherol, α-tocotrienol, β-tocotrienol, γ-tocotrienol, δ-tocotrienol, vitamin E, carotene, beta-carotene, ascorbate, vitamin C, cyanidine-3-glucoside, selenocysteine, or combinations thereof. In some embodiments, the non-thiol antioxidant is selected from the group consisting of α-tocopherol, 3-tocopherol, γ-tocopherol, δ-tocopherol, α-tocotrienol, β-tocotrienol, γ-tocotrienol, δ-tocotrienol, vitamin E, carotene, beta-carotene, ascorbate, vitamin C, cyanidine-3-glucoside, selenocysteine, and combinations thereof. In some embodiments, the non-thiol antioxidant is selected from the group consisting of α-tocopherol, γ-tocotrienol, and selenocysteine. In some embodiments, the antioxidant is ascorbic acid. In some embodiments, the antioxidant is ascorbate. In some embodiments, the antioxidant is vitamin C. In some embodiments, the antioxidant is N-acetylcysteine. In some embodiments, the antioxidant is glutathione. In some embodiments, the antioxidant is lipoic acid. In some embodiments, the antioxidant is uric acid. In some embodiments, the antioxidant is α-tocopherol. In some embodiments, the antioxidant is γ-tocotrienol. In some embodiments, the antioxidant is vitamin E. In some embodiments, the antioxidant is beta-carotene. In some embodiments, the antioxidant is vitamin A. In some embodiments, the antioxidant is retinol. In some embodiments, the antioxidant is vitamin A. In some embodiments, the antioxidant is selenocysteine. In some embodiments, the antioxidant is cyanidine-3-glucoside. In some embodiments, the antioxidant is ubiquinol.

In some embodiments, the pharmaceutical composition of this disclosure comprises any one of compounds 1-50 and an antioxidant. In some embodiments, the pharmaceutical composition of this disclosure comprises compound 42 and an antioxidant. In some embodiments, the pharmaceutical composition of this disclosure comprises compound 50 and an antioxidant. In some embodiments, the pharmaceutical composition of this disclosure comprises any one of compounds 1-50 and a non-thiol antioxidant. In some embodiments, the pharmaceutical composition of this disclosure comprises compound 42 and a non-thiol antioxidant. In some embodiments, the pharmaceutical composition of this disclosure comprises compound 50 and a non-thiol antioxidant. In some embodiments, the pharmaceutical composition of this disclosure comprises any one of compounds 1-50 and a non-thiol antioxidant, wherein the antioxidant is selected from the group consisting of α-tocopherol, γ-tocotrienol, and selenocysteine. In some embodiments, the pharmaceutical composition of this disclosure comprises compound 42 and a non-thiol antioxidant, wherein the antioxidant is selected from the group consisting of α-tocopherol, γ-tocotrienol, and selenocysteine. In some embodiments, the pharmaceutical composition of this disclosure comprises compound 50 and a non-thiol antioxidant, wherein the antioxidant is selected from the group consisting of α-tocopherol, γ-tocotrienol, and selenocysteine. In some embodiments, the pharmaceutical composition of this disclosure comprises any one of compounds 1-50 and α-tocopherol. In some embodiments, the pharmaceutical composition of this disclosure comprises compound 42 and α-tocopherol. In some embodiments, the pharmaceutical composition of this disclosure comprises compound 50 and α-tocopherol. In some embodiments, the pharmaceutical composition of this disclosure comprises any one of compounds 1-50 and γ-tocotrienol. In some embodiments, the pharmaceutical composition of this disclosure comprises compound 42 and γ-tocotrienol. In some embodiments, the pharmaceutical composition of this disclosure comprises compound 50 and γ-tocotrienol. In some embodiments, the pharmaceutical composition of this disclosure comprises any one of compounds 1-50 and selenocysteine. In some embodiments, the pharmaceutical composition of this disclosure comprises compound 42 and selenocysteine. In some embodiments, the pharmaceutical composition of this disclosure comprises compound 50 and selenocysteine.

In some embodiments, the pharmaceutical composition of this disclosure in combination with an antioxidant exhibits a synergistic radioprotective effect in mammals, mammalian tissues and/or cultured mammalian cells. In some embodiments, the pharmaceutical composition of this disclosure in combination with an antioxidant exhibits an additive radioprotective effect in mammals, mammalian tissues and/or cultured mammalian cells. In some embodiments, the pharmaceutical composition of this disclosure comprises a prodrug and a non-thiol antioxidant and exhibits a synergistic radioprotective effect in mammals, mammalian tissues and/or cultured mammalian cells. In some embodiments, the pharmaceutical composition of this disclosure in combination with an antioxidant reduces the side effects of the pharmaceutical composition.

Methods of Administration

Suitable routes of administration for one or more compounds, salts or compositions of this disclosure include, but are not limited to, inhalation, topical, cutaneous, transdermal, oral, rectal, transmucosal, intestinal, topical, cutaneous and parenteral, administration, including intramuscular, subcutaneous and intravenous injections. Appropriate methods of administering one or more compounds or compositions of the disclosure to a subject will depend, for example, on the age of the subject, the subject's physiological status including blood pressure, whether or not the subject is capable of taking oral medication, whether the subject is active or inactive at the time of administering, whether the subject is experiencing symptoms of a disease or condition at the time of administering, the extent of the symptoms, and the chemical and biological properties of the compound or composition (e.g. solubility, digestibility, bioavailability, stability and toxicity). In a preferred embodiment, the compounds or compositions of the disclosure are orally administered.

For any mode of administration, the actual amount of one or more compounds, salts or compositions of the disclosure delivered, as well as the dosing schedule necessary to achieve the advantageous pharmacokinetic profiles described herein, will be depend, in part, on such factors as the bioavailability of the one or more compounds of the disclosure, the disorder being treated or the potential radiation exposure being addressed, the desired therapeutic amount, and other factors that will be apparent to those of skill in the art. The actual amount delivered and an appropriate dosing schedule can be readily determined by those of skill without undue experimentation by monitoring the blood plasma levels of the administered compounds of the disclosure, and adjusting the dosage or dosing schedule as necessary to achieve the desired pharmacokinetic profile. In some embodiments, one or more compounds or compositions of the disclosure are administered once per day. In some embodiments, one or more compounds or compositions of the disclosure are administered once per day for several years. In some embodiments, one or more compounds, salts or compositions of the disclosure are administered once per day for one year, two years, three years, four years, five years, six years, seven years, eight years, nine years, ten years, 15 years, 20 years, 25 years, 30 years, 35 years, 40 years, 45 years, or 50 years. In some embodiments, one or more compounds or compositions of the disclosure are administered multiple times per day, e.g., two or three times per day. In some embodiments, one or more compounds, salts or compositions of the disclosure are administered multiple times per day for several years. In some embodiments, one or more compounds, salts or compositions of the disclosure are administered multiple times per day for one year, two years, three years, four years, five years, six years, seven years, eight years, nine years, ten years, 15 years, 20 years, 25 years, 30 years, 35 years, 40 years, 45 years, or 50 years.

In some embodiments, one or more compounds, salts or compositions of the disclosure may be administered singly, in combination simultaneously/concurrently, separately, or sequentially with other compounds or compositions, and/or in combination simultaneously/concurrently, separately, or sequentially with other therapeutic agents, including cancer chemotherapeutic agents. In some embodiments, one or more compounds or salts of the disclosure may be administered alone or in the form of a pharmaceutical composition, wherein the compound or salt of the disclosure is in admixture with one or more pharmaceutically acceptable carriers, excipients or diluents.

In some embodiments, the one or more compounds, salts or compositions of the disclosure are orally administered during the administration of radiation therapy or potential exposure to other sources of ionizing radiation. In some embodiments, the one or more compounds, salts or compositions of the disclosure are subcutaneously administered during the administration of radiation therapy or potential exposure to other sources of ionizing radiation. In some embodiments, the one or more compounds, salts or compositions of the disclosure are intravenously administered during the administration of radiation therapy or potential exposure to other sources of ionizing radiation. In some embodiments, the one or more compounds, salts or compositions of the disclosure are topically administered during the administration of radiation therapy or potential exposure to other sources of ionizing radiation. In some embodiments, the one or more compounds, salts or compositions of the disclosure are cutaneously administered during the administration of radiation therapy or potential exposure to other sources of ionizing radiation. In some embodiments, the one or more compounds, salts or compositions of the disclosure are orally administered during the administration of chemotherapy. In some embodiments, the one or more compounds, salts or compositions of the disclosure are subcutaneously administered during the administration of chemotherapy. In some embodiments, the one or more compounds, salts or compositions of the disclosure are intravenously administered during the administration of chemotherapy. In some embodiments, the one or more compounds, salts or compositions of the disclosure are topically administered during the administration of chemotherapy. In some embodiments, the one or more compounds, salts or compositions of the disclosure are cutaneously administered during the administration of chemotherapy.

In some embodiments, the one or more compounds, salts or compositions of the disclosure are administered orally at least about three hours prior to the administration of radiation therapy or potential exposure to other sources of ionizing radiation. In some embodiments, the one or more compounds, salts or compositions of the disclosure are orally administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the one or more compounds, salts or compositions of the disclosure are orally administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the one or more compounds, salts or compositions of the disclosure are orally administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the one or more compounds, salts or compositions of the disclosure are orally administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the one or more compounds, salts or compositions of the disclosure are orally administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the one or more compounds, salts or compositions of the disclosure are orally administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the one or more compounds, salts or compositions of the disclosure are administered subcutaneously at least about three hours prior to the administration of radiation therapy or potential exposure to other sources of ionizing radiation. In some embodiments, the one or more compounds, salts or compositions of the disclosure are subcutaneously administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the one or more compounds, salts or compositions of the disclosure are subcutaneously administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the one or more compounds, salts or compositions of the disclosure are subcutaneously administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the one or more compounds, salts or compositions of the disclosure are subcutaneously administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the one or more compounds, salts or compositions of the disclosure are subcutaneously administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the one or more compounds, salts or compositions of the disclosure are subcutaneously administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the one or more compounds, salts or compositions of the disclosure are administered intravenously at least about three hours prior to the administration of radiation therapy or potential exposure to other sources of ionizing radiation. In some embodiments, the one or more compounds, salts or compositions of the disclosure are intravenously administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the one or more compounds, salts or compositions of the disclosure are intravenously administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the one or more compounds, salts or compositions of the disclosure are intravenously administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the one or more compounds, salts or compositions of the disclosure are intravenously administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the one or more compounds, salts or compositions of the disclosure are intravenously administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the one or more compounds, salts or compositions of the disclosure are intravenously administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the one or more compounds, salts or compositions of the disclosure are administered topically at least about three hours prior to the administration of radiation therapy or potential exposure to other sources of ionizing radiation. In some embodiments, the one or more compounds, salts or compositions of the disclosure are topically administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the one or more compounds, salts or compositions of the disclosure are topically administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the one or more compounds, salts or compositions of the disclosure are topically administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the one or more compounds, salts or compositions of the disclosure are topically administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the one or more compounds, salts or compositions of the disclosure are topically administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the one or more compounds, salts or compositions of the disclosure are topically administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the one or more compounds, salts or compositions of the disclosure are administered cutaneously at least about three hours prior to the administration of radiation therapy or potential exposure to other sources of ionizing radiation. In some embodiments, the one or more compounds, salts or compositions of the disclosure are cutaneously administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the one or more compounds, salts or compositions of the disclosure are cutaneously administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the one or more compounds, salts or compositions of the disclosure are cutaneously administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the one or more compounds, salts or compositions of the disclosure are cutaneously administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the one or more compounds, salts or compositions of the disclosure are cutaneously administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the one or more compounds, salts or compositions of the disclosure are cutaneously administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the one or more compounds, salts or compositions of the disclosure are administered orally at least about three hours prior to the administration of chemotherapy. In some embodiments, the one or more compounds, salts or compositions of the disclosure are orally administered at least about 15 minutes prior to the administration of chemotherapy, such as at least about 5 minutes, or about 5 minutes to about 30 minutes prior to the administration of chemotherapy. In some embodiments, the one or more compounds, salts or compositions of the disclosure are orally administered at least about 30 minutes prior to the administration of chemotherapy, such as at least about 15 minutes, or about 15 minutes to about 60 minutes prior to the administration of chemotherapy. In some embodiments, the one or more compounds, salts or compositions of the disclosure are orally administered at least about 60 minutes prior to the administration of chemotherapy, such as at least about 30 minutes, or about 30 minutes to about 120 minutes prior to the administration of chemotherapy. In some embodiments, the one or more compounds, salts or compositions of the disclosure are orally administered at least about 2 hours prior to the administration of chemotherapy, such as at least about 1 hour, or about 1 hour to about 4 hours prior to the administration of chemotherapy. In some embodiments, the one or more compounds, salts or compositions of the disclosure are orally administered at least about 4 hours prior to the administration of chemotherapy, such as at least about 2 hours, or about 2 hours to about 8 hours prior to the administration of chemotherapy. In some embodiments, the one or more compounds, salts or compositions of the disclosure are orally administered at least about 6 hours prior to the administration of chemotherapy, such as at least about 8 hours, or about 8 hours to about 12 hours prior to the administration of chemotherapy.

In some embodiments, the one or more compounds, salts or compositions of the disclosure are administered subcutaneously at least about three hours prior to the administration of chemotherapy. In some embodiments, the one or more compounds, salts or compositions of the disclosure are subcutaneously administered at least about 15 minutes prior to the administration of chemotherapy, such as at least about 5 minutes, or about 5 minutes to about 30 minutes prior to the administration of chemotherapy. In some embodiments, the one or more compounds, salts or compositions of the disclosure are subcutaneously administered at least about 30 minutes prior to the administration of chemotherapy, such as at least about 15 minutes, or about 15 minutes to about 60 minutes prior to the administration of chemotherapy. In some embodiments, the one or more compounds, salts or compositions of the disclosure are subcutaneously administered at least about 60 minutes prior to the administration of chemotherapy, such as at least about 30 minutes, or about 30 minutes to about 120 minutes prior to the administration of chemotherapy. In some embodiments, the one or more compounds, salts or compositions of the disclosure are subcutaneously administered at least about 2 hours prior to the administration of chemotherapy, such as at least about 1 hour, or about 1 hour to about 4 hours prior to the administration of chemotherapy. In some embodiments, the one or more compounds, salts or compositions of the disclosure are subcutaneously administered at least about 4 hours prior to the administration of chemotherapy, such as at least about 2 hours, or about 2 hours to about 8 hours prior to the administration of chemotherapy. In some embodiments, the one or more compounds, salts or compositions of the disclosure are subcutaneously administered at least about 6 hours prior to the administration of chemotherapy, such as at least about 8 hours, or about 8 hours to about 12 hours prior to the administration of chemotherapy.

In some embodiments, the one or more compounds, salts or compositions of the disclosure are administered intravenously at least about three hours prior to the administration of chemotherapy. In some embodiments, the one or more compounds, salts or compositions of the disclosure are intravenously administered at least about 15 minutes prior to the administration of chemotherapy, such as at least about 5 minutes, or about 5 minutes to about 30 minutes prior to the administration of chemotherapy. In some embodiments, the one or more compounds, salts or compositions of the disclosure are intravenously administered at least about 30 minutes prior to the administration of chemotherapy, such as at least about 15 minutes, or about 15 minutes to about 60 minutes prior to the administration of chemotherapy. In some embodiments, the one or more compounds, salts or compositions of the disclosure are intravenously administered at least about 60 minutes prior to the administration of chemotherapy, such as at least about 30 minutes, or about 30 minutes to about 120 minutes prior to the administration of chemotherapy. In some embodiments, the one or more compounds, salts or compositions of the disclosure are intravenously administered at least about 2 hours prior to the administration of chemotherapy, such as at least about 1 hour, or about 1 hour to about 4 hours prior to the administration of chemotherapy. In some embodiments, the one or more compounds, salts or compositions of the disclosure are intravenously administered at least about 4 hours prior to the administration of chemotherapy, such as at least about 2 hours, or about 2 hours to about 8 hours prior to the administration of chemotherapy. In some embodiments, the one or more compounds, salts or compositions of the disclosure are intravenously administered at least about 6 hours prior to the administration of chemotherapy, such as at least about 8 hours, or about 8 hours to about 12 hours prior to the administration of chemotherapy.

In some embodiments, the one or more compounds, salts or compositions of the disclosure are administered topically at least about three hours prior to the administration of chemotherapy. In some embodiments, the one or more compounds, salts or compositions of the disclosure are topically administered at least about 15 minutes prior to the administration of chemotherapy, such as at least about 5 minutes, or about 5 minutes to about 30 minutes prior to the administration of chemotherapy. In some embodiments, the one or more compounds, salts or compositions of the disclosure are topically administered at least about 30 minutes prior to the administration of chemotherapy, such as at least about 15 minutes, or about 15 minutes to about 60 minutes prior to the administration of chemotherapy. In some embodiments, the one or more compounds, salts or compositions of the disclosure are topically administered at least about 60 minutes prior to the administration of chemotherapy, such as at least about 30 minutes, or about 30 minutes to about 120 minutes prior to the administration of chemotherapy. In some embodiments, the one or more compounds, salts or compositions of the disclosure are topically administered at least about 2 hours prior to the administration of chemotherapy, such as at least about 1 hour, or about 1 hour to about 4 hours prior to the administration of chemotherapy. In some embodiments, the one or more compounds, salts or compositions of the disclosure are topically administered at least about 4 hours prior to the administration of chemotherapy, such as at least about 2 hours, or about 2 hours to about 8 hours prior to the administration of chemotherapy. In some embodiments, the one or more compounds, salts or compositions of the disclosure are topically administered at least about 6 hours prior to the administration of chemotherapy, such as at least about 8 hours, or about 8 hours to about 12 hours prior to the administration of chemotherapy.

In some embodiments, the one or more compounds, salts or compositions of the disclosure are administered cutaneously at least about three hours prior to the administration of chemotherapy. In some embodiments, the one or more compounds, salts or compositions of the disclosure are cutaneously administered at least about 15 minutes prior to the administration of chemotherapy, such as at least about 5 minutes, or about 5 minutes to about 30 minutes prior to the administration of chemotherapy. In some embodiments, the one or more compounds, salts or compositions of the disclosure are cutaneously administered at least about 30 minutes prior to the administration of chemotherapy, such as at least about 15 minutes, or about 15 minutes to about 60 minutes prior to the administration of chemotherapy. In some embodiments, the one or more compounds, salts or compositions of the disclosure are cutaneously administered at least about 60 minutes prior to the administration of chemotherapy, such as at least about 30 minutes, or about 30 minutes to about 120 minutes prior to the administration of chemotherapy. In some embodiments, the one or more compounds, salts or compositions of the disclosure are cutaneously administered at least about 2 hours prior to the administration of chemotherapy, such as at least about 1 hour, or about 1 hour to about 4 hours prior to the administration of chemotherapy. In some embodiments, the one or more compounds, salts or compositions of the disclosure are cutaneously administered at least about 4 hours prior to the administration of chemotherapy, such as at least about 2 hours, or about 2 hours to about 8 hours prior to the administration of chemotherapy. In some embodiments, the one or more compounds, salts or compositions of the disclosure are cutaneously administered at least about 6 hours prior to the administration of chemotherapy, such as at least about 8 hours, or about 8 hours to about 12 hours prior to the administration of chemotherapy.

In some embodiments, the prodrugs or double prodrugs of the disclosure are administered orally at least about three hours prior to the administration of radiation therapy or potential exposure to other sources of ionizing radiation. In some embodiments, the prodrugs or double prodrugs of the disclosure are orally administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation.

In some embodiments, the prodrugs or double prodrugs of the disclosure are orally administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the o prodrugs or double prodrugs of the disclosure are orally administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the prodrugs or double prodrugs of the disclosure are orally administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the prodrugs or double prodrugs of the disclosure are orally administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the prodrugs or double prodrugs of the disclosure are orally administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the prodrugs or double prodrugs of the disclosure are administered subcutaneously at least about three hours prior to the administration of radiation therapy or potential exposure to other sources of ionizing radiation. In some embodiments, the prodrugs or double prodrugs of the disclosure are subcutaneously administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the prodrugs or double prodrugs of the disclosure are subcutaneously administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the prodrugs or double prodrugs of the disclosure are subcutaneously administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the prodrugs or double prodrugs of the disclosure are subcutaneously administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the prodrugs or double prodrugs of the disclosure are subcutaneously administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, prodrugs or double prodrugs of the disclosure are subcutaneously administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the prodrugs or double prodrugs compositions of the disclosure are administered intravenously at least about three hours prior to the administration of radiation therapy or potential exposure to other sources of ionizing radiation. In some embodiments, the prodrugs or double prodrugs of the disclosure are intravenously administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the prodrugs or double prodrugs of the disclosure are intravenously administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the one or more compounds, salts or compositions of the disclosure are intravenously administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the prodrugs or double prodrugs of the disclosure are intravenously administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the prodrugs or double prodrugs of the disclosure are intravenously administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the prodrugs or double prodrugs of the disclosure are intravenously administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the prodrugs or double prodrugs of the disclosure are administered topically at least about three hours prior to the administration of radiation therapy or potential exposure to other sources of ionizing radiation. In some embodiments, the prodrugs or double prodrugs of the disclosure are topically administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the prodrugs or double prodrugs of the disclosure are topically administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the prodrugs or double prodrugs of the disclosure are topically administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the prodrugs or double prodrugs of the disclosure are topically administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the prodrugs or double prodrugs of the disclosure are topically administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the prodrugs or double prodrugs of the disclosure are topically administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the prodrugs or double prodrugs of the disclosure are administered cutaneously at least about three hours prior to the administration of radiation therapy or potential exposure to other sources of ionizing radiation. In some embodiments, the prodrugs or double prodrugs of the disclosure are cutaneously administered at least about 15 minutes prior to the administration of radiation therapy or potential exposure to other sources of ionizing radiation, such as at least about 5 minutes, or about 5 minutes to about 30 minutes prior to the administration of radiation therapy or potential exposure to other sources of ionizing radiation. In some embodiments, the prodrugs or double prodrugs of the disclosure are cutaneously administered at least about 30 minutes prior to the administration of radiation therapy or potential exposure to other sources of ionizing radiation, such as at least about 15 minutes, or about 15 minutes to about 60 minutes prior to the administration of radiation therapy or potential exposure to other sources of ionizing radiation. In some embodiments, the prodrugs or double prodrugs of the disclosure are cutaneously administered at least about 60 minutes prior to the administration of radiation therapy or potential exposure to other sources of ionizing radiation, such as at least about 30 minutes, or about 30 minutes to about 120 minutes prior to the administration of radiation therapy or potential exposure to other sources of ionizing radiation. In some embodiments, the prodrugs or double prodrugs of the disclosure are cutaneously administered at least about 2 hours prior to the administration of radiation therapy or potential exposure to other sources of ionizing radiation, such as at least about 1 hour, or about 1 hour to about 4 hours prior to the administration of radiation therapy or potential exposure to other sources of ionizing radiation. In some embodiments, the prodrugs or double prodrugs of the disclosure are cutaneously administered at least about 4 hours prior to the administration of radiation therapy or potential exposure to other sources of ionizing radiation, such as at least about 2 hours, or about 2 hours to about 8 hours prior to the administration of radiation therapy or potential exposure to other sources of ionizing radiation. In some embodiments, the prodrugs or double prodrugs of the disclosure are cutaneously administered at least about 6 hours prior to the administration of radiation therapy or potential exposure to other sources of ionizing radiation, such as at least about 8 hours, or about 8 hours to about 12 hours prior to the administration of radiation therapy or potential exposure to other sources of ionizing radiation.

In some embodiments, the prodrugs or double prodrugs of the disclosure are administered orally at least about three hours prior to the administration of chemotherapy. In some embodiments, the prodrugs or double prodrugs of the disclosure are orally administered at least about 15 minutes prior to the administration of chemotherapy, such as at least about 5 minutes, or about 5 minutes to about 30 minutes prior to the administration of chemotherapy. In some embodiments, the prodrugs or double prodrugs of the disclosure are orally administered at least about 30 minutes prior to the administration of chemotherapy, such as at least about 15 minutes, or about 15 minutes to about 60 minutes prior to the administration of chemotherapy. In some embodiments, the prodrugs or double prodrugs of the disclosure are orally administered at least about 60 minutes prior to the administration of chemotherapy, such as at least about 30 minutes, or about 30 minutes to about 120 minutes prior to the administration of chemotherapy. In some embodiments, the prodrugs or double prodrugs of the disclosure are orally administered at least about 2 hours prior to the administration of chemotherapy, such as at least about 1 hour, or about 1 hour to about 4 hours prior to the administration of chemotherapy. In some embodiments, the prodrugs or double prodrugs of the disclosure are orally administered at least about 4 hours prior to the administration of chemotherapy, such as at least about 2 hours, or about 2 hours to about 8 hours prior to the administration of chemotherapy. In some embodiments, the prodrugs or double prodrugs of the disclosure are orally administered at least about 6 hours prior to the administration of chemotherapy, such as at least about 8 hours, or about 8 hours to about 12 hours prior to the administration of chemotherapy.

In some embodiments, the prodrugs or double prodrugs of the disclosure are administered subcutaneously at least about three hours prior to the administration of chemotherapy. In some embodiments, the prodrugs or double prodrugs of the disclosure are subcutaneously administered at least about 15 minutes prior to the administration of chemotherapy, such as at least about 5 minutes, or about 5 minutes to about 30 minutes prior to the administration of chemotherapy. In some embodiments, the prodrugs or double prodrugs of the disclosure are subcutaneously administered at least about 30 minutes prior to the administration of chemotherapy, such as at least about 15 minutes, or about 15 minutes to about 60 minutes prior to the administration of chemotherapy. In some embodiments, the prodrugs or double prodrugs of the disclosure are subcutaneously administered at least about 60 minutes prior to the administration of chemotherapy, such as at least about 30 minutes, or about 30 minutes to about 120 minutes prior to the administration of chemotherapy. In some embodiments, the prodrugs or double prodrugs of the disclosure are subcutaneously administered at least about 2 hours prior to the administration of chemotherapy, such as at least about 1 hour, or about 1 hour to about 4 hours prior to the administration of chemotherapy. In some embodiments, the prodrugs or double prodrugs of the disclosure are subcutaneously administered at least about 4 hours prior to the administration of chemotherapy, such as at least about 2 hours, or about 2 hours to about 8 hours prior to the administration of chemotherapy. In some embodiments, the prodrugs or double prodrugs of the disclosure are subcutaneously administered at least about 6 hours prior to the administration of chemotherapy, such as at least about 8 hours, or about 8 hours to about 12 hours prior to the administration of chemotherapy.

In some embodiments, the prodrugs or double prodrugs of the disclosure are administered intravenously at least about three hours prior to the administration of chemotherapy. In some embodiments, the prodrugs or double prodrugs of the disclosure are intravenously administered at least about 15 minutes prior to the administration of chemotherapy, such as at least about 5 minutes, or about 5 minutes to about 30 minutes prior to the administration of chemotherapy. In some embodiments, the o prodrugs or double prodrugs of the disclosure are intravenously administered at least about 30 minutes prior to the administration of chemotherapy, such as at least about 15 minutes, or about 15 minutes to about 60 minutes prior to the administration of chemotherapy. In some embodiments, the prodrugs or double prodrugs of the disclosure are intravenously administered at least about 60 minutes prior to the administration of chemotherapy, such as at least about 30 minutes, or about 30 minutes to about 120 minutes prior to the administration of chemotherapy. In some embodiments, the prodrugs or double prodrugs of the disclosure are intravenously administered at least about 2 hours prior to the administration of chemotherapy, such as at least about 1 hour, or about 1 hour to about 4 hours prior to the administration of chemotherapy. In some embodiments, the prodrugs or double prodrugs of the disclosure are intravenously administered at least about 4 hours prior to the administration of chemotherapy, such as at least about 2 hours, or about 2 hours to about 8 hours prior to the administration of chemotherapy. In some embodiments, the prodrugs or double prodrugs of the disclosure are intravenously administered at least about 6 hours prior to the administration of chemotherapy, such as at least about 8 hours, or about 8 hours to about 12 hours prior to the administration of chemotherapy.

In some embodiments, the prodrugs or double prodrugs of the disclosure are administered topically at least about three hours prior to the administration of chemotherapy. In some embodiments, the prodrugs or double prodrugs of the disclosure are topically administered at least about 15 minutes prior to the administration of chemotherapy, such as at least about 5 minutes, or about 5 minutes to about 30 minutes prior to the administration of chemotherapy. In some embodiments, the prodrugs or double prodrugs of the disclosure are topically administered at least about 30 minutes prior to the administration of chemotherapy, such as at least about 15 minutes, or about 15 minutes to about 60 minutes prior to the administration of chemotherapy. In some embodiments, the prodrugs or double prodrugs of the disclosure are topically administered at least about 60 minutes prior to the administration of chemotherapy, such as at least about 30 minutes, or about 30 minutes to about 120 minutes prior to the administration of chemotherapy. In some embodiments, the prodrugs or double prodrugs of the disclosure are topically administered at least about 2 hours prior to the administration of chemotherapy, such as at least about 1 hour, or about 1 hour to about 4 hours prior to the administration of chemotherapy. In some embodiments, the prodrugs or double prodrugs of the disclosure are topically administered at least about 4 hours prior to the administration of chemotherapy, such as at least about 2 hours, or about 2 hours to about 8 hours prior to the administration of chemotherapy. In some embodiments, the prodrugs or double prodrugs of the disclosure are topically administered at least about 6 hours prior to the administration of chemotherapy, such as at least about 8 hours, or about 8 hours to about 12 hours prior to the administration of chemotherapy.

In some embodiments, the prodrugs or double prodrugs of the disclosure are administered cutaneously at least about three hours prior to the administration of chemotherapy. In some embodiments, the prodrugs or double prodrugs of the disclosure are cutaneously administered at least about 15 minutes prior to the administration of chemotherapy, such as at least about 5 minutes, or about 5 minutes to about 30 minutes prior to the administration of chemotherapy. In some embodiments, the prodrugs or double prodrugs of the disclosure are cutaneously administered at least about 30 minutes prior to the administration of chemotherapy, such as at least about 15 minutes, or about 15 minutes to about 60 minutes prior to the administration of chemotherapy. In some embodiments, the o prodrugs or double prodrugs of the disclosure are cutaneously administered at least about 60 minutes prior to the administration of chemotherapy, such as at least about 30 minutes, or about 30 minutes to about 120 minutes prior to the administration of chemotherapy. In some embodiments, the prodrugs or double prodrugs of the disclosure are cutaneously administered at least about 2 hours prior to the administration of chemotherapy, such as at least about 1 hour, or about 1 hour to about 4 hours prior to the administration of chemotherapy. In some embodiments, the prodrugs or double prodrugs of the disclosure are cutaneously administered at least about 4 hours prior to the administration of chemotherapy, such as at least about 2 hours, or about 2 hours to about 8 hours prior to the administration of chemotherapy. In some embodiments, the prodrugs or double prodrugs of the disclosure are cutaneously administered at least about 6 hours prior to the administration of chemotherapy, such as at least about 8 hours, or about 8 hours to about 12 hours prior to the administration of chemotherapy.

In some embodiments, the one or more compounds, salts or compositions of the disclosure are useful in reducing the potential of future carcinogenesis of surviving cells after exposure to ionizing radiation or chemotherapy has occurred. In some embodiments, the one or more compounds, salts or compositions of the disclosure are administered before exposure to ionizing radiation or chemotherapy. In some embodiments, the one or more compounds, salts or compositions of the disclosure are administered simultaneously/concurrently with exposure to ionizing radiation or chemotherapy. In some embodiments, the one or more compounds, salts or compositions of the disclosure are administered after exposure to ionizing radiation or chemotherapy.

In some embodiments, the one or more compounds, salts or compositions of the disclosure are orally administered at least about 15 minutes after radiation exposure, such as at least about 5 minutes, or about 5 minutes to about 30 minutes after radiation exposure. In some embodiments, the one or more compounds, salts or compositions of the disclosure are orally administered at least about 30 minutes after radiation exposure, such as at least about 15 minutes, or about 15 minutes to about 60 minutes after radiation exposure. In some embodiments, the one or more compounds, salts or compositions of the disclosure are orally administered at least about 60 minutes after radiation exposure, such as at least about 30 minutes, or about 30 minutes to about 120 minutes after radiation exposure. In some embodiments, the one or more compounds, salts or compositions of the disclosure are orally administered at least about 2 hours after radiation exposure, such as at least about 1 hour, or about 1 hour to about 4 after radiation exposure. In some embodiments, the one or more compounds, salts or compositions of the disclosure are orally administered at least about 4 hours after radiation exposure, such as at least about 2 hours, or about 2 hours to about 8 hours after radiation exposure. In some embodiments, the one or more compounds, salts or compositions of the disclosure are orally administered at least about 6 hours after radiation exposure, such as at least about 8 hours, or about 8 hours to about 12 hours after radiation exposure.

In some embodiments, the one or more compounds, salts or compositions of the disclosure are administered subcutaneously at least about three hours after radiation exposure. In some embodiments, the one or more compounds, salts or compositions of the disclosure are subcutaneously administered at least about 15 minutes after radiation exposure, such as at least about 5 minutes, or about 5 minutes to about 30 minutes after radiation exposure. In some embodiments, the one or more compounds, salts or compositions of the disclosure are subcutaneously administered at least about 30 minutes after radiation exposure, such as at least about 15 minutes, or about 15 minutes to about 60 minutes after radiation exposure. In some embodiments, the one or more compounds, salts or compositions of the disclosure are subcutaneously administered at least about 60 minutes after radiation exposure, such as at least about 30 minutes, or about 30 minutes to about 120 minutes after radiation exposure. In some embodiments, the one or more compounds, salts or compositions of the disclosure are subcutaneously administered at least about 2 hours after radiation exposure, such as at least about 1 hour, or about 1 hour to about 4 hours after radiation exposure. In some embodiments, the one or more compounds, salts or compositions of the disclosure are subcutaneously administered at least about 4 hours after radiation exposure, such as at least about 2 hours, or about 2 hours to about 8 hours after radiation exposure. In some embodiments, the one or more compounds, salts or compositions of the disclosure are subcutaneously administered at least about 6 hours after radiation exposure, such as at least about 8 hours, or about 8 hours to about 12 hours after radiation exposure.

In some embodiments, the one or more compounds, salts or compositions of the disclosure are administered topically at least about three hours after radiation exposure. In some embodiments, the one or more compounds, salts or compositions of the disclosure are topically administered at least about 15 minutes after radiation exposure, such as at least about 5 minutes, or about 5 minutes to about 30 minutes after radiation exposure. In some embodiments, the one or more compounds, salts or compositions of the disclosure are topically administered at least about 30 minutes after radiation exposure, such as at least about 15 minutes, or about 15 minutes to about 60 minutes after radiation exposure. In some embodiments, the one or more compounds, salts or compositions of the disclosure are topically administered at least about 60 minutes after radiation exposure, such as at least about 30 minutes, or about 30 minutes to about 120 minutes after radiation exposure.

In some embodiments, the one or more compounds, salts or compositions of the disclosure are administered cutaneously at least about three hours after radiation exposure. In some embodiments, the one or more compounds, salts or compositions of the disclosure are cutaneously administered at least about 15 minutes after radiation exposure, such as at least about 5 minutes, or about 5 minutes to about 30 minutes after radiation exposure. In some embodiments, the one or more compounds, salts or compositions of the disclosure are cutaneously administered at least about 30 minutes after radiation exposure, such as at least about 15 minutes, or about 15 minutes to about 60 minutes after radiation exposure. In some embodiments, the one or more compounds, salts or compositions of the disclosure are cutaneously administered at least about 60 minutes after radiation exposure, such as at least about 30 minutes, or about 30 minutes to about 120 minutes after radiation exposure.

In some embodiments, the one or more compounds, salts or compositions of the disclosure are administered orally at least about three hours after administration of chemotherapy. In some embodiments, the one or more compounds, salts or compositions of the disclosure are orally administered at least about 15 minutes after administration of chemotherapy, such as at least about 5 minutes, or about 5 minutes to about 30 minutes after administration of chemotherapy. In some embodiments, the one or more compounds, salts or compositions of the disclosure are orally administered at least about 30 minutes after administration of chemotherapy, such as at least about 15 minutes, or about 15 minutes to about 60 minutes after administration of chemotherapy. In some embodiments, the one or more compounds, salts or compositions of the disclosure are orally administered at least about 60 minutes after administration of chemotherapy, such as at least about 30 minutes, or about 30 minutes to about 120 minutes after administration of chemotherapy. In some embodiments, the one or more compounds, salts or compositions of the disclosure are orally administered at least about 2 hours after the administration of chemotherapy, such as at least about 1 hour, or about 1 hour to about 4 hours after the administration of chemotherapy. In some embodiments, the one or more compounds, salts or compositions of the disclosure are orally administered at least about 4 hours after the administration of chemotherapy, such as at least about 2 hours, or about 2 hours to about 8 hours after the administration of chemotherapy. In some embodiments, the one or more compounds, salts or compositions of the disclosure are orally administered at least about 6 hours after the administration of chemotherapy, such as at least about 8 hours, or about 8 hours to about 12 hours after the administration of chemotherapy.

In some embodiments, the one or more compounds, salts or compositions of the disclosure are administered subcutaneously at least about three hours after the administration of chemotherapy. In some embodiments, the one or more compounds, salts or compositions of the disclosure are subcutaneously administered at least about 15 minutes after the administration of chemotherapy, such as at least about 5 minutes, or about 5 minutes to about 30 minutes after the administration of chemotherapy. In some embodiments, the one or more compounds, salts or compositions of the disclosure are subcutaneously administered at least about 30 minutes after the administration of chemotherapy, such as at least about 15 minutes, or about 15 minutes to about 60 minutes after the administration of chemotherapy. In some embodiments, the one or more compounds, salts or compositions of the disclosure are subcutaneously administered at least about 60 minutes after the administration of chemotherapy, such as at least about 30 minutes, or about 30 minutes to about 120 minutes after the administration of chemotherapy. In some embodiments, the one or more compounds, salts or compositions of the disclosure are subcutaneously administered at least about 2 hours after the administration of chemotherapy, such as at least about 1 hour, or about 1 hour to about 4 hours after the administration of chemotherapy. In some embodiments, the one or more compounds, salts or compositions of the disclosure are subcutaneously administered at least about 4 after the administration of chemotherapy, such as at least about 2 hours, or about 2 hours to about 8 hours after the administration of chemotherapy. In some embodiments, the one or more compounds, salts or compositions of the disclosure are subcutaneously administered at least about 6 hours after the administration of chemotherapy, such as at least about 8 hours, or about 8 hours to about 12 hours after the administration of chemotherapy.

In some embodiments, the one or more compounds, salts or compositions of the disclosure are administered topically at least about three hours after the administration of chemotherapy. In some embodiments, the one or more compounds, salts or compositions of the disclosure are topically administered at least about 15 minutes after the administration of chemotherapy, such as at least about 5 minutes, or about 5 minutes to about 30 minutes after the administration of chemotherapy. In some embodiments, the one or more compounds, salts or compositions of the disclosure are topically administered at least about 30 minutes after the administration of chemotherapy, such as at least about 15 minutes, or about 15 minutes to about 60 minutes after the administration of chemotherapy. In some embodiments, the one or more compounds, salts or compositions of the disclosure are topically administered at least about 60 minutes after the administration of chemotherapy, such as at least about 30 minutes, or about 30 minutes to about 120 minutes after the administration of chemotherapy. In some embodiments, the one or more compounds, salts or compositions of the disclosure are topically administered at least about 2 hours after the administration of chemotherapy, such as at least about 1 hour, or about 1 hour to about 4 hours after the administration of chemotherapy. In some embodiments, the one or more compounds, salts or compositions of the disclosure are topically administered at least about 4 after the administration of chemotherapy, such as at least about 2 hours, or about 2 hours to about 8 hours after the administration of chemotherapy. In some embodiments, the one or more compounds, salts or compositions of the disclosure are topically administered at least about 6 hours after the administration of chemotherapy, such as at least about 8 hours, or about 8 hours to about 12 hours after the administration of chemotherapy.

In some embodiments, the one or more compounds, salts or compositions of the disclosure are administered cutaneously at least about three hours after the administration of chemotherapy. In some embodiments, the one or more compounds, salts or compositions of the disclosure are cutaneously administered at least about 15 minutes after the administration of chemotherapy, such as at least about 5 minutes, or about 5 minutes to about 30 minutes after the administration of chemotherapy. In some embodiments, the one or more compounds, salts or compositions of the disclosure are cutaneously administered at least about 30 minutes after the administration of chemotherapy, such as at least about 15 minutes, or about 15 minutes to about 60 minutes after the administration of chemotherapy. In some embodiments, the one or more compounds, salts or compositions of the disclosure are cutaneously administered at least about 60 minutes after the administration of chemotherapy, such as at least about 30 minutes, or about 30 minutes to about 120 minutes after the administration of chemotherapy. In some embodiments, the one or more compounds, salts or compositions of the disclosure are cutaneously administered at least about 2 hours after the administration of chemotherapy, such as at least about 1 hour, or about 1 hour to about 4 hours after the administration of chemotherapy.

In some embodiments, the one or more compounds, salts or compositions of the disclosure are cutaneously administered at least about 4 after the administration of chemotherapy, such as at least about 2 hours, or about 2 hours to about 8 hours after the administration of chemotherapy.

In some embodiments, the one or more compounds, salts or compositions of the disclosure are cutaneously administered at least about 6 hours after the administration of chemotherapy, such as at least about 8 hours, or about 8 hours to about 12 hours after the administration of chemotherapy.

In some embodiments, one or more compounds, salts or compositions of the disclosure are useful as radioprotectants against the toxicities of ionizing radiation. In some embodiments, the amount of one or more compounds, salts of the disclosure is about 10 mg to about 10,000 mg. In certain such embodiments, the amount is at least about 500 mg, such as about 500 mg to 1500 mg, administered orally. In certain such embodiments, one or more compounds, salts or compositions of the disclosure are administered as two or more oral doses depending on the amount and duration of radiation exposure. In some embodiments, the amount of one or more compounds of the disclosure useful as radioprotectants is at least about 500 mg, such as about 500 mg to about 1500 mg, administered subcutaneously. In certain such embodiments, one or more compounds, salts or compositions of the disclosure are administered as two subcutaneous injections. In some embodiments, a circulating concentration of one or more compounds of the disclosure (and/or and a metabolite thereof) of about 2 µM to about 100 µM is effective as a radioprotectant. In certain such embodiments, the concentration of one or more compounds of the disclosure is about 5 µM to about 50 µM. Alternatively, or in addition to, a tissue concentration of one or more compounds of the disclosure (and/or a metabolite thereof) of about 4 µM to about 700 µM is effective as a radioprotectant. In certain such embodiments, the effective tissue concentration is about 20 µM to about 350 µM.

In some embodiments, one or more compounds, salts or compositions of the disclosure are useful in treating the toxicities associated ionizing radiation, especially in subjects with head and neck cancer. In certain such embodiments, oral, subcutaneous or intravenous administration reduces side effects. In certain such embodiments, oral administration reduces side effects. In some embodiments, subcutaneous administration reduces side effects. In certain such embodiments, intravenous administration reduces side effects. In some embodiments, subcutaneous administration reduces side effects.

In some embodiments, one or more compounds, salts or compositions of the disclosure are useful as chemoprotectants against the toxicities of chemotherapy. In some embodiments, the amount of one or more compounds or salts of the disclosure is about 10 mg to about 10,000 mg. In certain such embodiments, the amount is at least about 500 mg, such as about 500 mg to about 1500 mg, administered orally. In certain such embodiments, one or more compounds, salts or compositions of the disclosure are administered as two oral doses. In some embodiments, the amount of one or more compounds or salts of the disclosure useful as chemoprotectants is at least about 500 mg, such as about 500 mg to about 1500 mg, administered subcutaneously. In certain such embodiments, one or more compounds, salts or compositions of the disclosure are administered as two subcutaneous injections. In some embodiments, a circulating concentration of one or more compounds of the disclosure (and/or and a metabolite thereof) of about 2 µM to about 100 µM is effective as a chemoprotectant. In certain such embodiments, the concentration of one or more compounds of the disclosure is about 5 µM to about 50 µM. Alternatively, or in addition to, a tissue concentration of one or more compounds of the disclosure (and/or a metabolite thereof) of about 4 µM to about 700 µM is effective as a chemoprotectant. In certain such embodiments, the effective tissue concentration is about 20 µM to about 350 µM.

In some embodiments, one or more compounds, salts or compositions of the disclosure are useful in treating the toxicities associated with chemotherapy, especially in subjects with head and neck cancer. In certain such embodiments, oral or subcutaneous administration reduces side effects. In certain such embodiments, oral administration reduces side effects. In some embodiments, subcutaneous administration reduces side effects.

In some embodiments, one or more compounds, salts or compositions of the disclosure are useful in treating diseases requiring bone marrow growth, such as MDS, or in promoting recovery of bone marrow function. In certain such embodiments, a circulating concentration of one or more compounds of the disclosure (and/or a metabolite thereof) of about 2 µM to about 100 µM is effective. Alternatively, or in addition, a tissue concentration of one or more compounds of the disclosure (and/or a metabolite thereof) of about 0.1 µM to about 1000 µM is effective, such as about 10 µM to about 500 µM.

In some embodiments, usual subject doses for administration of one or more compounds or salts of the disclosure usually range from about 10 mg/day to about 10,000 mg/day. In some embodiments, the doses range from about 50 mg/day to about 6000 mg/day, about 100 mg/day to about 4000 mg/day, about 200 mg/day to about 3500 mg/day, about 50 mg/day to about 1000 mg/day, about 100 mg/day to about 900 mg/day, about 50 mg/day to about 1500 mg/day, about 100 mg/day to about 1000 mg/day, about 200 mg/day to about 750 mg/day, about 50 mg/day to about 1200 mg/day, about 100 mg/day to about 1100 mg/day, about 200 mg/day to about 1000 mg/day, or about 200 mg/day to about 800 mg/day.

Stated in terms of subject body weight, in some embodiments usual dosages range from about 0.5 mg/kg/day to about 16 mg/kg/day, about 1.1 mg/kg/day to about 15 mg/kg/day, about 0.6 mg/kg/day to about 100 mg/kg/day, about 1.1 mg/kg/day to about 66 mg/kg/day, about 2.2 mg/kg/day to about 58 mg/kg/day, about 0.5 mg/kg/day to about 25 mg/kg/day, about 1 mg/kg/day to about 16 mg/kg/day, about 3.3 mg/kg/day to about 12.5 mg/kg/day, about 0.5 mg/kg/day to about 20 mg/kg/day, about 1.1 mg/kg/day to about 18 mg/kg/day, about 2.2 mg/kg/day to about 16.2 mg/kg/day, or about 2.2 mg/kg/day to about 13.5 mg/kg/day.

Stated in terms of subject body surface areas, usual dosages range from about 22 $mg/m^2/day$ to about 666 $mg/m^2/day$, about 45 $mg/m^2/day$ to about 600 $mg/m^2/day$, about 23 $mg/m^2/day$ to about 4000 $mg/m^2/day$, about 45 $mg/m^2/day$ to about 2666 $mg/m^2/day$, about 90 $mg/m^2/day$ to about 2333 $mg/m^2/day$, about 22 $mg/m^2/day$ to about 1000 $mg/m^2/day$, about 45 $mg/m^2/day$ to about 666 $mg/m^2/day$, about 133 $mg/m^2/day$ to about 500 $mg/m^2/day$, about 22 $mg/m^2/day$ to about 800 $mg/m^2/day$, about 45 $mg/m^2/day$ to about 720 $mg/m^2/day$, about 90 $mg/m^2/day$ to about 650 $mg/m^2/day$, or about 90 $mg/m^2/day$ to about 540 $mg/m^2/day$.

In some embodiments, the one or more compounds, salts or compositions of the disclosure are administered orally. In certain such embodiments, usual subject doses for oral administration of one or more compounds or salts of the disclosure usually range from about 50 mg/day to about 6000 mg/day, commonly from about 100 mg/day to about 4000 mg/day, and typically from about 200 mg/day to about 3500 mg/day. Stated in terms of subject body weight, usual dosages range from about 0.6 mg/kg/day to about 100 mg/kg/day, commonly from about 1.1 mg/kg/day to about 66 mg/kg/day, and typically from about 2.2 mg/kg/day to about 58 mg/kg/day. Stated in terms of subject body surface areas, usual dosages range from about 23 $mg/m^2/day$ to about 4000 $mg/m^2/day$, commonly from about 45 $mg/m^2/day$ to about 2666 $mg/m^2/day$, and typically from about 90 $mg/m^2/day$ to about 2333 $mg/m^2/day$.

In some embodiments, the one or more compounds, salts or compositions of the disclosure are administered subcutaneously. In certain such embodiments, subject doses for subcutaneous administration of one or more compounds or salts of the disclosure usually range from about 50 mg/day to about 1500 mg/day, commonly from about 100 mg/day to about 1000 mg/day and typically from about 200 mg/day to about 750 mg/day. Stated in terms of body weight, usual dosages range from about 0.5 mg/kg/day to about 25 mg/kg/day, commonly from about 1 mg/kg/day to about 16 mg/kg/day and typically from about 3.3 mg/kg/day to about 12.5 mg/kg/day. Stated in terms of subject body surface areas, usual doses range from about 22 $mg/m^2/day$ to about 1000 $mg/m^2/day$, commonly from about 45 $mg/m^2/day$ to about 666 $mg/m^2/day$ and typically from about 133 $mg/m^2/day$ to about 500 $mg/m^2/day$.

In some embodiments when the one or more compounds, salts or compositions of the disclosure are administered subcutaneously, subject doses for subcutaneous administration of one or more compounds or salts of the disclosure usually range from about 50 mg/day to about 1200 mg/day, commonly from about 100 mg/day to about 1100 mg/day and typically from about 200 mg/day to about 1000 mg/day.

Stated in terms of body weight, usual dosages range from about 0.5 mg/kg/day to about 20 mg/kg/day, commonly from about 1.1 mg/kg/day to about 18 mg/kg/day and typically from about 2.2 mg/kg/day to about 16.2 mg/kg/day. Stated in terms of subject body surface areas, usual doses range from about 22 mg/m$^2$/day to about 800 mg/m$^2$/day, commonly from about 45 mg/m$^2$/day to about 720 mg/m$^2$/day and typically from about 90 mg/m$^2$/day to about 650 mg/m$^2$/day.

In some embodiments for parenteral administration by injection (e.g., by intramuscular, subcutaneous and intravenous injections, bolus injection or continuous infusion), one or more compounds, salts or compositions of the disclosure can be administered by continuous infusion subcutaneously over a period of 15 minutes to 24 hours.

For other modes of administration, dosage amount and interval can be adjusted individually to provide effective plasma and/or tissue levels of one or more compounds or salts of the disclosure, and/or a metabolite thereof, according to the pharmacokinetic profiles described herein, as previously described.

The actual amount of one or more compounds, salts or compositions of the disclosure administered will, of course, be dependent on the subject being treated, the condition being treated, the subject's weight, the severity of the affliction, the mode of administration and the judgment of the prescribing physician.

Methods and Uses of Treatment

One aspect of this disclosure is a method of treating or preventing a toxicity or condition associated with ionizing radiation exposure or chemotherapy in a subject in need thereof, comprising administering to said subject a therapeutically effective amount of a compound according to this disclosure, or a pharmaceutically acceptable salt, solvate, hydrate, polymorph or combination thereof or a hydrate, solvate or polymorph of the salt, or of a pharmaceutical composition according to this disclosure.

In some embodiments, the toxicity is one or more of bone marrow toxicity, central nervous system toxicity, immunological toxicity, gastrointestinal toxicity, neurotoxicity, nephrotoxicity, ototoxicity, cardiotoxicity, hepatotoxicity, cutaneous toxicity, alopecia mucositis, xerostomia, infertility, peripheral neuropathy, pulmonary toxicity or renal failure. In some embodiments the toxicity is an acute radiation toxicity. In some embodiments the toxicity is a late radiation toxicity (i.e., late onset toxicity). Ionizing radiation causes injury to cells and tissues. Damaged cells continue to function normally until they die while attempting to undergo mitosis. Accordingly, symptoms of ionizing radiation injury occur more rapidly for organs with rapid cell turnovers. Conversely, symptoms of ionizing radiation injury for organs with a slower turnover rate occur after a latency period. Symptoms associated with acute radiation toxicity can occur within hours, days or weeks, such as within 1 hour, 2 hours, 3 hours, 4 hours, 5 hours, 6 hours, 12 hours, 1 day, 2 days, 3 days, 4 days, 5 days, 6 days, 1 week, 2 weeks or 3 weeks after of the incident radiation exposure. Symptoms associated with late radiation toxicity can occur within several months or years, such as 2 months, 3 months, 4 months, 5 months, 6 months, 7 months, 8 months, 9 months, 10 months, 11 months, 1 year, 2 years, 3 years, or 4 years after the incident ionizing radiation exposure.

In some embodiments, one or more compounds, salts or compositions of this disclosure are useful in the treatment of Acute Radiation Syndrome (ARS), often referred to as radiation sickness. In humans, exposure to high doses of acute penetrating radiation can lead to the development of ARS. Depending on the radiation dose and extent of exposure, ARS can manifest as bone marrow syndrome, gastrointestinal syndrome, and cardiovascular (CV)/central nervous system (CNS) syndrome. ARS has three distinct stages—the prodromal phase, the latent asymptomatic phase, and the overt systemic illness phase. In some embodiments, one or more compounds, salts or compositions of this disclosure are useful in the treatment of the prodromal phase of ARS. In some embodiments, one or more compounds, salts or compositions of this disclosure are useful in the treatment of the latent asymptomatic phase of ARS. In some embodiments, one or more compounds, salts or compositions of this disclosure are useful in the treatment of the overt systemic illness phase of ARS.

In some embodiments, the one or more compounds, salts or compositions of this disclosure are useful in preventing, eliminating or alleviating one or more symptoms of ARS. In some embodiments, the one or more compounds, salts or compositions of this disclosure are useful in preventing, eliminating or alleviating one or more symptoms of ARS during the prodromal phase of ARS. In some embodiments, symptoms of ARS in the prodromal phase include, but are not limited to, nausea, vomiting, headache, diarrhea, loss of appetite, fatigue, fever, skin damage and hair loss.

In some embodiments, one or more compounds, salts or compositions are useful at preventing, eliminating or slowing the development of the overt systemic illness phase of ARS when administered during the latent phase of ARS.

In some embodiments, one or more compounds, salts or compositions of this disclosure are useful in preventing, eliminating or alleviating one or more symptoms of ARS during the overt systemic illness phase of ARS. In some embodiments, the overt systemic illness phase of ARS is associated with one or more of bone marrow syndrome, gastrointestinal syndrome or cardiovascular syndrome. The symptoms of bone marrow syndrome include, but are not limited to, anorexia, fever, malaise, drop in blood cell counts, infection and hemorrhage. In some embodiments, the overt systemic illness phase of ARS is associated with gastrointestinal syndrome. The symptoms of gastrointestinal syndrome include, but are not limited to malaise, anorexia, diarrhea, fever, dehydration, electrolyte imbalance, and infection. In some embodiments, the overt systemic illness phase of ARS is associated with cardiovascular syndrome. The symptoms associated with cardiovascular syndrome include, but are not limited to, diarrhea, convulsions and coma.

In some embodiments, the one or more compounds, salts or compositions of this disclosure are useful in the treatment of a toxicity or condition associated with acute radiation exposure. In some embodiments, the one or more compounds, salts or compositions of this disclosure are useful in the treatment of a toxicity or condition associated with chronic radiation exposure. Acute radiation exposure is short-term, high-level exposure that can occur from events such as a nuclear power plant accident, nuclear warfare, detonation of an explosive device that disperses radioactive material (dirty bomb), detonation of a nuclear weapon, the detonation of a small radioactive device, or space travel. Chronic radiation exposure is long-term, low-level exposure which can occur through events, such as, airplane travel, space travel, installation and/or decommissioning of nuclear reactors of naval vessels or land-based nuclear reactors, exposure to naturally occurring radioactive materials in the soil, water and vegetation, or exposure to small doses over time in the workplace such as, for example, medical professionals working with X-ray machines or researchers working with radioactive reagents, or regions contaminated by nuclear reactor accidents or terrorist attacks.

Astronauts are vulnerable to the enhanced levels of radiation present in outer space. Galactic cosmic rays are characterized by highly energetic and fully ionized nuclei. The charged particles within galactic cosmic rays are more damaging than terrestrial sources of radiation, and can lead to the development of, inter alia, severe and progressive cognitive defects and the development of neurological disorders such as premature aging, Alzheimer's disease and dementia (Parihar, V. K., ete al., "What happens to your brain on the way to Mars", Sci. Adv., 2015, no. 4, e1400256, DOI: 10.1126/sciadv.1400256; and Cucinotta, F. A., et al., "Space radiation risks to the central nervous system", *Life Sciences in Space Research*, 2014, 2, 54-69).

Another source of radiation exposure for astronauts is from the Sun in the form of solar flares or coronal mass ejections. Coronal mass ejections release large quantities of energetic protons and electromagnetic radiation. In some embodiments, one or more compounds, salts or compositions of this disclosure are useful in preventing, eliminating or reducing the development of cognitive disorders associated with exposure to ionizing radiation. In some embodiments, the ionizing radiation is one or more of galactic cosmic rays, chronic solar radiation, solar flares or coronal mass ejections. In some embodiments, the cognitive disorder is Alzheimer's disease or dementia. In some embodiments, one or more compounds, salts or compositions of this disclosure are useful in preventing, eliminating or reducing premature aging associated with exposure to ionizing radiation.

In some embodiments, one or more compounds, salts or compositions of this disclosure are useful in the treatment of individuals such as first-responders, nuclear power plant workers, pilots, flight attendants, and astronauts that have been exposed to high doses of radiation, acute and/or chronic, in the occupational setting. In some embodiments, one or more compounds, salts or compositions of the disclosure are useful in the treatment of emergency personnel such as policemen, firefighters, and military members that have been exposed to radiation while responding to an attack or accident involving radioactive material.

In some embodiments, one or more compounds, salts or compositions of the disclosure are useful in reducing the risk of tumor induction in a subject who has been exposed to, is being exposed to, or will be exposed to ionizing radiation. In some embodiments, the source of the ionizing radiation is nuclear warfare, a nuclear reactor, air travel, space travel, or radiation therapy. In one or more embodiments, one or more compounds, salts or compositions of the disclosure are administered to a subject in need thereof, before the subject has been exposed to ionizing radiation. In one or more embodiments, one or more compounds, salts or compositions of the disclosure are administered to a subject in need thereof, while the subject is being exposed to ionizing radiation. In one or more embodiments, one or more compounds, salts or compositions of the disclosure are administered to a subject in need thereof, after the subject has been exposed to ionizing radiation.

In some embodiments, the one or more compounds, salts or compositions of the disclosure are useful in reducing the risk of the development of cancer in a subject who has been exposed to, is being exposed to, or will be exposed to ionizing radiation. In some embodiments, the cancer is leukemia, lymphoma, rectal or colorectal cancer, breast cancer, prostate cancer, androgen-dependent prostate cancer, lung cancer, mesothelioma, head and neck cancer, esophageal cancer, gastric cancer, pancreatic cancer, gastrointestinal cancer, renal cell cancer, testicular cancer, ovarian cancer, germ cell cancer, glioma or any other primary, solid tumor or liquid tumor.

In some embodiments, one or more compounds, salts or compositions of the disclosure are useful in the treatment of subjects with cancer who are being treated, has been treated or will be treated with ionizing radiation or chemotherapy. In some embodiments, the cancer is a hematological cancer. In some embodiments, the cancer is bone cancer. In some embodiments, the cancer is leukemia. In some embodiments, the cancer is lymphoma, rectal or colorectal cancer, breast cancer, prostate cancer, androgen-dependent prostate cancer, lung cancer, mesothelioma, head and neck cancer, esophageal cancer, gastric cancer, pancreatic cancer, gastrointestinal cancer, renal cell cancer, testicular cancer, ovarian cancer, germ cell cancer, glioma or any other primary or solid tumor. In other embodiments, the subject suffers from a bone marrow disorder. In some embodiments, the subject has head and neck cancer.

In some embodiments, one or more compounds, salts or compositions of the disclosure are useful in treating or preventing a toxicity or condition associated with ionizing radiation in a subject with cancer who is also being treated with radiotherapy. In some embodiments, the radiotherapy is selected from gamma radiation, X-radiation, proton beam radiation, electron beam radiation or gamma radiation from cobalt-60 decay. In some embodiments, the radiotherapy is in the form of a radiopharmaceutical. In some embodiments, the radiopharmaceutical is selected from strontium-89, samarium-153 or radium-223.

In some embodiments, one or more compounds, salts or compositions of the disclosure are useful in reducing the risk of secondary tumor induction in a subject being treated with radiotherapy or chemotherapy. In some embodiments, one or more compounds, salts or compositions of the disclosure are useful in reducing the risk of secondary tumor induction in a subject being treated with radiotherapy. In some embodiments, one or more compounds, salts or compositions of the disclosure are useful in reducing the risk of secondary tumor induction in a subject being treated with chemotherapy.

In some embodiments, one or more compounds, salts or compositions of the disclosure are useful in treating or preventing a toxicity or condition associated with ionizing radiation in a subject with cancer who is also being treated with chemotherapy. In some embodiments, the chemotherapy is selected from the group consisting of cyclophosphamide, ifosfamide, etoposide, oxaliplatin, cisplatin, carboplatin, mechlorethamine, melphalan, chlorambucil, cyclophosphamide, streptozocin, carmustine, lomustine, bleomycin, busulfan, dacarbazine, doxorubicin, daunoubicin, temozolomide, thiotepa, altretamine, procarbaine, hexamethylmelamine, teniposide and mitoxantrone.

In another aspect, the one or more compounds, salts or compositions described herein are useful in selectively protecting normal tissues against the toxicities associated with ionizing radiation or chemotherapy. In some embodiments, one or more compounds, salts or compositions described herein are able to selectively protect normal tissues against the toxicities associated with ionizing radiation or chemotherapy with minimal adverse effects on the tumor response. Without wishing to be bound by theory, the ability of the phosphorylated prodrugs and double prodrugs of the disclosure to be metabolized to the active thiol form will be enhanced in healthy tissues as opposed to tumor tissues. This is due to the higher presence of alkaline phosphatase in healthy tissues versus tumor tissues. Therefore, the phosphorylated prodrugs and double prodrugs of the disclosure will be converted to their active thiol counterparts in healthy tissues to a greater extent than in tumor tissues, thus, protecting healthy tissues selectively over tumor tissues.

One or more compounds, salts or compositions described herein can be administered to cancer subjects receiving radiation therapy or chemotherapy. In some embodiments, administering one or more compounds, salts or compositions of the disclosure is useful in protecting the subjects against the toxicities or conditions associated with the exposure to the therapy. Such toxicities include, but are not limited to, bone marrow toxicity, central nervous system toxicity, immunological toxicity, neurotoxicity, nephrotoxicity, ototoxicity, cardiotoxicity, alopecia, peripheral neuropathy and mucositis. In some embodiments, the toxicities include xerostomia, infertility, pulmonary toxicity, and renal failure. In some embodiments, one or more compounds, salts or compositions described herein are able to protect tissues from the genotoxic and carcinogenic effects of radiation and certain forms of chemotherapy. In some embodiments, one or more compounds, salts or compositions described herein are able to protect tissues from radiation-induced fibrosis.

In some embodiments, one or more compounds, salts or compositions of the disclosure is useful as a cytoprotectant administered to cancer subjects in conjunction with therapeutic radiation or chemotherapy to ameliorate the harmful effects of ionizing radiation or chemotherapeutic agents to normal tissues.

In some embodiments, one or more compounds, salts or compositions of the disclosure are useful as a chemoprotectant administered to cancer subjects in conjunction with chemotherapy to ameliorate the harmful effects of chemotherapeutic agents to normal tissues.

In some embodiments, one or more compounds, salts or compositions of the disclosure are administered separately (before or after), sequentially or concurrently with a chemotherapeutic agent selected from the group consisting of cyclophosphamide, ifosfamide, etoposide, oxaliplatin, cisplatin, carboplatin, mechlorethamine, melphalan, chlorambucil, cyclophosphamide, streptozocin, carmustine, lomustine, bleomycin, busulfan, dacarbazine, doxorubicin, daunoubicin, temozolomide, thiotepa, altretamine, procarbaine, hexamethylmelamine, teniposide and mitoxantrone.

In some embodiments, one or more compounds, salts or compositions of the disclosure are useful as a radioprotectant administered to cancer subjects in conjunction with therapeutic radiation to ameliorate the harmful effects of ionizing radiation to normal tissues. In some embodiments, one or more compounds, salts or compositions of the disclosure are administered separately (before or after), sequentially or concurrently with radiotherapy, wherein the radiotherapy is selected from the group consisting of gamma radiation, X-radiation, proton beam radiation, electron beam radiation or gamma radiation from cobalt-60 decay. In some embodiments, one or more compounds or compositions of the disclosure are administered sequentially or concurrently with a radiopharmaceutical. In some embodiments, the radiopharmaceutical is selected from strontium-89, samarium-153 or radium-223.

In some embodiments, the subject being treated with one or more compounds, salts or compositions of the disclosure is a cancer subject. In some embodiments, the cancer is a hematological cancer. In some embodiments, the cancer is bone cancer. In some embodiments, the cancer is leukemia. In some embodiments, the cancer is lymphoma, rectal or colorectal cancer, breast cancer, prostate cancer, androgen-dependent prostate cancer, lung cancer, mesothelioma, head and neck cancer, esophageal cancer, gastric cancer, pancreatic cancer, gastrointestinal cancer, renal cell cancer, testicular cancer, ovarian cancer, germ cell cancer, glioma or any other primary or solid tumor. In other embodiments, the subject suffers from a bone marrow disorder. In some embodiments, the subject has head and neck cancer.

In some embodiments, the subject being treated with one or more compounds, salts or compositions of the disclosure is a cancer subject being treated with a chemotherapeutic agent, radiotherapy or both. In some embodiments, chemotherapeutic agent, radiotherapy or both are further combined with immunotherapy. In some embodiments the immunotherapy is selected from the group consisting of immune checkpoint inhibitors, T-cell transfer therapy, monoclonal antibodies, treatment vaccines and immune system modulators.

In some embodiments, one or more compounds, salts or compositions of the disclosure are useful in treating subjects suffering from diseases requiring bone marrow growth, such as myelodysplastic syndromes (MDS). In some embodiments, one or more compounds or compositions of the disclosure are useful in treating subjects in need of more rapid recovery of bone marrow function following chemotherapy. In some embodiments, one or more compounds, salts or compositions of the disclosure are useful in stimulating bone marrow production or function. In some embodiments, one or more compounds, salts or compositions of the disclosure are useful in preventing the development of or alleviating the existing symptoms of bone marrow dysfunction or prolonging the survival of the subject being treated.

In some embodiments, one or more compounds, salts or compositions of the disclosure are useful for treating or preventing radiation-induced cognitive impairment. Radiation-induced cognitive impairment has been reported to occur in up to 50-90% of adult cancer subjects with brain tumor who survive more than 6 months after undergoing whole-brain irradiation. Radiation-induced cognitive impairment is driven by oxidative stress and inflammatory responses. (Greene-Schloesser, D.; Robbins, M. E., "Radiation-induced cognitive impairment—from bench to bedside", *Neuro. Oncol.* 2012, 14, iv37-iv44). Without wishing to be bound by theory, treatment with a ROS scavenger will reduce the damaging effects caused by radiation-induced oxidative stress, and will prevent or alleviate the development of cognitive impairment in a subject that has been, will be or is being exposed to ionizing radiation.

In some embodiments, one or more compounds, salts or compositions of the disclosure are useful in the treatment of diseases or conditions associated with oxidative stress. Oxidative stress is caused by an imbalance between ROS and antioxidants, and can lead to the development of renal ischemia reperfusion injury, myocardial ischemia, spinal cord ischemia and reperfusion injury, ventilator induced lung injury, methotrexate-induced hepatoxicity, acute lung injury, Alzheimer's disease, Parkinson's disease, rheumatoid arthritis, myocardial infarction, cardiovascular disease, septic shock, chronic inflammation, Friedreich ataxia, Leber's hereditary optic neuropathy, myoclonus epilepsy, ragged red fiber disease, Mitochondrial Encephalopathy, Lactic Acidosis and Stroke (MELAS), COVID-19-associated cytokine storm, COVID-19-associated multisystem inflammatory syndrome in children (MIS-C), or post-COVID-19 SARS-CoV-2-induced autoimmunity (see Uttara et al., Oxidative Stress and Neurodegenerative Diseases: A Review of Upstream and Downstream Antioxidant Therapeutic Options, *Current Neuropharmacology,* 2009, Vol. 7, pp 65-74; Akbulut, S, et al, Cytoprotective effects of amifostine, ascorbic acid and N-acetylcystine against methotrexate-induced hepatoxicity in rats, *World J. Gastroenterol,* 2014, Vol. 20(9), pp 10158-10165; Fu, P., et al, Amifostine reduces lung vascular permeability via suppression of inflammatory signaling, *Eur. Respir. J,* 2009, Vol. 33(3), pp 612-624; Chronidou, F., et al, Beneficial effect of the oxygen free radical scavenger amifostine (WR-2721) on spinal cord ischemia/reperfusion injury in rabbits, *Thorac. Cardiovasc. Surg.,* 2009, Vol. 4(50), doi: 10.1186/1749-8090-4-50; Chok, M. K., et al, Renoprotective potency of amifostine in rat renal ischaemia-reprfusion, *Nephro Dial Translplant,* 2010, Vol 25, pp 3845-3851; and Wu, S., et al, Amifostine Pretreatment Attenuates Myocardial Ischemia/Reperfusion Injury by Inhibiting Apoptosis and Oxidative Stress, *Oxid. Med. Cell. Longev.,* 2017, doi: 10.1155/2017/4130824). Without wishing to be bound by theory, the compounds, salts and compositions of the disclosure reduce the adverse effects associated with oxidative stress caused by ROS.

In some embodiments, one or more compounds, salts or compositions of the disclosure are useful for slowing the rate of the aging process in a subject. Without wishing to be bound by theory, the accumulation of free radical damage to cells over time contributes to the aging process. The compounds, salts or compositions of the disclosure are useful as ROS scavengers and reduce the amount of damage to cells caused by ROS over time. This reduction in ROS associated cell damage slows the overall rate of aging and improves the health span of the subject.

In some embodiments, one or more compounds, salts or compositions of the disclosure are useful for treating or preventing COVID-19-associated cytokine storm, COVID-19-associated multisystem inflammatory syndrome in children (MIS-C), and post-COVID-19 SARS-CoV-2-induced autoimmunity. In some embodiments, one or more compounds, salts or compositions of the disclosure are useful for treating or preventing COVID-19-associated cytokine storm. In some embodiments, one or more compounds, salts or compositions of the disclosure are useful for treating or preventing COVID-19-associated multisystem inflammatory syndrome in children (MIS-C). In some embodiments, one or more compounds, salts or compositions of the disclosure are useful for treating or preventing post-COVID-19 SARS-CoV-2-induced autoimmunity.

Animal and Cell Models

For any compound, salt or composition described herein, the therapeutically effective or protective amount can be initially estimated from cell culture assays. In some embodiments, one or more compounds, salts or compositions of the disclosure can be used as research reagents and delivered to animals to understand bioactivity, enzymatic activity, gene expression, interactions with other molecules, and impacts on animal physiology in healthy or diseased animals or cells.

In some embodiments, healthy or diseased cells are contacted with one or more compounds, salts or compositions of the disclosure. In some embodiments, one or more compounds, salts or compositions of the disclosure can be formulated in animal models to achieve a circulating concentration range of compound, and/or a metabolite thereof, that includes an effective concentration as determined in cell culture. Such information can be used to more accurately determine useful doses in humans (Washburn, LC., Rafter, J J., and Hayes, R L (1976). Prediction of the Effective Radioprotective Dose of WR-2721 in Humans Through an Interspecies Tissue Distribution Study. Radiat. Res. 66:100-105).

In some embodiments, therapeutically or protective effective amounts of the compounds, salts or compositions of the disclosure for use in humans can also be estimated from animal models. For example, animal models can be used to develop a dose response curve that can be used to determine an effective or protective circulating concentration of the compounds and/or metabolites described herein. Based on those studies, a dose for humans can be formulated that achieves an efficacious circulating concentration.

EQUIVALENTS

The foregoing description and following examples detail certain specific embodiments of the disclosure and describe the best mode contemplated by the inventors. It will be appreciated, however, that no matter how detailed the foregoing may appear in text, the disclosure may be practiced in many ways and the disclosure should be construed in accordance with the appended claims and any equivalents thereof.

Although the disclosed teachings have been described with reference to various applications, methods, compounds, salts, and compositions, it will be appreciated that various changes and modifications can be made without departing from the teachings herein. The following examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

EXAMPLES

The following examples illustrate the synthesis of various compounds and salts according to the present disclosure. The skilled worker will readily appreciate that the following examples are merely illustrative and can be modified according to methods and techniques commonly known in the art.

One skilled in the art will recognize that in some cases, the compounds described herein can exist as a mixture of diastereomers and/or enantiomers. The skilled worker will also appreciate that such isomers may be separated at various stages of their synthesis using conventional techniques, or a combination of such techniques, such as, but not limited to, crystallization, normal phase chromatography, reverse phase chromatography, and chiral chromatography, to afford single enantiomers of the compounds described herein.

Example 1: Synthesis of di-tert-butyl (2-(mercaptomethyl)propane-1,3-diyl)bis (methylcarbamate) (PrC-210-Boc2)

Scheme 5. Proposed synthesis of the intermediate di-tert-butyl (2-(mercaptomethyl)propane-1,3-diyl)bis (methylcarbamate) (PrC-210-Boc2)

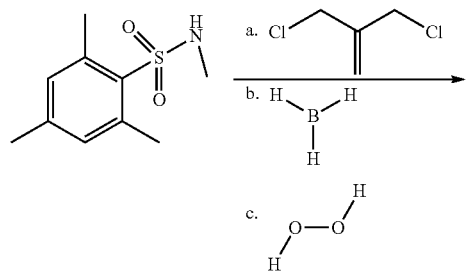

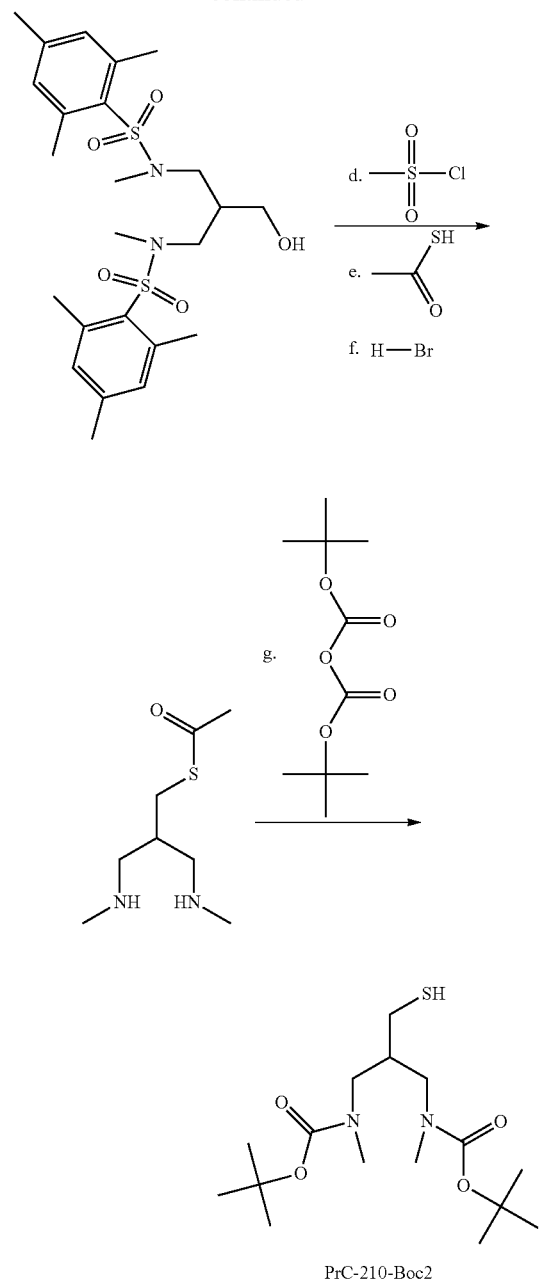

Intermediate PrC-210-Boc2 is synthesized according to Scheme 5. Double chloride displacement from 3-chloro-2-(chloromethyl)prop-1-ene with two equivalents of N-methyl mesitylene-sulfonamide followed by hydroboration-oxidation generates the corresponding sulfonamide alcohol. The alcohol is converted to a sulfonate ester upon addition of mesyl chloride to the reaction mixture. Subsequent treatment with thioacetic acid followed by deprotection of the amine under acidic conditions generates the deprotected thioate derivative. The tert-butoxycarbonyl (Boc) protected compound (PrC-210-Boc2) is then synthesized upon treatment with di-tert-butyl decarbonate. For exemplary reaction conditions, see Copp, R. R.; Peebles, D. D.; Fahl, W. E., Bioorg. Med. Chem. Lett., 2011, Vol. 21(24), pp 7426-7430; and US2014/107216.

Example 2: Synthesis of intermediate di-tert-butyl (2-((phosphonothio)methyl)propane-1,3-diyl)bis(methylcarbamate) (PrC-210-PT-Boc2)
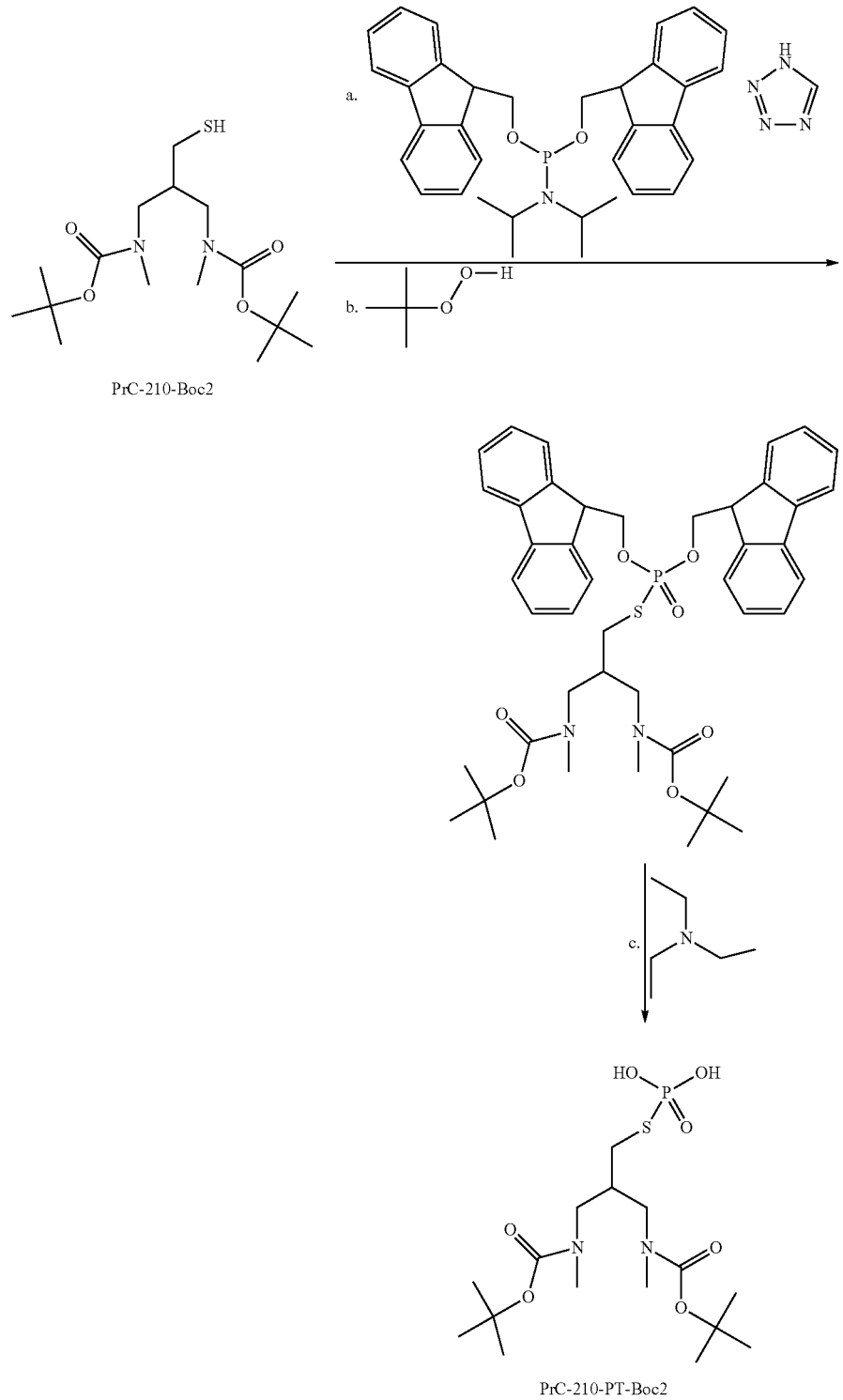
Scheme 6. Synthesis of intermediate di-tert-butyl (2-((phosphonothio)methyl)propane-1,3-diyl)bis(methylcarbamate) (PrC-210-PT-Boc2).

Intermediate PrC-210-PT-Boc2 is synthesized according to the procedure summarized in Scheme 6. Phosphorylation of PrC-210-Boc2 is afforded upon treatment with bis(9H-fluoren-9-ylmethyl)-diisopropylamidophosphite followed by oxidation with t-butyl hydroperoxide. Subsequent deprotection under basic conditions affords intermediate PrC-210-PT-Boc2. For exemplary reaction conditions, see Dorfmueller, H. C.; Borodkin, V. S.; Blair, D. E.; Pathak, S; Navratilova, I.; Van Aalten, D. M. F.; *Amino Acids,* 2011, Vol. 40, pp 781-792.

Example 3: Synthesis of compound 1—{[3-(methylamino)-2-[(methylamino)methyl]propyl]sulfanyl} phosphonic acid (PrC-210-PT)

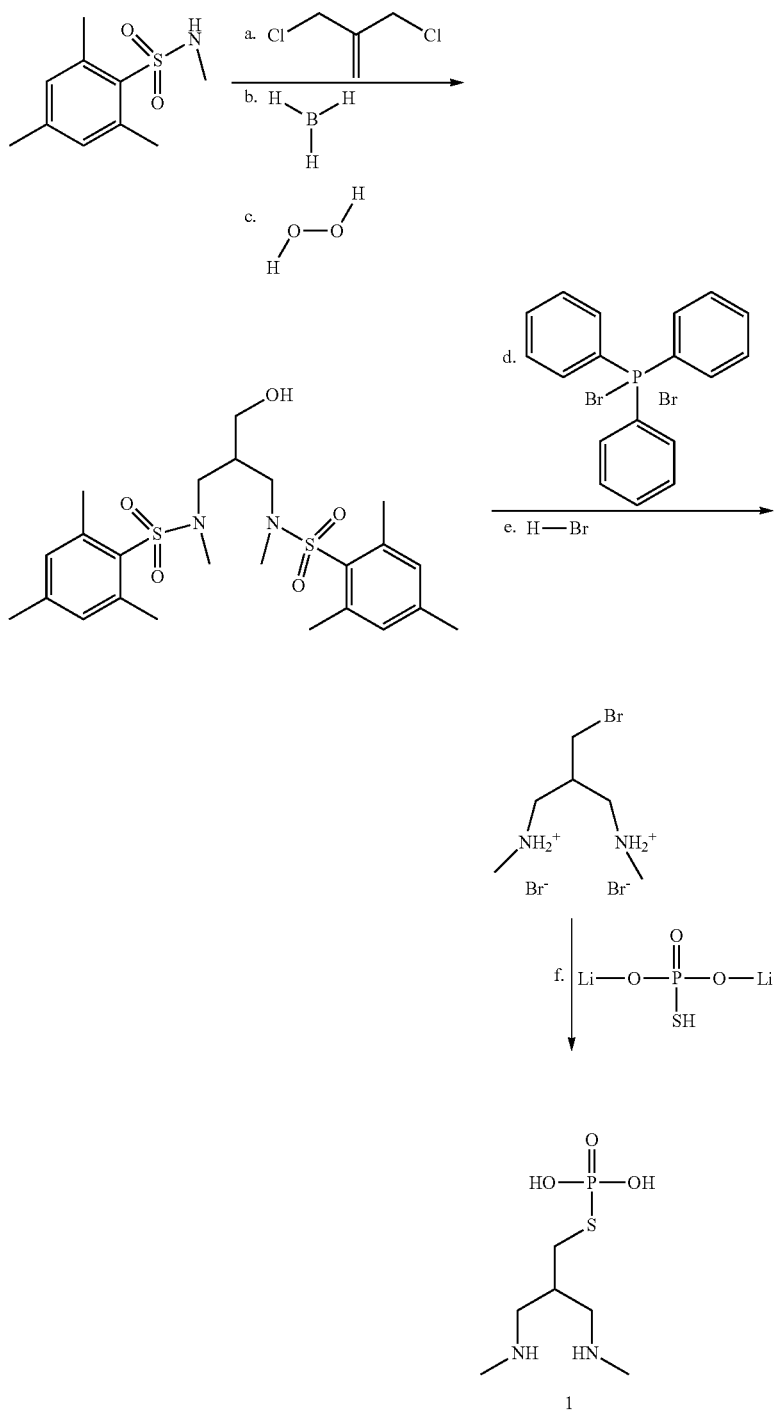

Scheme 7. Proposed synthesis of{[3-(methylamino)-2-[(methylamino)methyl]propyl]sulfanyl}phosphonic acid (PrC-210-PT, compound 1).

Compound 1 is synthesized as depicted in Scheme 7. Double chloride displacement from 3-chloro-2-(chloromethyl)prop-1-ene with two equivalents of N-methyl mesitylene-sulfonamide followed by hydroboration furnishes the corresponding sulfonamide alcohol. The alcohol is converted to the corresponding bromide upon treatment with triphenylphosphine dibromide. Subsequent addition of lithium thiophosphate affords compound 1 (PrC-210-PT). For exemplary reaction conditions see Laval, J. D.; Roman V; Laduranty, J.; Miginiac, L.; Lion, C.; et al., *Eur. J. Med. Chem.,* 1993, Vol. 28 (9), pp 709-714; Carrol, F. I.; Gopinathan, M. B.; Philip, A., *J Med. Chem.* 1990, Vol. 33(9), pp 2501-2508; Copp, R. R.; Peebles, D. D.; Fahl, W. E., *Bioorg. Med. Chem. Lett.,* 2011, Vol. 21(24), pp 7426-7430; Moene, W.; Vos, M.; Schakel, M.; De Kanter, F. J. J; Schmitz, R. F.; Klumpp, G. W., *Eur. J. Chem.,* 2000, Vol 6(2), pp 225-236.

Compound 13 is synthesized in an analogous manner to compound 1 using N-ethyl-2,4,6-trimethylbenzenesulfonamide as a starting material.

Example 4: Alternative Synthesis of Compound 1

Scheme 8. Alternative synthesis of compound 1.

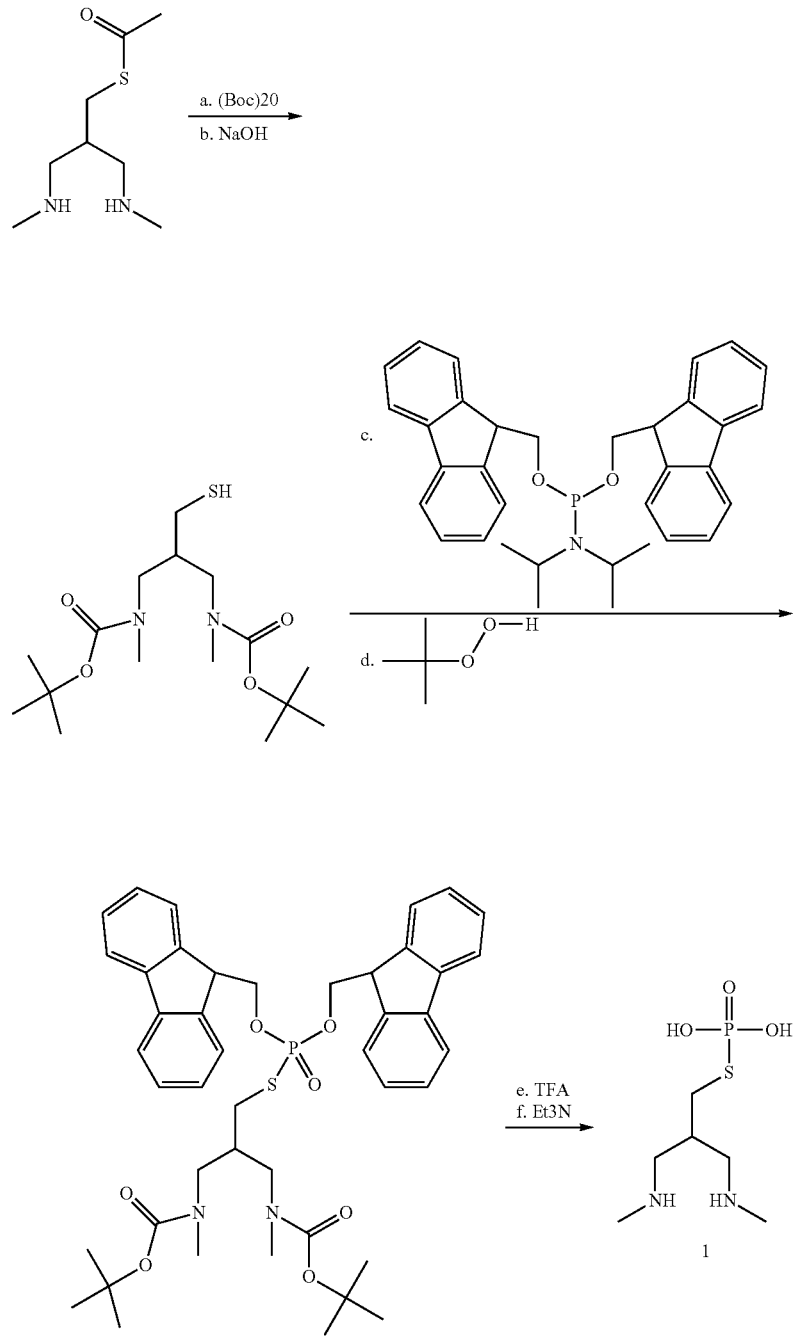

The synthesis of compound 1 is alternatively accomplished as depicted by Scheme 8. The PrC-210-thioacetate derivative is synthesized as shown in Scheme 5. Subsequent treatment with di-tert-butyl decarbonate affords the N-Boc protected thioester. Hydrolysis of the thioester upon the addition of NaOH to the reaction mixture affords the corresponding N-Boc protected thiol. S-phosphorylation of the thiol is achieved by the addition of bis(9H-fluoren-9-ylmethyl)-diisopropylamidophosphite followed by oxidation with t-butyl hydroperoxide. Deprotection of the amine with trifluoroacetic acid followed by deprotection of the phosphonate under basic conditions furnishes compound 1 (PrC-210-PT). For exemplary reaction conditions see Dorfmueller, H. C.; Borodkin, V. S.; Blair, D. E.; Pathak, S; Navratilova, I.; Van Aalten, D. M. F.; *Amino Acids*, 2011, Vol. 40, pp 781-792.

Example 5: Alternative Synthesis of PrC-210-PT

Scheme 9. Proposed synthesis of {[3-(methylamino)-2-[(methylamino)methyl]propyl]sulfanyl}phosphonic acid (PrC-210-PT).

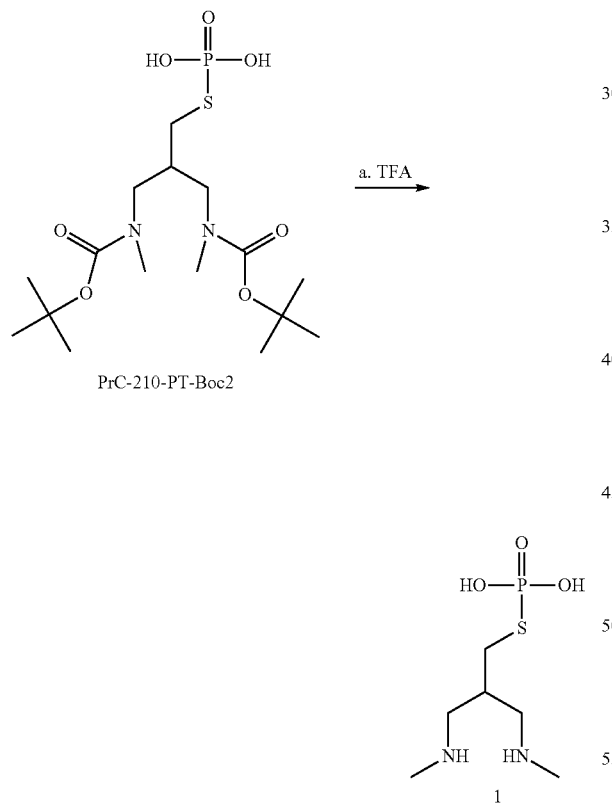

Compound 1 is alternatively synthesized according to Scheme 9. Intermediate PrC-210-PT-Boc2 is synthesized as shown in Scheme 6. Subsequent deprotection upon treatment with trifluoro acetic acid affords PrC-210-PT (compound 1). For exemplary reaction conditions, see WO2019/34866 A1.

Example 6: Synthesis of compound 2—({[(benzoyloxy)methoxy]({[3-(methylamino)-2-[(methylamino)methyl]propyl]sulfanyl}) phosphoryl}oxy)methyl benzoate (PrC-210-PT-BzOM)

Scheme 10. Synthesis of compound 2: ({[(benzoylox)methoxy]({[3-(methylamino)-2-[(methylamino)methyl]propyl]sulfanyl})phosphoryl}oxy)methyl benzoate (PrC-210-PT-BzOM).

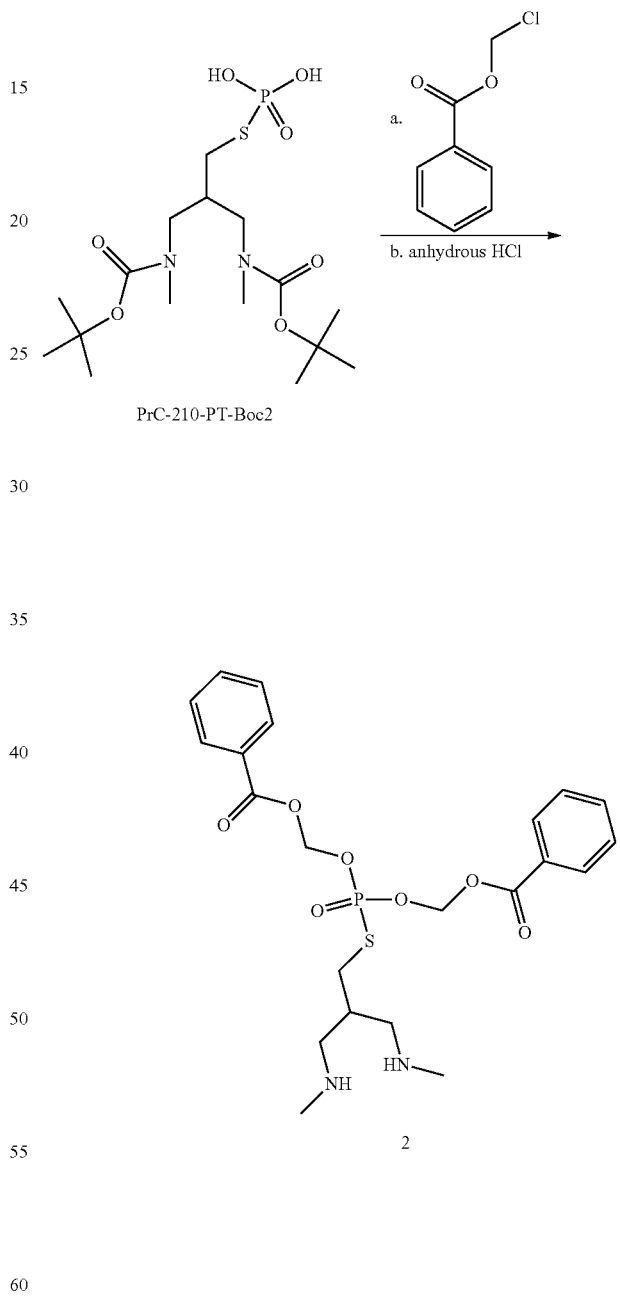

Compound 2 is synthesized according to Scheme 10. Intermediate PrC-210-PT-Boc2 is synthesized according to Scheme 6. Subsequent treatment with acyloxymethyl chloride followed by Boc deprotection affords compound 2 (PrC-210-PT-BzOM). For exemplary reaction conditions, see Ponaire, S., et al., Eur. J. Med. Chem., 2012, Vol. 51, pp. 277-285 and WO2009/69100.

Example 7: Synthesis of compound 3—]—[({1-[(2,2-dimethylpropanoyl)oxy]ethoxy}({[3-(methylamino)-2-[(methylamino)methyl] propyl]sulfanyl})phosphoryl)oxy]ethyl 2,2-dimethylpropanoate (PrC-210-PT-POE)

Example 8: Synthesis of compound 4:-bis{4-[(2,2-dimethylpropanoyl)sulfanyl]butyl} {[3-(methylamino)-2-[(methylamino)methyl]propyl]sulfanyl}phosphonate (PrC-210-PT-PivTB)

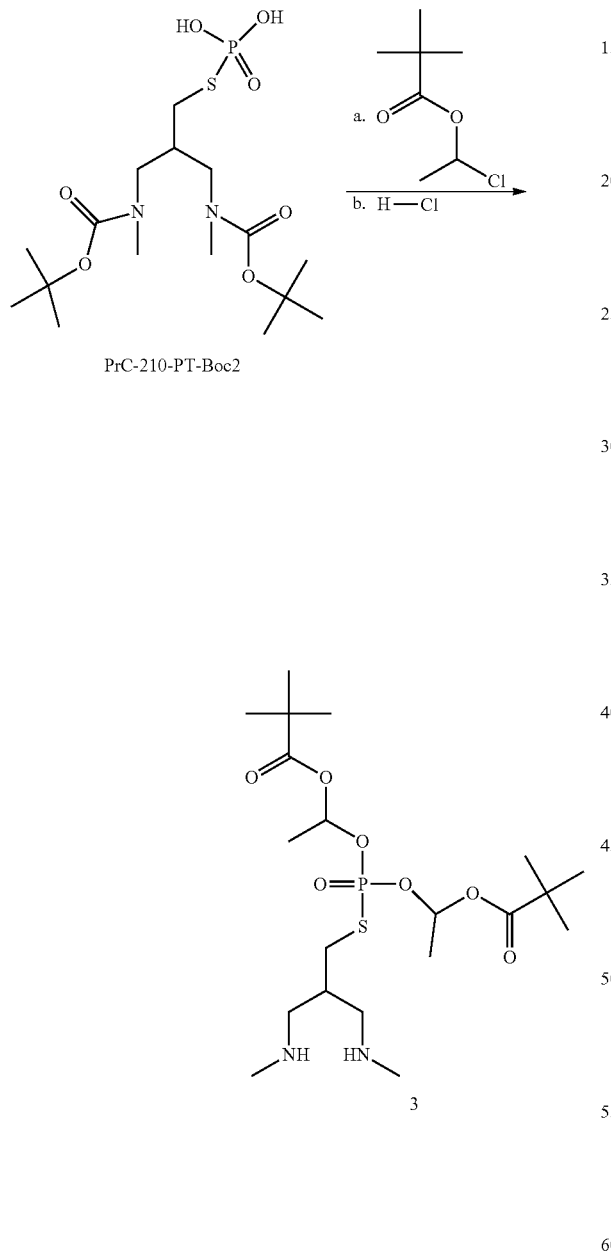

Scheme 11. Synthesis of compound 3: 1-[({1-[(2,2dimethylpropanoyl)oxy]ethoxy}({[3-(methylamino)-2-[(methylamino)methyl] propyl]sulfanyl})phosphoryl)oxy]ethyl 2,2-dimethylpropanoate (PrC-210-PT-POE)

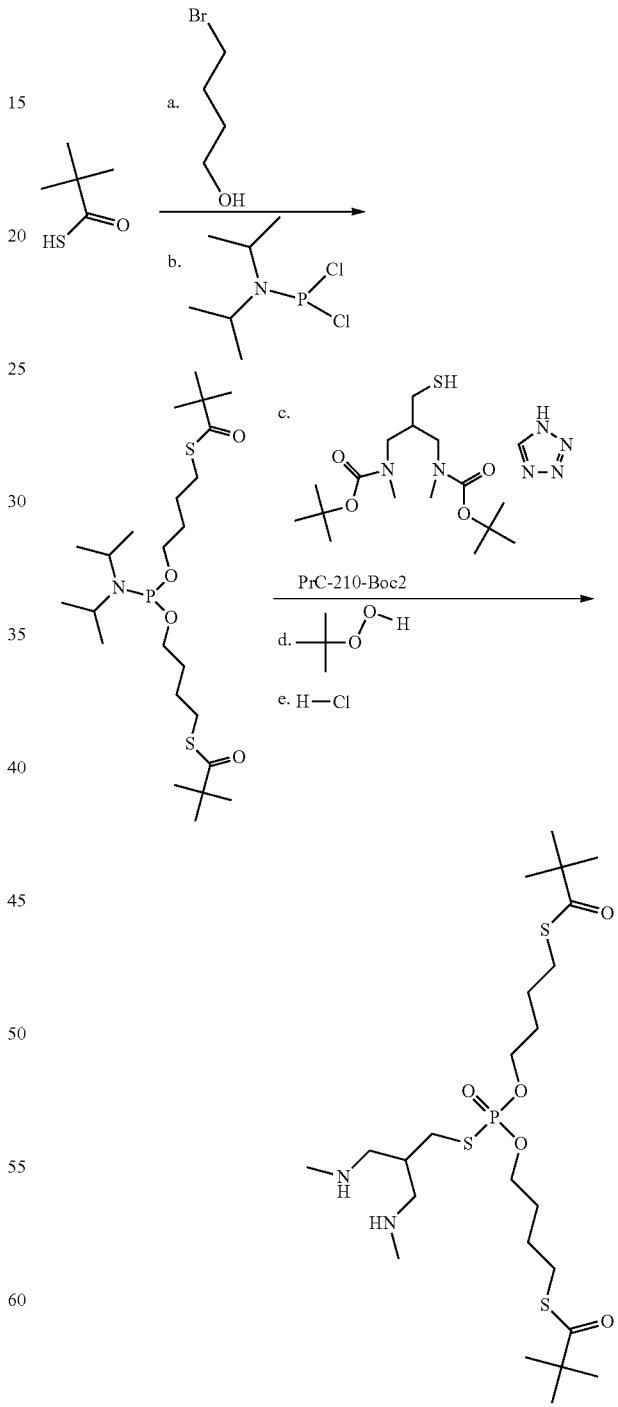

Scheme 12. Synthesis of compound 4: bis{4-[(2,2-dimethylpropanoyl)sulfanyl]butyl} {[3-(methylamino)-2-[(methylamino)methyl]propyl]sulfanyl}phosphonate (PrC-210-PT-PivTB).

Compound 3 is synthesized as shown in Scheme 11. Intermediate PrC-210-PT-Boc2 is synthesized according to Scheme 6. Subsequent treatment with 1-chloroethyl pivalate followed by Boc deprotection affords compound 3 (PrC-210-PT-POE). For exemplary reaction conditions see WO2009/69100 and CN108948084.

Compound 4 is synthesized as shown in Scheme 12. Nucleophilic substitution of 4-bromobutan-1-ol with 2,2-dimethylpropanethioic S-acid affords S-(4-hydroxybutyl) 2,2-dimethylpropanethioate. Addition of 1,1-dichloro-N,N-diisopropylphosphanamine to the reaction mixture affords S,S'-((((diisopropylamino)phosphanediyl) bis(oxy))bis(butane-4,1-diyl))bis(2,2-dimethylpropanethioate).

Intermediate PrC-210-Boc2 is synthesized according to Scheme 5. PrC-210-Boc2 is phosphorylated in the presence of tetrazole upon treatment with S,S'—((((diisopropylamino)phosphanediyl) bis(oxy))bis(butane-4,1-diyl)) bis(2, 2-dimethylpropanethioate) followed by oxidation with t-butyl hydroperoxide. Boc deprotection under acidic conditions affords compound 4 (PrC-210-PT-PivTB). For exemplary reaction conditions, see Egron,et. al., *Nucleosides and Nucleotides,* 1998, Vol. 17, pp 1725-1729, and Knapp, S., et al., *J. Org. Chem.,* 2002, 67(9), pp 2995-2999.

Compound 12 (PrC-210-PT-PivTP) is synthesized in an analogous manner to compound 4 (PrC-210-PivTB) using the appropriate starting materials.

Example 9: Synthesis of compound 5: bis{4-[(2,2-dimethylpropanoyl)sulfanyl]butyl}[3-(methylamino)-2-[(methylamino)methyl]propyl]sulfanyl}phosphonate (PrC-210-PT-POCE)

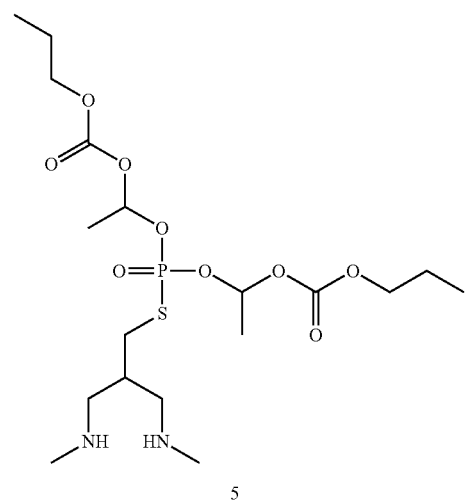

5

Compound 5 is synthesized according to Scheme 13. Intermediate PrC-210-PT-Boc2 is synthesized according to Scheme 6. Subsequent treatment with 1-chloroethyl propyl carbonate followed by Boc deprotection affords PrC-210-PT-POCE. For exemplary reaction conditions see US2017/233429 and CN108948084.

Example 10: Synthesis of compound 6: bis{4-[(2,2-dimethylpropanoyl)sulfanyl]butyl}[[3-(methylamino)-2-[(methylamino)methyl]propyl]sulfanyl}phosphonate (PrC-210-PT-POC)

Scheme 13. Synthesis of compound 5: bis{4-[(2,2-dimethylpropanoyl)sulfanyl]butyl}{[-3-(methylamino)-2-[(methylamino)methyl]propyl]sulfanyl}phosphonate (PrC-210-PT-POCE).

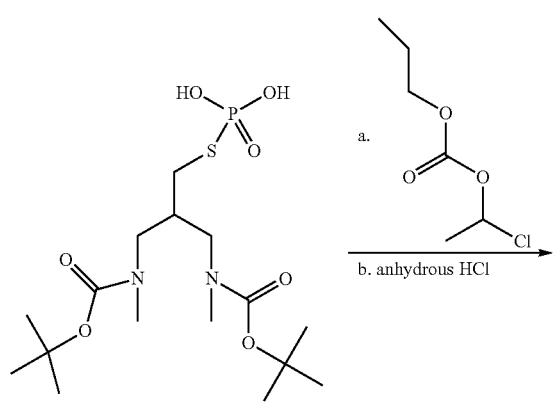

PrC-210-PT-Boc2

Scheme 14. Synthesis of compound 6: {4-[(2,2-dimethylpropanoyl)sulfanyl]butyl}{[-3-(methylamino)-2-[(methylamino)methyl]propyl]sulfanyl}phosphonate (PrC-210-PT-POC).

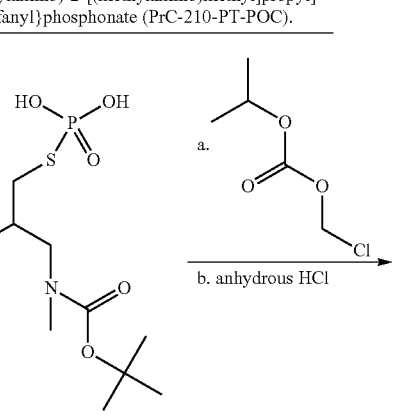

PrC-210-PT-Boc2

127

-continued

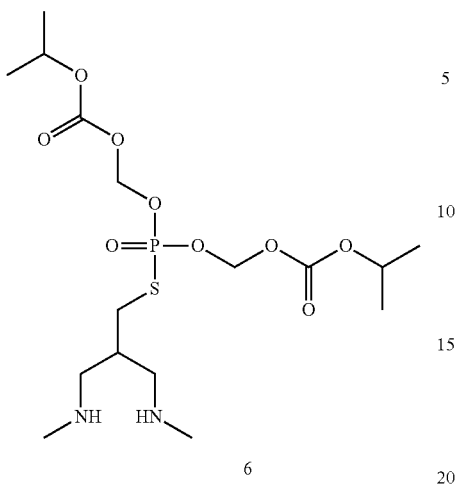

6

Compound 6 is synthesized as shown in Scheme 14. Intermediate PrC-210-PT-Boc2 is synthesized according to Scheme 6. Subsequent treatment with chloromethyl isopropyl carbonate followed by Boc deprotection affords compound 6 (PrC-210-PT-POCE). For exemplary reaction conditions, see Majer, et al., *J. Med. Chem.*, 2016, 59, pp 2810-2819, and CN108948084.

Example 11: Synthesis of compound 7: 4-(3-chlorophenyl)-2-{[3-(methylamino)-2-[(methylamino)methyl]propyl]sulfanyl}-1,3,215-dioxaphosphinan-2-one (PrC-210-PT-ClDOxP)

Scheme 15. Synthesis of compound 7 (PrC-210-PT-ClDOxP).

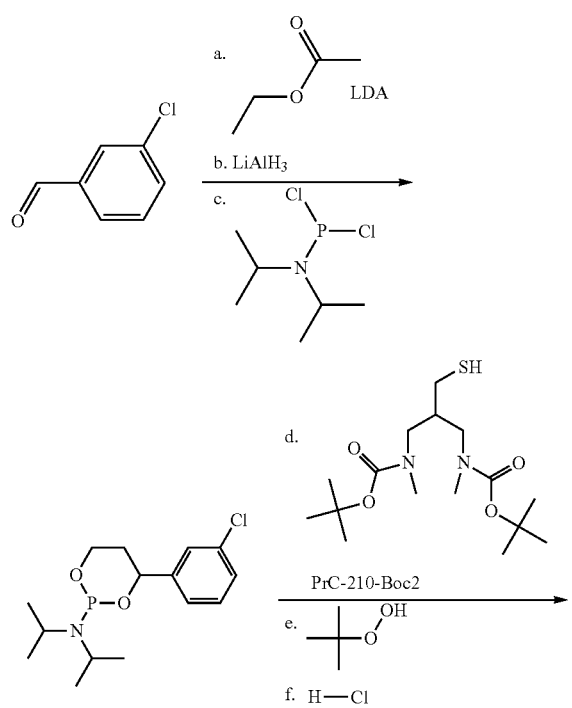

128

-continued

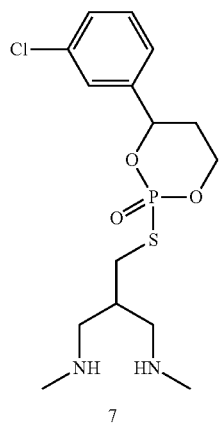

7

Compound 7 is synthesized as shown in Scheme 15. An Aldol addition between 3-chlorobenzaldehyde and ethyl acetate in the presence of lithium di-iso-propyl amine (LDA) affords ethyl 3-(3-chlorophenyl)-3-hydroxypropanoate. Subsequent reduction with lithium aluminum hydride followed by treatment with 1,1-dichloro-N,N-diisopropylphosphanamine results in the corresponding 1,3,2-dioxaphosphinane derivative.

Intermediate PrC-210-Boc2 is prepared according to Scheme 5. PrC-210-Boc2 is phosphorylated upon treatment of with the 1,3,2-dioxaphosphinane derivative followed by oxidation with t-butyl hydroperoxide. Subsequent Boc deprotection under acidic conditions affords compound 7 (PrC-210-PT-ClDOxP). For exemplary reaction conditions, see Erion, et al., JACS, 2004, 126, pp 5154-5163 and Knapp, S., et al, *J. Org. Chem.*, 2002, 67(9), pp 2995-2999.

Example 12: Synthesis of compound 8: 2-{[3-(methylamino)-2-[(methylamino)methyl]propyl]sulfanyl}-4-(2-methylpyridin-3-yl)-1,3,2 15-dioxaphosphinan-2-one (PrC-210-PT-PyDOxP)

Scheme 16. Synthesis of compound 8 (PrC-210-PT-PyDOxP)

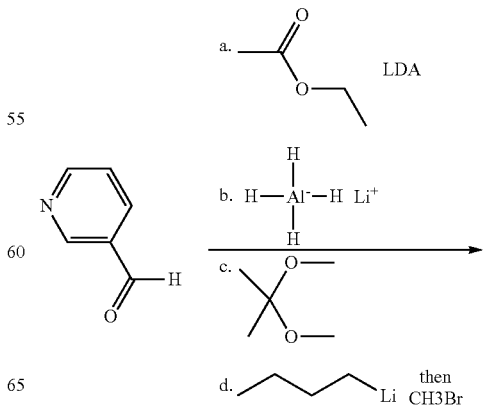

129

-continued

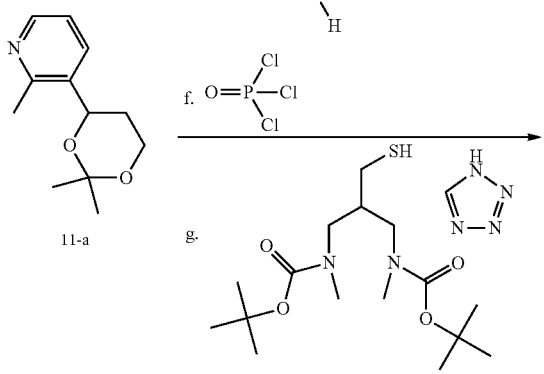

130

Example 13: Synthesis of Appropriate Starting Materials for Compounds 9, 10 and 11 (PrC-210-PT-PivTB2, Prc-210-PT-PivTB3 and Prc-210-PT-PivTB4)

Scheme 17. Synthesis of appropriate thioate precursor (PivTB2) for the synthesis of compound 9 (PrC-210-Pt-PivTB2).

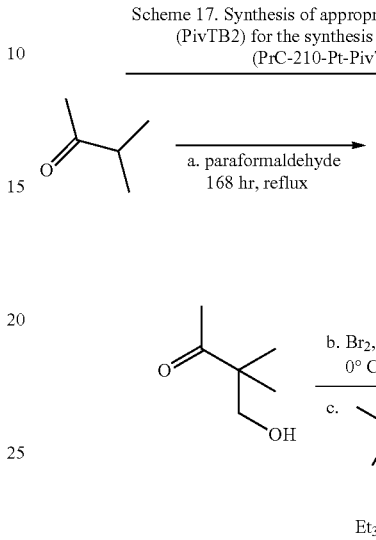

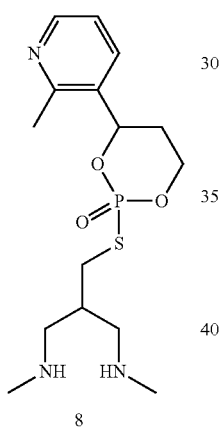

8

Compound 8 is synthesized as shown in Scheme 16. An Aldol addition reaction between pyridine-3-carboxaldehyde and ethyl acetate in the presence of lithium di-iso-propyl amine (LDA) affords ethyl 3-hydroxy-3-(2-methylpyridin-3-yl)propanoate. Subsequent reduction with lithium aluminum hydride produces the corresponding diol. The diol is next reacted with 2,2-dimethoxypropane to furnish the isopropylidene derivative. Treatment with n-butyl lithium to selectively deprotonate the 2-position using the ortho-directing activity of the 1,3-dioxane ring and reaction with bromomethane affords intermediate 11-a.

Intermediate 11-a is next converted to the corresponding diol under acidic conditions. Subsequent addition of phosphoryl chloride furnishes the dioxaphosphinane derivative. Subsequent Boc deprotection affords compound 8. For exemplary reaction conditions, see Tsukada, et al, *Bioorganic and Medicinal Chemistry Letters*, 2010, 20, pp 2938-2941 and Eliel, et al, *J Am. Chem. Soc.*, 1986, pp 6651.

3-methylbutan-2-one is refluxed with paraformaldehyde to afford 4-hydroxy-3,3-dimethylbutan-2-one. Subsequent bromination followed by nucleophilic substitution upon treatment with 2,2-dimethylpropanethioic S-acid in the presence of triethylamine furnishes the corresponding thioate (PivTB2). For exemplary reaction conditions, see Kiuru, E.; Ahmed, Z.; Lonnberg, H.; Beigelman, L.; Ora, M, *J Org. Chem.*, 2012, Vol. 78(3), p. 950-959.

Scheme 18. Synthesis of appropriate precursor (PivTB3) for the synthesis of compound 10 (PrC-210-Pt-PivTB3).

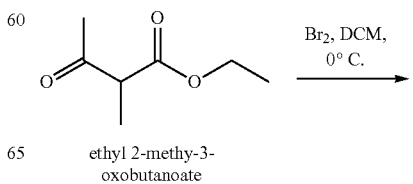

ethyl 2-methy-3-oxobutanoate

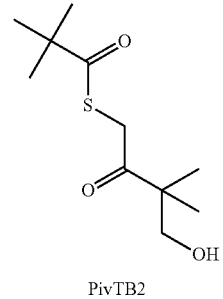

PivTB2

-continued

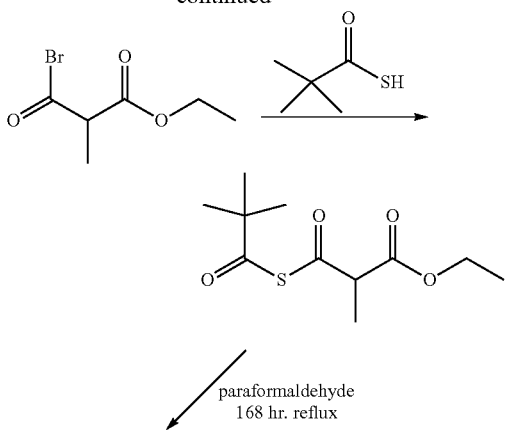

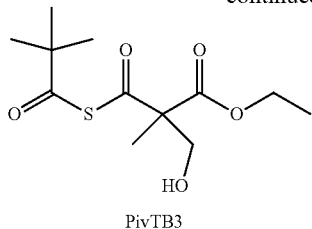

PivTB3

Bromination of ethyl 2-methyl-3-oxobutanoate followed by nucleophilic substitution with thioacetic acid furnishes the corresponding thioanhydride. Reflux of the thioanhydride with paraformaldehyde affords the alcohol (PivTB3). For exemplary reaction conditions, see Kiuru, E.; Ahmed, Z.; Lonnberg, H.; Beigelman, L.; Ora, M, J. Org. Chem., 2012, Vol. 78(3), p. 950-959.

Scheme 19. Synthesis of appropriate precursor (PivTB4) for the synthesis of compound 11 (PrC-210-Pt-PivTB4).

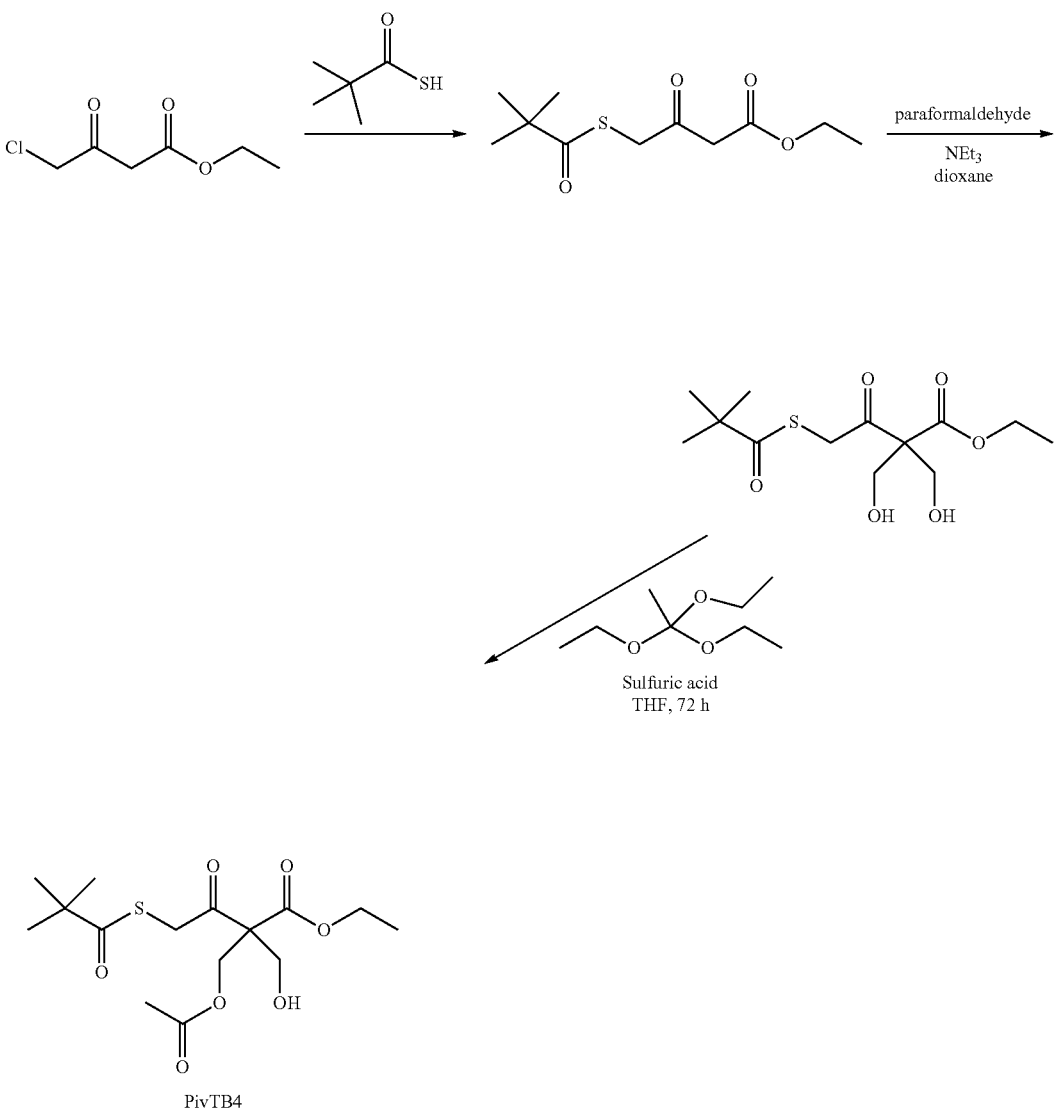

PivTB4

Nucleophilic substitution of ethyl 4-chloro-3-oxobutanoate with 2,2-dimethylpropanethioic S-acid affords the corresponding thioate derivative. Reflux of the thioate derivative with paraformaldehyde in the presence of triethyl amine furnishes the diol intermediate. Subsequent Johnson-Claisen rearrangement upon treatment of the diol with 1,1,1-triethoxyethane generates the precursor (PivTB4). For exemplary reaction conditions, see Kiuru, E.; Loennberg, H.; Ora, M. Helv. Chim., 2013, Vol. 96(11), p. 1997-2008 and US2008/125483.

Example 14: Synthesis of compound 9: {4-[(2,2-dimethylpropanoyl)sulfanyl]-2,2-dimethyl-3-oxobutoxy}({[3-(methylamino)-2-[(methylamino)methyl]propyl]sulfanyl})phosphinic acid (PrC-210-PivTB2)

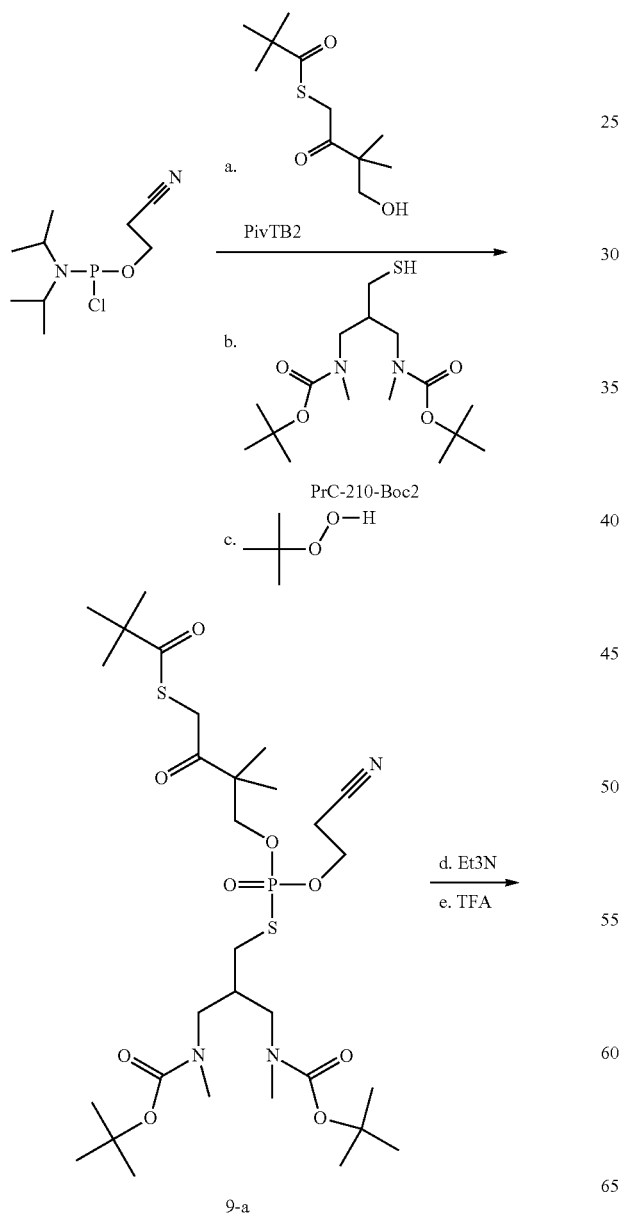

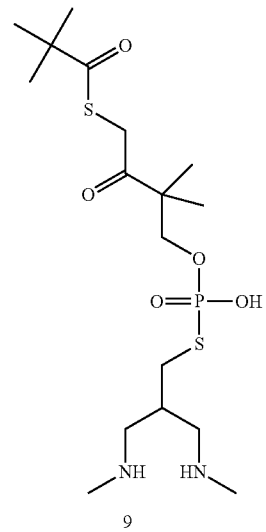

Compound 9 (PrC-210-PivTB2) is prepared according to Scheme 20. Treatment the appropriate precursor (PivTB2, Example 13) with 3-((chloro(diisopropylamino) phosphaneyl)oxy)propanenitrile affords the corresponding phosphane derivative. Subsequent treatment of PrC-210-Boc2 (Scheme 5) with the phosphane derivative followed by oxidation with tert-butyl hydroperoxide furnishes intermediate 9-a. Cyanoethyl deprotection with triethylamine followed by Boc deprotection with anhydrous trifluoroacetic acid affords compound 9. For exemplary reaction conditions, see Romanucci, V., et al., Bioorg. Med. Chem. 2014, Vol. 22(3), pp. 960-966; Kulesza, A., Frank, C. G.; Aebi, M.; Vasella, A., Helv. Chim., 2004, Vol. 87(12), pp. 3106-3118; Bazin, H. G.; Bess, L. S.; Livesay, M. T.; Mwakwari, S. C.; Johnson, D. A., Tetrahedron Lett., 2016, Vol. 57(19), pp. 2063-2066; and U.S. Pat. No. 6,949,528 B1

Compounds 10 and 11 will be synthesized in an analogous manner to compound 9 using the appropriate precursors, i.e., PivTB3 and PivTB4 (Example 13).

Example 15: Synthesis of compound 14: 1-{[(1-{[2-(2-methoxyethoxy)acetyl]oxy}ethoxy)({[3-(methylamino)-2-[(methylamino)methyl]propyl]sulfanyl})phosphoryl]oxy}ethyl 2-(2-methoxyethoxy)acetate (PrC-210-PT-PEGOE1)

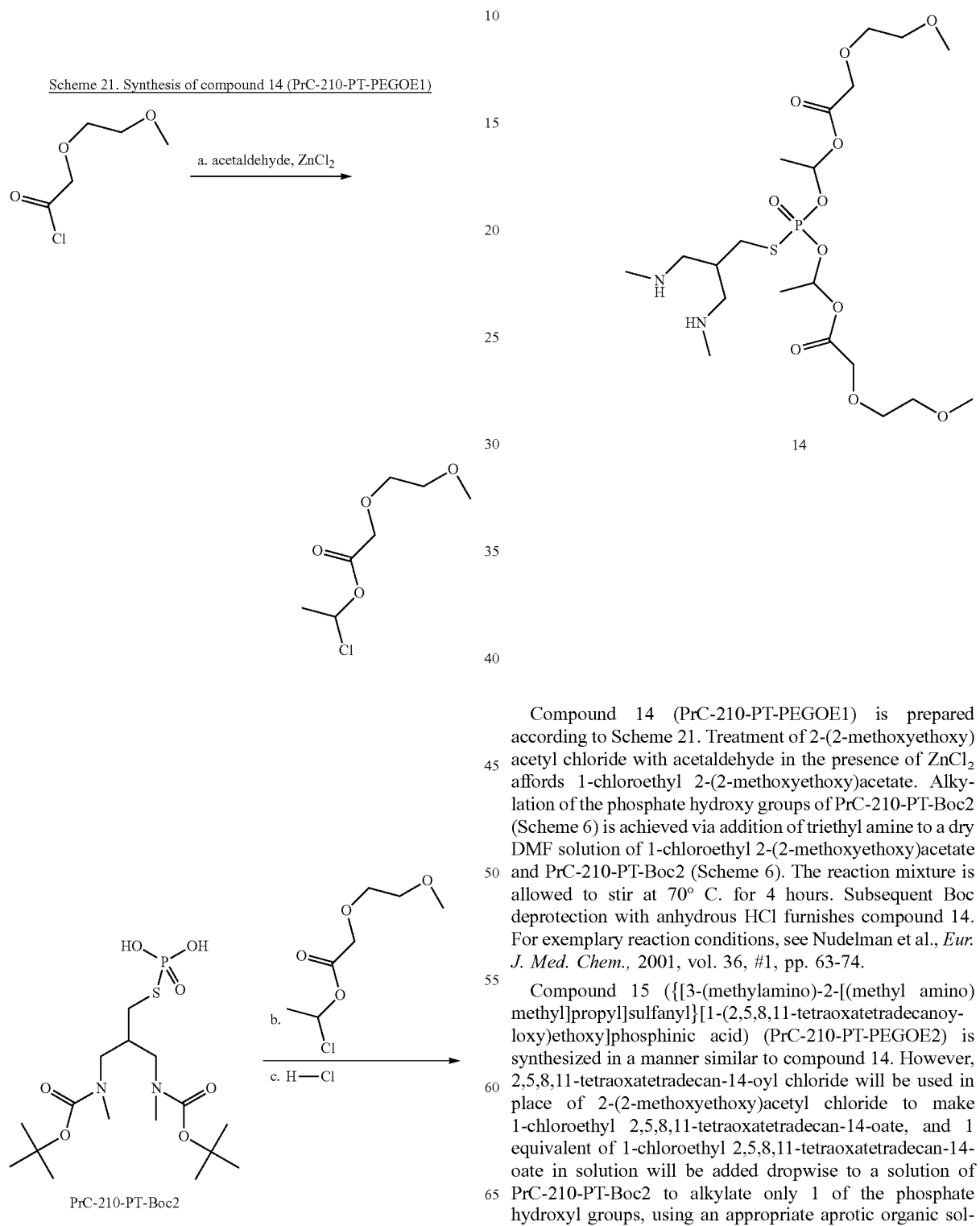

Compound 14 (PrC-210-PT-PEGOE1) is prepared according to Scheme 21. Treatment of 2-(2-methoxyethoxy)acetyl chloride with acetaldehyde in the presence of $ZnCl_2$ affords 1-chloroethyl 2-(2-methoxyethoxy)acetate. Alkylation of the phosphate hydroxy groups of PrC-210-PT-Boc2 (Scheme 6) is achieved via addition of triethyl amine to a dry DMF solution of 1-chloroethyl 2-(2-methoxyethoxy)acetate and PrC-210-PT-Boc2 (Scheme 6). The reaction mixture is allowed to stir at 70° C. for 4 hours. Subsequent Boc deprotection with anhydrous HCl furnishes compound 14. For exemplary reaction conditions, see Nudelman et al., *Eur. J. Med. Chem.*, 2001, vol. 36, #1, pp. 63-74.

Compound 15 ({[3-(methylamino)-2-[(methyl amino)methyl]propyl]sulfanyl}[1-(2,5,8,11-tetraoxatetradecanoyloxy)ethoxy]phosphinic acid) (PrC-210-PT-PEGOE2) is synthesized in a manner similar to compound 14. However, 2,5,8,11-tetraoxatetradecan-14-oyl chloride will be used in place of 2-(2-methoxyethoxy)acetyl chloride to make 1-chloroethyl 2,5,8,11-tetraoxatetradecan-14-oate, and 1 equivalent of 1-chloroethyl 2,5,8,11-tetraoxatetradecan-14-oate in solution will be added dropwise to a solution of PrC-210-PT-Boc2 to alkylate only 1 of the phosphate hydroxyl groups, using an appropriate aprotic organic solvent such as THF.

Example 16: Synthesis of compound 16 {[3-(methylamino)-2-[(methylamino)methyl]propyl]sulfanyl}[ ]—(2,5,8,11,14-pentaoxaicosanoyloxy)ethoxy] phosphinic acid (PrC-210-PT-PEGOE3)

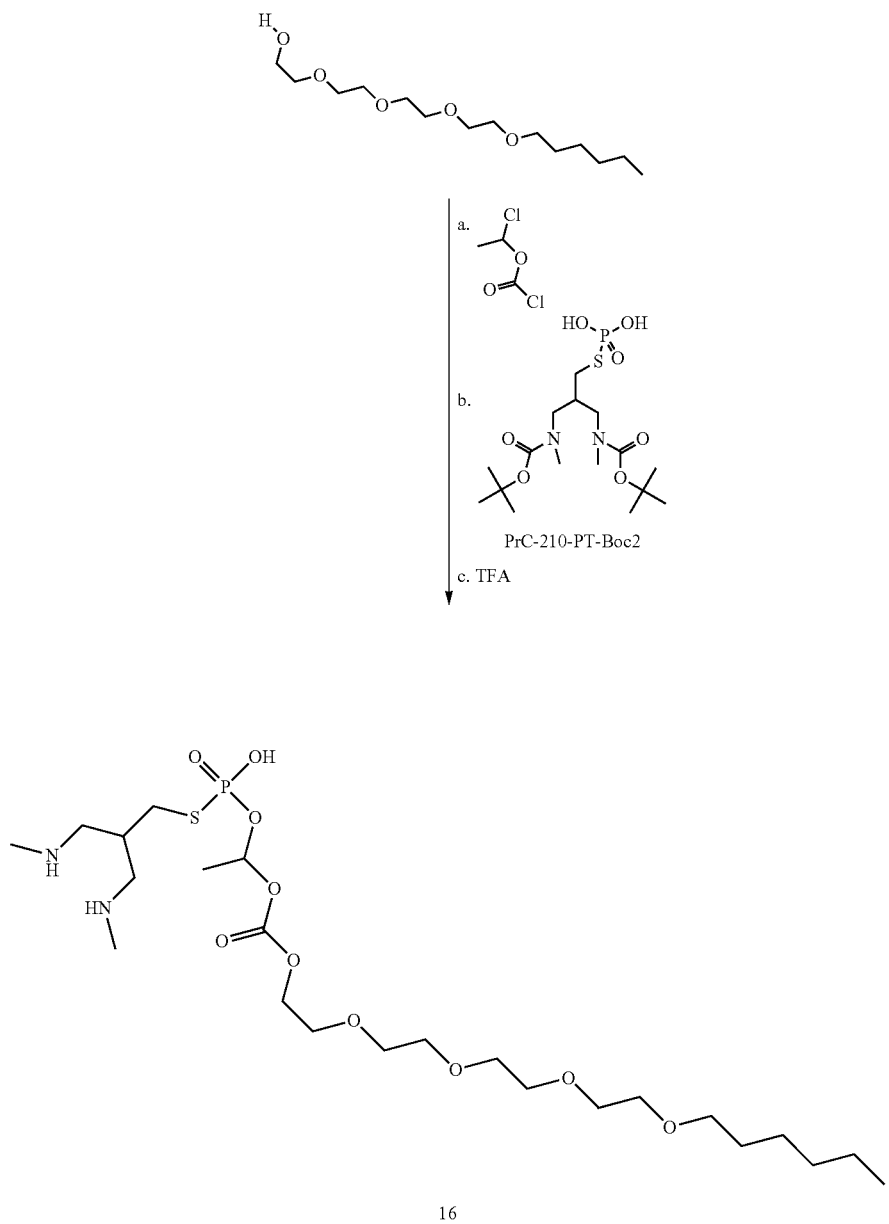

Compound 16 is synthesized according to Scheme 22. Nucleophilic substitution of 1-chloroethyl carbonochloridate with 3,6,9,12-tetraoxaoctadecan-1-ol provides the PEG precursor, 1-chloroethyl (3,6,9,12-tetraoxaoctadecyl) carbonate. Dropwise addition of a solution containing only 1 equivalent of the PEG precursor to PrC-210-PT-Boc2 (Scheme 6) will serve to alkylate only 1 of the phosphate hydroxyl groups, resulting in the Boc protected derivative of compound 16. Subsequent Boc deprotection under acidic conditions affords compound 16. For exemplary reaction conditions, see US 2008/0125483.

Example 17: Synthesis of compound 18 propan-2-yl (2S)-2-[((R+S)-{[3-(methylamino)-2-[(methylamino)methyl]propyl]sulfanyl}(phenoxy)phosphoryl)amino]propanoate (S, R+S-PrC-210-PT-alaf)

Scheme 23. Synthesis of compound 18 ((S, R+S)-PrC-210-PT-alaf).

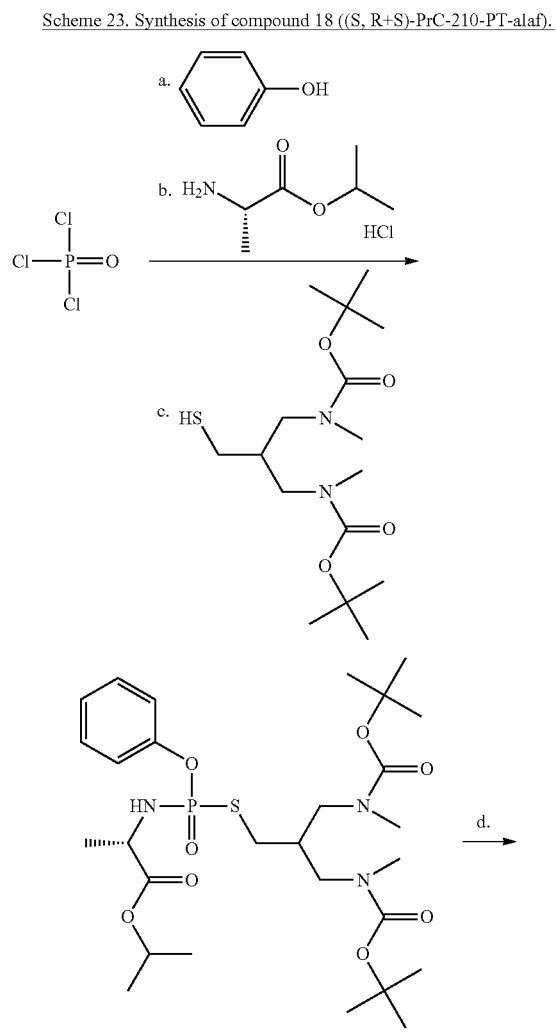

18-(S,S)

a. Triethyl phosphate, 0-20° C. b. triethylamine, 0-20° C. c. 1,8-diazabicyclo[5.4.0]undec-7-ene in acetonitrile d. TFA, DCM Double prodrug S, R+S-PrC-210-PT-alaf (compound 18) is prepared according to Scheme 24. Conversion of phosphoryl chloride to the corresponding aryl ester is afforded upon treatment with phenol. Addition of L-Alanine isopropyl ester hydrochloride and triethylamine to the reaction mixture affords the alafenamide derivative. Subsequent treatment with PrC-210-Boc2 (see Scheme 5) in the presence of 1,8-diazabicyclo[5.4.0]undec-7-ene (DBU) generates the Boc protected analogue of (S, R+S)—PrC-210-PT-alaf Subsequent Boc deprotection furnishes compound 18. For exemplary reaction conditions, see US2014/248242 and WO2016/41877.

To isolate the pure diastereomers of 18, (S,S)—PrC-210-PT-alaf and (S,R)—PrC-210-PT-alaf, the Boc protected analogue of the mixture of diastereomers (S, R+S)—PrC-210-PT-alaf is purified by recrystallization or silica gel chromatography to yield Boc protected analogs of (S, S)—PrC-210-PT-alaf and (S, R)—PrC-210-PT-alaf. Each of these could be deprotected with anhydrous TFA to yield the pure (S, S)—and (S, R)— diastereomers of 18. Alternately, the two diastereomers (S, R+S)—PrC-210-PT-alaf could be separated by fractional recrystallization of salts of appropriate chiral anions or dianions such as the dibenzoyl tartrate salt followed by neutralization to yield the pure (S, S)—and (S, R)— diastereomers of 18.

Example 18: Synthesis of 2,2-dimethyl-1-{[3-(methylamino)-2-[(methylamino)methyl]propyl]sulfanyl}propan-1-one (compound 19, S-acyl-PrC-210)

Scheme 24. Synthesis of compound 19 (S-acyl-PrC-210).

-continued

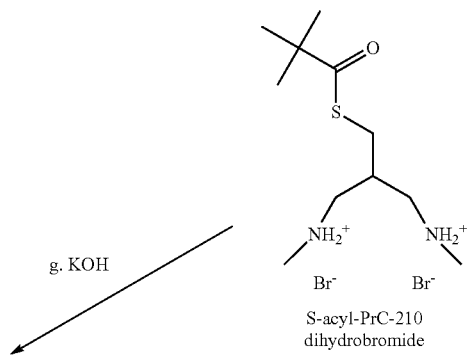

g. KOH

S-acyl-PrC-210 dihydrobromide

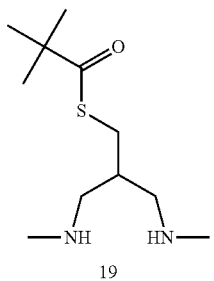

19

Compound 19 is prepared according to Scheme 25. Double chloride displacement from 3-chloro-2-(chloromethyl)prop-1-ene with two equivalents of N-methyl mesitylene-sulfonamide followed by hydroboration-oxidation generates the corresponding sulfonamide alcohol. Mesylation of the alcohol upon addition of mesyl chloride to the reaction mixture followed by treatment with lithium 2,2-dimethylpropanethioate affords the S-acyl derivative. Subsequent removal of the mesitylene protecting groups under acidic conditions results in the hydrobromide salt form of S-acyl-PrC-210. Other salt forms can be made from the hydrobromide using anion exchange resin. Alternately, the free base 19 can be made using careful treatment with 2 equivalents of aqueous KOH, added dropwise at 5° C. The base can be converted to more stable salts by treatment with the appropriate acid. For exemplary reaction conditions see Copp, R. R.; Peebles, D. D.; Fahl, W. E., Bioorg. Med. Chem. Lett., 2011, Vol. 21(24), pp 7426-7430.

Example 19: Synthesis of compound 20 ethyl 4-(benzoylthio)-2-(((hydroxy((3-(methylamino)-2-((methylamino)methyl)propyl)thio)phosphoryl)oxy)methyl)-2-methyl-3-oxobutanoate (PrC-210-PT-BzTB1)

Scheme 25. Synthesis of compound 20 (PrC-210-PT-BzTB1)

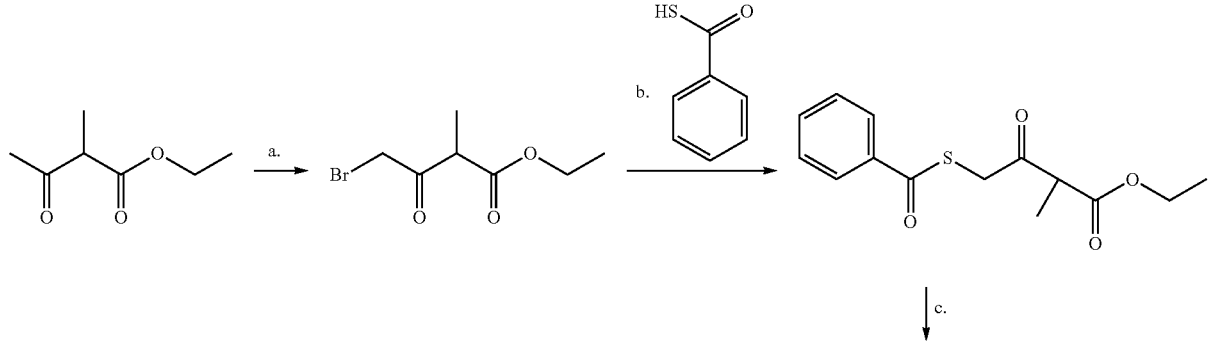

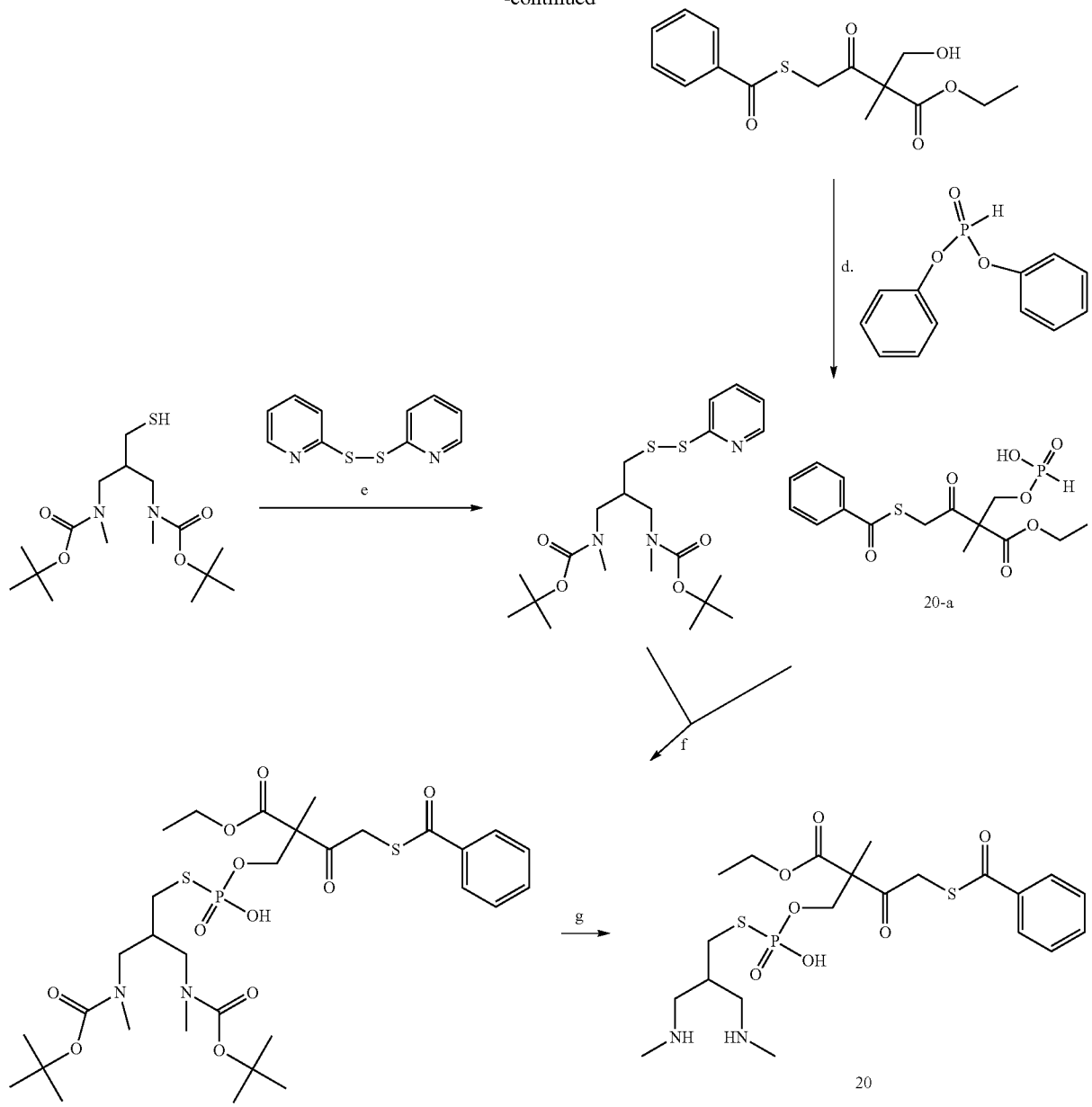

Compound 20 is synthesized according to Scheme 25. Bromination of ethyl 2-methyl-3-ketobutyrate upon addition of Br₂ in a DCM solution affords the corresponding bromide. Substitution of the bromide upon treatment with benzenecarbothioc S-acid in the presence of triethylamine affords the benzoylthioester derivative. Hydroxymethylation upon treatment of the bonzoylthioester with formaldehyde in the presence of triethylamine in dioxane affords the hydroxyl intermediate. Subsequent treatment with diphenylphosphite in pyridine at 20° C. for 1 h followed by treatment with triethylamine and pyridine in water at 0° C. affords intermediate 20-a. For Exemplary reaction conditions see Kiuru, E.; Ahmed, Z.; Lonnberg, H.; Beigelman, L.; Ora, M, J *Org. Chem.*, 2012, Vol. 78(3), p. 950-959; and Chevolot et al., *Angew.*, 2007, Vol. 46, pp 2398-2402.

To a THE solution of PrC-210-Boc2 (Scheme 5), 1,2-di (pyridine-2-yl)disulfane is added to afford the disulfide derivative. After work up, the disulfide is dissolved in dry THF. The phosphinic acid (20-a) and N,O-bis(trimethylsilyl) trifluoroacetamide are dissolved in a separate dry THE solution, followed by subsequent addition to the disulfide solution. The reaction mixture is stirred under reflux for 3 to 5 hours. Subsequent Boc deprotection using trifluoroacetic acid affords compound 20. For exemplary reaction conditions, see Dugave, C., Kessler, P., *Tetrahedron Lett.*, 1994, Vol. 35, #51, pp 9557-9560.

Compound 17 is synthesized via an analogous procedure to that of compound 20 using the appropriate starting materials. In particular 2-methoxy-2'-ethoxy-238-ethoxyethyl 2-methyl-3-ketobutyrate in place of ethyl 2-methyl-3-ketobutyrate in step a, and 2-dimethylpropanethioic S-acid in place of benzenecarbothioic S-acid in step b.

Example 20: Synthesis of (2-(piperazin-2-yl)propane-2-thiol) (Compound 21,2Pip-2PrSH)

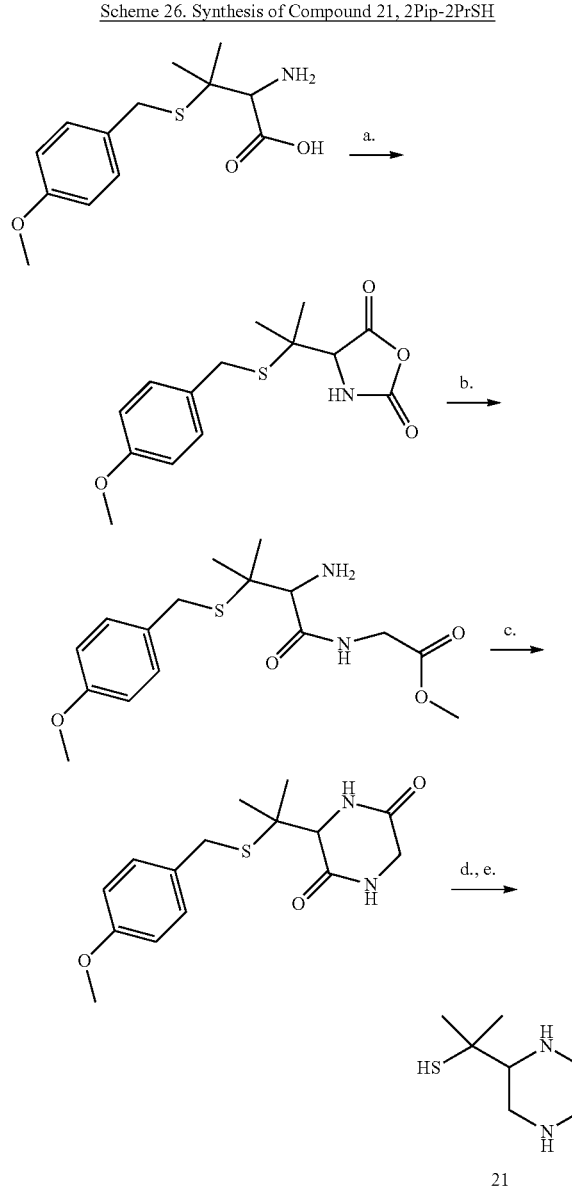

Scheme 26. Synthesis of Compound 21, 2Pip-2PrSH

Reagents and conditions: a. phosgene, THF, 25° C., 24 h; b. glycine methyl ester hydrochloride, chloroform, TEA, -78° C. to 0° C., 16 h; c. toluene, reflux, 24 h, 62% overall; d. trifluoromethanesulfonic acid, dichloromethane, anisole, 25° C., 30 min 87%; e. LAH, THF, 0° C.

Compound 21 is synthesized according to Scheme 26. Ring closure of 2-amino-3-((4-methoxybenzyl)thio)-3-methylbutanoic acid upon treatment with phosgene generates the oxazole-dione derivative. Subsequent treatment with glycine methyl ester hydrochloride under basic conditions followed by reflux affords the piperazinedione derivative. PMB (p-methoxybenzyl) deprotection followed by reduction with lithium aluminum hydride affords compound 21. For exemplary reaction conditions, see Richter, L. S.; Gadek, T. R., Tetrahedron: *Asymmetry*, 1996, Vol. 7(2), pp 427-434.

Example 21: Synthesis of ((1,4-diazepan-6-yl)methanethiol HBr) (Compound 22 HBr, DzCH2SH)

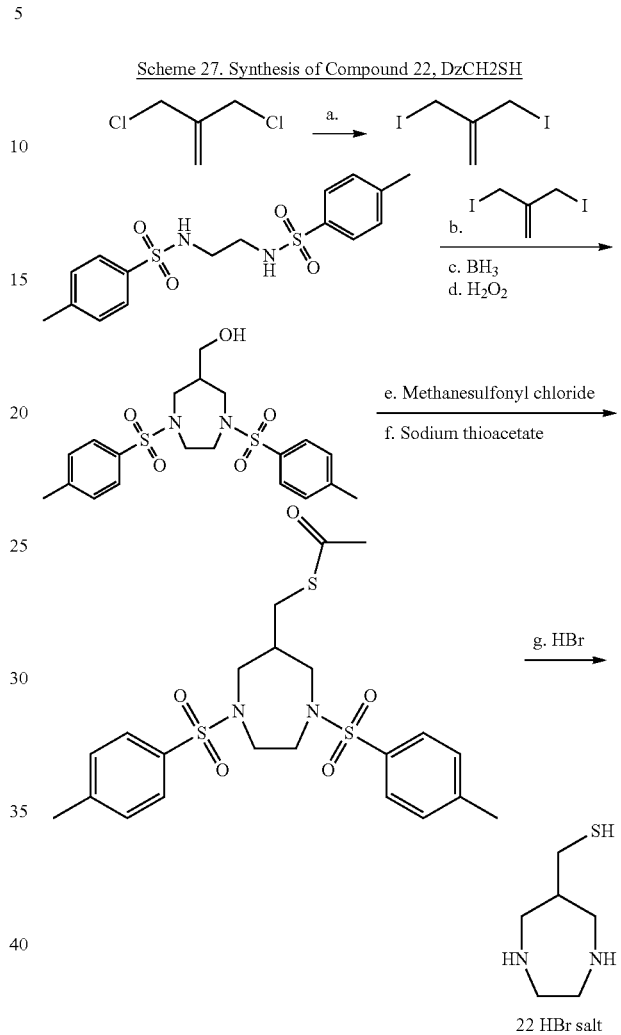

Scheme 27. Synthesis of Compound 22, DzCH2SH a. sodium iodide in acetone for 10 h, inert atmosphere, reflux; b. sodium hydride in DMF for 80° C. for 1 h, then 3-iodo-2-(iodomethyl)-1-propene in DMF at 80° C. for 1.5 h; c. borane; d. hydrogen peroxide, NaOH; e. methanesulfonyl chloride, TEA; f. sodium thioacetate; g. HBr, heat Compound 22 is prepared according to Scheme 27. Halogen exchange of 3-chloro-2-(chloromethyl)prop-1-ene upon treatment with sodium iodide in acetone affords 3-iodo-2-iodomethylpropene. Cyclization of N,N'-(ethane-1,2-diyl)bis(4-methylbenzenesulfonamide) upon treatment with 3-iodo-2-iodomethylpropene to give the corresponding olefin, followed by hydroboration-oxidation generates the corresponding sulfonamide alcohol. Mesylation of the alcohol upon addition of methanesulfonyl chloride to the reaction mixture followed by treatment with sodium thioacetate affords the S-acyl derivative. Subsequent removal of the mesitylene protecting groups under acidic conditions results in the hydrobromide salt form of compound 22. Treatment of the salt with a base, such as sodium hydroxide affords the compound 22 as the free base. For exemplary reaction conditions, see Copp, R. R.; Peebles, D. D.; Fahl, W. E., *Bioorg. Med. Chem. Lett.*, 2011, Vol. 21(24), pp 7426-7430; Matsumoto, K.; Tomioka, K., *Chem. Pharm. Bull.* 2001, Vol 49(12), pp 1653-1657.

Example 22: Synthesis of 2-methyl-4-(methyl-amino)-3-((methylamino)methyl)butane-2-thiol (Compound 23, DM-PrC-210)

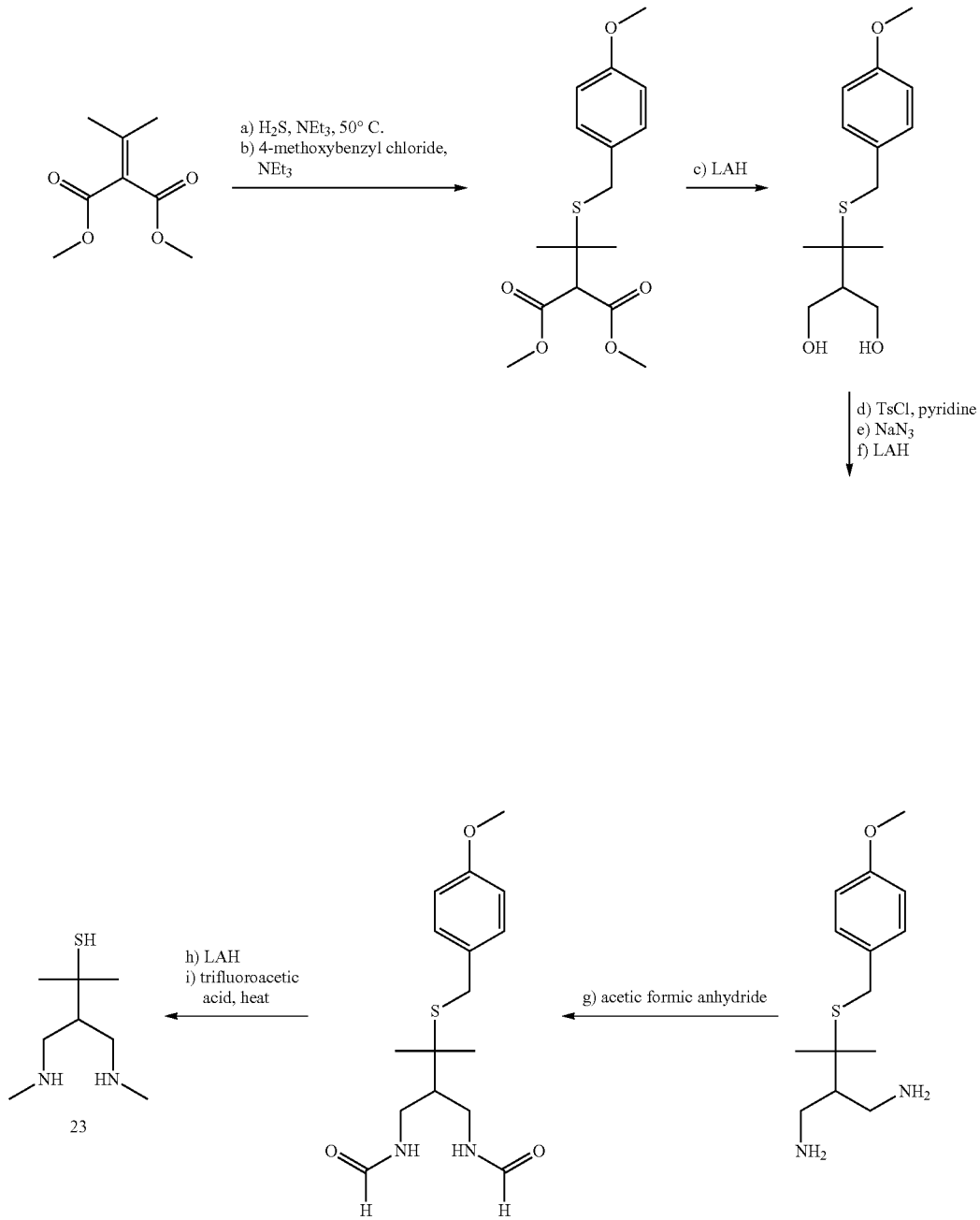

Compound 23 is prepared according to Scheme 28. Treatment of dimethyl isopropylidenemalonate with hydrogen sulfide affords the thiol analogue. Subsequent addition of 4-methoxybenzyl chloride results in formation of the PMB protected derivative. The diol is next formed upon reduction with lithium aluminum hydride. Conversion of the diol to the diamine is afforded by conversion of the diol to the tosylate followed by treatment with sodium azide and subsequent reduction with LAH. Carboxylation with acetic formic anhydride followed by reduction LAH and subsequent PMB deprotection under acidic conditions affords DM-PrC-210. For exemplary reaction conditions, see Foldi, Z., Kollonitsch, J., *J. Chem. Sci,* 1948, pp 1683-1685; Cullen W. R., Hall, L. D., Price, J. T., Spendjian, G., *Can. J. Chem.,* 1975, Vol. 53(3), pp 366-372; and Richter, L. S.; Gadek, T. R., Tetrahedron: Asymmetry, 1996, Vol. 7(2), pp 427-434.

Example 23: Alternative Synthesis of 2-methyl-4-(methylamino)-3-((methylamino)methyl)butane-2-thiol (Compound 23, DM-PrC-210)

technique to detect γ-H2AX-foci. The detection of γ-H2AX-foci is indicative of DNA damage and is recognized as a biomarker for radiation-induced double-strand breaks (DSBs). See for example, Brand, M., Sommer, M., Jer-

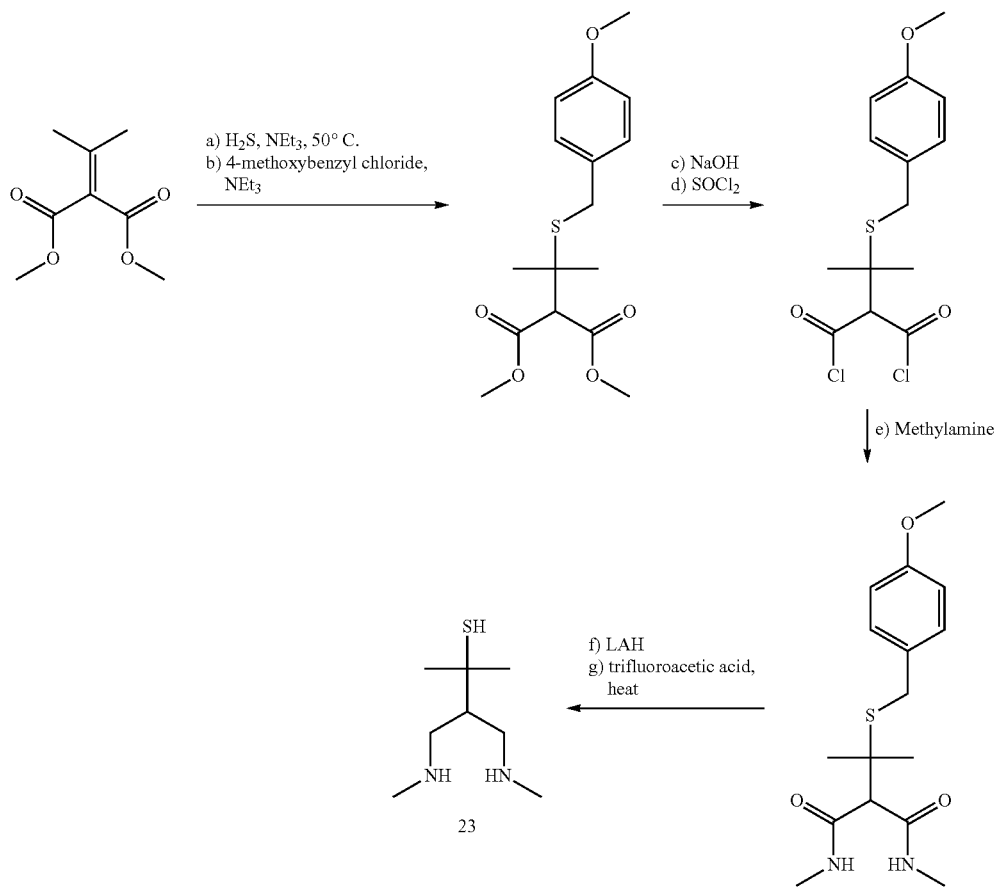

Scheme 29. Alternative Synthesis of compound 23.

Compound 23 is prepared according to Scheme 29. Treatment of dimethyl isopropylidenemalonate with hydrogen sulfide affords the thiol analogue. Subsequent addition of 4-methoxybenzyl chloride results in formation of the PMB protected derivative. Treatment with NaOH followed by addition of thionyl chloride results in the chlorinated derivative. Substitution with methylamine affords the corresponding amide. Reduction with LAH and subsequent PMB deprotection under acidic conditions affords DM-PrC-210. For exemplary reaction conditions see Foldi, Z., Kollonitsch, J., *J. Chem. Sci*, 1948, pp 1683-1685; Walli, A., Dechert, S., Meyer, F., *Eur. J Org. Chem.*, 2013, No. 31, pp 7044-7049; and Richter, L. S.; Gadek, T. R., *Tetrahedron: Asymmetry*, 1996, Vol. 7(2), pp 427-434.

Example 24: Protection of DNA from Radiation-Induced Damage

The radioprotective efficacy of the thiol-containing compounds of this disclosure, as well as the thiol derivatives of the prodrugs and double prodrugs of this disclosure, is assessed in vitro. The ability of the compounds to suppress X-ray induced DNA damage in normal human cells can be determined using a H2AX-immunofluorescense microscopy musek, F., Fahl, W. E., Uder, M., *Biology Open*, 2018, 7, bio035113. doi:10.1242/bio.035113.

The thiols of this disclosure (SH), and the thiol derivatives of the pro-drugs and double pro-drugs of this disclosure (PD-SH) are compared to PrC-210, as well as to a control sample (containing no additive). A baseline measurement of γ-H2AX-foci for each sample is determined prior to exposure to radiation and prior to the addition of the test compounds. The efficacy of each compound is assessed at varying concentrations of 1, 10, 25, 50, 75 and 100 mM. The blood samples are incubated with the test compounds for 4 hrs, 3 hrs, 2 hrs, 1 hr, 30 min or 15 min before the sample is exposed to radiation. Each concentration at each incubation time period is assessed for efficacy in reducing radiation-induced DNA damage after exposure to 10 mGy, 50 mGy or 100 mGy radiation. Some samples are exposed to radiation 10 min, 15 min, 30 min or 1 hr prior to the addition of a test compound to the sample.

The blood samples are layered into 6 mL of lymphocyte separation medium and centrifuged. The separated lymphocytes are stained and incubated overnight using an antibody against γ-H2AX. Fluorescence analyses are performed, and the γ-H2AX-foci are counted. The amount of γ-H2AX-foci induced by radiation exposure is determined by subtracting the baseline value of γ-H2AX-foci from the measurement.

The test compounds (SH and PD-SH) are found to be useful in reducing radiation-induced DNA damage.

Example 25: Protection of Mice from Lethal Radiation

The radioprotective efficacy of the thiols, prodrugs and double prodrugs according to this disclosure is assessed in mice. The compounds of the disclosure are administered via oral gavage to mice, and are compared to mice that have been administered 3-(methylamino)-2-(methylaminomethyl)propane-1-thiol (PrC-210), as well as to a control group or mice that are administered vehicle (i.e., containing no radioprotective additive).

More specifically, mice are assigned to three groups (Groups 1, 2 and 3). A control group, Group 1, is treated via oral gavage with vehicle (Lactated Ringer's and 5% dextrose, adjusted to pH 7.3 with sodium bicarbonate) 15-90 minutes prior to a dose of 8 Gy ($LD_{100}$) radiation. Group 2 is treated via oral gavage with PrC-210, as a positive control, dissolved in Lactated Ringer's at a dose of 200 mg/kg 15-90 minutes prior to irradiation with 8 Gy ($LD_{100}$). Group 3 is treated via oral gavage with compound 1 (PrC-210-PT) dissolved in Lactated Ringer's at a dose of 308 mg/kg 15-90 minutes prior to irradiation with 8 Gy ($LD_{100}$). The mortality of the three groups is assessed for 60 days post irradiation. The experiment is repeated with doses of PrC-210 ranging from 200 mg/kg to 450 mg/kg. Molar equivalent dosages of the test compound (compound 1, Prc-210-PT) to PrC-210 are also assessed.

The experiment is repeated to assess the efficacy of compounds 2-23 as radioprotectors. The control group demonstrates a reduced rate of survival compared to the mice treated with PrC-210 and the thiols, prodrugs and double prodrugs according to the disclosure (i.e., compounds 1-23).

Example 26: Reduction of LD50 in Mice

The affect of the compounds according to the disclosure on the dose of radiation required to kill 50% of mice ($LD_{50}$) is assessed.

Mice are assigned to three groups (Groups 1, 2 and 3). A control group, Group 1, is treated via oral gavage with vehicle (Lactated Ringer's and 5% dextrose, adjusted to pH 7.3 with sodium bicarbonate) 60 minutes prior to whole body irradiation (2 Gy). Group 2 is treated via oral gavage with PrC-210, as a positive control, dissolved in Lactated Ringer's at a dose of 200 mg/kg 60 minutes prior to whole body irradiation (2 Gy). Group 3 is treated via oral gavage with compound 1 (PrC-210-PT) dissolved in Lactated Ringer's at a dose of 308 mg/kg 60 minutes prior to whole body irradiation (2 Gy). The mortality of the three groups is assessed for 30 days post irradiation.

The experiment is repeated using varying radiation doses of 4, 6, 8, 10 and 12 Gy. The $LD_{50}$ for each group was determined.

The experiment is repeated to assess compounds 2-23 as radioprotectors. The control group demonstrates a lower $LD_{50}$ compared to the mice treated with PrC-210 and the mice treated with the thiols, prodrugs and double prodrugs according to the disclosure (i.e., compounds 1-23).

Example 27. Efficacy and Maximum Tolerated Dose of PrC-210, DzCH2SH and 2Pip-2PrSH in Mice Male mice were randomized and assessed in two phases: 1) for maximum tolerated doses (MTDs) of PrC-210, DzCH2SH, and 2Pip-2PrSH to determine dose levels for the efficacy study and 2) to evaluate the efficacy of the compounds when administered 60+5 minutes prior to exposure to total body irradiation (TBI) at an $LD_{100/30}$ dose (990 cGy) (Tables 1 and 2).

For Phase 1 or 2, sterile water (vehicle), PrC-210, DzCH2SH, and 2Pip2PrSH were administered at 10 mL/kg calculated based on the most recent body weight via oral gavage. Animals were not fasted prior to administration of the compounds or vehicle. Mice in Phase 1 were administered the dose on Day 1 and mice in Phase 2 were administered the dose 60+5 minutes prior to TBI on Day 0.

Irradiation was administered once to the whole body. TBI of mice were performed using a 6 MV LINAC photon source (TrueBeam STx source). Animals were irradiated at a dose rate of up to 80 cGy/min to the midline of the animals. The source irradiated animals to 50% of the dose from anterior-posterior direction and complete irradiation from the posterior-anterior direction. Dose measurements were performed with a PTW 31010 0.1 cc Semiflex Ion chamber.

All surviving animals were observed once daily for clinical signs (e.g., unusually low or high activity, lethargy, shivering, appearance of fur, bloody and water stool, and other symptoms of moribundity) at 1-2 hours post-irradiation and/or post-dose and once daily on non-dosing days until Day 4 (Phase 1) or Day 30 (Phase 2). The mortality rate was assessed at 8-days post-irradiation (Table 2), which show efficacious effects of DzCH2SH to protect mice after irradiation.

In Phase 1 (Table 1), all animals were normal when observed and all body weights were within normal range. The dose level of 1000 mg/kg was selected for Phase 2.

In Phase 2 (Table 2), survival curves of mice treated with vehicle, PrC-210, DzCH2SH or 2Pip-PrSH prior to TBI with 9.9 Gy were measured (FIG. 1). Mice administered with vehicle before TBI 9.9 Gy (Group 13) did not survive until Day 30. Five mice were moribund sacrificed, and 6 mice were found dead. Survival in the Group 13 animals was 0% and median survival time was 8 days. In mice administered with PrC-210 before TBI (Group 14), 4 animals survived until scheduled sacrifice (Day 30) while 7 mice were moribund sacrificed. Survival in the Group 14 mice was 36.4% and median survival time was 11 days. The survival in the Group 14 mice was statistically significantly higher when compared to the Group 13 mice by Log-rank (Mantel-Cox) ($p<0.001$) and Chi-square tests ($p<0.05$). In mice administered with DzCH2SH before TBI (Group 15), 3 animals survived until scheduled sacrifice (Day 30) while 7 mice were moribund sacrificed, and one mouse was found dead. Survival in the Group 15 mice was 27.3% and median survival time was 11 days. The survival in the Group 15 mice was statistically significantly higher when compared to the Group 13 mice by Log-rank (Mantel-Cox) test ($p<0.001$). In mice administered with 2Pip-2PrSH before TBI at 9.9 Gy (Group 16), no animals survived until scheduled sacrifice (Day 30). Five mice were moribund sacrificed and six mice were found dead. Survival in the Group 16 mice was 0% and median survival time was 10 days. The survival in the Group 16 mice was statistically significantly higher when compared to the Group 13 mice by Log-rank (Mantel-Cox) test ($p<0.02$) and was not statistically significantly different when compared by Chi-square test ($p>0.05$).

Rough coat, hunched posture, decreased activity and eye closed were observed in most mice in all groups. Eye discharge was seen in one animal each in Groups 13, 14 and 16, and in 2 animals in Group 15. Lethargy and swollen head were observed in one mouse each in Groups 15 and 16. Hypoactivity was seen 3 animals in Group 13 and in 5 animals each in Groups 14, 15 and 16. Tremor was seen in 4 mice in Group 14. Labored breathing was observed in one mouse in Group 15. Cold to touch skin was seen in one animal each in Groups 13 and 15, and in 4 mice in Group 16. Swollen eye was seen in one animal in Groups 13, 14 and 16, and in 2 mice in Group 15, while sunken eye and eye cloudy were observed in 1 and 2 animals, respectively, in Group 15. Eye opacity was seen in one mouse each in Groups 13 and 15.

There were no statistically significant differences in body weights between the vehicle group (Group 13) and the test article-dosed groups (Groups 14-16) although the mean body weight in the Group 14 animals was higher than body weights in the Groups 13, 15 and 16 on Day 9. It was confirmed by body weight gain which was significantly higher in Group 14 on Days 5 to 9 when compared to the vehicle group (Group 13). Animals in Groups 13, 15 and 16 did not gain body weights over the Days 5 to 9 period.

At the highest tested dose (1,000 mg/kg), PrC-210, DzCH2SH and 2Pip-2PrSH did not produce any toxicity. Mice treated PrC-210 or DzCH2SH prior to total body irradiation ($LD_{100}/30$) was performed, increased survival of animals through 30 days post exposure. Survival beyond 30 days was not assessed.

TABLE 1

Phase 1 Dose Groups for MTD determination

| Group Number | Number of Animals | Compound | Dose (mg/kg) | Dose Volume (mL/kg) | Concentration (mg/mL) |
|---|---|---|---|---|---|
| 1 | 3 | PrC-210 | 30 | 10 | 3 |
| 2 | 3 | PrC-210 | 100 | 10 | 10 |
| 3 | 3 | PrC-210 | 300 | 10 | 30 |
| 4 | 3 | PrC-210 | 1,000 | 10 | 100 |
| 5 | 3 | DzCH2SH | 30 | 10 | 3 |
| 6 | 3 | DzCH2SH | 100 | 10 | 10 |
| 7 | 3 | DzCH2SH | 300 | 10 | 30 |
| 8 | 3 | DzCH2SH | 1,000 | 10 | 100 |
| 9 | 3 | 2Pip-2PrSH | 30 | 10 | 3 |
| 10 | 3 | 2Pip-2PrSH | 100 | 10 | 10 |
| 11 | 3 | 2Pip-2PrSH | 300 | 10 | 30 |
| 12 | 3 | 2Pip-2PrSH | 1,000 | 10 | 100 |

TABLE 2

Phase 2 Dose Groups for Efficacy study

| Group Number | Number of Animals | Compound | Dose (mg/kg) | Dose Volume (mL/kg) | Concentration (mg/mL) |
|---|---|---|---|---|---|
| 13 | 11 | Vehicle | 0 | 10 | 0 |
| 14 | 11 | PrC-210 | 1000 | 10 | 100 |
| 15 | 11 | DzCH2SH | 1000 | 10 | 100 |
| 16 | 11 | 2Pip-2PrSH | 1000 | 10 | 100 |

Example 28. Efficacy of PrC-210 and DzCH2SH in Irradiated Mice

The efficacy of PrC-210 and DzCH2SH is evaluated in male mice administered with the compounds 60±10 minutes prior to exposure to total body irradiation (TBI) at a range of radiation levels of $LD_{20/30}$, $LD_{40/30}$, $LD_{60/30}$, $LD_{80/30}$, and $LD_{100130}$ (Table 3). Sterile water (vehicle), PrC-210 and DzCH2SH are administered by oral gavage at 10 mL/kg calculated based on the most recent body weight. Animals are not fasted prior to administration. After 60+10 minutes, mice are administered with doses of 7.19 Gy, 7.96 Gy, 8.73 Gy, 9.50 Gy and 9.90 Gy to the whole body using a 6 MV LINAC photon source (TrueBeam STx source). Animals are irradiated at a dose rate of up to 80 cGy/min to the midline of the animals, in which the source will irradiate animals to 50% of the dose from anterior-posterior direction and complete irradiation from the posterior-anterior direction. Dose measurements will be performed with a PTW 31010 0.1 cc Semiflex Ion chamber. Following administration of the TBI dose, there is a 30-day observation period.

All surviving animals are observed for mortality and moribundity twice daily at least 6 hours apart for the duration of the study. In addition, all surviving animals are observed once daily for clinical signs (e.g., unusually low or high pap activity, lethargy, shivering, appearance of fur, bloody and water stool, and other symptoms of moribundity) at 1-2 hours post-irradiation and once daily on non-dosing days until the end of the study. All observations are individually recorded.

TABLE 3

Dose Groups

| Group Number | Compound | TBI Level | TBI Dose (Gy) | Number of Animals | Dose (mg/kg) | Dose Volume (mL/kg) | Concentration (mg/mL) |
|---|---|---|---|---|---|---|---|
| 1 | Vehicle | $LD_{20/30}$ | 7.19 | 35 | 0 | 10 | 0 |
| 2 | Vehicle | $LD_{40/30}$ | 7.96 | 15 | 0 | 10 | 0 |
| 3 | Vehicle | $LD_{60/30}$ | 8.73 | 15 | 0 | 10 | 0 |
| 4 | Vehicle | $LD_{80/30}$ | 9.50 | 15 | 0 | 10 | 0 |
| 5 | Vehicle | $LD_{100/30}$ | 9.90 | 11 | 0 | 10 | 0 |
| 6 | PrC-210 | $LD_{20/30}$ | 7.19 | 35 | 1,000 | 10 | 100 |
| 7 | PrC-210 | $LD_{40/30}$ | 7.96 | 15 | 1,000 | 10 | 100 |
| 8 | PrC-210 | $LD_{60/30}$ | 8.73 | 15 | 1,000 | 10 | 100 |
| 9 | PrC-210 | $LD_{80/30}$ | 9.50 | 15 | 1,000 | 10 | 100 |
| 10 | PrC-210 | $LD_{100/30}$ | 9.90 | 11 | 1,000 | 10 | 100 |
| 11 | DzCH2SH | $LD_{20/30}$ | 7.19 | 35 | 1,000 | 10 | 100 |
| 12 | DzCH2SH | $LD_{40/30}$ | 7.96 | 15 | 1,000 | 10 | 100 |
| 13 | DzCH2SH | $LD_{60/30}$ | 8.73 | 15 | 1,000 | 10 | 100 |
| 14 | DzCH2SH | $LD_{80/30}$ | 9.50 | 15 | 1,000 | 10 | 100 |
| 15 | DzCH2SH | $LD_{100/30}$ | 9.90 | 11 | 1,000 | 10 | 100 |

Example 29. Analogues of DzCH2SH

The compounds of this disclosure include (1,4-diazepan-6-yl)methanethiol (DzCH2SH) and derivatives or analogues thereof (Table 2).

TABLE 4

Analogues of DzCH2SH

| Compound | Structure | IUPAC Name |
|---|---|---|
| 24 | (structure: bicyclic diazabicyclo with SH substituent, HN and NH groups) | [(1R,4s,7S)-2,6-diazabicyclo[5.1.0]octan-4-yl]methanethiol |

TABLE 4-continued

Analogues of DzCH2SH

| Compound | Structure | IUPAC Name |
|---|---|---|
| 25 | 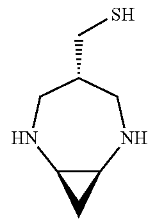 | [(1R,4r,7S)-2,6-diaza-bicyclo[5.1.0]octan-4-yl]methanethiol |
| 26 | 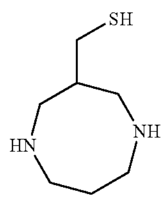 | (1,5-diazocan-3-yl)methanethiol |
| 27 | 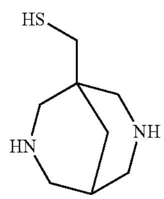 | {3,7-diazabicyclo[3.3.1]nonan-1-yl}methanethiol |
| 28 | 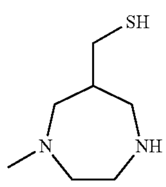 | (1-methyl-1,4-diazepan-6-yl)methanethiol |
| 29 | 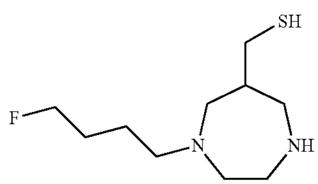 [SMILES: FCCCCN1CCNCC(CS)C1] | [1-(4-fluorobutyl)-1,4-diazepan-6-yl]methanethiol |
| 30 | 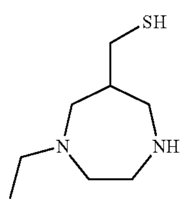 | (1-ethyl-1,4-diazepan-6-yl)methanethiol |
| 31 | 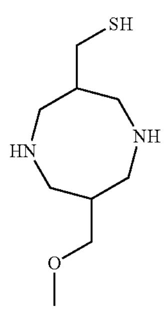 | [7-(methoxymethyl)-1,5-diazocan-3-yl]methanethiol |
| 32 | 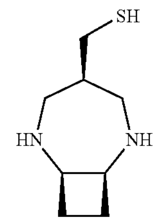 | [(1R,4S,7S)-2,6-diazabicyclo[5.2.0]nonan-4-yl]methanethiol |
| 33 | 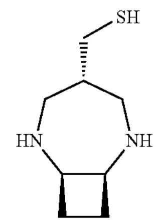 [SMILES: SC[C@@H]1CN[C@H]2CC[C@H]2NC1] | [(1R,4R,7S)-2,6-diazabicyclo[5.2.0]nonan-4-yl]methanethiol |
| 34 | 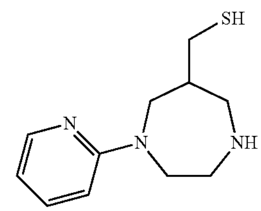 [SMILES: SCC1CNCCN(c2ccccn2)C1] | [1-(pyridin-2-yl)-1,4-diazepan-6-yl]methanethiol |
| 35 | 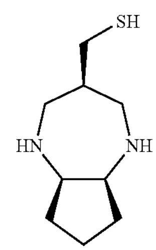 | [(3S,5aR,8aS)-decahydro-cyclopenta[b][1,4]diazepin-3-yl]methanethiol |
| 36 | 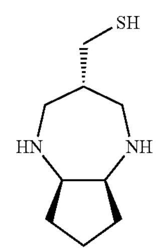 | [(3R,5aR,8aS)-decahydro-cyclopenta[b][1,4]diazepin-3-yl]methanethiol |
| 37 | 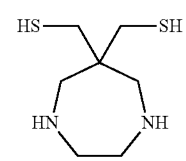 | [6-(sulfanylmethyl)-1,4-diazepan-6-yl]methanethiol |

TABLE 4-continued

Analogues of DzCH2SH

| Compound | Structure | IUPAC Name |
|---|---|---|
| 38 | 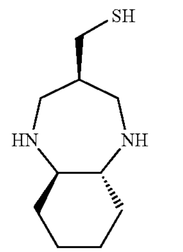 | [(5aR,9aR)-decahydro-1H-1,5-benzodiazepin-3-yl]methanethiol |
| 39 | 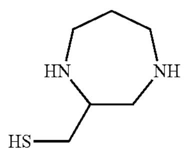 | (1,4-diazepan-2-yl)methanethiol |
| 40 | 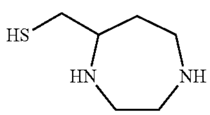 | (1,4-diazepan-5-yl)methanethiol |
| 41 | 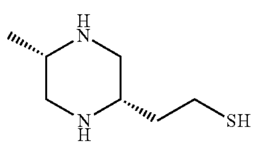 | 2-[(2S,5S)-5-methylpiperazin-2-yl]ethane-1-thiol |
| 42 | 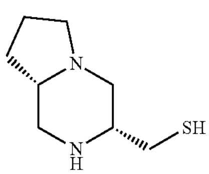 [SMILES: SC[C@H]1CN2CCC[C@H]2CN1] | [(3R,8aS)-octahydropyrrolo[1,2-a]pyrazin-3-yl]methanethiol |
| 43 | 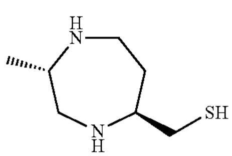 | [(2S,5S)-2-methyl-1,4-diazepan-5-yl]methanethiol |
| 44 | 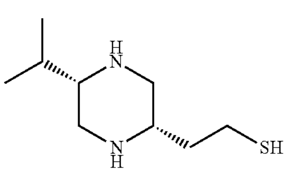 | 2-[(2S,5S)-5-(propan-2-yl)piperazin-2-yl]ethane-1-thiol |
| 45 | 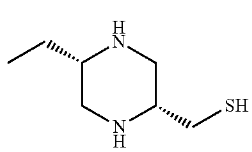 | [(2R,5S)-5-ethylpiperazin-2-yl]methanethiol |
| 46 | 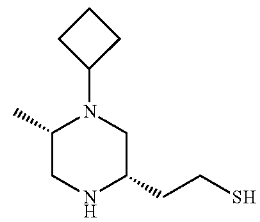 | 2-[(2S,5S)-4-cyclobutyl-5-methylpiperazin-2-yl]ethane-1-thiol |
| 47 | 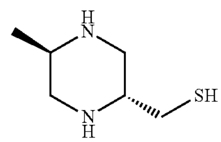 | [(2R,5R)-5-methylpiperazin-2-yl]methanethiol |
| 48 | 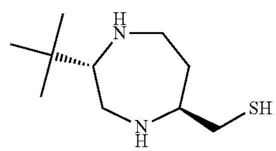 | [(2S,5S)-2-tert-butyl-1,4-diazepan-5-yl]methanethiol |
| 49 | 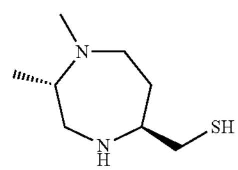 | [(2S,5S)-1,2-dimethyl-1,4-diazepan-5-yl]methanethiol |
| 50 | 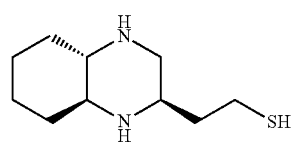 [SMILES: SCC[C@@H]1CN[C@H]2CCCC[C@@H]2N1] | [2-((2R,4aS,8aS)-decahydroquinoxalin-2yl)ethane-1-thiol] |

Example 30. Synthesis of 3-(methylamino)-2-((methylamino)methyl)propane-1-thiol) (PrC-210 diHCl)

Scheme 30. Synthesis of 3-(methylamino)-2-((methylamino)methyl)propane-1-thiol) (PrC-210 diHCl)

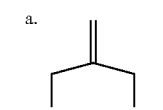

a.
b. c.
NaH, DMF
75%

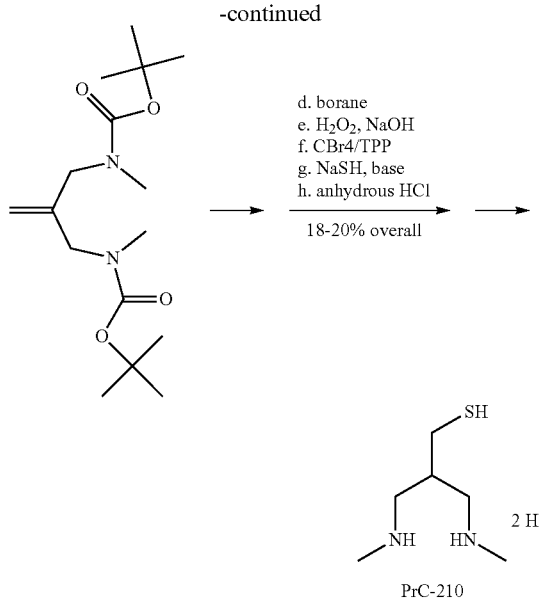

PrC-210 is synthesized according to Scheme 30. Double chloride displacement from 3-chloro-2-(chloromethyl)prop-1-ene with two equivalents of tert-butyl methylcarbamate followed using sodium hydride and dimethylformamide (DMF) furnishes the corresponding di-tert-butyl (2-methylenepropane-1,3,-diyl)bis(methylcarbamate). The di-tert-butyl intermediate is converted to 3-(methylamino)-2-((methylamino)methyl)propane-1-thiol) (PrC-210) after subsequent treatment with 1) borane, 2) hydrogen peroxide, sodium hydroxide, 3) carbon tetrabromide (CBr4)/tetraphenylporphyrin (TPP), 4) addition of a hydrosulfide group with sodium hydrosulfide and base. The addition of anhydrous HCl leads to formation of the PrC-210 dihydrochloride salt form.

Example 31. Alternative Synthesis of ((1,4-diazepan-6-yl)methanethiol HBr) (Compound 22 diHCl, DzCH2SH)

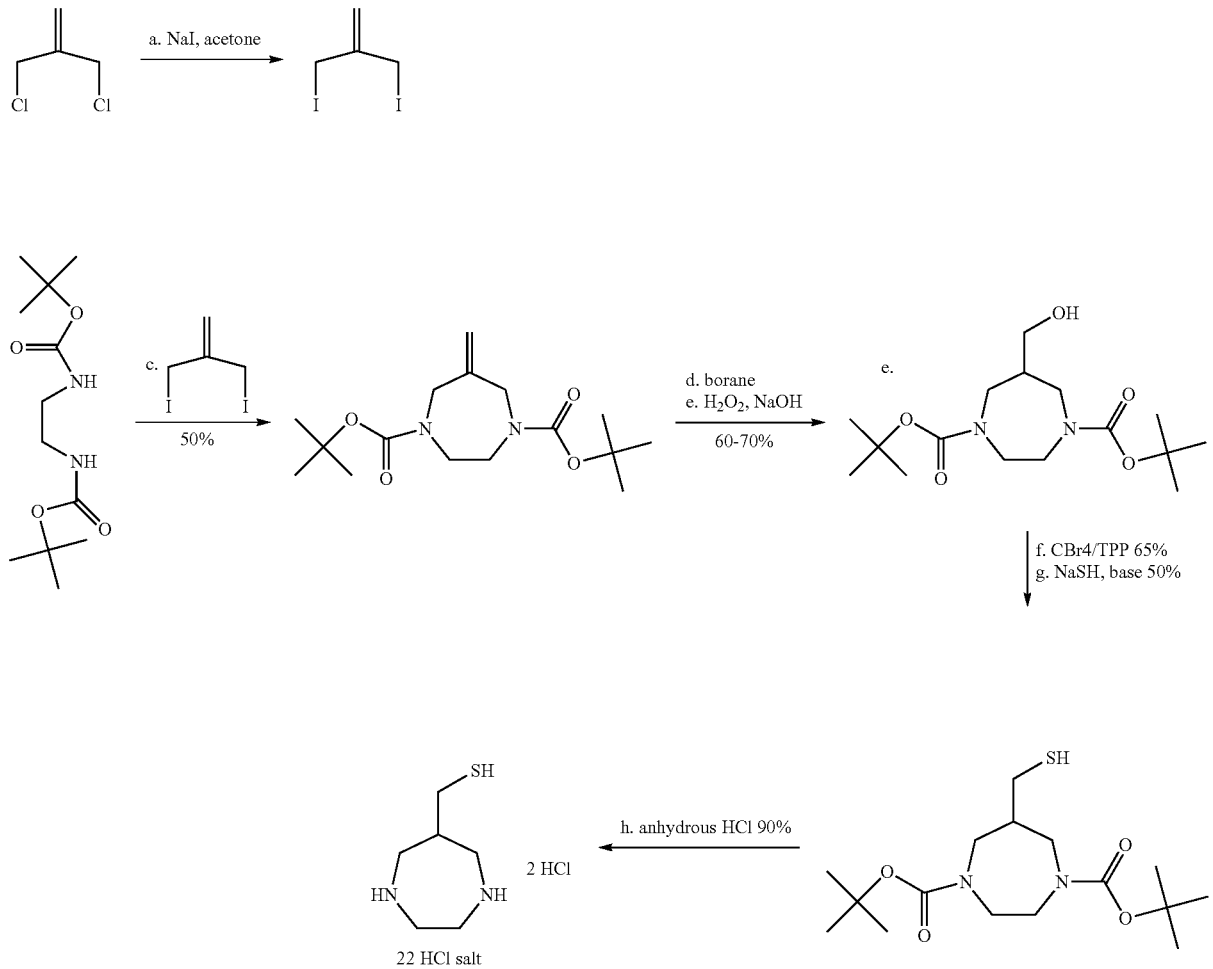

Compound 22 is alternatively prepared according to Scheme 31. Halogen exchange of 3-chloro-2-(chloromethyl)prop-1-ene upon treatment with sodium iodide in acetone affords 3-iodo-2-iodomethylpropene. Cyclization of N,N'-(ethane-1,2-diyl)bis(4-methylbenzenesulfonamide) with 3-iodo-2-iodomethylpropene gives the corresponding olefin, followed by hydroboration-oxidation generates the corresponding sulfonamide alcohol. The alcohol is converted to di-tert-butyl 6-(mercaptomethyl)-1,4-diazepane-1,4-dicarboxylate on treatment with carbon tetrabromide (CBr4)/ tetraphenylporphyrin (TPP) and sodium hydrosulfide and base. Subsequent removal of the tert-butyl formate groups in anhydrous hydrochloride results in the dihydrochloride salt form of compound 22.

Example 32: Alternative Synthesis of (2-(piperazin-2-yl)propane-2-thiol) (Compound 21 di HCl, 2Pip-2PrSH)

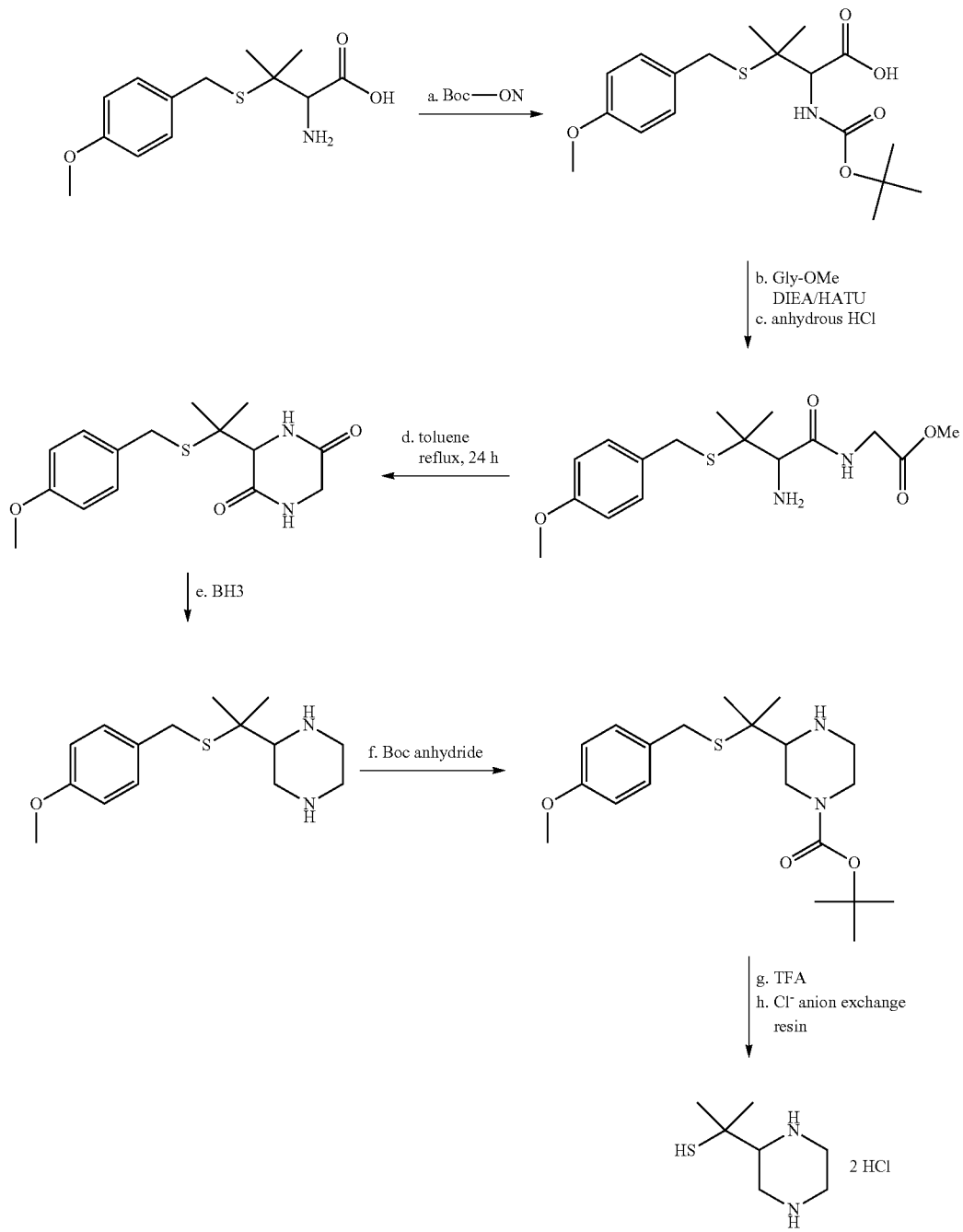

Compound 21 is alternatively prepared according to Scheme 32. 2-amino-3-((4-methoxybenzyl)thio)-3-methylbutanoic acid is treated with 2-(tert-butoxycarbonyloxyimino)-2-phenylacetonitrile (Boc-ON) to add a tert-butyl formate group and generate 2((tert-butoxycarbonyl)amino)-3-((4-methoxybenzyl)thio)-3-methylbutanoic acid. Subsequently, glycine methyl ester (Gly-OMe) and diisopropylethylamine (DIEA)/hexafluorophosphate azabenzotriazole tetramethyl uronium (HATU) and anhydrous hydrochloride are used to generate methyl (2-amino-3-((4-methoxybenzyl)thio)-3-methylbutanoyl)glycinate. The mixture is refluxed in toluene for 24 hours to produce 3-(2-((4-methoxybenzyl)thio)propan-2-yl)piperazine-2,5-dione. Treatment with borane produces (2-((4-methoxybenzyle)thio)propan-2-yl)piperazine. After treatment with di-tert-butyl decarbonate (Boc anhydride), tert-butyl 3-(2-((4-methoxybenzyl)thio)propan-2-yl)piperazine-1-carboxylate is formed and is treated with 2,2,2-Trifluoroacetic acid (TFA) and is processed in a C1- anion exchange resin to generate Compound 21 as a di HCl salt form.

Example 33. Synthesis of [(1R,4s, 7S)-2,6 diazabicyclo [5.1.O]octan-4-yl]methanethiol (Compound 24) and [(1R,4r, 7S)-2,6-diazabicyclo [5.1.O]octan-4-yl]methanethiol (Compound 25)

Scheme 33. Synthesis of Compound 24 and Compound 25

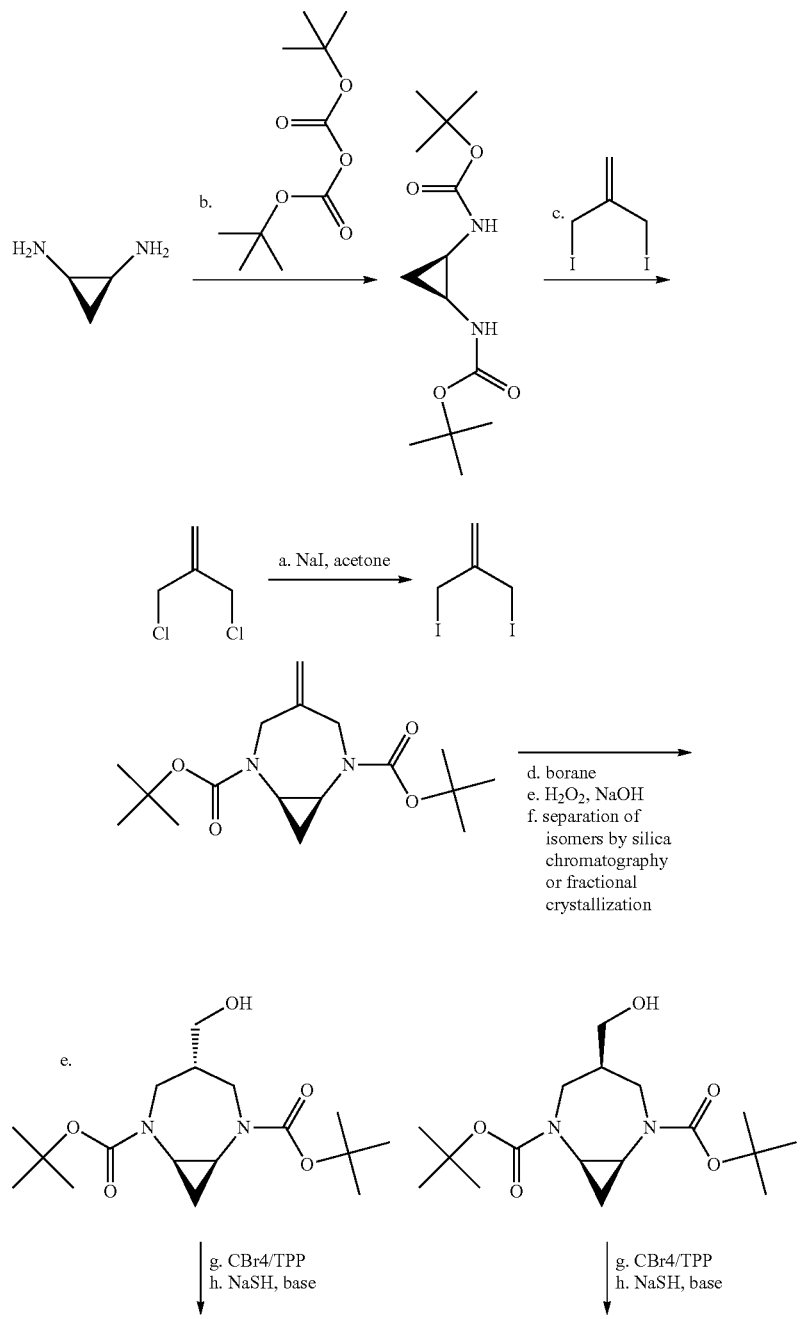

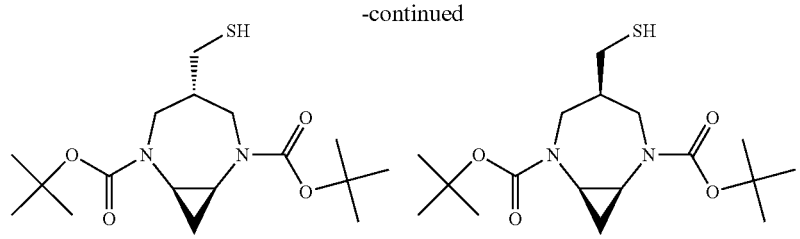

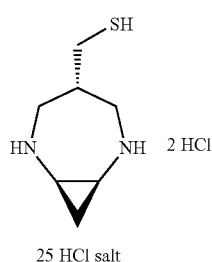

25 HCl salt

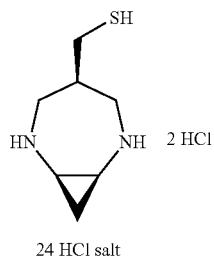

24 HCl salt

Compounds 24 and 25 are prepared according to Scheme 33. Halogen exchange of 3-chloro-2-(chloromethyl)prop-1-ene upon treatment with sodium iodide in acetone affords 3-iodo-2-iodomethylpropene. (1R, 2S)-cyclopropane-1,2-diamine is converted to di-tert-butyl ((1R,2S)-cyclopropane-1,2,-diyl)dicarbamate) with the addition of di-tert-butyl decarbonate. Subsequent addition of 3-iodo-2-iodomethyl-propene leads to cyclization of di-tert-butyl ((1R,2S)-cyclopropane-1,2,-diyl)dicarbamate), forming di-tert-butyl (1R, 7S)-4-methylene-2,6-diazabicyclo[5.1.0]octane-2,6-dicarboxylate. Subsequent hydroboration-oxidation generates isomers that are separated by silica chromatography or fractional crystallization. Treatment of each isomer with carbon tetrabromide (CBr4)/tetraphenylporphyrin (TPP) and sodium hydrosulfide and base converts the hydroxide group to a thiol group, then subsequent treatment with anhydrous hydrochloride results in the dihydrochloride salt form of compound 24 or compound 25.

Example 34. Synthesis of (1,5-diazocan-3-yl)methanethiol (Compound 26)

Scheme 34. Synthesis of Compound 26

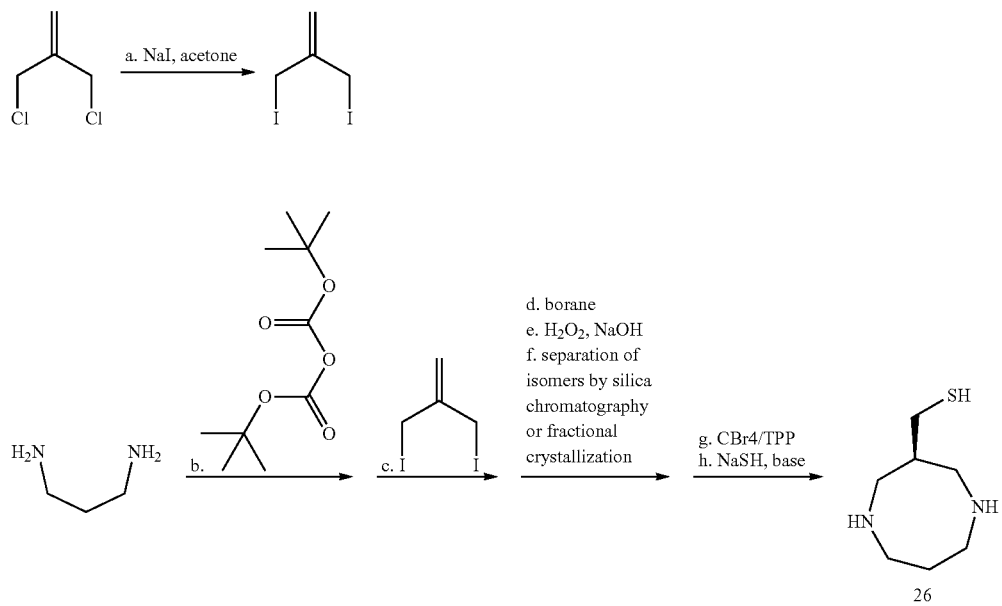

Compound 26 is prepared according to Scheme 34. (1,5-diazocan-3-yl)methanethiol (Compound 26) can be synthesized by similar methods as described in Example 32 using the appropriate diamine (e.g., propane-1,3,-diamine).

Example 35. Synthesis of [(1R,4R, 7S)-2,6-diazabicyclo[5.2.0]nonan-4-yl]methanethiol (Compound 32) and [(R,4S, 7S)-2,6-diazabicyclo[5.2.0]nonan-4-yl]methanethiol (Compound 33)

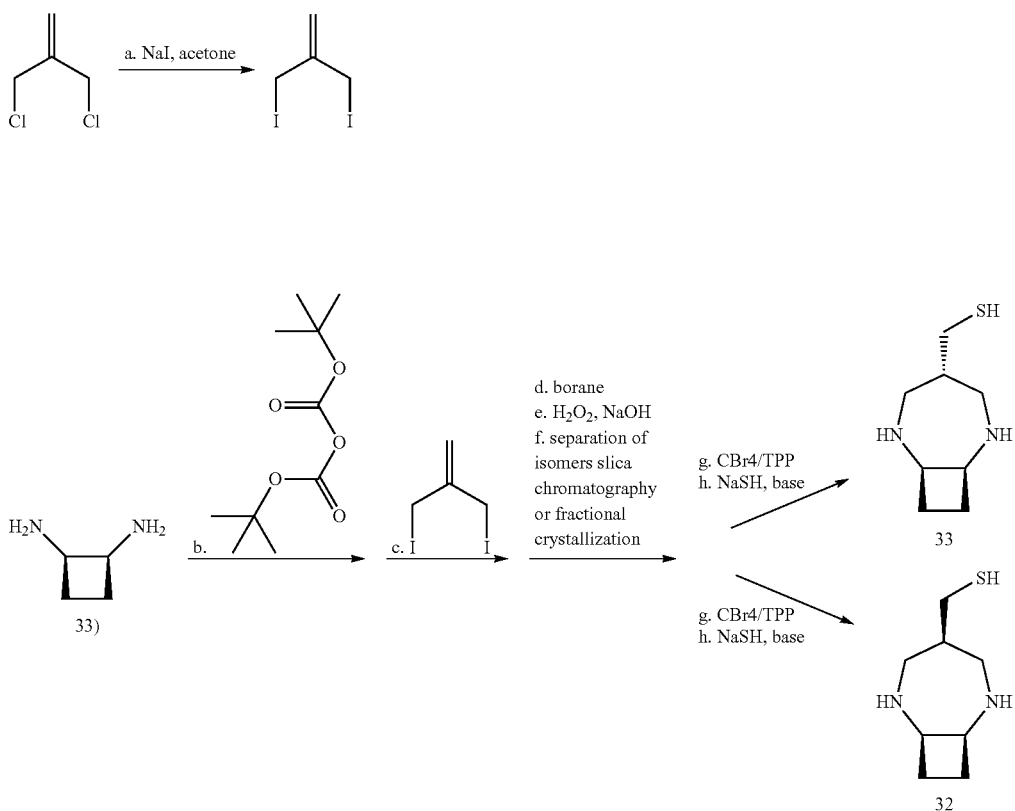

Compounds 32 and 33 are prepared according to Scheme 35. [(1R,4R,7S)-2,6-diazabicyclo[5.2.0]nonan-4-yl]methanethiol (Compound 32) and [(1R,4S,7S)-2,6-diazabicyclo[5.2.0]nonan-4-yl]methanethiol (Compound 33) can be synthesized by similar methods as described in Example 32 using the appropriate diamine (e.g., a cyclobutene-1,2,- diamine including (1R,2S)-cyclobutane-1,2-diamine) and separating the desired isomer.

Example 36. Synthesis of [(3R,5aR,8aS)-decahydrocyclopenta[b][ ],4]diazepin-3-yl]methanethiol (Compound 35) and [(3S,5aR,8aS)-decahydrocyclopenta[b][ ],4]diazepin-3-yl]methanethiol (Compound 36)

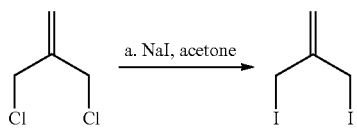

-continued

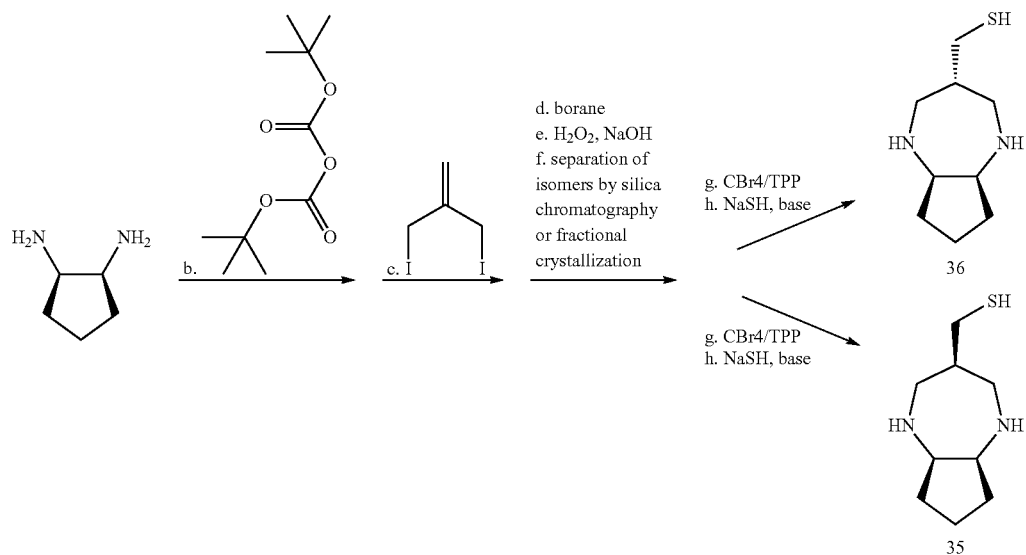

Compounds 35 and 36 are prepared according to Scheme 36. [(3R,5aR,8aS)-decahydrocyclopenta[b][1,4]diazepin-3-yl]methanethiol (Compound 35) and [(3S,5aR,8aS)-decahydrocyclopenta[b][1,4]diazepin-3-yl]methanethiol (Compound 36) can be synthesized by similar methods as described in Example 32 using the appropriate diamine (e.g., a cyclopentane-1,2,-diamine including (1R,2S)-cyclopentane-1,2-diamine) and separating the desired isomer.

Example 37. Synthesis of [(5aR,9aR)-decahydro-1H-1,5-benzodiazepin-3-yl]methanethiol (Compound 38)

Scheme 37. Synthesis of Compound 38

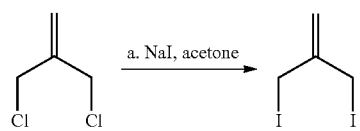

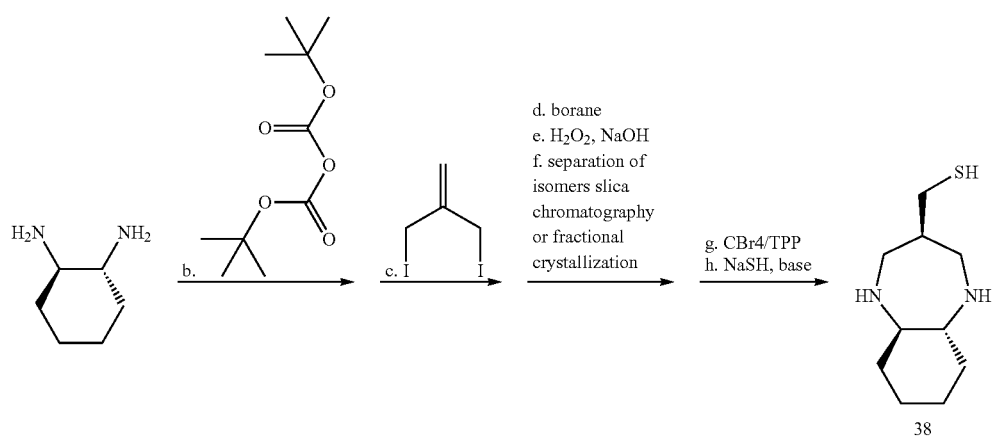

Compound 38 is prepared according to Scheme 37. [(5aR,9aR)-decahydro-1H-1,5-benzodiazepin-3-yl]methanethiol (Compound 38) can be synthesized by similar methods as described in Example 32 using the appropriate diamine (e.g., a cyclopentane-1,2,-diamine including (1R,2S)-cyclopentane-1,2-diamine) and separating the desired isomer.

Example 38. Synthesis of [(3R,8aS)-octahydropyrrolo[1,2-a]pyrazin-3-yl]methanethiol (Compound 42)

Scheme 38. Synthesis of Compound 42

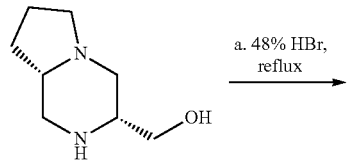

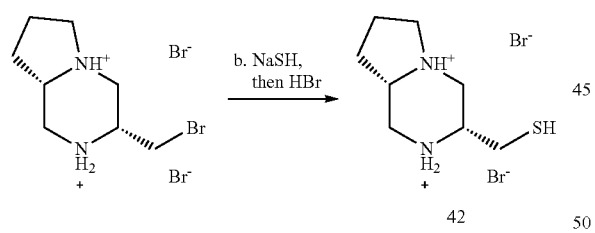

Compound 42 is prepared according to Scheme 38. In the presence of 48% hydrogen bromide (HBr), reflux, ((3R,8aS)-oxtahyddropyrrolo[1,2-a]pyrazin-3-yl)methanol is converted to (3R,8aS)-3-(bromomethyl)octahydro-1H-pyrrolo[1,2-a]pyrazine-2,5-diium. Subsequently, addition of sodium hydrosulfide, then HBr, leads to the synthesis of [(3R,8aS)-octahydropyrrolo[1,2-a]pyrazin-3-yl]methanethiol (Compound 42) as the diHBr salt.

Example 39. Alternative Synthesis of [(3R,8aS)-octahydropyrrolo[ ],2-a]pyrazin-3-yl]methanethiol (Compound 42)

Scheme 39. Alternative Synthesis of Compound 42

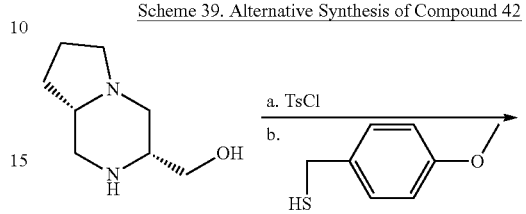

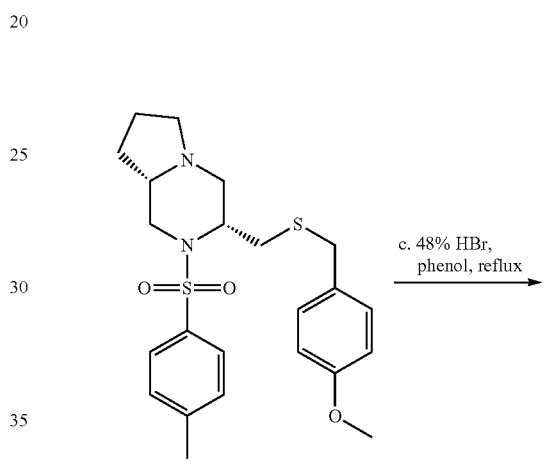

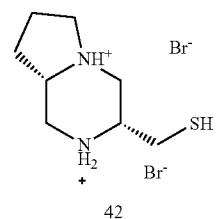

Compound 42 is prepared according to Scheme 39. In the presence of 4—toluenesulfonyl chloride, and then (4-methoxyphenyl)methanethiol, ((3R,8aS)-oxtahyddropyrrolo[1,2-a]pyrazin-3-yl)methanol is converted to (3R,8aS)-3-(((4-methoxybenzyl)thio)methyl)-2-tosyloctahydropyrrolo[1,2-a]pyrazine. Subsequent addition of 48% hydrobromide (HBr), phenol, reflux leads to the synthesis of [(3R,8aS)-octahydropyrrolo[1,2-a]pyrazin-3-yl]methanethiol (Compound 42) as the diHBr salt.

Example 40. Synthesis of [(2S,5S)-2-methyl-1,4-diazepan-5-yl]methanethiol (Compound 43)

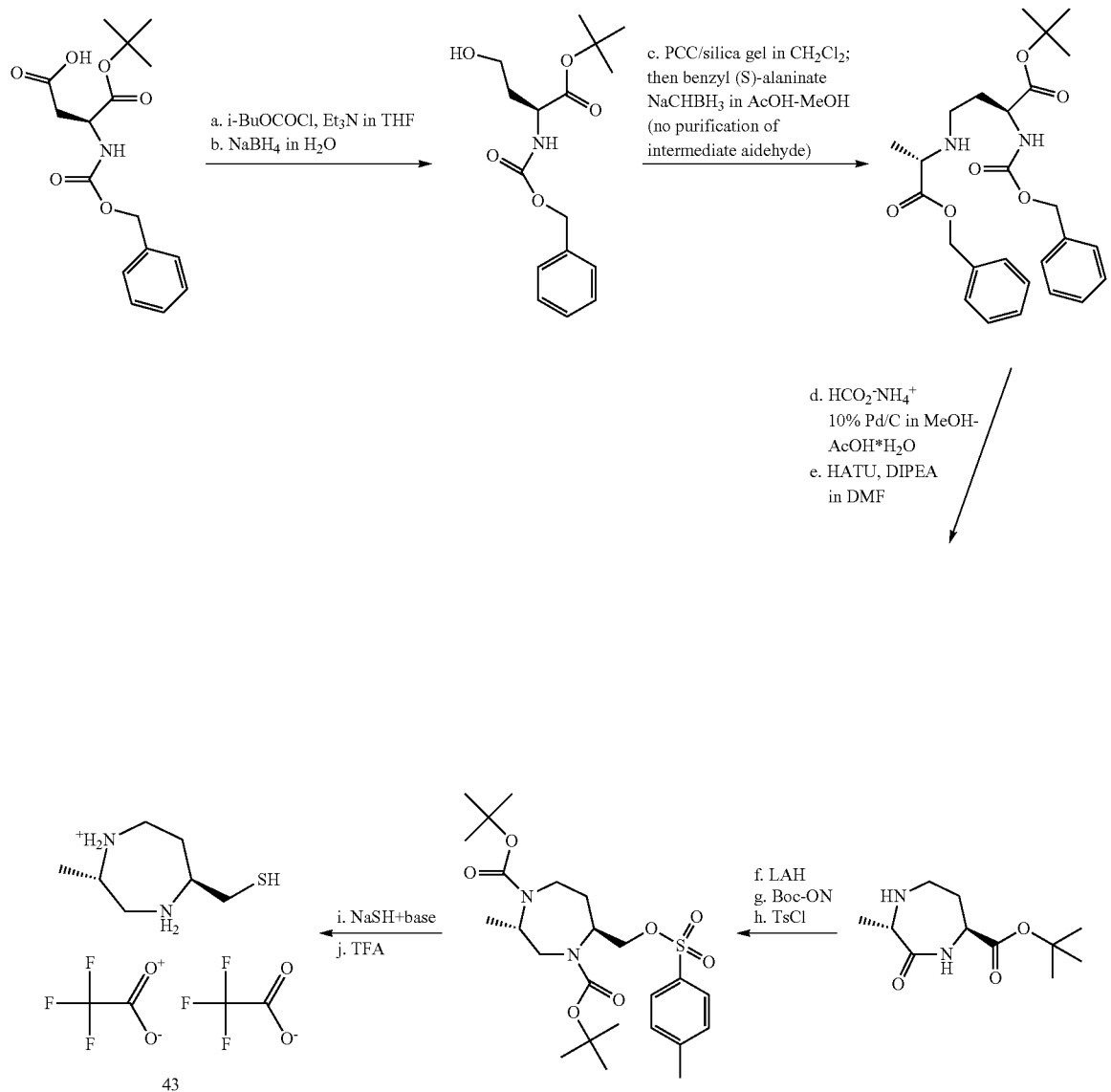

Compound 43 is prepared according to Scheme 40. Treatment of [(S)-3-(((benzyloxy)carbonyl)amino)-4-(tert-butoxy)-4-oxobutanoic acid] with isobutyl chloroformate (i-BuOCOCl) and triethylamine (Et₃N) in tetrahydrofuran (THF), followed by sodium borohydride (NaBH₄) in water forms tert-butyl ((benzyloxy)carbonyl)-L-homoserinate. Chromatography (PCC/silica gel) in dichloromethane (CH₂C2), then reaction with benzyl (S)-alaninate, sodium cyanoborohydride (NaCNBH₃) in acetic acid-methanol forms the tert-butyl (S)-4-(((S)-1-(benzyloxy)-1-oxopropan-2-yl)amino)-2-(((benzyloxy)carbonyl)amino)butanoate. Subsequent treatment with $HCO_2^-$ $NH_4^+$ in 10% Pd/C in methanol-acetic acid*H₂O and HATU, DIPEA in DMF leads to formation of tert-butyl (2S,5S)-2-methyl-3-oxo-1,4-diazepane-5-carboxylate. Subsequent treatment with lithium aluminum hydride (LAH), Boc-ON and 4—toluenesulfonyl chloride forms di-tert-butyl (2S,5S)-2-methyl-5-((tosyloxy)methyl)-1,4-diazepane-1,4-dicarboxylate. Subsequent treatment with sodium hydrosulfide plus a base, then trifluoroacetic acid (TFA) forms [(2S,5S)-2-methyl-1,4-diazepan-5-yl]methanethiol (Compound 43).

Example 41. Alternative Synthesis of [(2S,5S)-2-methyl-1,4-diazepan-5-yl]methanethiol (Compound 43)

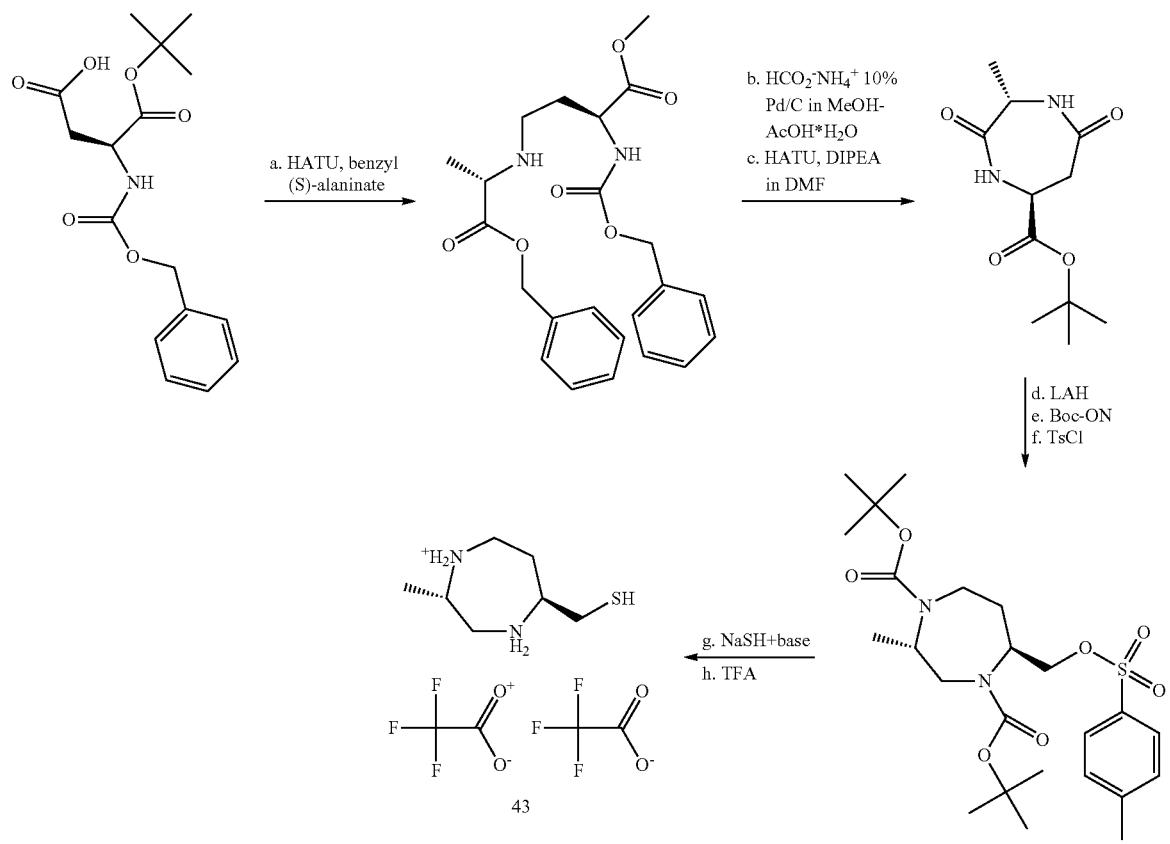

Scheme 41. Alternative Synthesis of Compound 43

Compound 43 is prepared according to Scheme 41. In the presence of HATU and benzyl (S)-alaninate, [(S)-3-(((benzyloxy)carbonyl)amino)-4-(tert-butoxy)-4-oxobutanoic acid]is converted to tert-butyl (S)-4-(((S)-1-(benzyloxy)-1-oxopropan-2-yl)amino)-2-(((benzyloxy)carbonyl)amino) butanoate. Subsequent treatment with HCO$_2$NH$_4$ in 10% Pd/C in methanol-acetic acid*H$_2$O and HATU, DIPEA in DMF leads to formation of tert-butyl (2S,5S)-2-methyl-3,7-dioxo-1,4-diazepane-5-carboxylate. Subsequent treatment with lithium aluminum hydride (LAH), Boc-ON and 4—toluenesulfonyl chloride forms di-tert-butyl (2S,5S)-2-methyl-5-((tosyloxy)methyl)-1,4-diazepane-1,4-dicarboxylate. Subsequent treatment with sodium hydrosulfide plus a base, then trifluoroacetic acid (TFA) forms [(2S,5S)-2-methyl-1,4-diazepan-5-yl]methanethiol (Compound 43) as the diTFA salt.

Example 42. Synthesis of [2-((2R,4aS,8aS)-decahydroquinoxalin-2-yl)ethane-1-thiol](Compound 50)

Scheme 42. Synthesis of Compound 50

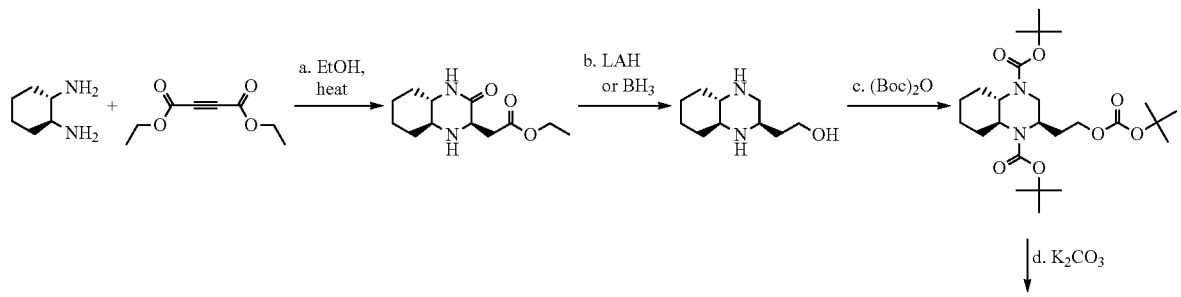

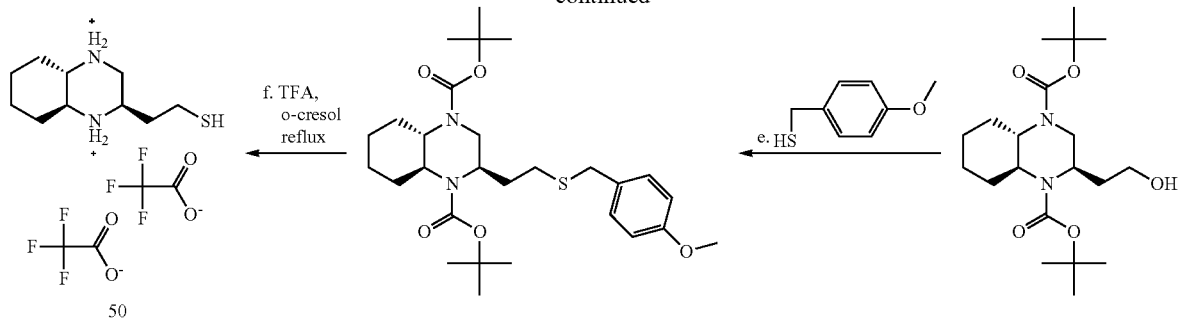

Compound 50 is prepared according to Scheme 42. (1S, 2S)-cyclohexane-1,2-diamine is combined with diethyl but-2-ynedioate in the presence of ethanol and heat to form ethyl 2-((2R,4aS,8aS)-3-oxodecahydroquinoxalin-2-yl)acetate. Subsequent addition of lithium aluminum hydride (LAH) or borane (BH$_3$) forms 2-((2R,4aS,8aS)-decahydroquinoxalin-2-yl)ethan-1-ol, then subsequent addition of di-tert-butyl decarbonate ((Boc)$_2$0 forms di-tert-butyl (2R,4aS,8aS)-2-(2-((tert-butoxycarbonyl)oxy)ethyl)octahydroquinoxaline-1,4-dicarboxylate. Subsequent addition of potassium carbonate forms di-tert-butyl (2R,4aS,8aS)-2-(2-hydroxyethyl)octahydroquinoxaline-1,4-dicarboxylate. When reacted with (4-methoxyphenyl)methanethiol, di-tert-butyl (2R,4aS,8aS)-2-(2-((4-methoxybenzyl)thio)ethyl)octahydroquinoxaline-1,4-dicarboxylate is formed. Subsequent treatment with trifluoroacetic acid (TFA). O-cresol, reflux forms [2-((2R,4aS,8aS)-decahydroquinoxalin-2-yl)ethane-1-thiol] (Compound 50) as the diTFA salt.

Example 43. Synthesis of 3-(methylamino)-2-((methylamino)methyl)propane-1-thiol) (PrC-210 diHCl)

Scheme 43. Synthesis of 3-(methylamino)-2-((methylamino)methyl)propane-1-thiol) (PrC-210)

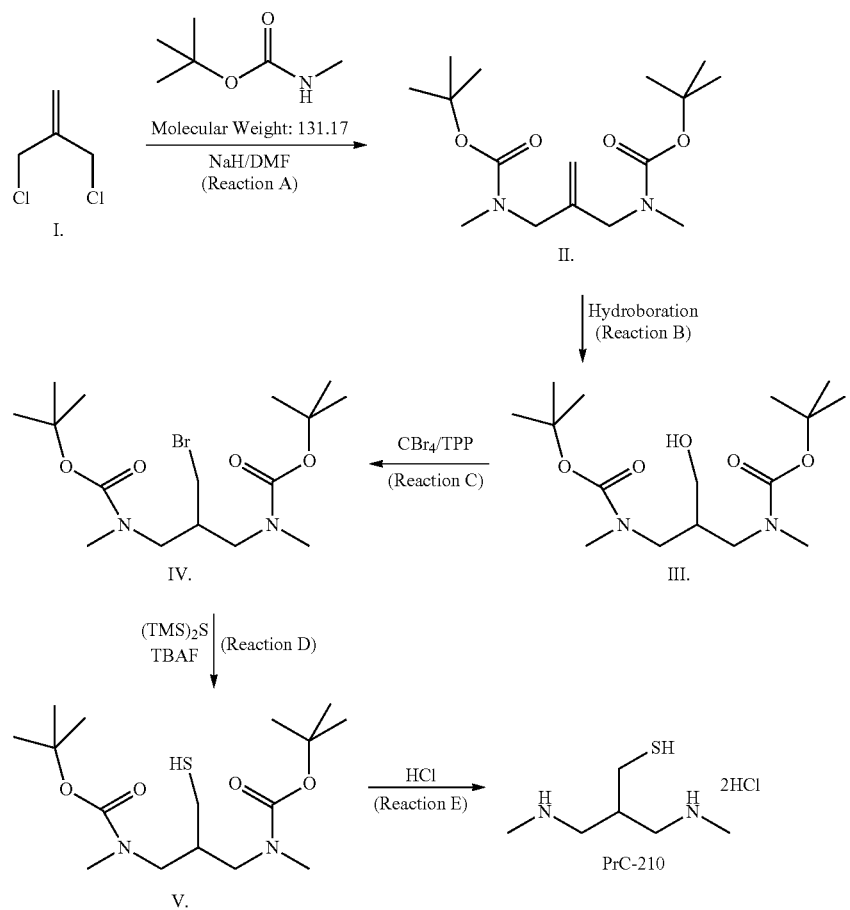

PrC-210 was synthesized according to Scheme 43. In Reaction A: Tert-Butylmethylcarbamate (CAS: 16066-84-5), 10 grams, 0.076 moles and 50 ml dry dimethylformamide (DMF) were added to a flame-dried round bottom flask, under argon, that was set up for magnetic stirring. The flask was cooled in an ice bath, then sodium hydride, 3.34 grams, 1.1 eq. (60% dispersion in mineral oil, Aldrich #452912) was added portion wise over 10 minutes (caution, gas evolution) and the reaction was allowed to stir for 1 hour while warming to room temperature. 3-chloro-2-chloromethyl-1-propene (CAS: 1871-57-4, Aldrich #C31104), 3.80 g, 0.4 eq. pre-dried over 4A molecular sieves, in 3 ml anhydrous DMF, was added to this mixture slowly over 15 min at room temperature. The reaction was then heated to 60° C. for 24 hours until the reaction was determined to be complete using TLC. The reaction was then cooled in an ice bath and quenched with aqueous saturated NaCl and extracted with ethyl acetate, (3×100 ml). The combined extracts were dried over $MgSO_4$, filtered, concentrated. The crude material was purified by silica gel flash column chromatography eluting with hexane/ethylacetate mixtures providing 6.8 grams (71%) of compound II (i.e., di-tert-butyl (2-methylenepropane-1,3-diyl)bis(methylcarbamate)) as a solid. The structure was confirmed by NMR.

In Reaction B: Compound II, 6 grams, 0.018 moles and 35 ml anhydrous THE were added to a flame-dried round bottom flask, under argon, set up for magnetic stirring. The reaction was cooled to 0° C. A solution of borane in THF, 1M (Aldrich #176192), 19.8 mL, 1.1 eq. was added via syringe and the reaction was allowed to warm up to room temperature and allowed to stir for 1 hour. TLC analysis (10% EtOAc in Hexane) showed complete disappearance of starting material. The reaction was opened to the air and quenched with 1 ml $H_2O$, added dropwise. NaOH, 3M solution (25 ml) was then added followed by dropwise addition of 5 ml of 30% $H_2O_2$ keeping the solution close to room temperature with an ice bath as needed. The reaction was stirred for another hour at room temperature. Solid NaCl was added until the solution was saturated and the mixture was extracted with ethyl acetate, (3×100 ml). The combined extracts were dried over $MgSO_4$, filtered and concentrated. The crude material was purified by silica gel flash column chromatography eluting with hexane/ethylacetate mixtures providing 5.2 grams (84%) of compound III (i.e., di-tert-butyl (2-(hydroxymethyl)propane-1,3-diyl)bis(methylcarbamate)) as a solid. Structure was confirmed by NMR, MS. Purity by TLC.

In Reaction C: A solution of 5 grams, 0.015 moles, of compound III (dried in vacuo over $P_2O5$) in 50 mL of dry dichloromethane and magnetically stirred under argon at room temperature was treated with 6.5 grams, 1.3 eq $CBr_4$. The solution was then cooled (−30° C.) and triphenylphosphine 5.3 grams, 1.35 eq. was added in 3 portions over 30 minutes. The reaction was allowed to reach 0° C. over 30 minutes and maintained at that temperature for 4 hours. TLC analysis (10% EtOAc in Hexane) of the reaction showed complete conversion of the starting material. The mixture was concentrated and applied to a silica gel column and eluted with mixtures of dichloromethane and methanol of increasing polarity. The combined fractions were pooled and evaporated providing compound IV as a low-melting waxy solid, 5.35 grams (90%). The structure was confirmed by NMR, MS. The purity was determined by TLC.

In Reaction D: 25 ml of distilled anhydrous THE was added to compound IV, 5 g, 0.013 moles, in a flask under argon and equipped for magnetic stirring and cooled to −10° C. Hexamethyldisilathiane, CAS 3385-94-2 (Aldrich #283134), 2.78 grams, 1.2 eq. was added followed by dropwise addition of Tetrabutylammonium fluoride solution, 1 M in THF, (TBAF, Aldrich #216143) 15.6 mL, 1.2 eq over 5 minutes. The reaction was stirred at −10° C. for 30 minutes and then allowed to warm to room temperature over 30 minutes. TLC analysis (5% EtOAc in Hexane) showed disappearance of starting material. The reaction was quenched with 10 mL of saturated $NH_4Cl$ solution. The mixture was extracted with ethyl acetate, (3×100 mL). The combined extracts were washed with brine, dried over $MgSO_4$, filtered and concentrated. The crude material was purified by silica gel flash column chromatography and eluted with hexane/ethylacetate mixtures providing 3.7 grams (82%) of compound V as a waxy solid. The structure was confirmed by NMR, MS and the purity determined by TLC. The compound had a characteristic thiol-like odor.

In Reaction E: 48 ml of HCl in methanol, 6 eq. (1.25 M solution, Aldrich #17935) was added to a solution of compound V, 3.5 g, 0.010 moles dissolved in 10 ml dry methanol in a flask under argon and equipped for magnetic stirring and the reaction was stirred at room temperature for 24 hours. TLC analysis (20% EtOAc in Hexane) showed the disappearance of starting material and the appearance of a highly polar compound that stained positive with ninhydrin. The solution was degassed by gently bubbling argon into the solution for 30 minutes.

Concentration (rotary evaporator at ambient temperature) provided a crude oily residue which was triturated with hexane producing a white solid. The hexane was removed (via pipette suction) and replaced with dry THE (25 ml). After an additional 10 minutes of trituration, the THF was removed and replaced with dry hexane (25 ml). After an additional 10 minutes of trituration, the hexane was removed and the resulting white solid was dried in vacuo over $P_2O5$ providing 1.95 grams of diHCl salt of PrC-210 (88%). A 10 minutes exposure of a small amount of PrC-210 to the atmosphere did not show any signs of hygroscopicity. PrC-210 showed HPLC purity of >98%, NMR and MS were fully consistent with the structure.

Example 45. Synthesis of ((1,4-diazepan-6-yl)methanethiol HBr) (Compound 22 HCl, DzCH2SH)

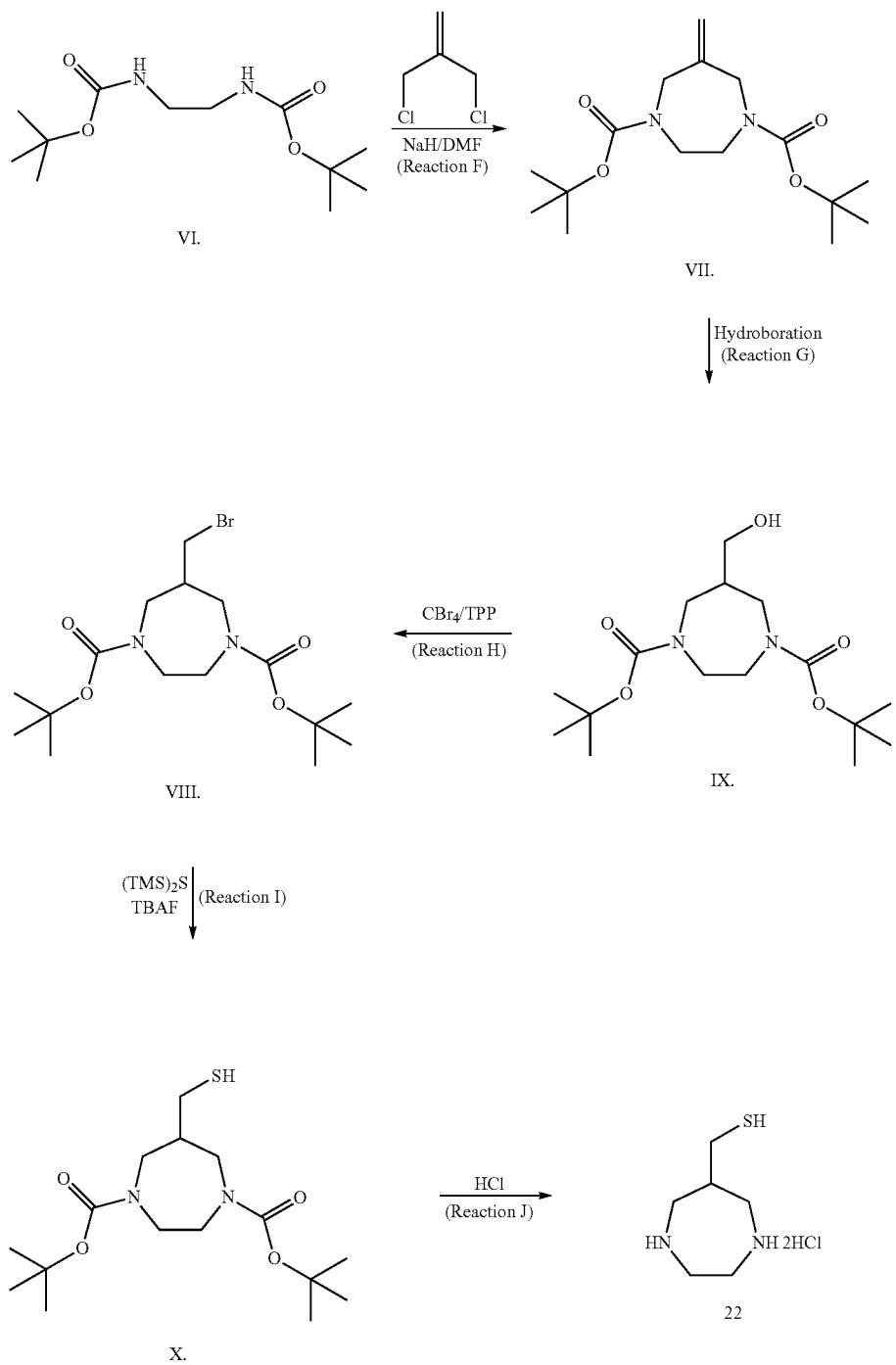

Scheme 45. Synthesis of Compound 22, DzCH2SH

Compound 22 was synthesized according to Scheme 45. In Reaction F: Di-tert-butyl ethane-1,2-diyldicarbamate (compound VI; CAS: 33105-93-0, Combi-Blocks # QK-1806), 10 grams, 0.038 moles and 150 ml dry dimethylformamide (DMF) were added to a flame-dried round bottom flask, under argon, set up for magnetic stirring. The flask was cooled in an ice bath, then sodium hydride, 3.38 grams, 2.2 eq. (60% dispersion in mineral oil, Aldrich #452912) was added portion wise over 10 minutes (caution, hydrogen gas evolution) and the reaction was allowed to stir for 1 hour while warming to room temperature. 3-chloro-2-chloromethyl-1-propene (CAS: 1871-57-4, Aldrich # C31104), 4.8 grams, 1.0 eq., pre-dried over 4A molecular sieves, in 6 ml anhydrous DMF was rapidly added to the mixture at room temperature. The reaction was then heated to 60° C. for 24 hours and the reaction was determined to be complete by TLC. The reaction was then cooled in an ice bath and quenched with aqueous saturated NaCl and extracted with ethyl acetate, (3×100 ml). The combined extracts were dried over MgSO$_4$, filtered and concentrated. The crude material was purified by silica gel flash column chromatography eluting with hexane/ethylacetate mixtures providing 7.4 grams (63%) of compound VII as a solid. The structure was confirmed by NMR and MS.

In Reaction G: compound VII, 7 grams, 0.022 moles and 42 mL anhydrous THE were added to a flame-dried round bottom flask, under argon, equipped for magnetic stirring. The reaction was cooled to 0° C. A solution of borane in THF, 1M (Aldrich #176192), 24.2 mL, 1.1 eq. was added via syringe and the reaction was allowed to warm up to room temperature and allowed to stir for 1 hour. TLC analysis showed complete disappearance of starting material.

The reaction was opened to the air and quenched with 2 mL H$_2$O added dropwise. NaOH, 3M solution (30 mL) was then added followed by dropwise addition of 6 mL of 30% H$_2$O$_2$ keeping the solution close to room temperature with an ice bath as needed. The reaction was stirred for another hour at room temperature. Solid NaCl was added until the solution was saturated and the mixture was extracted with ethyl acetate, (3×100 ml). The combined extracts were dried over MgSO$_4$, filtered and concentrated. The crude material was purified by silica gel flash column chromatography eluting with hexane/ethylacetate mixtures providing 6.14 grams (83%) of compound VIII as a solid. The structure was confirmed by NMR.

In Reaction H: A solution of 6 grams, 0.018 moles, of compound VIII (dried in vacuo over P$_2$O$_5$) in 75 mL of dry dichloromethane and magnetically stirred under argon at room temperature was treated with 7.8 grams, 1.3 eq CBr$_4$. The solution was then cooled (−30° C.) and triphenylphosphine 6.37 grams, 1.35 eq. was added in 3 portions over 30 minutes. The reaction was allowed to reach 0° C. over 30 minutes and maintained at that temperature for 4 hours. TLC of the reaction showed complete conversion of starting material. The mixture was concentrated and applied to a silica gel column and eluted with mixtures of dichloromethane and methanol of increasing polarity. The combined fractions were pooled and evaporated providing compound IX as a viscous oil, 6.21 grams (87%). The structure was confirmed by NMR.

In Reaction I: 25 ml of distilled anhydrous THE was added to compound IX, 4 grams, 0.010 moles, in a flask under argon and equipped for magnetic stirring and was cooled to −10° C. Hexamethyldisilathiane, CAS 3385-94-2 (Aldrich Cat #283134), 2.18 grams, 1.2 eq. was added, followed by dropwise addition of tetrabutylammonium fluoride solution, 1 M in THF, (TBAF, Aldrich Cat #216143) 12.0 mL, 1.2 eq. over 5 minutes. The reaction was stirred at −10° C. for 30 minutes and then allowed to warm to room temperature over 30 minutes. TLC analysis showed disappearance of starting material. The reaction was quenched with 10 mL of saturated NH$_4$Cl solution. The mixture was extracted with ethyl acetate, (3×100 ml). The combined extract was washed with brine, dried over MgSO$_4$, filtered and concentrated. The crude material was purified by silica gel flash column chromatography eluting with hexane/ethylacetate mixtures providing 2.88 grams (83%) of compound X as a waxy solid. The structure was confirmed by NMR and the compound had a characteristic mercaptan-like order.

In Reaction J: 34 ml of HCl in methanol, 6 eq. (1.25 M solution, Aldrich Cat #17935) was added to a solution of compound X, 2.5 grams, 0.007 moles dissolved in 10 mL dry methanol in a flask under argon and equipped for magnetic stirring and the reaction was stirred at room temperature for 24 hours. TLC analysis showed the disappearance of starting material and the appearance of a highly polar compound that stained positive with ninhydrin. The solution was degassed by gently bubbling argon into the solution for 30 minutes. The concentration (rotary evaporator at ambient temp) provided a crude oily residue which was triturated under argon with hexane producing a white solid. The hexane was removed (via pipette suction) and replaced with dry THE (20 mL). After a further 10 minutes of trituration under argon, the THF was removed and replaced with dry hexane (20 mL). After an additional 10 minutes of trituration under argon, the hexane was removed and the resulting white solid was dried in vacuo over P$_2$O$_5$ providing 1.4 g of Compound 22 (91%). A 10 minute exposure of a small amount of DzCH2SH to the atmosphere did not show any signs of hygroscopicity. The DzCH2SH as the diHCl salt produced in this manner showed HPLC purity of >98%, and NMR and MS analysis were fully consistent with the structure.

Example 46: Synthesis of (2-(piperazin-2-yl)propane-2-thiol) (Compound 21,2Pip-2PrSH)

Scheme 46. Synthesis of Compound 21, 2Pip-2PrSH

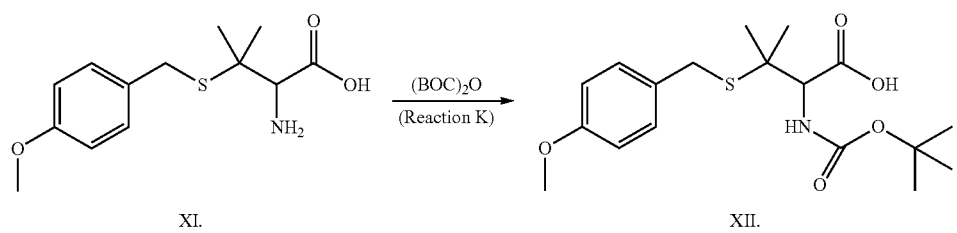

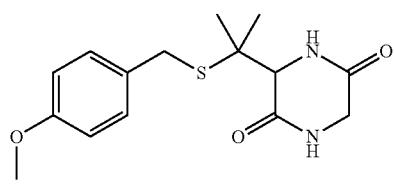

XIV.

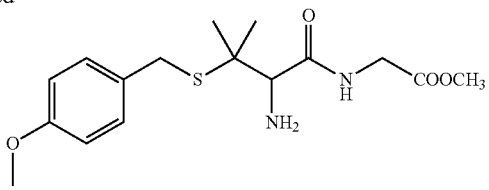

XIII.

BH3/THF (Reaction N)

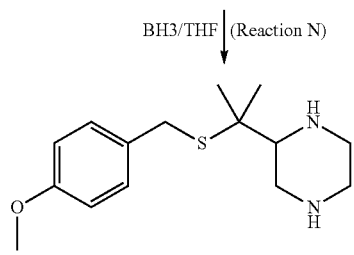

XV.

(BOC)₂
(Reaction O)

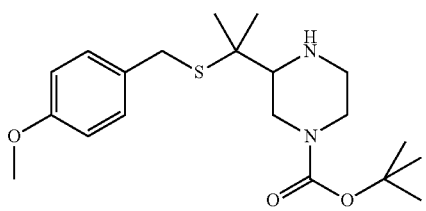

6

TFA
Ion exchange
HCl
(Reaction P)

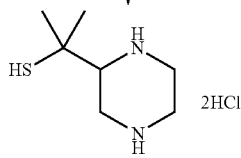

2HCl

21

Compound 21 was synthesized according to Scheme 46. In Reaction K: 2-Amino-3-((4-methoxybenzyl)thio)-3-methylbutanoic acid (compound XI), 10 grams, 0.037 moles was placed in a round-bottom flask, equipped for magnetic stirring and 200 mL 1:1 mixture of THF/H$_2$O was added. The flask was cooled in an ice bath and BOC anhydride, 9.71 grams, 1.2 eq. (Aldrich #34660) was added in one portion followed by sodium bicarbonate (NaHCO$_3$) 3 grams, 5 eq. and the reaction was allowed to stir for 1 hour. Subsequently, the flask was removed from the ice bath and stirred for 14 hours at room temperature. The reaction was determined to be complete by TLC and the THF was then stripped off using a rotary evaporator and the resulting mixture was treated with NaCl (saturation) and extracted with ethyl acetate, (3×200 ml). The combined extracts were dried over MgSO$_4$, then filtered and concentrated. The resulting solid was purified by recrystallization with ethanol providing 13.1 grams (94%) of compound XII as a white solid. The structure was confirmed by NMR and MS.

In Reaction L: Compound XII, 12 grams, 0.032 moles was placed in a flame-dried round bottom flask, under argon, equipped for magnetic stirring along with glycine methyl-ester, 2.85 grams, 1 eq. followed by 100 mL anhydrous dimethylformide. To this solution was added diisopropyl-ethylamine (DIEA, Aldrich 387649) 4.95 grams, 1.2 eq. followed by N-[(Dimethylamino)-1H-1,2,3-triazolo-[4,5-b]pyridin-1-ylmethylene]-N-methylmethanaminium hexafluorophosphate N-oxide, (HATU, Aldrich 445460) 13.4 grams, 1.1 eq. and the reaction was stirred overnight at room temperature. TLC analysis indicated that the reaction was complete. The reaction was poured into 400 mL of ice-cold water and stirred while warming to room temperature. The resulting precipitate was collected by filtration and washed with distilled water (100 mL) followed by diethyl ether (25 mL) and dried in vacuo over P$_2$O$_5$ providing 13.5 grams of intermediate BOC-protected amide, without further purification. The BOC group was removed by first dissolving the intermediate (11.5 g) in 75 mL dry methanol in a flask under argon, equipped for magnetic stirring. Then a solution of HCl in methanol, 52 mL, 2 eq. (1.25 M solution, Aldrich Cat #17935) was added and the reaction was stirred at room temperature for 24 hours. TLC analysis showed the disappearance of starting material and the appearance of a more polar product that stained positive with ninhydrin. The solution was degassed by bubbling argon into the solution for 30 minutes. The solution was made alkaline by addition of excess 1 M aqueous NaOH (with cooling) and the resulting solution was extracted with dichloromethane (3×200 mL) followed by concentration (rotary evaporator) which provided a crude oily residue. Flash column chromatography with CH$_2$Cl$_2$/CH$_3$OH mixtures provided pure compound XIII, 7.8 grams, 72% yield as a waxy solid. The structure was confirmed by NMR and MS.

In Reaction M: Compound XIII, 7 grams, 0.020 moles, was placed in a round-bottom flask equipped for magnetic stirring, then 100 mL toluene was added and the flask was fitted with a condenser. The solution was refluxed for 24 hours whereupon TLC analysis showed a complete reaction.

The solution was concentrated and the crude product was then subjected to flash column chromatography on silica gel eluting with CH$_2$Cl$_2$/CH$_3$OH mixtures which provided pure compound XIV, 4.3 grams, 68% yield as a white solid. The structure was confirmed by NMR and MS.

In Reaction N: Compound XIV, 4 grams, 0.013 moles and 10 mL anhydrous THF were added to a flame-dried round bottom flask, under argon, equipped for magnetic stirring. A solution of borane in THF, 1M (Aldrich #176192), 39 mL, 3 eq. was added slowly via syringe. The reaction was then refluxed for 4 days. TLC analysis shows complete disappearance of starting material. The reaction was opened to the air and quenched with 5 mL H$_2$O. The reaction was stirred for another 30 minutes at room temperature. The solution was then concentrated to dryness using a rotary evaporator and the solids washed exhaustively with chloroform/methanol (1:1) solution, 200 mL. The combined washings were concentrated and the crude product (3.6 grams of compound XV) was carried directly into the subsequent reaction without purification.

In Reaction 0: the crude product compound XV was BOC-protected so it could be purified by column chromatography. Crude compound XV, 3.6 grams, 0.013 moles was placed in a round-bottom flask equipped for magnetic stirring and 50 mL 1:1 mixture of THF/H$_2$O was added. The flask was cooled in an ice bath and BOC anhydride, 3.1 grams, 1.2 eq. (Aldrich #34660) was added in one portion followed by sodium bicarbonate (NaHCO$_3$) 5.4 grams, 5 eq. and the reaction was allowed to stir for 1 hour, then removed from the ice bath and was stirred for 14 hours at room temperature. The reaction was determined to be complete by TLC. The THF was then stripped off using a rotary evaporator and the resulting mixture was treated with NaCl (saturation) and extracted with ethyl acetate, (4×50 mL). The combined extracts were dried over MgSO$_4$, filtered and concentrated. The resulting solid was purified by flash column chromatography on silica gel eluting with CH$_2$Cl$_2$/CH$_3$OH mixtures which provided pure compound XVI, x 2.4 grams, 49% yield from compound XIV as a white solid. The structure was confirmed by NMR and MS.

In Reaction P: Compound XVI, 2.2 grams, 0.0058 moles was placed in a round-bottom flask equipped for magnetic stirring followed by 15 mL anhydrous trifluoroacetic acid (CF$_3$COOH, Aldrich #8.08260). The flask was fitted with a condenser and the solution was refluxed for 5 hours whereupon it was determined that the reaction was complete using TLC by observing the disappearance of starting material and the appearance of a highly polar product, which stained positive with ninhydrin. The solution was concentrated using a rotary evaporator to a solid residue. This crude product was converted to the free base by first adding 20 mL of CH$_2$Cl$_2$/CH$_3$OH (1:1) to the flask under an argon atmosphere with a magnetic stir bar. Then Amberlyst A-21 ion exchange resin, 6 grams (Alfa Aesar # A17956), which was prewashed by three successive treatments with 20 mL of CH$_2$Cl$_2$/CH$_3$OH (1:1), was added to the solution. The mixture was stirred at room temperature for 3 hours followed by rapid filtration under argon. The resin was washed with an additional 20 mL CH$_2$Cl2/CH$_3$OH (1:1) and was concentrated using a rotary evaporator at room temperature, forming a waxy residue. This waxy residue product was then converted to the HCl salt by adding the residue to 10 mL dry methanol followed by addition of 14.5 mL of HCl in methanol, 2.5 eq. (1.25 M solution, Aldrich Cat #17935), which produced a clear solution which was allowed to stand for 15 minutes. The solution was then degassed by bubbling argon through the solution for 15 minutes. Concentrating with a rotary evaporator at ambient temperature provided a crude residue which was triturated under argon with hexane (25 mL) produced a white solid. The hexane was removed (via pipette suction) and replaced with dry THF (10 mL). After an additional 10 minutes of trituration under argon, the THF was removed and replaced with dry hexane (20 mL). After an additional 10 minutes of trituration under argon, the hexane was removed and the resulting white solid was dried in vacuo over P$_2$O$_5$ providing 1.2 grams of Compound 21 as the diHCl salt (89%). A 10-minute exposure of a small amount of Compound 22 to the atmosphere did not show any signs of hygroscopicity. The compound produced in this manner showed HPLC purity of >98%, and NMR and MS analysis were consistent with the structure.

Example 47. Synthesis of [(3R,8aS)-octahydropyrrolo[1,2-a]pyrazin-3-yl]methanethiol (Compound 42)

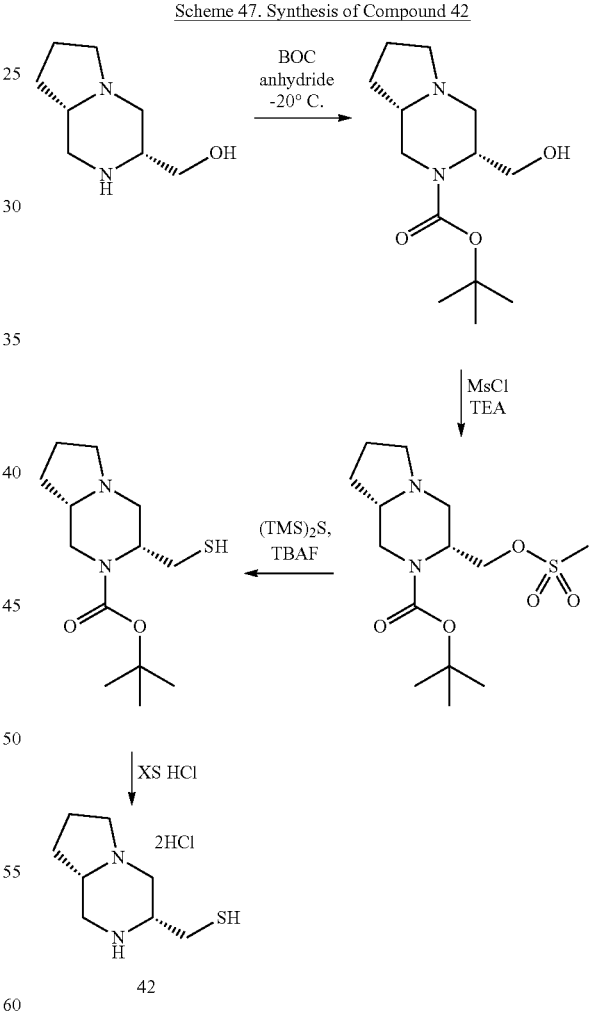

Compound 42 is prepared according to Scheme 47. BOC anhydride is added to ((3R, 8aS)-octahydropyrrolo[1,2-a]pyrazin-3-yl)methanol and chilled (e.g., −20° C.) to form tert-butyl (3R,8aS)-3-(hydroxymethyl)hexahydropyrrolo[1,2-a]pyrazine-2(1H)-carboxylate. Subsequently, MsCl and triethanolamine (TEA) is added to form tert-butyl (3R,8aS)-

3-(((methylsulfonyl)oxy)methyl)hexahydropyrrolo[1,2-a]pyrzine-2(1H)-carboxylate. Next, Bis(trimethylsilyl)sulfide ((TMS)$_2$S) and tetra-n-butylammonium fluoride (TBAF) is added to to form tert-butyl (3R,8aS)-3-(mercaptomethyl)hexahydropyrrolo[1,2-a]pyrazine-2(1H)-carboxylate. Then excess of HCl leads to the synthesis of [(3R,8aS)-octahydropyrrolo[1,2-a]pyrazin-3-yl]methanethiol (Compound 42) as the diHCl salt.

Example 48. Synthesis of [2-((2R,4aS,8aS)-decahydroquinoxalin-2-yl)ethane-1-thiol](Compound 50)

Compound 50 is prepared according to Scheme 48. (1S,2S)-cyclohexane-1,2-diamine and dimethyl but-2-ynedioate are combined and heated in the presence of ethanol to form methyl 2-((4aS,8aS,Z)-3-oxooctahydroquinoxalin-2(1H)-ylidene)acetate. Subsequent addition of hydrogen and palladium (Pd) leads to the formation of two stereoisomers: 1. methyl 2-((2R,4aS,8aS)-3-oxodecahydroquinoxalin-2-yl)acetate and 2. methyl 2-((2S,4aS,8aS)-3-oxodecahydroquinoxalin-2-yl)acetate. When the stereoisomers are in the presence of lithium aluminum hydride or borane, 2-((2R,4aS,8aS)-decahydroquinoxalin2-yl)ethan-1-ol or its isomer forms. Subsequent addition of di-tert-butyl decarbonate

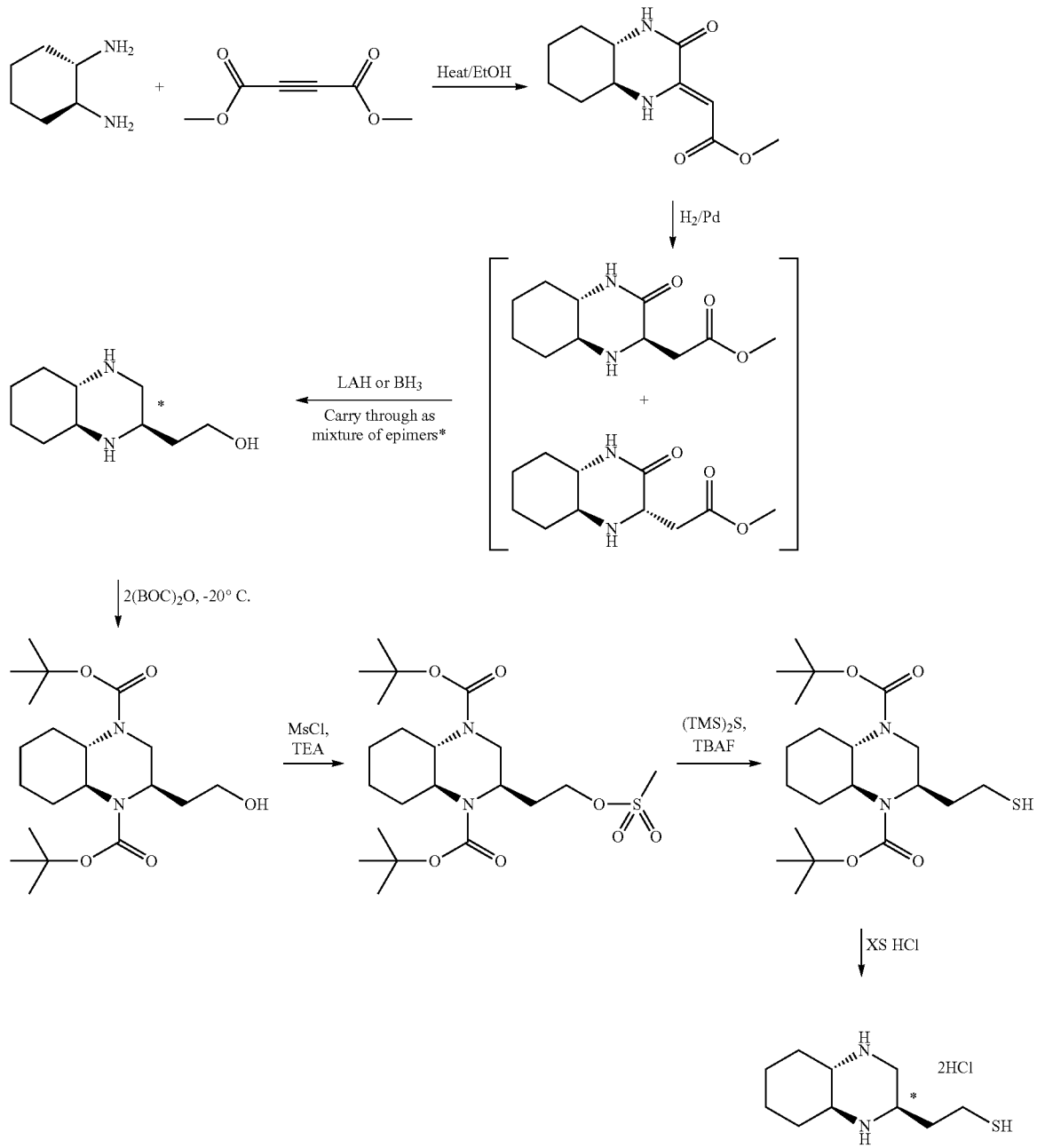

((2BOC)$_2$O), chilled (e.g., −20° C.) forms di-tert-butyl (2R,4aS,8aS)-2-(2-hydroxyethyl)octahydroquinoxaline-1,4-dicarboxylate, or its isomer. Exposure of the intermediate to methanesulfonyl chloride (MsCl) and triethylamine forms di-tert-butyl (2R,4aS,8aS)-2-(2-((methylsulfonyl)oxy)ethyl)octahydroquinoxaline-1,4-dicarboxylate, or its isomer. Subsequent addition of bis(trimethylsilyl) sulfide ((TMS)$_2$S) and tetra-n-butylammonium fluoride (TBAF) forms di-tert-butyl (2R,4aS,8aS)-2-(2-mercaptoethyl)octahydroquinoxaline-1,4-dicarboxylate, or its isomer. In the presence of excess HCl, 2-((2R,4aS,8aS)-decahydroquinoxalin-2-yl)ethane-1-thiol (Compound 50) as the diHCl salt, or its isomer, is formed. The stereoisomers can be optionally separated by silica chromatography or recrystallization to yield one or both stereoisomers of the final product.

Example 49. Synthesis of [2-((2R,4aS,8aS)-decahydroquinoxalin-2-yl)ethane-1-thiol](Compound 50)

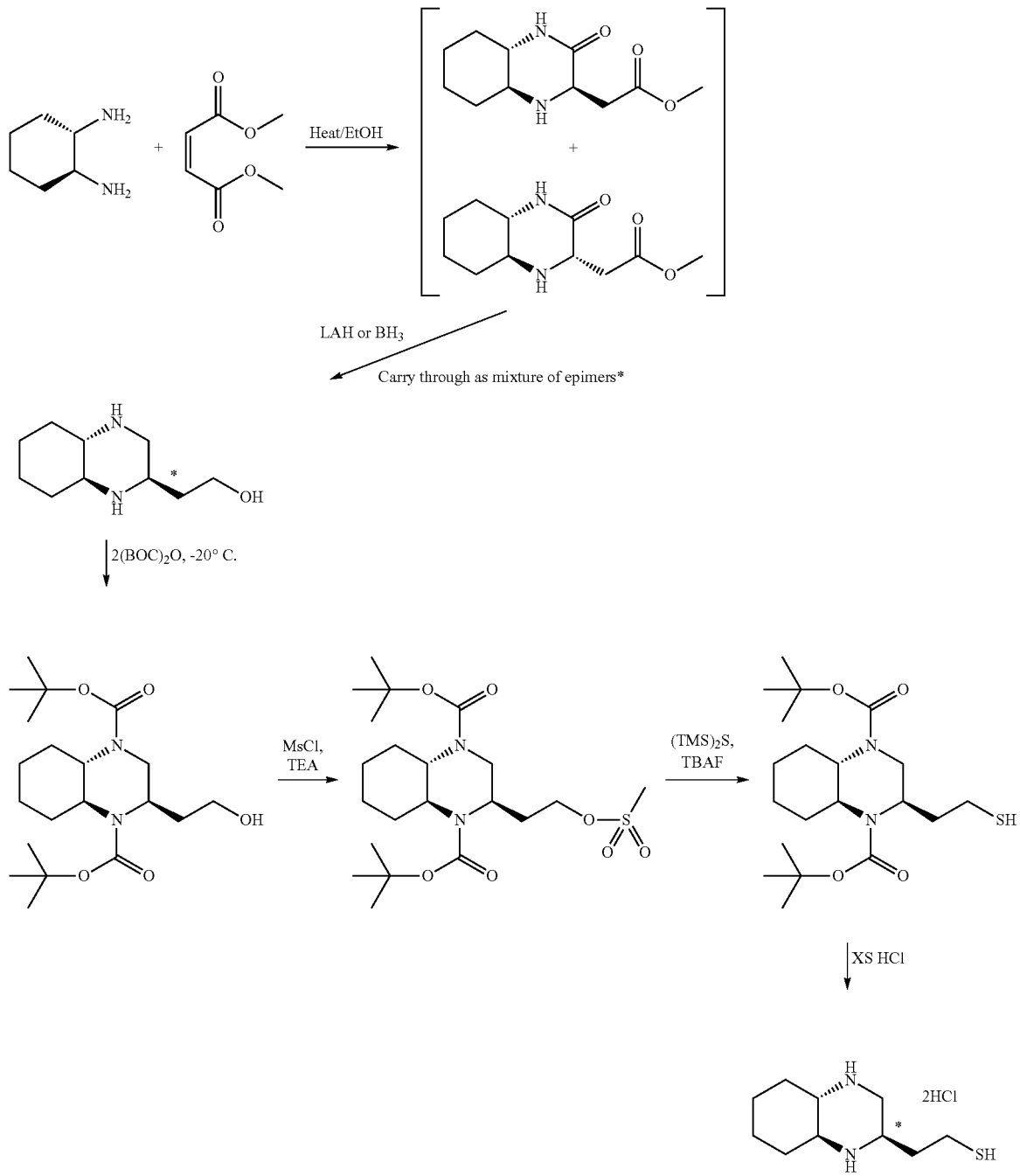

Compound 50 is prepared according to Scheme 49. (1S, 2S)-cyclohexane-1,2-diamine and dimethyl maleate are combined and heated in the presence of ethanol to form two stereoisomers. 1. methyl 2-((2R,4aS,8aS)-3-oxodecahydroquinoxalin-2-yl)acetate and 2. methyl 2-((2S,4aS,8aS)-3-oxodecahydroquinoxalin-2-yl)acetate. When the stereoisomers are in the presence of lithium aluminum hydride or borane, 2-((2R,4aS,8aS)-decahydroquinoxalin2-yl)ethan-1-ol, or its isomer, forms. Subsequent addition of di-tert-butyl decarbonate ((2BOC)₂O), chilled (e.g., −20° C.), forms di-tert-butyl (2R,4aS,8aS)-2-(2-hydroxyethyl)octahydroquinoxaline-1,4-dicarboxylate, or its isomer. Exposure of the intermediate to methanesulfonyl chloride (MsCl) and triethylamine forms di-tert-butyl (2R,4aS,8aS)-2-(2-((methylsulfonyl)oxy)ethyl)octahydroquinoxaline-1,4-dicarboxylate, or its isomer. Subsequent addition of bis(trimethylsilyl) sulfide ((TMS)₂S) and tetra-n-butylammonium fluoride (TBAF) forms di-tert-butyl (2R,4aS,8aS)-2-(2-mercaptoethyl)octahydroquinoxaline-1,4-dicarboxylate, or its isomer. In the presence of excess HCl, 2-((2R,4aS,8aS)-decahydroquinoxalin-2-yl)ethane-1-thiol (Compound 50) as the diHCl salt, or its isomer, is formed. The stereoisomers can be optionally separated by silica chromatography or recrystallization to yield one or both stereoisomers of the final product.

What is claimed is:

1. A compound according to formula I:

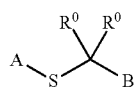

formula I each R⁰ is independently H or (C1-C3)alkyl;
A is H; and
B is:

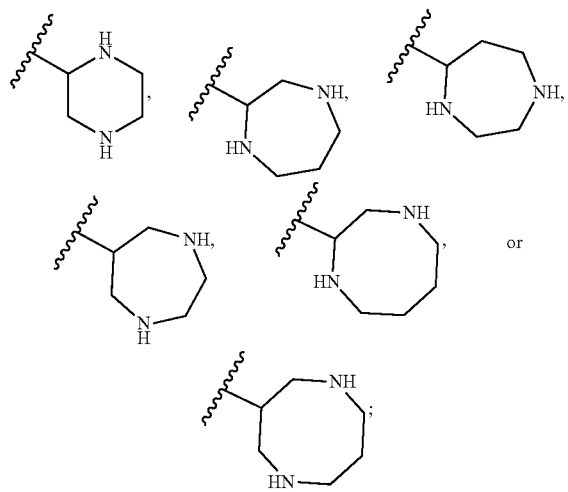

wherein the piperazin-2-yl is substituted with 1, 2, or 3 substituents independently selected from the group consisting of (C2-C4)alkyl, (C2-C4)alkenyl, (C2-C4)alkynyl, (C1-C4)acyl, cyclopropyl, cyclobutyl, cyclopentyl, cyclohexyl, aryl, and heteroaryl;
wherein the 1,4-diazepan-2-yl, 1,4-diazepan-5-yl, 1,4-diazepan-6-yl, 1,4-diazocan-2-yl, or 1,5-diazocan-3-yl is optionally substituted with 1, 2, or 3 substituents independently selected from the group consisting of (C1-C4)alkyl, (C2-C4)alkenyl, (C2-C4)alkynyl, (C1-C4)acyl, cyclopropyl, cyclobutyl, cyclopentyl, cyclohexyl, aryl, and heteroaryl; and
wherein each (C1-C4)alkyl, (C2-C4)alkyl, (C2-C4)alkenyl, and (C2-C4)alkynyl substituent is optionally and independently substituted with 1, 2, or 3 substituents independently selected from the group consisting of halogen, O(C1-C4)alkyl, and SH.

2. The compound according to claim 1, or a pharmaceutically acceptable salt or stereoisomer thereof, wherein B is:

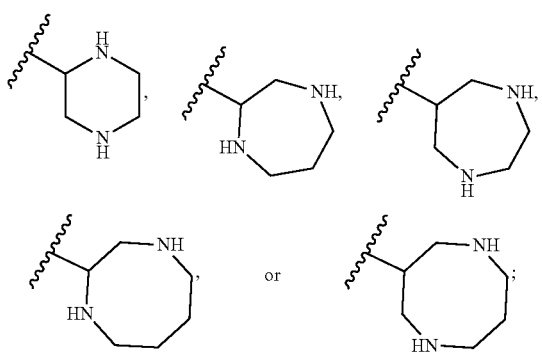

wherein the piperazin-2-yl is substituted with 1, 2, or 3 substituents independently selected from the group consisting of (C2-C4)alkyl, (C2-C4)alkenyl, (C2-C4)alkynyl, (C1-C4)acyl, cyclopropyl, cyclobutyl, cyclopentyl, cyclohexyl, aryl, and heteroaryl;
wherein the 1,4-diazepan-2-yl, 1,4-diazepan-6-yl, 1,4-diazocan-2-yl, or 1,5-diazocan-3-yl is optionally substituted with 1, 2, or 3 substituents independently selected from the group consisting of (C1-C4)alkyl, (C2-C4)alkenyl, (C2-C4)alkynyl, (C1-C4)acyl, cyclopropyl, cyclobutyl, cyclopentyl, cyclohexyl, aryl, and heteroaryl; and
wherein each (C1-C4)alkyl, (C2-C4)alkyl, (C2-C4)alkenyl, and (C2-C4)alkynyl substituent is optionally and independently substituted with 1, 2, or 3 substituents independently selected from the group consisting of halogen, O(C1-C4)alkyl, and SH.

3. A pharmaceutical composition comprising the compound according to claim 1, or a pharmaceutically acceptable salt or stereoisomer thereof, and a pharmaceutically acceptable carrier.

4. The pharmaceutical composition according to claim 3, wherein the pharmaceutical composition is formulated for oral administration.

5. The pharmaceutical composition according to claim 3, wherein the pharmaceutical composition is formulated for parenteral administration.

6. The pharmaceutical composition according to claim 5, wherein the parenteral administration is subcutaneous, intravenous, intramuscular, or intrathecal.

7. The pharmaceutical composition according to claim 3, wherein the pharmaceutical composition further comprises an antioxidant.

8. A compound according to formula I:

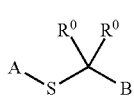

formula I or a pharmaceutically acceptable salt or stereoisomer thereof,
wherein:
each $R^0$ is independently (C1-C3)alkyl;
A is H; and
B is:

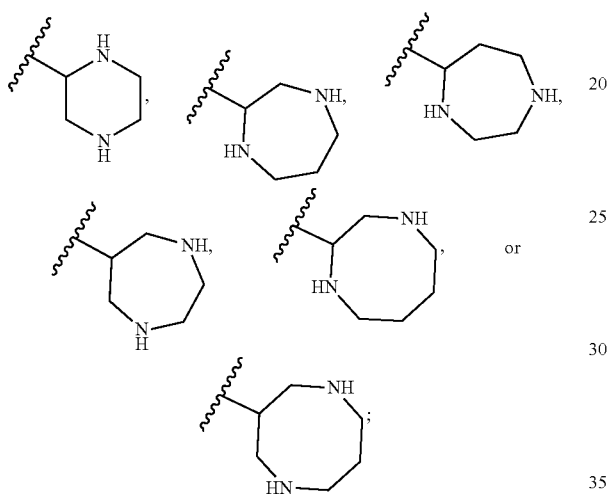

wherein the piperazin-2-yl, 1,4-diazepan-2-yl, 1,4-diazepan-5-yl, 1,4-diazepan-6-yl, 1,4-diazocan-2-yl, or 1,5-diazocan-3-yl is optionally substituted with 1, 2, or 3 substituents independently selected from the group consisting of (C1-C4)alkyl, (C2-C4)alkenyl, (C2-C4)alkynyl, (C1-C4)acyl, cyclopropyl, cyclobutyl, cyclopentyl, cyclohexyl, aryl, and heteroaryl; and
wherein each (C1-C4)alkyl, (C2-C4)alkenyl, and (C2-C4)alkynyl substituent is optionally and independently substituted with 1, 2, or 3 substituents independently selected from the group consisting of halogen, O(C1-C4)alkyl, and SH.

9. A pharmaceutical composition comprising the compound according to claim 8, or a pharmaceutically acceptable salt or stereoisomer thereof, and a pharmaceutically acceptable carrier.

10. The pharmaceutical composition according to claim 9, wherein the pharmaceutical composition is formulated for oral administration.

11. The pharmaceutical composition according to claim 9, wherein the pharmaceutical composition is formulated for parenteral administration.

12. The pharmaceutical composition according to claim 11, wherein the parenteral administration is subcutaneous, intravenous, intramuscular, or intrathecal.

13. The pharmaceutical composition according to claim 9, wherein the pharmaceutical composition further comprises an antioxidant.

14. A compound selected from the group consisting of:

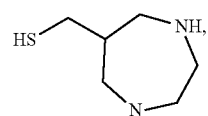  22

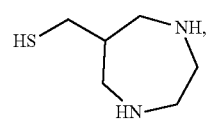  26

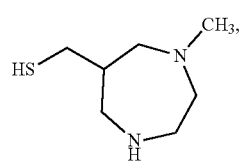  28

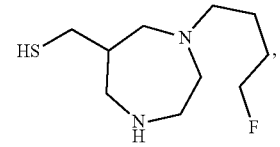  29

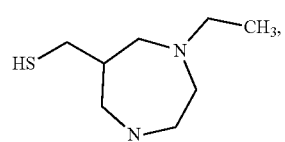  30

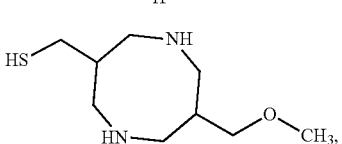  31

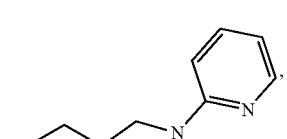  34

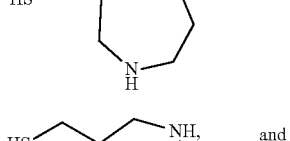  39 and

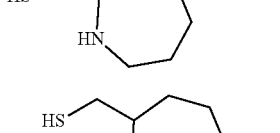  40 or a pharmaceutically acceptable salt or stereoisomer thereof.

15. A pharmaceutical composition comprising the compound according to claim 14, or a pharmaceutically acceptable salt or stereoisomer thereof, and a pharmaceutically acceptable carrier.

16. The pharmaceutical composition according to claim 15, wherein the pharmaceutical composition is formulated for oral administration.

17. The pharmaceutical composition according to claim 15, wherein the pharmaceutical composition is formulated for parenteral administration.

18. The pharmaceutical composition according to claim 17, wherein the parenteral administration is subcutaneous, intravenous, intramuscular, or intrathecal.

19. The pharmaceutical composition according to claim 15, wherein the pharmaceutical composition further comprises an antioxidant.

20. A compound selected from the group consisting of:

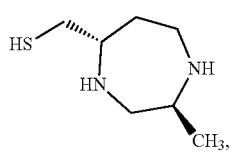
43

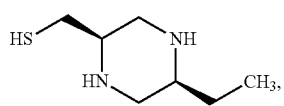
45

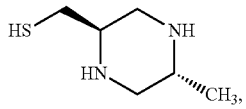
47

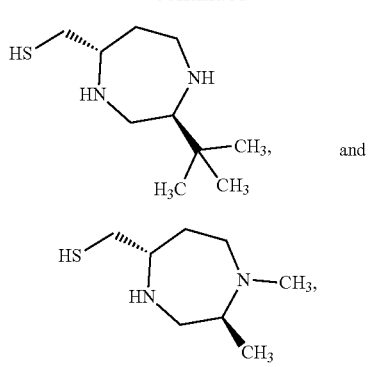
48 and

49 or a pharmaceutically acceptable salt thereof.

21. A pharmaceutical composition comprising the compound according to claim 20, or a pharmaceutically acceptable salt thereof, and a pharmaceutically acceptable carrier.

22. The pharmaceutical composition according to claim 21, wherein the pharmaceutical composition is formulated for oral administration.

23. The pharmaceutical composition according to claim 21, wherein the pharmaceutical composition is formulated for parenteral administration.

24. The pharmaceutical composition according to claim 23, wherein the parenteral administration is subcutaneous, intravenous, intramuscular, or intrathecal.

25. The pharmaceutical composition according to claim 21, wherein the pharmaceutical composition further comprises an antioxidant.

* * * * *

UNITED STATES PATENT AND TRADEMARK OFFICE
CERTIFICATE OF CORRECTION

| | |
|---|---|
| PATENT NO. | : 11,566,032 B2 |
| APPLICATION NO. | : 17/315258 |
| DATED | : January 31, 2023 |
| INVENTOR(S) | : Philip S. Schein et al. |

It is certified that error appears in the above-identified patent and that said Letters Patent is hereby corrected as shown below:

In the Claims

In Claim 1, Column 193, Line 31, please move "formula I" to Line 35 so that it is placed under the chemical structure between Lines 32-34

In Claim 1, Column 193, Line 36, please insert --or a pharmaceutically acceptable salt or stereoisomer thereof, wherein:-- before Line 37 starting "each. . ."

In Claim 1, Column 193, Line 37, please change "$R^O$" to --$R^0$--

In Claim 8, Column 195, Line 4, please move "formula I" to Line 8 so that it is placed under the chemical structure shown between Lines 5-7

In Claim 8, Column 195, Line 12, please change "$R^O$" to --$R^0$--

Signed and Sealed this
Twenty-first Day of March, 2023

Katherine Kelly Vidal
*Director of the United States Patent and Trademark Office*